US008399827B1

(12) United States Patent
Grothe

(10) Patent No.: US 8,399,827 B1
(45) Date of Patent: Mar. 19, 2013

(54) MASS SPECTROMETRY SYSTEMS

(75) Inventor: Robert A. Grothe, Burlingame, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 13/397,161

(22) Filed: Feb. 15, 2012

Related U.S. Application Data

(63) Continuation of application No. 12/207,435, filed on Sep. 9, 2008, now abandoned.

(60) Provisional application No. 60/971,158, filed on Sep. 10, 2007.

(51) Int. Cl.
*G01N 33/53* (2006.01)

(52) U.S. Cl. .......................... 250/282; 250/292; 702/23

(58) Field of Classification Search .................. 250/282
See application file for complete search history.

(56) References Cited

U.S. PATENT DOCUMENTS 4,945,234 A 7/1990 Goodman et al.
4,959,543 A 9/1990 McIver, Jr. et al.
6,498,340 B2 * 12/2002 Anderson et al. .......... 250/252.1
6,608,302 B2 8/2003 Smith et al.
6,906,320 B2 6/2005 Sachs et al.
7,348,553 B2 3/2008 Wang et al.
7,451,052 B2 * 11/2008 Wang et al. ..................... 702/85
7,493,225 B2 2/2009 Wang et al.
7,499,807 B1 * 3/2009 Tolmachev et al. ............ 702/23
7,577,538 B2 8/2009 Wang
2002/0130259 A1 9/2002 Anderson et al.
2004/0113063 A1 6/2004 Davis
2005/0026198 A1 2/2005 Balac Sipes
2005/0029441 A1 2/2005 Davis
2005/0086017 A1 4/2005 Wang
2005/0092910 A1 * 5/2005 Geromanos et al. .......... 250/282
2006/0169883 A1 8/2006 Wang
2006/0217911 A1 9/2006 Wang

FOREIGN PATENT DOCUMENTS

WO WO0070649 11/2000
WO WO2006130787 12/2006
WO WO2007140341 12/2007

OTHER PUBLICATIONS

Bruce, et al. "Obtaining more accurate Fourier transform ion cyclotron resonance mass measurements without internal standards using mulitply charged ions," J. Am. Soc. Mass Spectrom., 2000, vol. 11, 416-421.

Cooper, et al. "Electrospray ionization Fourier transform mass spectrometric analysis of wine," J. Agric. Food Chem., 2001, vol. 49, 5710-5718.

Dempster, et al., "Maximum likelihood from incomplete data via the $EM$ algorithm," Journal of the Royal Statistical Society, Series B (Methodological), vol. 39, No. 1 (1977), pp. 1-38.

Easterling, M.L. et al., "Routine Part-per-Milliion Mass Accuracy for High-Mass Ions: Space-Charge Effects in MALDI FT-ICR", Anal. Chem., 1999, 71(3):624-632.

Feng Xian et al., Automated broadband phase correction of Fourier transform ion cyclotron resonance mass spectra. Analytical Chemistry 2010 vol. 82 pp. 8807-8812.

(Continued)

*Primary Examiner* — Phillip A Johnston
(74) *Attorney, Agent, or Firm* — Hema Vakharia-Rao; Nixon Peabody LLP

(57) ABSTRACT

Described herein are methods that may be used related to mass spectrometry, such as mass spectrometry analysis, mass spectrometry calibration, identification of proteins/peptides by mass spectrometry and/or mass spectrometry data collection strategies. In one embodiment, the subject matter discloses a phase-modeling analysis method for identification of proteins or peptides by mass spectrometry.

5 Claims, 32 Drawing Sheets frequency (Hz)

OTHER PUBLICATIONS

Giancaspro, C. et al., Exact interpolation of Fourier transform spectra. Allied Spectroscopy 1993 vol. 37 pp. 153-165.
Gorshkov, et al. "Analysis and elimination of systematic errors originating from Coulomb mutual interaction and image charge in Fourier transform ion cyclotron resonance precise mass difference measurements," J. Am. Soc. Mass Spectrom., 1993, vol. 4, 855-868.
Hubbard, T. et al., "Ensembl 2005", Nucleic Acids Research, 2005, vol. 33, Database issue D447-D453.
Ledford, E.B. et al., "Space charge effects in fourier transform mass spectrometry. Mass calibration", Anal. Chem., 1984, 56:2744-2748.
Marshall, et al. "Fourier transform ion cyclotron resonance mass spectrometry: A primer," Mass Spectrometry Reviews, 1998, vol. 17, 1-35.
Marshall, et al. "Petroleomics: The next grand challenge for chemical analysis," Acc. Chem. Res., 2004, vol. 37, 53-59.
Masseslon, C. et al., "Mass measurement errors caused by "local" frequency perturbations in FTICR mass spectrometry", Journal of the American Society for Mass Spectrometry. 2002, 13:99-106.
Meier, J. et al., Pure absorption-mode spectra from Bayesian maximum entropy analysis of ion-cyclotron resonance time-domain signals. Analytical Chemistry 1991 vol. 63 pp. 551-560.
Wool, A. et al., "Precalibration of matrix-assisted laser desorption/ionization-time of flight spectra for peptide mass fingerprinting", Proteomics, 2002, 2:1365-1373.
Yanofsky, et al. "Multicomponent internal recalibration of an LC-FTICR-MS analysis employing a partially characterized complex peptide mixture: Systematic and random errors," Anal. Chem., 2005, vol. 7, 7246-7254.
Zhang, et al. "Accurate mass measurements by Fourier transform mass spectrometry," Mass Spectrometry Reviews, 2005, vol. 24, 286-309.
Bernauth, P. Fourier techniques. Encyclopedia of Analytical Science 2005 vol. 3 pp. 498-504.
Sylwester et al., ANDRIL-Maximum likelihood algorithm for deconvolution of SXT images. Acta Astronomica 1998 vol. 48 pp. 519-545.
Extended EP Search Report for EP App No. 07797803.9, dated Oct. 5, 2011.
ISR for PCT/US2006121321, dated Apr. 26, 2007.
Office Action in U.S. Appl. No. 11/914,588, dated Apr. 19, 2010.
Office Action in U.S. Appl. No. 11/914,588, dated Oct. 19, 2010.
Office Action in U.S. Appl. No. 11/914,588, Feb. 3, 2011.
Office Action in U.S. Appl. No. 11/914,588, dated Jun. 15, 2011.
Supplemental EP Search Report for EP App No. EP 06 77 1860, dated May 6, 2010.
IPRP and Written Opinion for PCT/US2006/21321, Apr. 26, 2007.
IPRP and Written Opinion for PCT/US2007/69811, dated Jan. 23, 2008.
ISR for PCT/US2007/69811, dated Jan. 23, 2008.
ISR for PCT/US2006/21321, dated Apr. 26, 2007.
Beu, S.C. et al., Broadband Phase Correction of FT-ICR Mass Spectra via Simultaneous Excitation and Detection, Analytical Chemistry, 2004, 76:19, pp. 5756-5761.
Meek, "Prediction of peptide retention times in high-pressure liquid chromatography on the basis of amino-acid compositon," Procceedings of the National Adademy of Sciences, 1980, 77(3): 1632-1636.
Pardee, "Calculations on paper chromatography of peptides," The Journal of Biological Chemistry, 1951, 190:757-762.
Spengler, "De Novo Sequencing, Peptide Composition Analysis, and Composition-Based Sequencing: A New Strategy Employing Accurate Mass Detemnation by Fourier Transform Ion Cyclotron Resonance Mass Sepctrometry," Journal of the American Society for Mass Spectrometry, 2004, 15:703-714.
Vining, B.A. et al., Phase Correction for Collision Model Analysis and Enhanced Resolving Power of Fourier Transform Ion Cyclotron Resonance Mass Spectra, Analytical Chemistry, 1999, 71:2, pp. 460-467.
Zubarev et al., "Electron Capture Dissociation of Multiply Charged Protein Cations. A Nonergodic Process," J. Am. Chem. Soc., 1998, 120(13): 3265-3266.
Zubarev, "Electron-capture dissociation tandem mass spectrometry," Current Opinion in Biotechnology, 2004, 15: 12-16.

* cited by examiner (a)

(b)

Figure 6 (contd.)
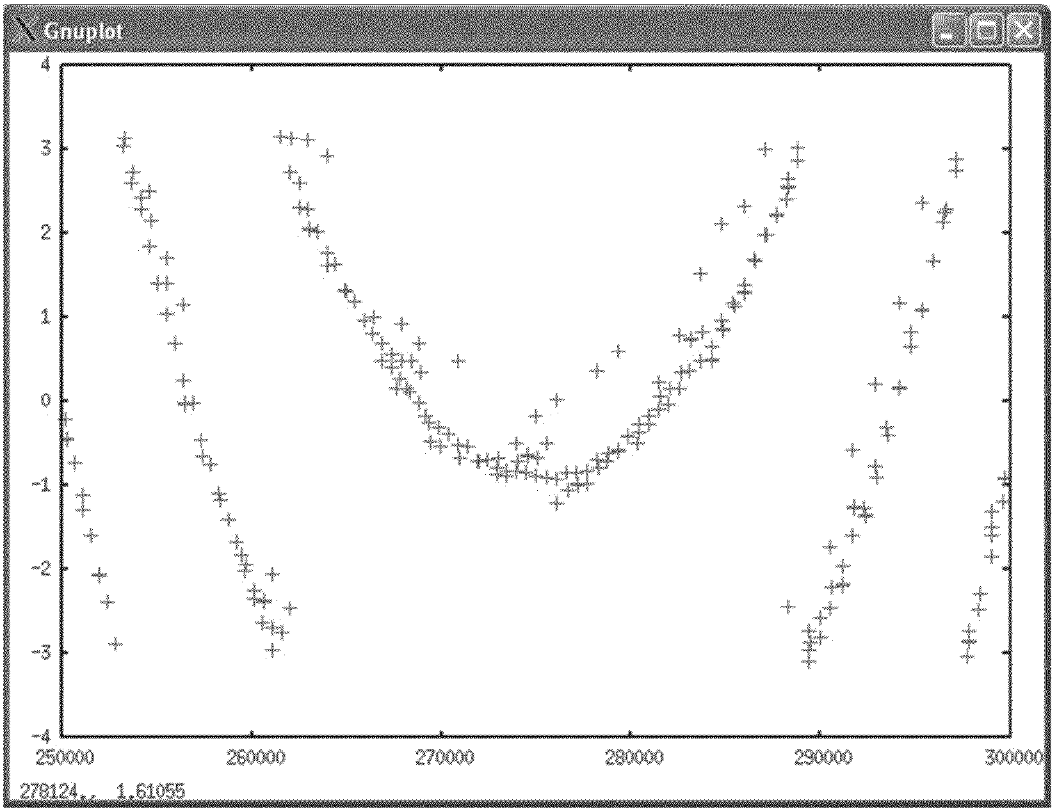
(c)

(a)

(b)

Figure 7 (Contd)
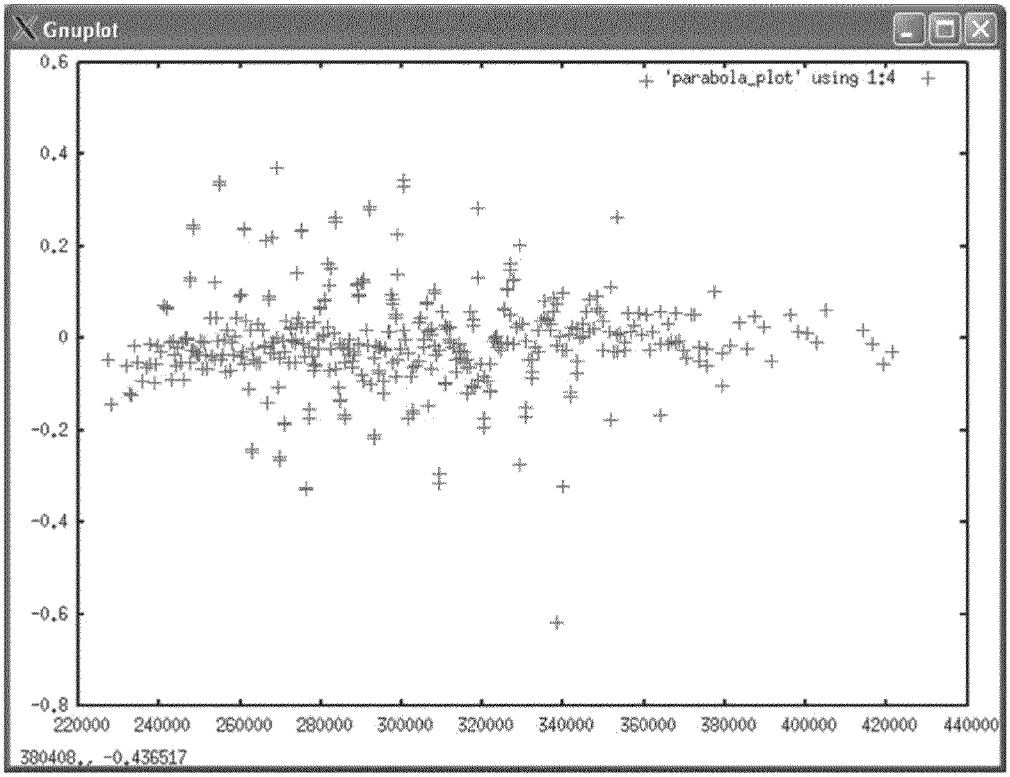
(c)

(a)

(b)

(a)

(b)

MASS SPECTROMETRY SYSTEMS

CROSS-REFERENCE TO RELATED APPLICATIONS

This application is a continuation of U.S. Ser. No. 12/207,435, filed Sep. 9, 2008, now abandoned, which claims the priority benefit of U.S. provisional application No. 60/971,158, filed Sep. 10, 2007, the contents of all of which are herein incorporated by reference in their entirety.

FIELD OF THE INVENTION

The invention relates to mass spectrometry; specifically, to mass spectrometry systems and improvements to the same.

BACKGROUND OF THE INVENTION

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Mass spectrometry addresses two key questions: (1) "what's in the sample?" and (2) "how much is there?". Both questions are addressed in the instant application. Several of the embodiments described herein focus on the first question; that is, identification of the components in a mixture. Embodiments of the present invention relate to software that has demonstrated substantial improvements in mass accuracy, sensitivity and mass resolving power. Certain of these gains follow directly from estimation and modeling of ion resonances using a physical model described by Marshall and Comisarow. Other embodiments described herein focus upon applications of estimation and modeling of the phases of ion resonances. Such methods can be divided into functional groups: phase-based methods, calibration, adaptive data-collection strategies, and miscellaneous auxiliary functions.

The traditional approach to analysis of Fourier transform mass spectrometry ("FTMS") spectra is bottom-up. Resonances are detected in the spectra, from which inferences are made about the composition of the analyzed sample. Most of the embodiments described herein involve approaches to bottom-up analysis. Key steps in bottom-up analysis of FTMS data are detection and estimation of ion resonances, mass calibration, and identification. Various embodiments of the present invention involve reducing the 4 MB of data representing an FTMS (MS-1) spectrum to a list of candidate elemental compositions for each detected peak with probabilities assigned to these identities and abundance estimates. The essential information represents a data reduction of roughly three orders of magnitude relative to the unprocessed spectrum. In the bottom-up approach to data analysis, peaks are detected and characterized by estimation first, and then knowledge about the sample is used to calibrate and identify the components. The ability to perform these calculations in real-time creates exciting possibilities for adaptive workflows that actively direct acquisition of optimally informative data.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 10 shows two ion resonances, real and imaginary spectra before phase correction. The phase for both ions is approximately 5π/4.

FIG. 11 shows the phase corrected spectra; the real part has even symmetry about the centroid and the imaginary part has odd symmetry. Some distortion in the peak shape is due to a display artifact (linear interpolation).

DETAILED DESCRIPTION

Figure 1:
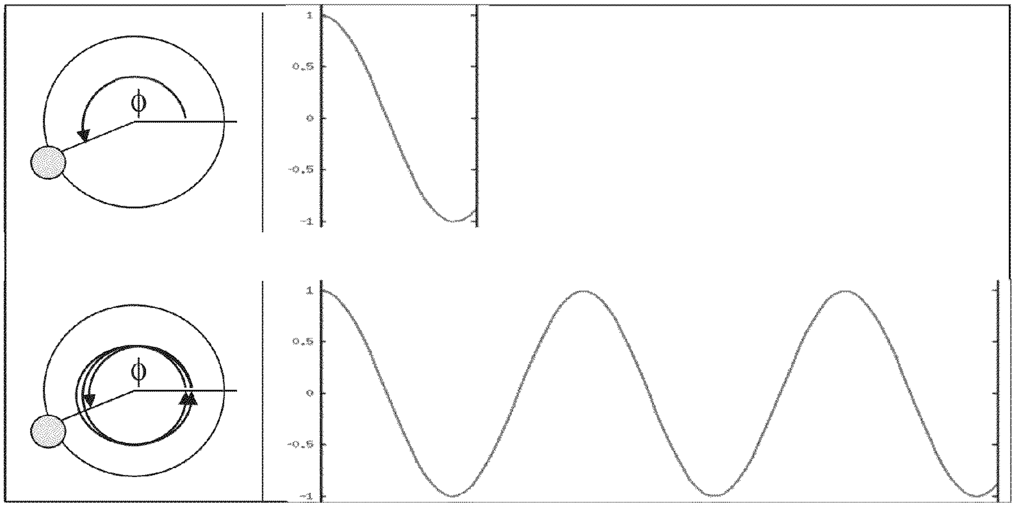
FIG. 1 illustrates that the relative phase indicates the position of an ion relative to the origin of its oscillation cycle, in accordance with an embodiment of Component 1 of the present invention. The absolute phase refers to the angular displacement of the ion swept out over some interval of time. The absolute phase differs from the absolute phase by an integer multiple of 2p. Phase models describe the relationship between ion frequencies and absolute phases. However, in connection with Component 1, the relative phase, and not the absolute phase, is observed. The discrepancy between the relative and absolute phases is known as the "phase wrapping" problem.

Described herein are Components that have been developed to improve and/or modify various aspects of mass spectrometry equipment and techniques, as well as the attendant scientific fields of study, such as proteomics and the analysis of petroleum, although the invention is in no way limited thereto. In various embodiments, the Components may be implemented independently or together in any number of combinations as will be readily apparent to those of skill in the art. Furthermore, certain of the Components may be implemented by way of software instructions that can be developed by routine effort based on the information provided herein and the ordinary level of skill in the relevant art. The inventive methods, software, electronic media on which the software resides, computer and/or electronic equipment that operates based on the software's instructions and combinations thereof are each contemplated as being within the scope of the present invention. Furthermore, some Components may be implemented by mechanical alteration of existing mass spectrometric equipment, as described in greater detail herein.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001); and Sambrook and Russel, Molecular Cloning: A Laboratory Manual 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

Model Based Estimation

In Components 1-8, a family of estimators and detectors are described that make use of the fact that the Marshall-Comisarow (MC) model provides a highly accurate description of FTMS data. In the MC model, observed ion resonances are characterized by an initial magnitude and phase, a frequency and an (exponential) decay constant. The (noise-free) peak shape in the frequency domain depends upon these four parameters as well as the duration that the signal is observed (assumed to be known). The observed FTMS data (in either the time or frequency domain) consists of a linear superposition of these ion resonances and additive white Gaussian noise. The close correspondence between the MC model and observed FTMS data, collected on both the LTQ-FT and Orbitrap™ (available from ThermoFisher, Inc.) instruments, suggest that this model provides a solid theoretical foundation for developing analytic software and performing calculations to predict the relative performance of various analysis methods.

International PCT patent application No. PCT/US2007/069811, filed May 25, 2007 and incorporated by reference herein in its entirety, describes the estimation of ion resonance parameters from FTMS data, and serves is a foundation for much of the estimation work described herein. For each detected ion resonance signal, maximum-likelihood estimates of the four parameters described by the MC model are computed. Initially, the goal was to generate more accurate frequency estimates. Success in reaching this goal was validated by comparing mass estimates calculated by the inventor's software versus that of Xcalibur™ software (available from ThermoFisher, Inc.) on the same data sets, when frequency estimates were calibrated using the same internal calibration least-squares technique. The mass accuracy gain was about 30%.

The magnitude of the peak is another parameter estimated at the same time as frequency in the estimator described in international PCT patent application No. PCT/US2007/069811. These estimates are expected to be accurate based upon the excellent correspondence between model and observed data. Conversely, existing methods for abundance estimation have limitations. These methods are expected to provide substantially improved estimates of ion abundances.

The phase of the ion resonance is yet another parameter estimated by the method described in international PCT patent application No. PCT/US2007/069811. At first, phase was viewed as a "nuisance parameter"—a parameter that had to be estimated accurately only to allow accurate estimation of other parameters that have intrinsic value. However, it was eventually realized that accurate phase estimation allowed one to model the relationship between the phases and frequencies of the ion resonances. This work is described in Component 1, below. Models were determined that accurately matched the phases of all detected ion resonances in both Orbitrap™ and FT-ICR data without assuming prior knowledge of what the theoretical relationship should be. Then, the models were validated by showing that the coefficients found by de novo curve fitting agreed with values computed using theoretical principles to 100 parts-per-million or better.

The ability to accurately model ion resonance phases permits improvements in mass spectrometry performance along several lines of development: phase-correction (Component 2), phase-enhanced detection (Components 3 and 4), phase-enhanced frequency estimation (Component 5) and linear decomposition of phased spectra (Component 6)

In phase correction (described in Component 2), the concept is to apply a complex-valued scale factor to the phase of each frequency sample in the spectrum to rotate its phase back to zero. The phase-corrected spectrum is what the spectrum would look like if it were physically possible to place all the ions on a common starting line when the detection process begins. The real component of the phase-corrected spectrum is called the absorption spectrum. The absorption spectrum is the projection of the complex-valued resonance that has the narrowest line shape, making it ideal for graphical display and for simplifying the complexity of the calculations described in Component 7.

The idea behind phase-enhanced detection (Components 3 and 4) is that the phase of a putative ion resonance—if it can be predicted—leads to substantially improved discrimination of weak ion resonances from noise. It is established in the field that when an accurate signal model exists, the optimal detection strategy is matched filtering. For FTMS, the matched filter is the MC model. A matched filter returns a number indicating the overlap between the signal model when at each location in the data (i.e., a frequency value in a spectrum). Filtering of FTMS data can be performed in the time of frequency domain, but is more computationally efficient (by four orders of magnitude) in the frequency domain. Because the frequency domain data and model are complex-valued, the matched filter returns a complex-valued overlap value, which can be represented as a magnitude and a phase.

It is convenient to use a fixed zero-phase signal model. In this case, the expected phase of the overlap value is equal to the phase of the ion resonance. If the ion resonance is known a priori (i.e., specified by a model as produced by Component 1), the projection of the overlap value along the direction of the predicted phase may be used to detect the presence of a signal. If not, the magnitude of the overlap may be used. In the absence of phase, noise fluctuations of occasionally high magnitude are mistaken for ion resonances. However, noise has a uniformly random distribution of phases, but ion resonance signals do not. Therefore, it is possible to rule out noisy fluctuations that do not have the correct phase.

Component 3 describes a phase-enhanced detector and compares its performance to a phase-naïve detector by calculating theoretical receiver operating characteristic ("ROC") curves. The phase-enhanced detector achieves a level of performance that is equivalent to boosting the signal-to-noise ratio ("SNR") by 0.34 units relative to the phase-naïve detector. At a false alarm rate chosen to give 100 false positive per spectra, the phase-enhanced detector detects over twice as many peaks with SNR=2 as the phase-naïve detector Component 4 describes detection of entire isotope envelopes rather than individual ion resonances. This development further enhances the ability to detect weak signals. For example, for a peptide containing approximately 90 carbons (mass about 1800 Daltons), the number of monoisotopic molecules is about the same as the number of molecules with exactly one C-13 atom. Detecting an isotope envelope of two equal peaks (rather than either peak in isolation as in Component 3) boosts SNR by a factor of $\sqrt{2}$. Therefore, one would expect a slightly larger gain for peptides of mass around 1800 Daltons. The gain factor would increase quadratically in the peptide length from approximately 1 for very small peptides up to about 1.5 for peptides of length 16.

Component 5 is a departure from detectors described in Components 2-4 and a return to the problem of estimation. Component 1 demonstrates that the phase and frequency of ion resonances are not independent variables as had been assumed in the development of the estimator in international PCT patent application No. PCT/US2007/069811. A new estimator is described in Component 5, in which the phase of the resonance is assumed to be a function of the resonant frequency. The coupling of phase and frequency adds an important constraint that improves estimation in the presence of noise.

Components 1-5 address the typical scenario in which the observed signal is (effectively) separated from other signals. Component 6 addresses the less common, but very important, situation in which the separation between two resonant frequencies is less than several times the width of the resonance peak (i.e., signal overlap). In many cases, overlap between two signals is visually apparent and easily detected by automated software. In other cases, overlap was apparent only because of an atypical degree of deviation between the observed signal and a signal model of a single ion resonance. In Component 6, a detector is described that evaluates the likelihood of the hypothesis that a feature arises from one, and not multiple signals and an estimator that determines the parameters describing each individual ion resonance. Signal overlaps are particularly common is situations where complex mixtures are not amenable to fractionation (e.g., petroleum).

Components 1-6 describe detection of ion resonances and estimation of parameters following detection. As mentioned above, this can be described as "bottom-up" analysis because information about the sample is inferred from detected ion resonances. Components 7 and 8 describe an alternative—top-down analysis—in which the potential components in the sample have been enumerated. In top-down analysis, the goal is to determine how much of each component is present in a sample. For components that are not present, the abundance estimate should be zero.

Top-down analysis is particularly well-suited to petroleum analysis, among other things, where the number of detected species is less than an order of magnitude less than the number of "likely" species. For example, Alan Marshall's group at the National High Magnetic Field Laboratory reported identification of 28,000 distinct species in a single spectrum. The number of possible elemental compositions is roughly 100,000.

Abundance estimates are computed by solving a system of linear equations involving the overlap among pairs of ion resonance signal models and between these models and the observed spectrum. Linear equations result only when the model and data are viewed as complex-valued. Magnitudes of ion resonances are not additive. The use of a phase model, as described in Component 1, improves the accuracy of the estimates. Application of the method using the absorption spectrum from phase-corrected data can reduce overlaps between signal models, simplifying and thus speeding up the calculation. The signal models can be individual ion resonances or entire isotope envelopes. In either case, the basic equation describing the estimator is the same.

Component 8 extends the concept in Component 7 of decomposing an entire proteomic LC-MS run into a superposition of protein images. Protein images would be the idealized LC-MS run that would result from analysis of a purified protein under a given set of experimental conditions. Given the theoretical (or observed) image of each purified protein in an LC-MS experiment, the same equations described in Component 7 would be used to calculate abundance estimates. The challenge addressed in Component 8 is a mechanism for determining protein images from large repositories of proteomic data.

Component 1: Modeling the Phases of Ion Resonances in Fourier-Transform Mass Spectrometry FTMS involves inducing ions to oscillate in an applied field and determining the oscillation frequency of each ion to infer its mass-to-charge ratio (m/z). The Fourier transform is used to resolve the superposition of signals from ion packets with distinct frequencies. The signal from each ion packet is characterized by five parameters: amplitude, frequency, phase, decay constant and the signal duration. The signal duration is known; the other four parameters are estimated for each signal in a spectrum from the observed data.

Phase is the unique property that distinguishes FTMS from other types of mass spectrometry. As a consequence of phase differences among signals, the magnitudes of overlapping signals do not add. Instead, overlapping signals interfere with each other like waves. Similarly, the noise interferes with a signal constructively and destructively with equal probability. The opportunities that accompany the properties of phase have yet to be exploited in FTMS analysis. In fact, heretofore FTMS analysis has deliberately avoided consideration of phase by using phase-invariant magnitude spectra.

This Component is concerned with modeling the relationship between the phases of an ion's oscillation and its oscillation frequency. There are two different types of instruments for performing FTMS experiments: traditional FT-ICR devices and the Orbitrap™ instrument. The phase behavior is analyzed for each instrument.

In Fourier-transform ion cyclotron resonance mass spectrometry ("FT-ICR MS"), ions are injected into a cell in which there is a constant, spatially homogeneous magnetic field.

Each ion orbits with a frequency that is inversely proportional to its m/z value. Orbital radii are small and phases are essentially uniformly random. To allow detection of ion frequencies, the ions are resonantly excited by a transient radio-frequency pulse. After the pulse is turned off, ions with the same frequency (and thus also m/z) orbit in coherent packets at a large radius. The motion of the ion packets is detected by measuring the voltage induced by difference in the image charges induced upon two conducting detector plates. The line between the detectors forms an axis that lies in the orbital plane. The voltage between the plates is linearly proportional to the ion's displacement along detector axis. Therefore, an ion in a circular orbit would generate a sinusoidal signal.

The Orbitrap™ instrument performs FTMS using a modified design. A central electrode, rather than a magnetic field, provides the centripetal force that traps ions in an orbital trajectory. As in FT-ICR, a harmonic potential perpendicular to the orbital plane is used to trap ions in the direction perpendicular to the orbital plane. However, in the Orbitrap™ instrument the detector axis is perpendicular to the orbital plane, measuring linear ion oscillations induced by the harmonic potential. The Orbitrap™ instrument has the advantage that ions can be injected off-axis (i.e., displaced relative to the vertex of the harmonic potential) as a coherent packet, eliminating the need for excitation to precede detection. The injection process, like excitation, does interfere somewhat with detection, and a waiting time is required before detection.

In either type of FTMS, the observed signal is the sum of contributions from ion packets, each with a distinct m/z value, and each component signal is a decaying sinusoid. Analysis of FTMS data involves detecting ion signals (i.e., discriminating ion signals from noisy voltage fluctuations), estimating the resonant frequency of each signal, converting frequencies into m/z values (i.e., mass calibration), and identifying the elemental composition of each ion from an accurate estimate of its m/z value. Fundamental challenges in mass spectrometry analysis include the detection of very weak signals (sensitivity), accurate determination of m/z (mass accuracy), and resolution of signals with very similar m/z values (mass resolving power). In fact, these three performance metrics are the primary specifications by which mass spectrometry platforms are evaluated. Significant investment in hardware for FTMS and other types of mass spectrometry has led to performance gains. Additional improvement as assessed by all three metrics is possible by improving analytical software, and in particular, by modeling the phases of ion resonances in FTMS.

The relative phase of an oscillating particle is its displacement relative to an arbitrarily defined origin of the cycle expressed as a fraction of a complete cycle and multiplied by $2\pi$ radians/cycle. For example, the phase of an FT-ICR signal is equivalent to the ion's angular displacement relative to a defined origin. A natural origin is one of the two points of intersection between the orbit and the detector axis. The origin is chosen as the point that is closer to an arbitrarily defined reference detector (FIG. 1).

A second notion of "phase" arises from the fact that each sample value of the discrete Fourier transform (i.e., evaluated at a given frequency) is a complex number that can be thought of as representing the amplitude and phase of a wave of that frequency. The phase of the DFT evaluated at cyclic frequency f represents the angular shift that results in the largest overlap between a sinusoid of frequency f and the observed signal. For a sinusoidal signal, and also for the FT-ICR signal model described in Component 1, the phase of the DFT at frequency f for an ion oscillating at frequency f is identical to the initial angular displacement of the ion (i.e., the first notion of phase described above).

In the theoretical limit where the ion's amplitude is constant with time (i.e., no decay) and the observation duration goes to infinity, the DFT is zero except at f. In reality, the signal decays and is observed for a finite duration. As a result, the DFT has non-zero values for frequencies not equal to f. The phases for these "off-resonance" values can be computed directly and are uniformly shifted by the initial angular displacement of the ion.

The two notions of phase described above can be thought of as "relative" to a single oscillation cycle. Relative phases take values in $[0,2\pi)$, or $[-\pi,+\pi)$ depending upon convention. Another notion of phase that is useful in the analysis below takes into account the number of cycles completed by an ion over some arbitrary interval of time. The absolute phase at time t is the relative phase of a signal or an ion at some initial time $t_0$ plus the total phase swept out by the oscillating ion during an interval of time from $t_0$ to t (Equation 1). The phase at $t=t_0$ is denoted by $\phi_0$.

$$\phi^{abs}(t)=\phi(t_0)+\int_{t_0}^{t}2\pi f(t')dt'=\phi_0+\int_{t_0}^{t}2\pi f(t')dt' \quad (1)$$

The "initial time" $t_0$ has different meanings in different contexts. For example, in Orbitrap™ MS, $t_0$ usually denotes the instant that ions are injected into the cell. The meaning of $t_0$ will be made clear when it is used in various contexts below.

An important special case of Equation 1 is oscillations of constant frequency. In this case, the absolute phase can be written as the initial phase plus a term that is linear in both frequency and elapsed time.

$$\phi^{abs}(t)=\phi_0+2\pi f(t-t_0) \quad (2)$$

Note that the initial phase of an ion may depend upon its frequency. To show this explicitly, we write:

$$\phi^{abs}(f,t)=\phi_0(f)+2\pi f(t-t_0) \quad (3)$$

Note that the initial phase $\phi_0$ may have polynomial (e.g., quadratic) dependence upon f. In this case, the overall dependence off upon f may be non-linear, despite the appearance of a linear relationship as suggested by Equation 2.

The absolute phase differs from the relative phase by an integral multiple (n) of $2\pi$ (Equation 4), where n denotes the number of full oscillations completed by the ion during the prescribed time interval.

$$\phi^{abs}(f,t)=\phi^{rel}(f)+2\pi n \quad (4)$$

The relative phase can be computed from the absolute phase by applying the modulo $2\pi$ operation, as shown in Equation 5.

$$\phi^{rel}=\phi^{abs} \bmod 2\pi=\phi^{abs}-2\pi\lfloor\phi^{abs}/2\pi\rfloor \quad (5)$$

Figure 2:
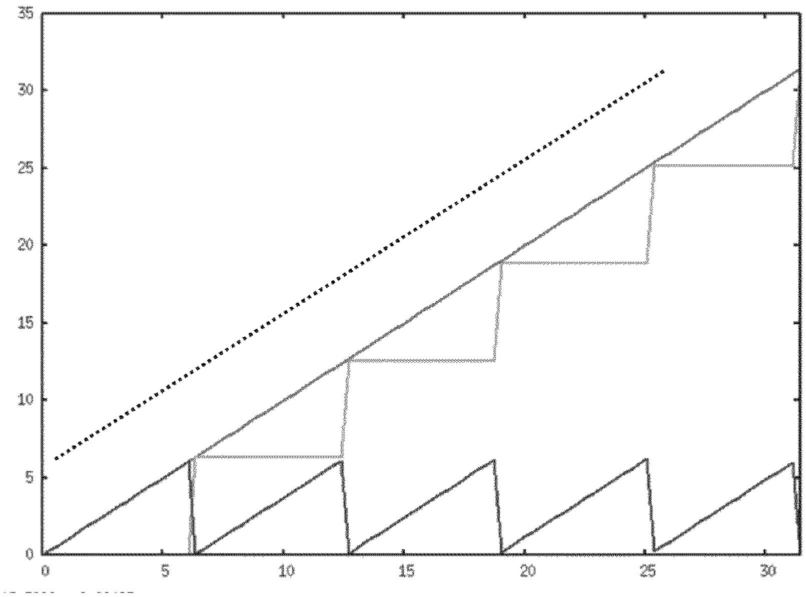
FIG. 2 depicts a graph in which a (fictional) model for absolute phase is illustrated by the dotted line, in accordance with an embodiment of Component 1 of the present invention. In this case, the absolute phase varies linearly with frequency. The zigzag line along the x-axis shows the relative phase, defined on the interval $[0,2\pi]$. Estimated phases for detected resonances would lie on this line. To construct the dotted line, it is necessary to determine the number of complete cycles completed by various ion resonances. The other zigzag line represents the number of complete cycles multiplied by $2\pi$, the phase term that needs to be added to the relative phase (the first zigzag line) to produce the absolute phase (dotted line).

The relative phase of an ion at some point during the detection interval (e.g., the instant that signal detection begins) can be estimated by fitting the observed signal to a signal model. The evolution of an ion's phase as a function of time is most naturally expressed in terms of absolute phase (as in Equation 1). However, absolute phase cannot be directly observed, but must be inferred from the observation of relative phases. This fundamental difficulty is commonly referred to as "phase wrapping" (FIG. 2).

A phase model maps frequencies to relative or absolute phases. A phase model is derived from estimation of the frequencies and phases of a finite number of ions and extended to the entire continuum of frequencies in the spectrum. An ab initio solution of the phase wrapping problem involves evaluating various trial solutions of the phase wrapping problem (i.e., by adding integer multiples of $2\pi$ to each observed relative phase). The resulting mapping is considering successful if the absolute phases show high correspondence with a curve with a small number of degrees of freedom (i.e., a low-order polynomial). Theoretical considerations described below place constraints upon likely models.

Orbitrap™ Instrument

A simple model for the Orbitrap™ instrument is that ions are injected into the cell instantaneously. We call this instant $t=t_0$, and for convenience set $t_0=0$. The injected ions are compressed into a point cloud and injected in the orbital plane. Because the detector axis is orthogonal to the orbital plane, the ions have zero velocity along the detector axis. Thus, the ions sit at a turning point in the oscillation, and their phases at t=0 are all identically zero.

$$\phi_0=0 \tag{6}$$

Each packet of ions with a given m/z value undergoes coherent simple harmonic motion with constant frequency f. Therefore, from Equations 3 and 6, we see that the absolute phase of an on with oscillation frequency fat time t is 2λft.

$$\phi^{abs}(f,t)=2\pi ft \tag{7}$$

Let $t_d$ denote the elapsed time between the instant of that ions are injected into the cell and the instant that detection begins. This is often referred to as the ion's initial phase.

$$\phi^{abs}(f,t_d)=2\pi ft_d \tag{8}$$

In the ideal situation, a plot of absolute phase versus frequency would be linear. The slope of the line would be $2\pi t_d$. Therefore, the elapsed time between injection and detection can be estimated from the slope of the line of best fit, after the relative phases are mapped to absolute phases by adding the appropriate integer multiple of 2π to each observed resonant signal.

In practice, the injection is not instantaneous and results in some dephasing of the ions (i.e., lighter ions accelerate away from heavier ions). This introduces a phase lag, so that Equation 6 does not strictly hold. Analysis of Orbitrap™ instrument data indicates that the phase dependence has a slight quadratic dependence, which may reflect frequency drift during the detection interval or non-linear effects during the injection process.

FT-ICR

As discussed above, detection of ions by FT-ICR requires the ions to be excited by a radio-frequency pulse. The pulse serves two purposes: (1) to cause all ions of the same m/z to oscillate (approximately) in phase, and (2) to increase the orbital radius, thus amplifying the observed voltage signal. A commonly used excitation waveform is a "chirp" pulse—a signal whose frequency increases linearly with time. The design goal is to produce equal energy absorption by ions of all frequency, so that each is excited to the same radius, and thus each the signal from each ion is amplified by the same gain factor. Typically, the applied excitation pulse is allowed to decay before detection begins. The phase dependence of ion's frequency in an FT-ICR experiment varies depending upon the details of the experiment.

An expression for the absolute phase at time t is given by Equation 9.

$$\phi^{abs}(f,t)=\phi(f,t_x(f))+2\pi f(t-t_x(f)) \tag{9}$$

Equation 9 is essentially the same as Equation 3, except that $t_0$ is replaced by $t_x(f)$. $t_x(f)$ denotes the "instant" at which the pulse excites ions orbiting at frequency f. Because excitation involves resonance, $t_x(f)$ also denotes the instant at which the pulse has instantaneous frequency f. For example, a linear "chirp" pulse is an oscillating signal whose instantaneous frequency $f_x$ increases linearly over the range $[f_{lo}, f_{hi}]$ with "sweep rate" r.

$$f_x(t) = \begin{cases} f_{lo} + rt & t \in \left[0, \dfrac{f_{hi} - f_{lo}}{r}\right] \\ 0 & \text{else} \end{cases} \tag{10}$$

In the simplest model, an ion with resonant frequency f is instantaneously excited by the RF pulse at the instant where the chirp sweeps through frequency f. The instant that ions resonating at frequency f are excited can be calculated from Equation 10.

$$t_x(f) = \frac{f - f_{lo}}{r} \quad f \in [f_{lo}, f_{hi}] \tag{11}$$

At that moment, the induced phase of the ion is equal to the instantaneous phase of the RF pulse plus a constant offset (undetermined, but fixed for all frequencies).

The phase of the excited ion at the instant of excitation $t_x$ is determined by the phase of the chirp pulse at this same instant. That is, at time $t_x$ all ions with the resonant frequency f have the phase $\phi(f, t_x)$, which is a constant offset from the phase of the excitation pulse. This constant offset does not depend upon the frequency, and its value is not modeled here. Without loss of generality, we equate the phases of the excitation pulse and the resonant ion at the instant of excitation.

$$\phi(f,t_x)=\phi_x(t) \tag{12}$$

The left-hand side of Equation 12 is the first term in Equation 9. The second term in Equation 9 involves linear propagation of the phase following the "instantaneous" excitation.

The phase of the excitation pulse can be calculated by integrating Equation 10.

$$\phi_x(t) = 2\pi\int_0^t (f_{lo} + rt')\,dt' = 2\pi\left(f_{lo}t + \frac{1}{2}rt^2\right) \quad t \in \left[0, \frac{f_{hi} - f_{lo}}{r}\right] \tag{13}$$

Now, we use equations 12 and 13 to rewrite the expression for the phase in Equation 9.

$$\phi^{abs}(f, t) = 2\pi\left(f_{lo}t_x(f) + \frac{1}{2}rt_x^2\right) + 2\pi f(t - t_x(f)) \quad f \in [f_{lo}, f_{hi}],\ t > t_x(f) \tag{14}$$

Finally, we rewrite equation 14 by replacing $t_x$ using Equation 11. Collecting terms in f, we have:

$$\phi^{abs}(f, t) = C + 2\pi\left(t + \frac{f_{lo}}{r}\right)f - \frac{\pi}{r}f^2 \quad f \in [f_{lo}, f_{hi}],\ t > t_x(f) \tag{15}$$

In particular, we are interested in the value of the phase evaluated $t=t_d$, the beginning of the detection interval. Define t=0 to be the beginning of the excitation pulse and let $t_w$ denote the "waiting" time between the end of the pulse and the beginning of detection. The pulse duration is given by the frequency range divided by the sweep rate, so we have:

$$t_d = \frac{f_{hi} - f_{lo}}{r} + t_w \quad (16)$$

Combining Equations 15 and 16 and simplifying yields the desired expression for the absolute phase in terms of the FT-ICR data acquisition parameters:

$$\phi^{abs}(f, t_d) = C' + 2\pi\left(\frac{f_{hi}}{r} + t_w\right)f - \frac{\pi}{r}f^2 \;\; f \in [f_{lo}, f_{hi}] \quad (17)$$

C' denotes a constant phase lag that will be inferred from observed data, but not directly modeled. The coefficients multiplying f and $f^2$ in Equation 17 can be computed from the maximum excitation frequency $f_{hi}$, the sweep rate r, and the "waiting" time $t_w$. Up to a constant offset, the phases induced a chirp pulse do not depend upon the minimum frequency $f_{lo}$.

Phase modeling algorithms are simplified by constructing an initial model based upon knowledge of the data acquisition parameters. The values of these parameters are assumed to be imperfect, but accurate enough to solve the "phase-wrapping" problem. That is, we assume that the errors in the absolute phases across the spectrum are less than 2π, so that we can determine the number of oscillations completed by each ion packet. Then, it is possible to fit a polynomial (e.g., second-order) to the absolute phases. When an initial model is not available, a trial solution to the phase-wrapping problem must be constructed.

The phase modeling algorithm is, in general, iterative and proceeds from an initial model by alternating steps of retracting and extending the region of the spectrum for which the model is evaluated. Refinement can be applied only to the region of the spectrum for which wrapping numbers have been correctly determined. This region can be determined by examining the difference between the observed relative phases and the calculated relative phases (i.e., the calculated absolute phases modulo 2π). Phase wrapping is apparent when the error gradually drifts to and crosses the boundaries +/−π.

To further refine the model, it is necessary to restrict the model to the region where no phase wrapping occurs. The refined model evaluated on this retracted region will be more accurate, because points outside the region have incorrectly assigned absolute phases and thus introduce large errors. The improved accuracy of the refined model derived from observed phases on this retracted region may make it possible to correctly assign absolute phases to a larger region of the spectrum. The model is assessed against the entire spectrum. If no phase wrapping is apparent, then no further extension is necessary. Alternatively, additional rounds of retraction and extension may be warranted. If an attempt at extension fails to increase the region, then the order of polynomial must be incremented allowing extension to continue until the entire spectrum is covered. Once the phase-wrapping problem has been solved for the entire spectrum, higher-order polynomial can be used to fit the absolute phases to eliminate systematic errors.

When an initial model is not available (e.g., data acquisition parameters are not available), the approach taken here is to assume that the phases are approximately linear over the spectrum (or at least part of the spectrum). The number of cycles completed by various phases is approximately linear and can be specified by the integer number of cycles completed (wrapping number) for the ion packets of highest frequency. All integer differences from zero to an arbitrarily high maximum value can be evaluated.

For example, a sample may contain m detected signals with frequencies $[f_1 \ldots f_m]$ and observed relative phases $[\phi_1 \ldots \phi_m]$. The absolute phase for $\phi_m = \phi_m + 2\pi n_m$, where $n_m$ is the wrapping number for packet m. All integer values for $n_m$ will be tried. Suppose that in a particular trial that $n_m$ is assigned to n. This defines a linear relationship between phase and frequency with slope $r = \phi_m^{abs}/f_m$. This trial model is used to assign wrapping numbers of signals 1 . . . m−1. For example, the $i^{th}$ signal (with frequency $f_i$) has absolute phase $\phi_i = rf_i$ according to the linear model, but absolute phase $\phi_i = \phi_i + 2\pi n_i$ according to the observation of the relative phase. The integer value of $n_i$ that minimizes the difference between the model and the observation is given by Equation 18.

$$n_i = \left\lfloor \frac{(rf_i - \phi_i)}{2\pi} + \frac{1}{2} \right\rfloor \quad (18)$$

After wrapping numbers $[n_1 \ldots n_m]$ have been assigned for a particular trial value of n, the absolute phases are computed and a line of best fit (e.g., least squares) is calculated.

This process is repeated for all integer values of n up to a specified maximum value. The value of n that produces the best fit is kept. The best model discovered by this process is used as the initial model and submitted to the refinement process via retraction and extension described above.

Example 1

Analysis of Thermo "Calmix" by Orbitrap™ MS

A specially formulated mixture of known molecules ("Calmix") was analyzed using an Orbitrap™ instrument. The time-dependent voltage signals (transients) for eight such runs on the same machine were provided. In each run, ion signals for the monoisotopic peaks of ten species (all charge state one) were detected. For each signal, the frequency and initial phase of the ion packet were estimated.

At the time of analysis, the time delay between injection of the ions into the analytic cell and the initiation of the detection interval was not known. It was hypothesized that the phase of each ion packet at the initiation of detection (the "initial" phase) should vary approximately linearly with phase. (See "Theory" section above.) The wrapping number for the highest frequency was allowed to vary from 0 to 100000. (See "Methods" section above.)

For each of the eight runs, a linear fit was found to solve the phase-wrapping problem for the entire spectrum, as predicted by Equation 8. In each case, the collection of observed phases demonstrated a small systematic error relative to the linear model. A second-order polynomial was subsequent fit to the data, eliminating the systematic error.

Example 2

Petroleum Analysis by FT-ICR MS

A transient signal obtained by FT-ICR analysis of a petroleum sample was provided by Alan Marshall's lab at the National High Magnetic Field Laboratory. 666 ion signals were detected, ranging in frequency from 217 kHz to 455 kHz. All species were charge state one, with ion masses ranging from 320.5 Da to 664.7 Da. Maximum-likelihood estimates were produced for the frequency and phase of each detected signal.

A trial linear phase model (expected to fit only part of the spectrum) was constructed exhaustively by allowing the wrapping number of the highest detected frequency to vary from 0 to 100,000, calculating the wrapping numbers for the other frequencies as in Equation 18, and determining the line of best-fit through the absolute phases that result from the observed phases and wrapping numbers as in Equation 4.

After determining the second-order model from the observed phases ab initio, the estimated coefficients were compared to the values predicted from the theoretical model (Equation 17) using the known data acquisition parameters: $f_{lo}$=96161 Hz, $f_{hi}$=627151 kHz, r=150 MHz/sec, $t_w$=0.5 ms.

Results

1. Orbitrap

The fit between the linear model and the observed data is shown for one of the eight runs (FIG. 2). In all cases, discrepancies are too small to visualize at this scale. The affine coefficients for each of the eight runs are shown in Table 1. A linear model was sufficient to fit the entire spectrum to an accuracy of about 0.04 radians rmsd.

TABLE 1

Linear Phase Model for Orbitrap Data (8 spectra)

| $c_0$ (rad) | $c_1$ (rad/Hz) | rmsd (rad) | $t_d$ (ms, $1000c_1/2\pi$) |
|---|---|---|---|
| 0.2667 | 0.1256334 | 0.032 | 19.99518 |
| 0.2503 | 0.1256333 | 0.044 | 19.99516 |
| 0.2408 | 0.1256338 | 0.041 | 19.99523 |
| 0.2734 | 0.1256336 | 0.045 | 19.99520 |
| 0.2724 | 0.1256333 | 0.040 | 19.99516 |
| 0.2796 | 0.1256332 | 0.048 | 19.99515 |
| 0.2466 | 0.1256335 | 0.046 | 19.99518 |
| 0.2723 | 0.1256340 | 0.036 | 19.99528 |

The apparent delay time is about 19.9951 ms, with a standard deviation of less than 0.1 μs across 8 runs. It was later learned that the intended delay between injection and detection was 20 ms. The 5 μs difference between the instrument specification and the observed delay is clearly significant, relative to the variation among runs, but is not understood.

Figure 3:
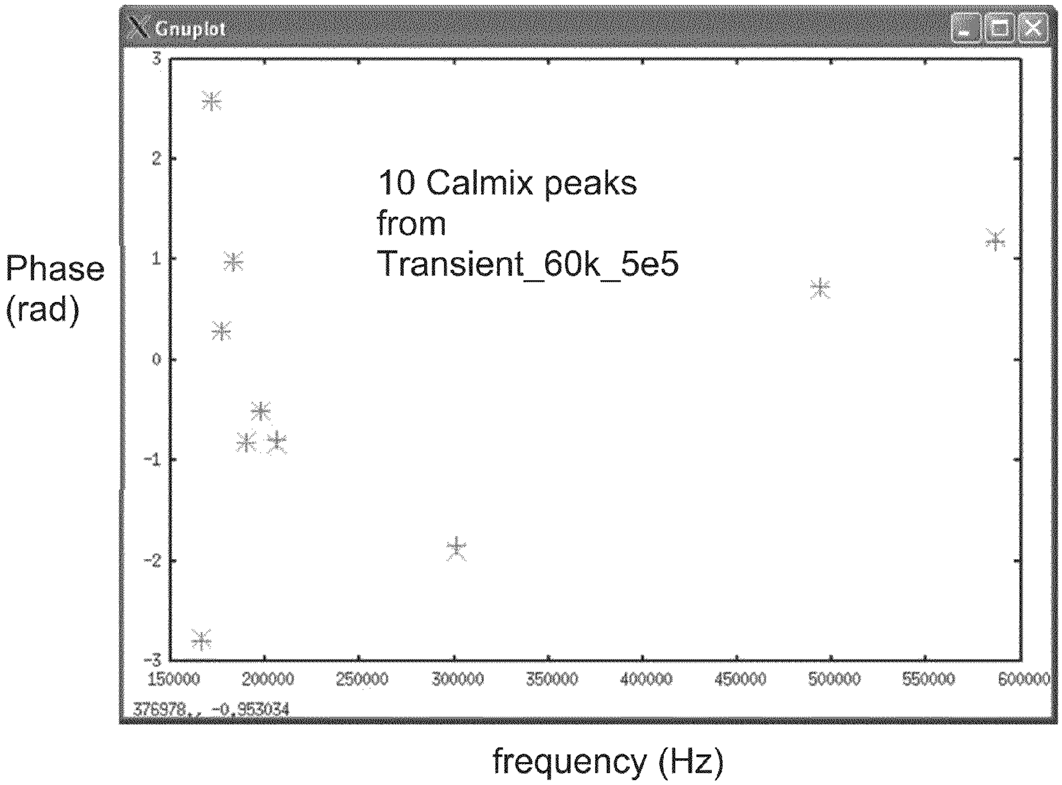
FIG. 3 illustrates a graph in which calculated relative phases (depicted by "x") show high correspondence to estimated relative phases (depicted by "+") of observed ion resonances on the Orbitrap™ instrument, in accordance with an embodiment of Component 1 of the present invention. The continuous phase model "wraps" every 50 Hz. The phase wraps over 10,000 times for the highest resonant frequencies in the spectrum. The line depicting the relative phases (analogous to the zigzag line along the x-axis in FIG. 2) is not easily displayed at this scale.
Figure 4:
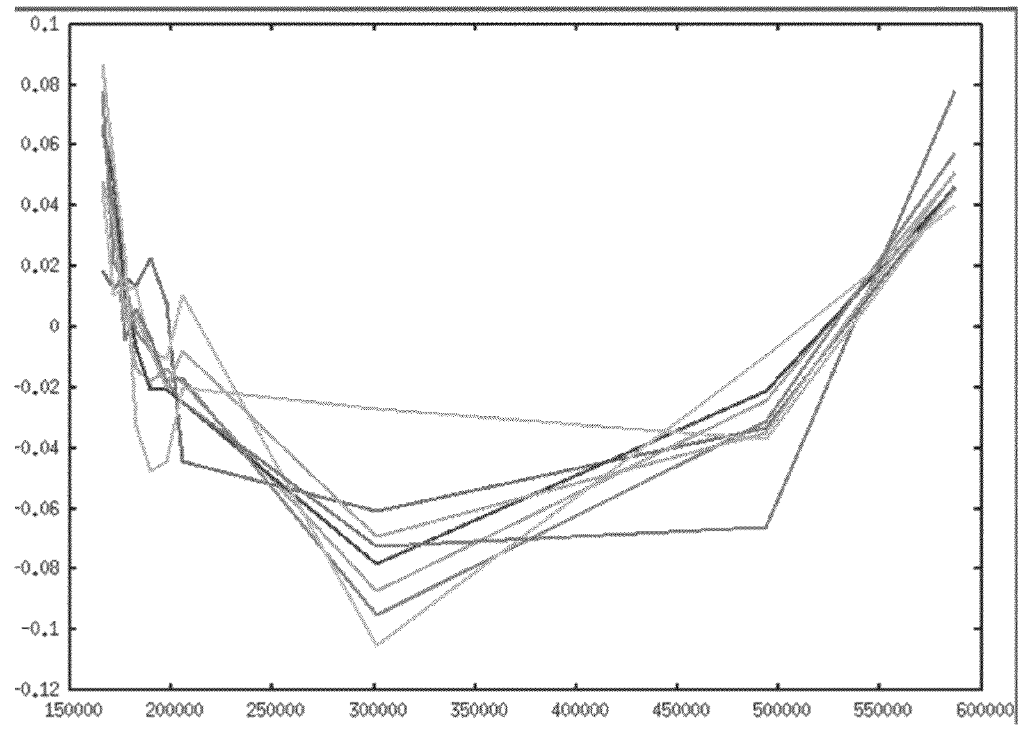
FIG. 4 illustrates a difference between linear model and observed Orbitrap™ phases, in accordance with an embodiment of Component 1 of the present invention. Differences between the linear phase model and observed Orbitrap™ phases show a small (less than 0.1 rad) but systematic quadratic dependence that was reproducible across eight runs.
Figure 5:
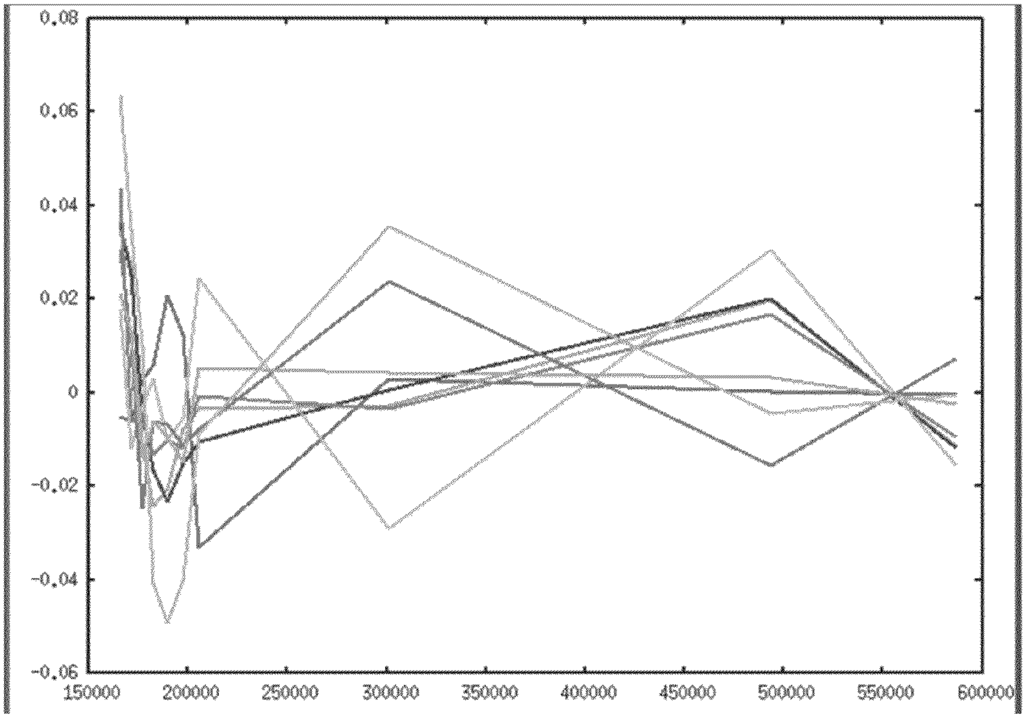
FIG. 5 illustrates the difference between a quadratic model and observed Orbitrap™ phases, in accordance with an embodiment of Component 1 of the present invention. Including a quadratic term (of undetermined physical origin) in the model for Orbitrap™ phases eliminated the systematic error in the phases, and reduced the overall rmsd error by roughly a factor of two.

A small systematic error remained in the data, evident in all eight datasets (FIG. 3). The systematic error was removed by fitting the data with a second-order polynomial (FIG. 4). The coefficients of best-fit and resulting error are shown in Table 2. The simple model for Orbitrap™ phases (Equation 8) has $c_0$=$c_2$=0. The physical interpretation of coefficients $c_0$ and $c_2$ requires more detailed modeling.

TABLE 2

Quadratic Model for Orbitrap Phases

| $c_0$ (rad) | $c_1$(rad/Hz) | $c_2$(rad/Hz$^2$) | rmsd (rad) | $t_d$ (ms, $1000c_1/2\pi$) |
|---|---|---|---|---|
| 0.0124 | 0.1256352 | −2.46e−12 | 0.0134 | 19.99546 |
| −0.0872 | 0.1256357 | −3.27e−12 | 0.0191 | 19.99554 |
| −0.0746 | 0.1256360 | −3.05e−12 | 0.0192 | 19.99559 |
| −0.0919 | 0.1256362 | −3.54e−12 | 0.0166 | 19.99562 |
| −0.0318 | 0.1256355 | −2.94e−12 | 0.0179 | 19.99551 |
| −0.1052 | 0.1256359 | −3.72e−12 | 0.0167 | 19.99558 |
| −0.0033 | 0.1256352 | −2.42e−12 | 0.0352 | 19.99547 |
| −0.0201 | 0.1256361 | −2.83e−12 | 0.0110 | 19.99561 |

Example 2

Petroleum Analysis by FT-ICR MS

A collection of transient voltages obtained by FT-ICR analysis of a petroleum sample was provided by Alan Marshall's lab at the National High Magnetic Field Laboratory. 666 ion signals were detected, ranging in frequency from 217 kHz to 455 kHz. All species were charge state one, with ion masses ranging from 320.5 Da to 664.7 Da. Maximum-likelihood estimates were produced for the frequency and phase of each detected signal.

Figure 6:
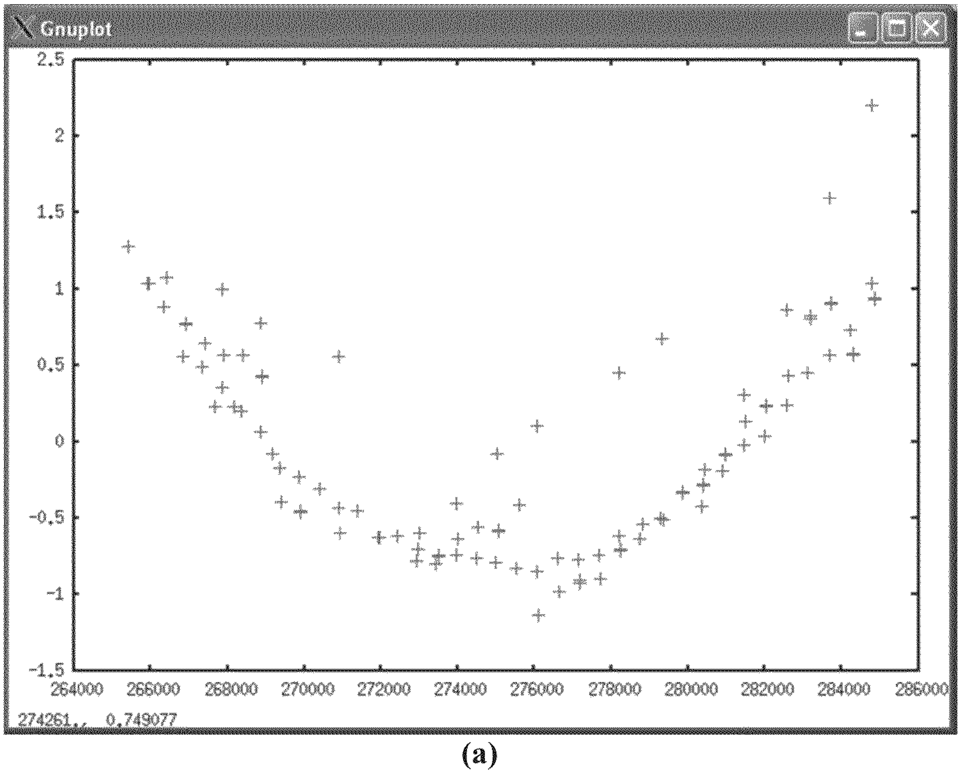
FIG. 6 illustrates various graphs, in which panel (a) shows the error resulting from fitting a linear model to 117 peaks in the region of the spectrum (265 kHz-285 kHz), in accordance with an embodiment of Component 1 of the present invention. The selected region is the largest region that can be fit without phase wrapping. Panel (b) shows the residual error of this model over the entire spectrum; phase-wrapping is evident from diagonal lines in the relative phase error separated by discontinuous jumps from $+\pi$ to $-\pi$. Panel (c) shows the region (250 kHz-300 kHz) where the phase wrapping is more easily visualized. The parabolic dependence of the phase error is evident.
Figure 6:
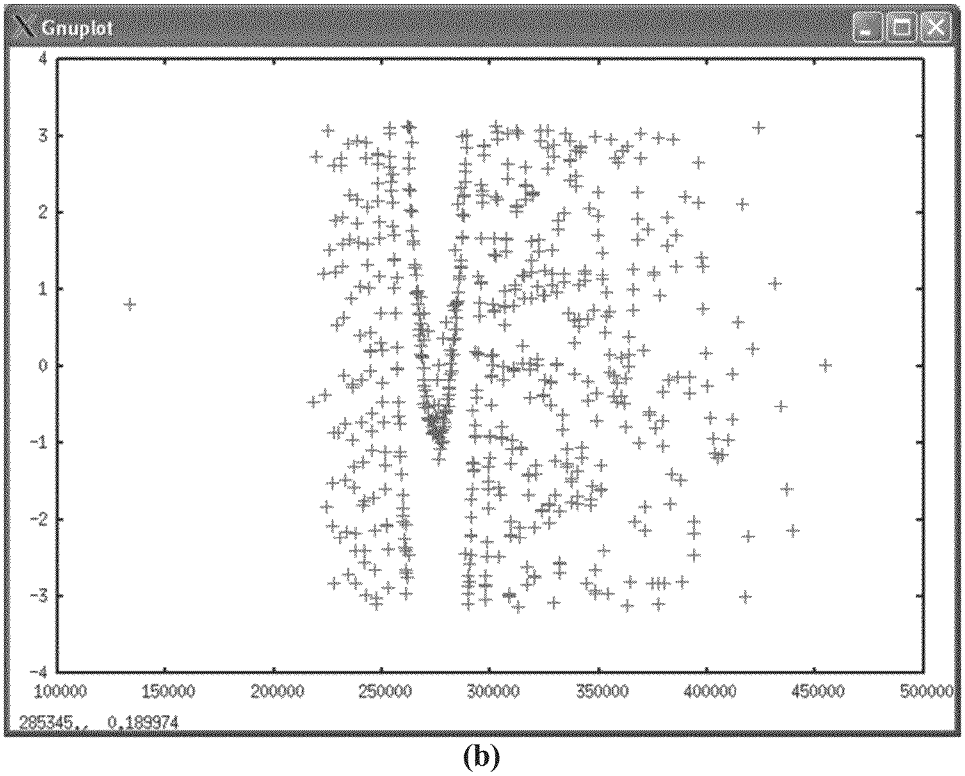

A trial phase model (expected to fit only part of the spectrum) is a linear model with two parameters (slope and intercept). A line of best fit can be constructed through the phases after exhaustive trials of unwrapping the phases. The result of these trials is shown in FIG. 6. A linear model fit only a band of the spectrum 20 kHz wide (265 kHz-285 kHz) without phase wrapping errors.

Figure 7:
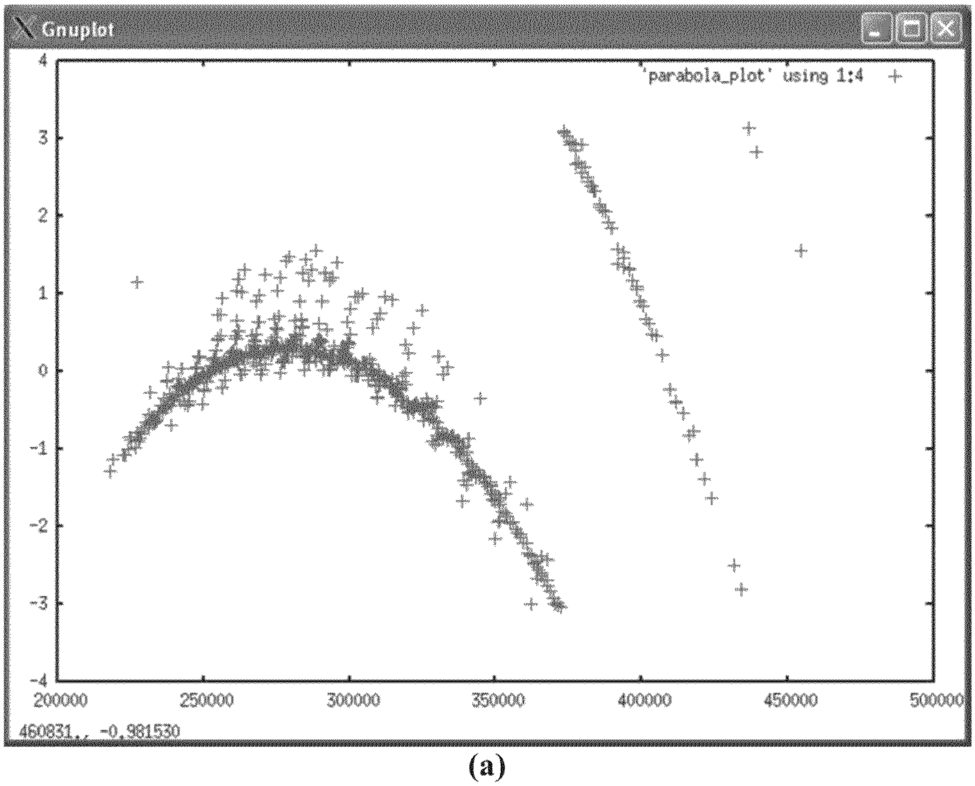
FIG. 7 illustrates several graphs, in which panel (a) shows the first attempt to fit a parabola model to the residual error over the entire spectrum, in accordance with an embodiment of Component 1 of the present invention. Two diagonal lines in the right side of the plot indicate phase wrapping of one and two cycles respectively. The left side of the plot also shows a parabolic residual error because the parabola of best fit is distorted by the peaks at the right hand where the phase wrapping was not properly modeled. Panel (b) shows the residual error resulting from using the model in panel (a) to construct an initial model of the absolute phases to the 583 peaks in the region (215 kHz-365 kHz). The model in panel (b) was then used as an initial model of the absolute phases over the entire spectrum (215 kHz-440 kHz), 666 peaks, resulting in the residual error shown in panel (c). No systematic deviation was apparent in this model.
Figure 7:
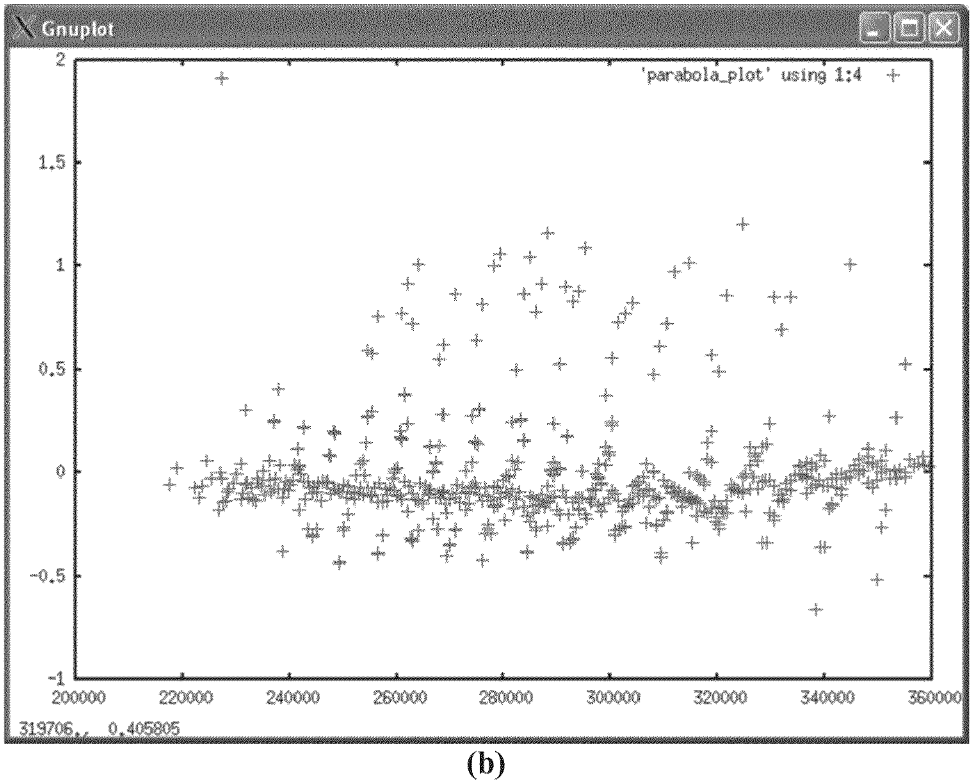

This linear model was used to determine absolute phases in this region, and the resulting curve was fit to a parabola—a second-order model. This model (not shown) was used to compute absolute phases over the entire spectrum. The resulting absolute phases were fit by another parabola, resulting in the residual error function shown in FIG. 7*a*. The absolute phase model was not correct, as indicated by the phase wrapping effects seen above 365 kHz in FIG. 7*a*. A parabola was fit to the region below 365 kHz, where the phase wrapping had been correctly determined. The resulting residual error (FIG. 7*b*) showed no phase wrapping and no systematic error. This model was then used to compute absolute phases over the entire spectrum. The resulting absolute phases were fit to a parabola one last time. The residual error is shown in FIG. 7*c*. This model correctly fit the entire spectrum without phase wrapping.

Figure 8:
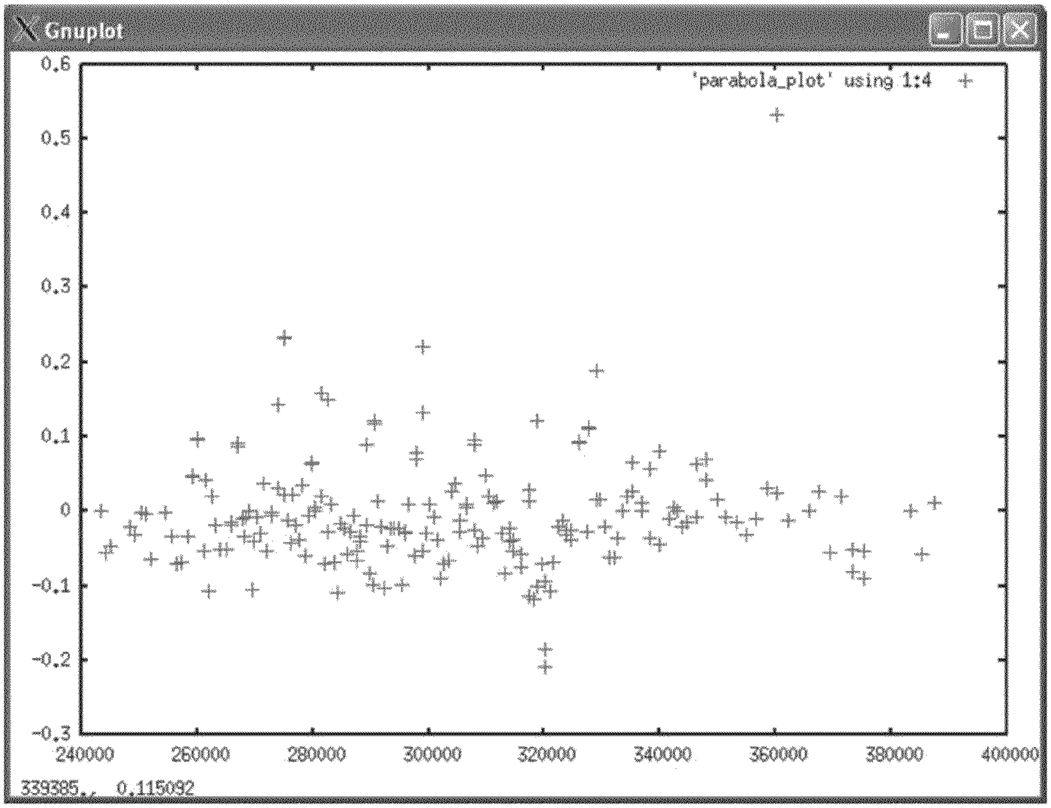
FIG. 8 illustrates a graph, in which the final parabolic model has an rmsd error of 0.079 rad for a fit of the 200 peaks of highest magnitude (out of 666), in accordance with an embodiment of Component 1 of the present invention. The final coefficients in the model are (−1588.94 0.0294012-2.09433e-08). The first coefficient (a constant) was not explicitly modeled. The other two coefficients agree to better than 100 ppm against theoretical values 0.0294116 and −2.09440e-08.

It was noticed that most of the residual error was due to peaks of low SNR, where presumably the phases were not estimated correctly. In some cases, the phase errors were due to overlaps with large neighboring peaks. An improved model was generated by fitting the absolute phases of the 200 largest peaks. The final coefficients were $c_0$=−1588.94 rad, $c_1$=0.0294012 rad/Hz, and $c_2$=−2.09433e-8 rad/Hz$^2$. The residual error is shown in FIG. 8. The rmsd error was 0.079 radians.

After determining the second-order model from the observed phases ab initio, the estimated coefficients were compared to the values predicted from the theoretical model (Equation 17) using the known data acquisition parameters: $f_{lo}$=96161 Hz, $f_{hi}$=627151 kHz, r=150 MHz/sec, $t_w$=0.5 ms. The theoretical model for FT-ICR phases would predict $c_1$=0.0294116 rad/Hz and $c_2$=−2.09440e-8 rad/Hz$^2$. The deviation of the observed coefficients was less than 1 part per 10,000, or 100 parts per million.

Figure 9:
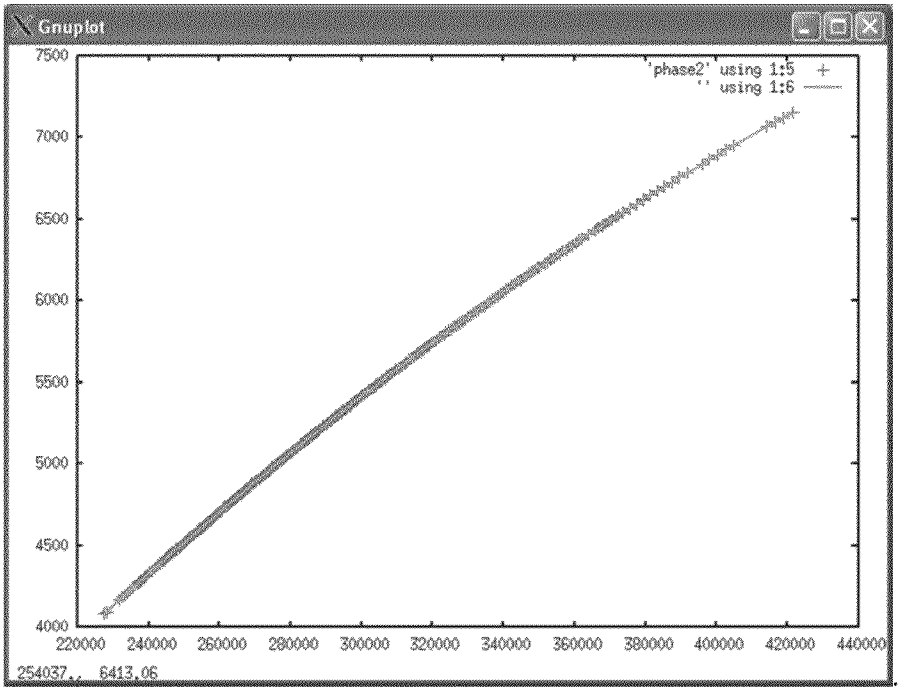
FIG. 9 illustrates the correspondence of the phase model and the observed phases, in accordance with an embodiment of Component 1 of the present invention. The model for the absolute phase is shown in panel (a) along with inferred observed absolute phases that result from estimating the number of cycles completed by the ions before detection. The observed relative phases are shown in panel (b) along with the relative phases implied by the absolute phase model. To create an intelligible display, the relative phases are shown only in the region (262 kHz-265 kHz). The model indicates nearly 9 cycles of phase wrapping between 262 kHz and 265 kHz.
Figure 9:
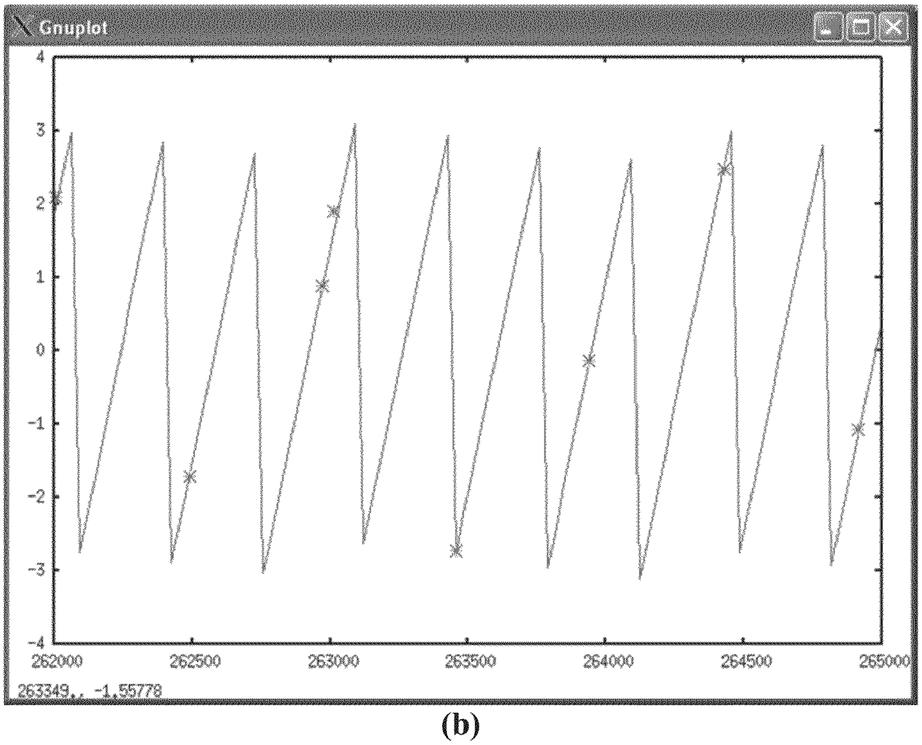

Representations of the absolute and relative phase models are shown in FIG. 9. The curvature of the absolute phase is apparent in FIG. 9*a*.

The phases observed in both Orbitrap™ instrument and FT-ICR spectra showed close correspondence with the behavior predicted by simple theoretical models for the instruments. In the Orbitrap™, the apparent delay time between injection and detection differed from the value inferred from observed phases by less than 1 part in 4000 (20 ms vs 19.995 ms). Furthermore, the variation between estimates of this value across 8 runs differed by less than 1 part in 200,000 (0.1 us vs 19.995 ms). In the FT-ICR, the observed phases were fit to a second-order polynomial. The linear coefficient, representing the time required to sweep from zero to the highest frequency plus the delay time until detection, agreed to 1 part in 10000. The quadratic coefficient, inversely proportional to the sweep rate, showed even higher correspondence, a deviation of less than 4 ppm.

Orbitrap™ phase modeling is not difficult, even without prior knowledge of the delay time, because of the approximate linearity of phases as a function of frequency. De novo FT-ICR modeling is more challenging because the curvature in the phase model induced by the excitation of different resonant frequencies at different times makes solving the phase-wrapping problem non-trivial. An iterative algorithm was used to fit a linear model to as much of the curve as possible without phase-wrapping errors. This region of the curve was then fit to a second-order polynomial that was sufficient to solve the phase-wrapping problem over the rest of the spectrum. In the next step, a refined model was computed using the entire spectrum.

Petroleum samples provide excellent spectra for de novo determination of phase modeling because of the large number of distinct species analyzed in a single spectrum. Multiple detectable species for each unit m/z can be detected over a broad band of the spectrum. Construction of higher-order models that attempt to accurately model subtle effects like the ion injection process, off-resonance or finite-duration excitation, or frequency drift during detection would require a large number of observed phases in a single spectrum.

When a set of parameters sufficient to describe a simple model of the data acquisition process are known (as in Equations 8 and 17), an approximate absolute phase model can be used to solve the phase-wrapping problem over the entire spectrum without multiple iterations. A second-order polynomial of best fit can be easily determined from the correctly assigned absolute phases to correct small errors in the initial model.

An accurate phase model provides the ability to use the phases of observed signals to infer the relative phases of resonant ions that have not been directly detected. Thus, a phase model can enhance detection. Typically, a feature is identified as ion signal because its magnitude is significantly larger than typical noise fluctuations. However, features with smaller magnitudes can be discriminated from noise by requiring also that the phase characteristics of the feature agree with the phase model.

An accurate phase model also makes it possible to apply broadband phase correction to a spectrum. In broadband phase correction, each sample in the spectrum (indexed by frequency) is multiplied by a complex scalar of unit magnitude (i.e., a rotation in the complex plane) to exactly cancel the predicted phase at that sample point. The result approximates the spectrum that would have been observed if all ions had zero phase. The real and imaginary parts of such a spectrum are called the absorption and dispersion spectra respectively. An absorption spectrum is similar in appearance to a magnitude spectrum, except that its peaks are narrower by as much as a factor of two. Consequently, the overlap between two peaks with similar m/z is greatly reduced in absorption spectra relative to magnitude spectra. The ability to extract the absorption spectrum is a visual demonstration of the improved resolving power that comes with phase modeling and estimation. However, further investigation is necessary to compare the relative performance of algorithms that use the absorption spectrum to those that use the uncorrected complex-valued spectrum.

Whether the phase model is use to phase correct the spectrum or not, phase models can be used to calculate phased isotope envelopes (i.e., to calculate the phase relationships between signals from the various isotopic forms of the same molecule). Detection by filtering a spectrum with a phased isotope envelope, rather than by fishing for a single peak, improves the chances of finding weak signals. Furthermore, weak signals that are obscured by overlap with larger signals may be discovered more frequently and discovered more accurately using phased isotope envelopes.

FTMS analysis is typically performed upon magnitude spectra (i.e., without considering ion phases). The advantage of magnitude spectra is phase-invariance: the peak shape does not depend upon the ion's phase. This invariance simplifies analysis.

Component 1 demonstrates that it is possible to accurately determine the broadband relationship between phase and frequency in both Orbitrap™ instrument and FT-ICR spectra de novo. Theoretical models were also derived for the phases on both instruments. The coefficients of polynomials of best-fit to observed phases showed very high correspondence with the values predicted by the theoretical models. As is shown in other embodiments of the invention described herein, the additional effort required to model and estimate phases yields improved mass accuracy, mass resolving power, and sensitivity. Thus, phase modeling and estimation improves the overall performance of FTMS instruments.

Component 2: Broadband Phase Correction of FTMS Spectra

Phase correction is a synthetic procedure for generating an FTMS spectrum (the frequency-domain representation of the time-domain signal) that would have resulted if all the ions were lined up with the reference detector at the instant that detection begins. That is, the corrected spectrum appears to contain ions of zero phase. The motivation for generating zero-phase signals arises from the properties of the real and imaginary components of the zero-phase signal, called the absorption and dispersion spectra respectively. Heretofore, analysis of FTMS spectra has involved magnitude spectra, which do not depend upon the phases of the ions. The magnitude spectrum is formed by taking the square root of the sums of the squares of the real and imaginary parts of the complex-valued spectra. Ion resonances in the absorption spectrum are narrower than those in the magnitude spectra by approximately a factor of two; resulting in improved mass resolving power. Furthermore, the absorption spectra from multiple ion resonances sum to produce the observed absorption spectrum. Therefore, it is possible to display the contributions from individual ion resonances superimposed upon the observed absorption spectrum. In contrast, magnitude spectra are not additive.

Component 2 relates to a procedure for phase-correcting entire spectra. "Broadband phase correction" refers to correcting the entire spectra, including ion resonances that are not directly detected, rather than correcting individual detected ion resonances. Broadband phase correction requires a model relating the phases and frequencies of ion resonances. The construction of such a model from observed FTMS data and its subsequent theoretical validation is described in Component 1.

Collection of FTMS data involves measurement of a time-dependent voltage signal produced by a resonating ion in an analytic cell. Let vector y denote a collection of N voltage measurements acquired at uniform intervals from time 0 to time T. y[n] is the voltage measured at time nT/N. Let Y denote the discrete Fourier transform of y. Y is called the frequency spectrum and is a vector of N/2 complex values. Y[k] is defined by Equation 1.

$$Y[k] = \sum_{n=0}^{N-1} y[n]e^{-i2\pi kn/N} \quad (1)$$

The real part and imaginary parts of Y[k] represent the overlap between the observed signal y and either a cosine or sine (respectively) with cyclic frequency k/T. The phase of Y[k], denoted by $\phi_k$ corresponds to the sinusoid of cos(2πtkt/T−ϕ) that maximizes the overlap with signal y, among all possible values of ϕ.

To simplify subsequent analysis, assume that Y is the spectrum resulting from a single ion resonance. In the MC model of FTMS, the signal from an ion resonance (in the absence of measurement noise) is given by Equation 2.

$$y(t) = \begin{cases} ce^{-t/\tau}\cos(2\pi f_0 t - \phi) & t \in [0, T] \\ 0 & \text{else} \end{cases} \quad (2)$$

The phase ϕ that appears in Equation 2 refers to the position of the ion relative to its oscillation. For example, the phase fin FT-ICR is equal to the angular displacement of the ion in its orbit relative to a reference detector.

Frequency spectrum Y is calculated from the time-dependent signal y by discrete Fourier transform, Equation 1. The result is shown in Equation 3.

$$Y[k] = ce^{-i\phi}\frac{1-e^{-q}}{1-e^{-q/N}} = ce^{-i\phi}Y_0[k] \quad (3)$$

$$q = \left[\frac{1}{\tau} + i2\pi\left(\frac{k}{T} - f_0\right)\right]T$$

Y0 denotes the spectrum from an ion with zero phase. The signal from an ion with arbitrary phase is related to the signal from a zero-phase ion, denoted by $Y_0$, by a factor of $e^{-i\Phi}$ (Equation 4).

$$Y[k]=e^{-i\Phi}Y_0[k] \quad (4)$$

If $f_0$ happens to be an integer multiple of 1/T (e.g., $f_0=k_0/T$), then the phase of $Y[k_0]$ is equal to the phase ϕ that appears in Equations 2 and 3.

The complex-valued vector Y can be written in terms of its real and imaginary components, denoted by real-valued value R and I respectively (Equation 5).

$$Y[k]=R[k]+iI[k] \quad (5)$$

R and I can be thought of as two related spectra representing the ion resonance. The appearance of these components depends upon the phase of the resonant ion. Note that the magnitude spectrum does not depend upon the ion's phase.

Likewise, the zero-phase signal can be expressed in terms of its real and imaginary components. The real and imaginary components of the zero-phase ion are called the absorption and dispersion spectra and are denoted by A and D respectively (Equation 5).

$$Y_0[k]=R_0[k]+iI_0[k]=A[k]+iD[k] \quad (5)$$

It is convenient to write R and I—the spectrum for a resonance of arbitrary phase—in terms of the absorption and dispersion spectra.

$$R[k] = \mathrm{Re}[Y[k]] = \mathrm{Re}[(A[k]+iD[k])(\cos\phi - i\sin\phi)] = (\cos\phi)A[k] + (\sin\phi)D[k] \quad (6)$$

$$I[k] = \mathrm{Im}[Y[k]] = \mathrm{Im}[(A[k]+iD[k])(\cos\phi - i\sin\phi)] = (-\sin\phi)A[k] + (\cos\phi)D[k]$$

The real and imaginary components of a signal from an ion with arbitrary phase are linear combinations of the absorption and dispersion spectra. When the complex-valued components are viewed as vectors in the complex plane, signal components of the signal with phase ϕ correspond to rotating the signal components of the zero phase signal by −ϕ. (Equation 7)

$$\begin{bmatrix} R[k] \\ I[k] \end{bmatrix} = \begin{bmatrix} \cos\phi & \sin\phi \\ -\sin\phi & \cos\phi \end{bmatrix}\begin{bmatrix} A[k] \\ D[k] \end{bmatrix} = R_{-\phi}\begin{bmatrix} A[k] \\ D[k] \end{bmatrix} \quad (7)$$

As indicated by Equation 4, phase correcting an FTMS spectrum containing an ion resonance of phase ϕ involves multiplying the entire spectrum by $e^{i\Phi}$ (Equation 8).

$$Y_0[k]=e^{i\Phi}Y[k] \quad (8)$$

Figure 10:
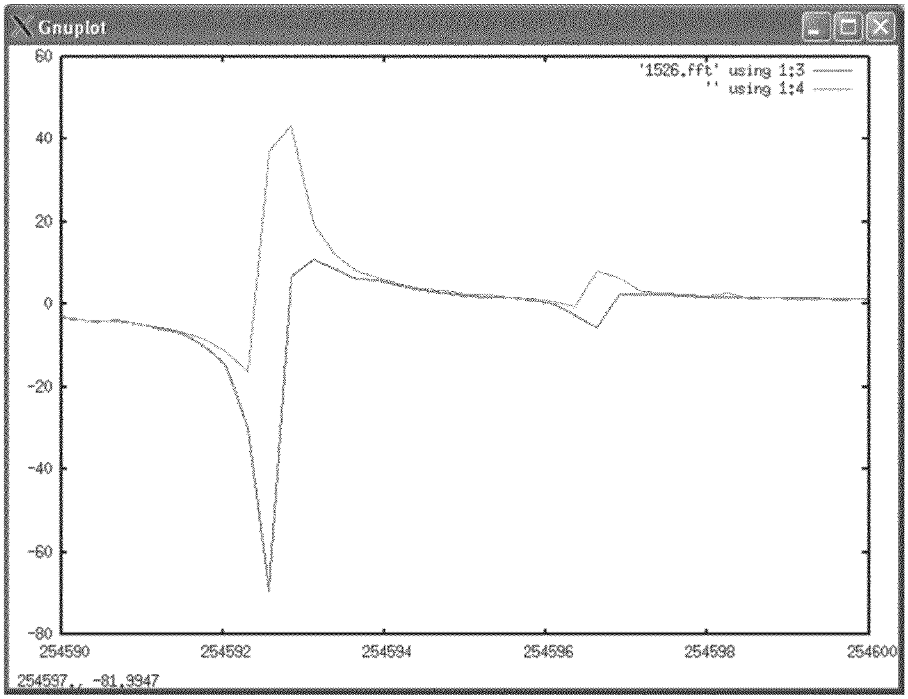
FIG. 10 illustrates phase correction, in accordance with an embodiment of Component 2 of the present invention.
Figure 11:
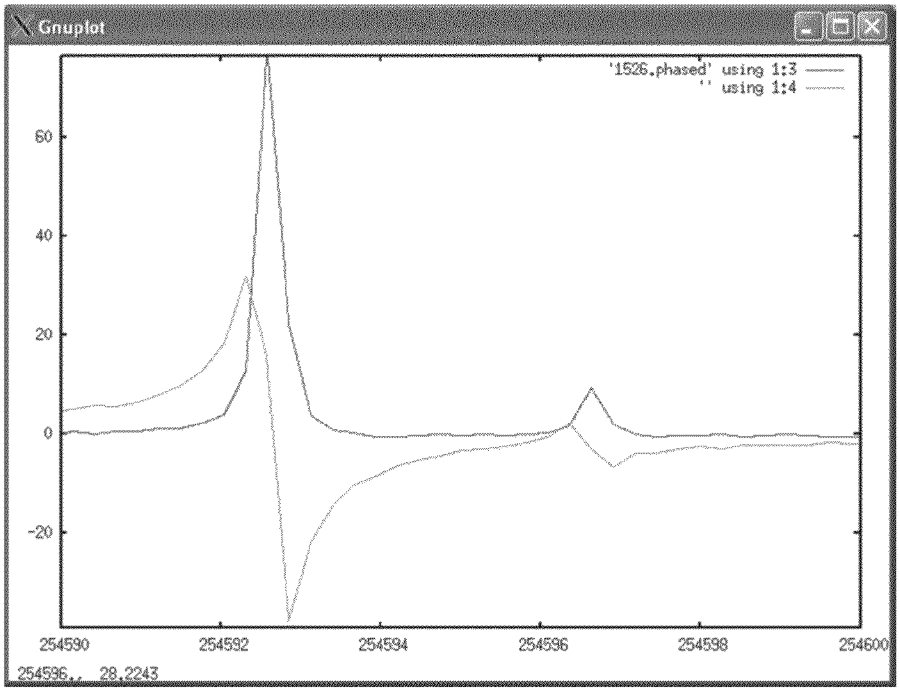
FIG. 11 illustrates phase correction, in accordance with an embodiment of Component 2 of the present invention.

This is equivalent to rotating each complex-valued sample of the Fourier transform by angle cp. It is also equivalent to rotating the ion in an FT-ICR cell about the magnetic field vector by angle −cp. The phase of the signal can be estimated from the data as described in international PCT patent application No. PCT/US2007/069811, to determine the necessary correction factor (or angle of rotation). FIGS. 10 and 11 shows phase correction of two resonances with the same phase in an FT-ICR spectrum.

It is not possible, strictly speaking, to phase correct multiple ion resonances in the same spectra with different phases because each requires a different correction factor. In practice, however, it may be possible to approximately correct numerous phases simultaneously by rotating each component in the spectrum by a phase angle that changed very slowly as a function of frequency. Because peaks are narrow, the phase would be effectively constant over a region large enough to contain the peak. Very accurate phase correction of multiple detected ion resonances has been demonstrated using Equation 9 where f[k] denotes a phase function that varies with frequency.

$$Y_0[k]=e^{i\Phi[k]}Y[k] \quad (9)$$

It is a small step from correcting multiple detection resonances to broadband phase correction. In broadband phase correction, the goal is to phase correct not only detected peaks, but also regions of the spectrum where ion resonances may be present but are not directly observed. If the phase function ϕ[k] that appears in Equation 9 predicts the phases of all resonances in the spectrum, then Equation 9 can be used for broadband correction.

Component 1 demonstrates that a phase model can be determined essentially by "connecting the dots" between pairs of estimates of phase and frequency for numerous peaks in a spectrum. Further, the empirical phase model was validated by deriving an essentially identical relationship using data acquisition parameters describing the excitation pulse (in FT-ICR) and delay between excitation (FT-ICR) or injection (Orbitrap™) and detection.

Given this phase model, it is possible to phase correct a spectrum. However, it is important to demonstrate that the variation of phase with frequency is sufficiently slow so that individual peaks are not "twisted." The rotation applied to an individual resonance signal should be constant, while the variation in the phase model across a single peak induces a twist. The variation in the phase is roughly proportional to the delay time between excitation/injection and detection. The breadth of the peak (full-width-half-maximum; "FWHM") is roughly 2/T, where T is the acquisition time. Therefore, a useful figure of merit is the ratio of the delay time and the acquisition time. For a 60 k resolution scan on the Orbitrap™ instrument, the figure of merit is 768 ms/20 ms=38.4. For FT-ICR data provided by National High Magnetic Field Laboratory, the figure of merit is 3690 ms/4 ms~900. The figure of merit is roughly twice the number of peak widths per phase cycle. For example, a peak in Orbitrap™ instrument data undergoes a twist of about 1/20 cycle (18 degrees). The twist is much less for FT-ICR data.

Figure 12:
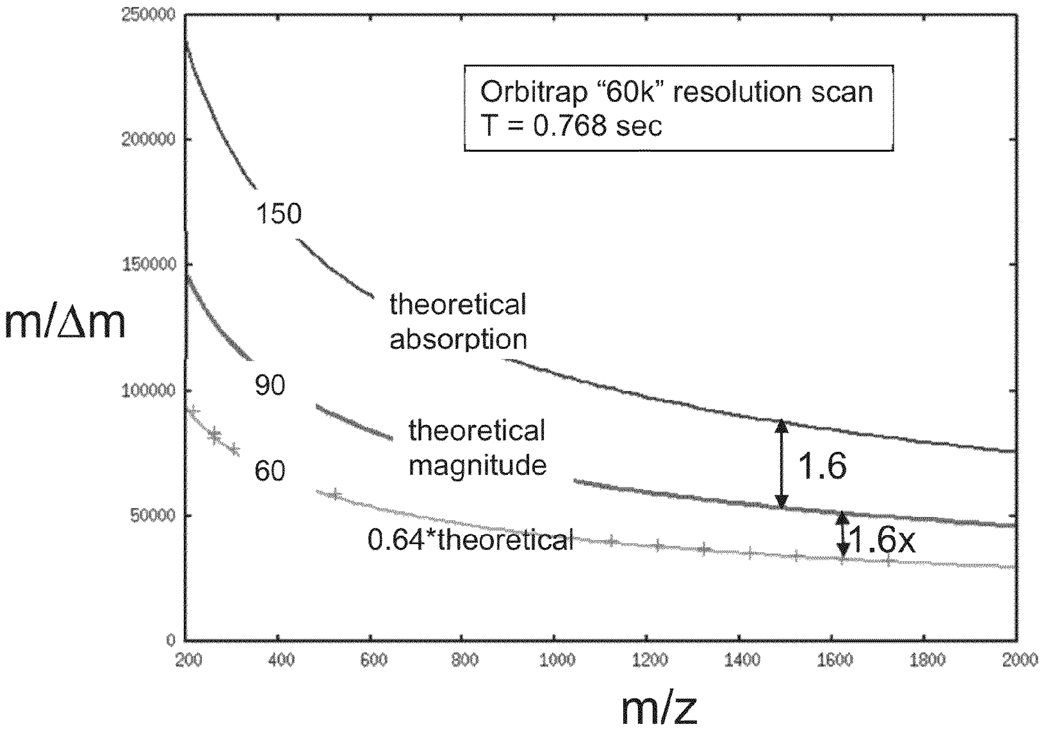
FIG. 12 depicts an Orbitrap™ "60k" resolution scan (T=0.768 sec), in accordance with an embodiment of Component 2 of the present invention. The "theoretical absorption" curve shows theoretical peak width (FWHM) of absorption spectra. The theoretical magnitude curve shows theoretical peak width for magnitude spectra. The black crosses are the observed "resolution" returned by XCalibur™ software for an Orbitrap™ instrument spectrum of "Calmix." The "theoretical" curve is 0.64 times the "theoretical magnitude" curve. The loss of mass resolving power is due to apodization of the time-domain signal before Fourier transformation. Phase correction results in a resolving power gain of 2.5×.

The primary goal of phase correction is to obtain the absorption spectrum. As mentioned above, peaks in an absorption spectrum have roughly half the width of magnitude spectra. In fact, a difference of 2.5 times was found between peak widths in apodized magnitude spectra produced by XCalibur™ software and those in (unapodized) absorption spectra (FIG. 12). Apodization is a filtering process used to reduce the ringing artifact that appears in zero-padded (interpolated) spectra. The process has the undesired side-effect of broadening peaks. Apodization reduced the mass resolving power by a factor of 1.6, on top of an additional factor of 1.6 relating absorption and magnitude peak widths before apodization. Note that zero-padding and thus apodization is unnecessary in phased spectra; all the information is contained in the (non-zero-padded) complex-valued spectrum.

The absorption spectrum is useful for display because it has the appearance of a magnitude spectrum with roughly twice the mass resolving power. The zero-phase signal has the special property that its real and imaginary components—the absorption and dispersion spectra, respectively—represent extremes of peak width. The absorption spectrum is the narrowest line shape; the dispersion spectrum is the broadest line shape. The absorption spectrum decreases as the square of frequency away from the centroid, while the dispersion spectrum decreases only as frequency.

Because the real and imaginary components of a signal of arbitrary phase are linear combinations of the absorption and dispersion spectra, their peak widths fall in between these two extremes. Likewise, the magnitude spectrum, which is the square-root of the sum of the squares of the absorption and dispersion spectra, has a peak width (at FWHM) that is wider than the absorption spectrum, but not as wide as the dispersion spectrum. It should be noted that the tail of the magnitude spectrum is dominated by the dispersion spectrum. The 1/f dependency of the dispersion introduces a very long tail in magnitude peaks relative to absorption peaks. Peaks that overlap significantly in a magnitude spectrum may have little observable overlap in an absorption spectrum.

Another important property is that the superposition of peaks is linear in an absorption spectrum: the observed absorption spectrum is the sum of the contributions from individual peaks. Therefore, it is possible to compute contributions from individual resonances, and to show the individual resonances on the display as lines superimposed upon the observed absorption spectrum. Conversely, linearity does not hold for magnitude spectra.

Calculations such as signal detection, frequency estimation, mass calibration can be enhanced using a phase model. In some cases, the calculation applies the phase correction implicitly, without actually applying the phase correction to the spectra directly. However, explicit phase correction does provide a benefit in one particular application. As described previously by the inventor, the complex valued spectrum containing multiple (possibly overlapping) ion resonances can be written as a sum of the signals from the individual resonances. The calculations utilized both the real and imaginary parts of the signal. The complexity of the calculation depends upon the number of overlapping signals and can be reduced when absorption spectra are used.

It can be determined theoretically whether frequency estimates computed from zero-padded absorption spectra will be more accurate than estimates computed from complex-value spectra (non-zero padded absorption and dispersion).

Broadband phase correction is a simple calculation when a phase model for the spectrum is available. The approximation that resonances of nearly identical frequencies have nearly identical phases is very good; otherwise, it would not be possible to simultaneously correct both resonances. A primary benefit of phase correction is the ability to display absorption spectra. The absorption spectrum has two advantages over magnitude spectrum for display: narrower peaks and linearity. The linearity property allows the display of absorption components from individual resonances along with the observed (total) signal; thereby improving the visualization of overlapping signals. In addition, the calculation to decompose signals into individual resonances can be made more efficient using the zero-padded absorption spectrum rather than the uncorrected complex-valued spectrum.

Component 3: Phase-Enhanced Detection of Ion Resonance Signals in FTMS Spectra

Component 3 relates to a phase-enhanced detector that uses estimates of both the magnitude and the phases of ion resonances to distinguish true molecular signals in an FTMS spectrum from instrument fluctuations (noise). Because of the nature of FTMS data collection, whether on an FT-ICR machine or an Orbitrap™ instrument, there is a predictable, reproducible relationship between the phases and frequencies of ion resonances. Component 1 relates to a method for discovering this relationship by fitting a curve to estimates of (frequency, phase) pairs for observed resonances. In contrast, noise has a uniformly random phase distribution. The estimated phase of a putative resonance signal can be compared to the predicted value to provide better discriminating power than would be possible using its magnitude alone. For typical operating parameters, the phase-enhanced detector yields a gain of 0.35 units in SNR over an analogous phase-naïve detector. That, for the same rate of false positives, the phase-enhanced detection rate for SNR=2 is the same as the phase-naïve detection rate for SNR=2.35. For example, at a false alarm rate of $10^{-4}$, the phase-enhanced detector successfully detects more than twice as many ion resonances with SNR=2 as the phase-naïve detector.

Detection of low-abundance components in a mixture is a key problem in mass spectrometry. It is especially important in proteomic biomarker discovery. Hardware improvements and depletion of high-abundance species in sample preparation are two approaches to the problem. Improving detection software is a complementary approach that would multiply gains in sensitivity yielded by these other strategies.

The fundamental problem in designing detection software is to develop a rule that optimally distinguishes noisy fluctuations from weak ion resonance signals in FTMS spectra. Matched-filter detection is an optimal detection strategy when a good statistical model for observed data is available. A signal model for FTMS was first described by Marshall and Comisarow in a series of papers in the 1970's. The Marshall- Comisarow (MC) model describes the time-dependent FTMS signal (transient) produced a single resonant ion as the product of a sinusoid and an exponential. The total FTMS signal is the linear superposition of multiple resonance signals and additive white Gaussian noise. The Fourier transform of such a signal can be determined analytically and corresponds very closely with observed FTMS signals obtained on the LTQ-FT and Orbitrap™ instrument. The MC signal model is well-suited for matched-filter detection in FTMS.

A matched-filter detector applies a decision rule that declares a signal to be present when the overlap (i.e., inner product) between the observed spectrum and a signal model exceeds a given threshold. As the threshold increases, both the false positive rate and detection rate of true signals decrease. The choice of threshold is arbitrary and application-dependent. Matched-filter detection is optimal in the following sense: under conditions where the matched-filter detector and some other detector produce the same rate of false positives, the matched-filter detector is guaranteed to have a rate of detection of true signals greater than or equal to that of the alternative detector.

The construction of a phase-naïve detector will be described first to illustrate the concept of matched-filter detection. It should be noted that even the phase-naïve detector represents an advance over current detectors used in FTMS analysis: the phase-naïve detector matches the complex-valued MC signal model to the observed complex-valued Fourier transform. Outside of this work, FTMS detection and analysis has used only the Fourier transform magnitudes. The phase-naïve detector uses the relative phases of the observed transform values to detect ion resonances; it is naïve about the absolute relationship between ion resonance phases and frequencies.

The overlap between signal and data is calculated at each location in the spectrum (i.e., frequency sample). The overlap value is a complex number that can be thought of as a magnitude and a phase. The phase of the overlap value corresponds to the phase of the ion resonance. In connection with Component 1, it was shown that the relationship between the phase and frequency of each ion resonance can be inferred from FTMS spectra. This relationship is referred to as a phase model. The phase-naïve detector assumes no knowledge of a phase model and uses a detector criterion based upon the magnitude of the overlap value. In contrast, the phase-enhanced detector uses both the magnitude and phase of the overlap value to discriminate true ion resonances from noise.

Let y denote an observed FTMS spectrum, a vector of complex-valued samples of the discrete Fourier transform of a voltage signal that was measured at a finite number of uniformly-spaced time intervals. For simplicity, assume that y consists of a single ion resonance signal As and additive white Gaussian noise n (Equation 1).

$$y=As+n \tag{1}$$

s denotes a vector of complex-valued samples specified by the MC signal model for an ion resonance of unit rms magnitude and zero phase, and shifted to some arbitrary location in the spectrum. A is the complex-valued scalar that multiplies s. The magnitude and phase of A correspond to the magnitude and phase of the ion resonance, in particular the initial magnitude and phase of the sinusoidal factor in the MC model. This fact can be demonstrated by noting that the signal of unit norm and phase ϕ is equal to $e^{i\Phi}s$.

Noise vector n is also a complex-valued vector whose real and imaginary components are independent and identically distributed.

Given these assumptions, the optimal detector for detecting signal s is a matched filter. Matched-filter detection involves computing the overlap or inner product between the observed signal vector y and the normalized signal model vector s (Equation 2).

$$S=\langle y\,|\,s\rangle=\sum_k y_k s_k^* \tag{3}$$

Each term in the sum is the product of the data and the complex-conjugate (denoted by *) of the model each evaluated at position (i.e., frequency) k in the spectrum. In theory, the sum is computed over the entire spectrum. In practice, the magnitude of s is significantly different from zero on only a small interval and so truncation of the sum does not introduce noticeable error.

The matched filter "score," denoted by S in Equation 2, is a complex-valued quantity whose value is used as the detection criterion. In the absence of noise and signal overlap (i.e., y=As) the magnitude and phase of S correspond to the magnitude and phase of signal s. (Equation 3).

$$S=\langle y|s\rangle=\langle As|s\rangle=A\langle s|s\rangle=A\|s\|^2=A \tag{3}$$

Noise added to a signal (y=As+n, Equation 1) will obscure the true magnitude and phase of the signal (Equation 4).

$$S=\langle y|s\rangle=\langle (As+n)|s\rangle=A\langle s|s\rangle+\langle n|s\rangle=A+v \tag{4}$$

Because the inner product is linear, the presence of additive noise introduces an additive error term in the inner product, denoted by n. Because the noise is white Gaussian noise, any projection with a unit vector is a (complex-valued) Gaussian random variable with independent, identically distributed real and imaginary parts whose mean and variance are the same as any sample of the original noise vector.

This property makes it relatively simple to calculate the distribution of S.

Without loss of generality, assume that the noise has a mean magnitude of one. That is, the real and imaginary components for any sample of n (and thus also for v) are uncorrelated Gaussian random variables, each with mean zero and variance ½. Then, the SNR is |A|. Then S is also a Gaussian random variable. The mean of S is A and its real and imaginary components each have variance ½.

The phase-naïve detector does not differentiate between values of S with the same magnitude. That is, the detection criterion depends upon |S|. A signal is judged to be present whenever |S|>T for some threshold. The choice of the threshold is governed by the number of false alarms that the user is willing to tolerate. A very high threshold will reduce the false alarm rate, but reduce the sensitivity of the detector, resulting in a lot of missed signals. Conversely, a very low threshold will be very sensitive to the presence of signals, but also will produce many false alarms.

The relative performance of two detectors can be assessed by a receiver-operator characteristic ("ROC") curve. An ROC curve is constructed by plotting the probability of detection $P_D$ versus the probability of false alarm $P_{FA}$ for each possible value of the threshold T. As the T increases, both $P_D$ and $P_{FA}$ go to zero. As T decreases, both $P_D$ and $P_{FA}$ go to one. A detector is useful if for some intermediate values of the threshold, $P_D$ is significantly greater than $P_{FA}$. $P_D$ and $P_{FA}$ can be computed as a function of SNR and T by theory, by simulation, or by experiment. In this case, the probabilities can be computed directly for both the phase-sensitive and the phase-enhanced detectors.

Detector A is superior to detector B if every point on the ROC curve for A lies above the ROC curve for B. That is, for a given level of false positives—a vertical intercept through the ROC curves—detector A detects more true signals than detector B. The ROC curve for the phase-naïve detector will be calculated below. Later, the ROC curve for the phase-enhanced detector will be calculated, and the two detectors will be compared.

The probability of detection of signal of magnitude |A| in the presence of unit-magnitude noise (i.e., SNR=|A|) is the probability that |S|>T, where S is defined by Equation 4.

The condition |S|>T corresponds to the exterior of a circle centered at the origin of the complex radius with radius T (FIG. 1). The probability that |S|>T is the probability density of S integrated over all points in the exterior of the circle (Equation 5).

$$P(|S|>T)=\int_0^{2\pi}\int_T^{\infty}p_s(r,\theta)r\,dr\,d\theta \tag{5}$$

The probability density of S is the probability density of n evaluated at (r,q)−A (Equation 6).

$$p_S(r,\theta)=p_N[(r,\theta)-A] \tag{6}$$

The integral formed by combining Equations 5 and 6 does not depend upon the phase of A and so without loss of generality we take the phase of A to be zero (as shown in FIG. 1). The result is Equation 7.

$$P(|S|>T)=\int_0^{2\pi}\int_T^{\infty}\frac{1}{\pi}e^{-[(r\sin\vartheta)^2+(r\cos\vartheta-|A|)^2]}r\,dr\,d\theta \tag{7}$$

The integral on the right-hand side of Equation 7 can be simplified using the modified Bessel function of order zero (Equation 8) to produce Equation 9.

$$I_0(z)=\frac{1}{\pi}\int_0^{\pi}e^{z\cos\vartheta}d\theta \tag{8}$$

$$P_D(A,T)=P(|S|>T)=e^{-A^2}\int_T^{\infty}re^{-r^2}I_0(2Ar)\,dr \tag{9}$$

Equation 9 gives the probability that a signal of magnitude |A| would produce a matched-filter score greater than T, and thus be detected when the detector threshold is T. The expression on the right hand side is the complementary cumulative Rice distribution evaluated at T.

In the special case of A=0, the right-hand side is the probability that noise, in the absence of a signal, will have a score magnitude above T, and thus result in a false alarm when the detector threshold is T.

$$P_{FA}(T)=P_D(0,T)=\int_T^{\infty}re^{-r^2}dr \tag{10}$$

This expression on the right hand side of Equation 10 is the complementary cumulative Rayleigh distribution evaluated at T.

The probability of detection and false alarm are computed similarly for the phase-enhanced detector. However, when the phase of the signal is known (e.g., suppose the phase is ϕ) one applies the phase to the signal model by multiplying by a complex phasor $e^{-i\Phi}$ before taking the inner product with the observed spectrum as in Equation 3.

$$S=\langle y|se^{-i\Phi}\rangle=\langle e^{i\Phi}y|s\rangle=e^{i\Phi}\langle y|s\rangle \tag{11}$$

As a result of linearity, this inner project is equivalent to taking the inner product between the phase-corrected spectrum (formed by multiplying the spectrum by the conjugate phasor $e^{-i\Phi}$) and the zero-phase model. The inner product is also equivalent to the inner product between the uncorrected spectrum and the zero-phase model multiplied by the conjugate phasor $e^{-i\Phi}$. The three equivalent expressions are shown in Equation 11.

The last expression is the simplest to compute as it involves scalar, rather than vector, multiplication.

The complex scale factor A can be written as $|A|e^{-i\Phi}$ when the phase of the signal is θ. Now, we combine Equations 2 and 11, to produce the phase-enhanced score (analogous to the phase-naïve score of Equation 3).

$$S=e^{i\Phi}\langle y|s\rangle=e^{i\phi}(A\langle s|s\rangle+\langle n|s\rangle)=e^{i\Phi}(A+v)=e^{i\Phi}(|A|e^{-i\Phi}+v)=|A|+v' \tag{12}$$

The phase-enhanced score is a real scalar, corresponding to the magnitude of the true signal, plus a complex-valued noise term v', which, like v, is a Gaussian random variable with mean zero and independent components with variance ½.

The maximum-likelihood estimate of |A| from S is the real component of S, denoted by Re[S]. Our decision rule for the phase-enhanced detector, therefore, will involve the value of Re[S].

$$Re[S]=Re[|A|+v']=|A|+Re[v'] \tag{13}$$

Figure 13:
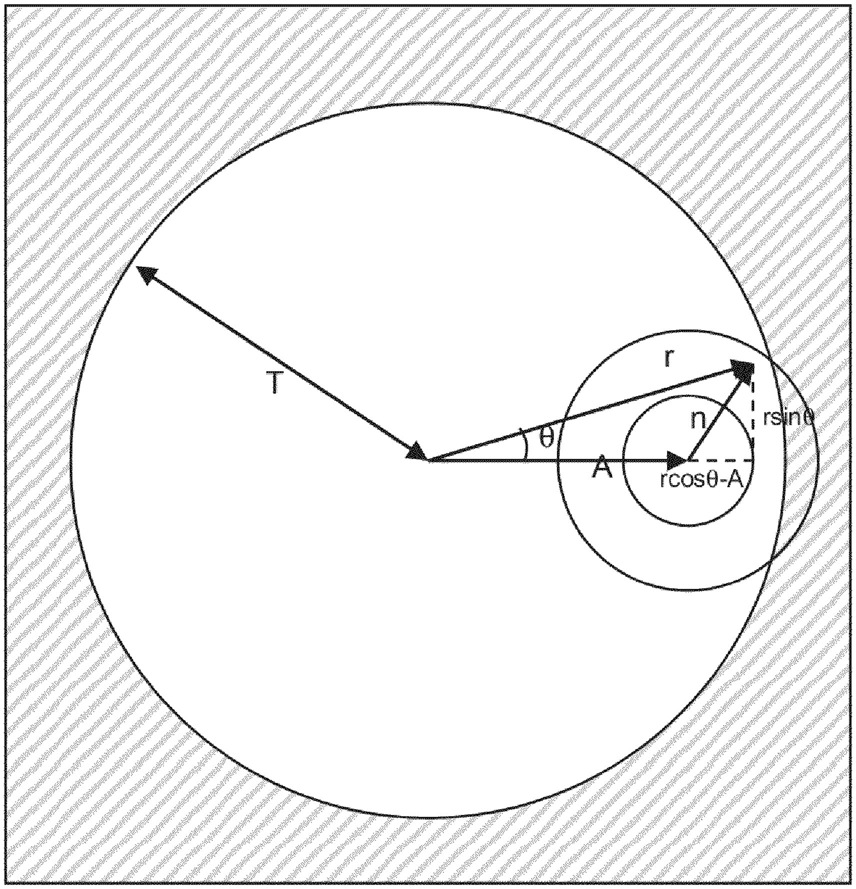
FIG. 13 depicts diagrams in accordance with an embodiment of Component 3 of the present invention, in which (a) the shaded region (extended over the infinite complex plane) represents the magnitudes (noise-free signal plus noise) greater than threshold T. The smaller circles (centered about the tail of the noise-free signal A) represent the contours of probability density of noise vector n. The probability density of observing a signal with magnitude r and phase θ given additive noise is the probability density for the noise vector evaluated at (r cos θ-A,r sin θ). (b) In the phase-enhanced detector, the projection of noise adds to the signal magnitude.
Figure 13:

Re[S] is Gaussian distributed with mean |A| and variance ½ (FIG. 13*b*). Therefore, the probability that Re[S] exceeds T is the one-sided complementary error function evaluated at T-|A|.

$$P_D(|A|,T)=P(\mathrm{Re}[S]>T)=\frac{1}{\pi}\int_T^{\infty}e^{-[x-|A|]^2}dx=\frac{1}{\pi}\int_{T-|A|}^{\infty}e^{-x^2}dx=\frac{1}{2}\mathrm{erfc}(T-|A|) \tag{14}$$

erfc denotes the two-sided complementary error function. The expression in Equation 14 gives the probability of detection for a signal of magnitude |A|, when |A|>0.

The special case |A|=0 gives the probability of false alarm.

$$P_{FA}(T)=P_D(0,T)=\frac{1}{2}\mathrm{erfc}(T) \tag{15}$$

Figure 14:
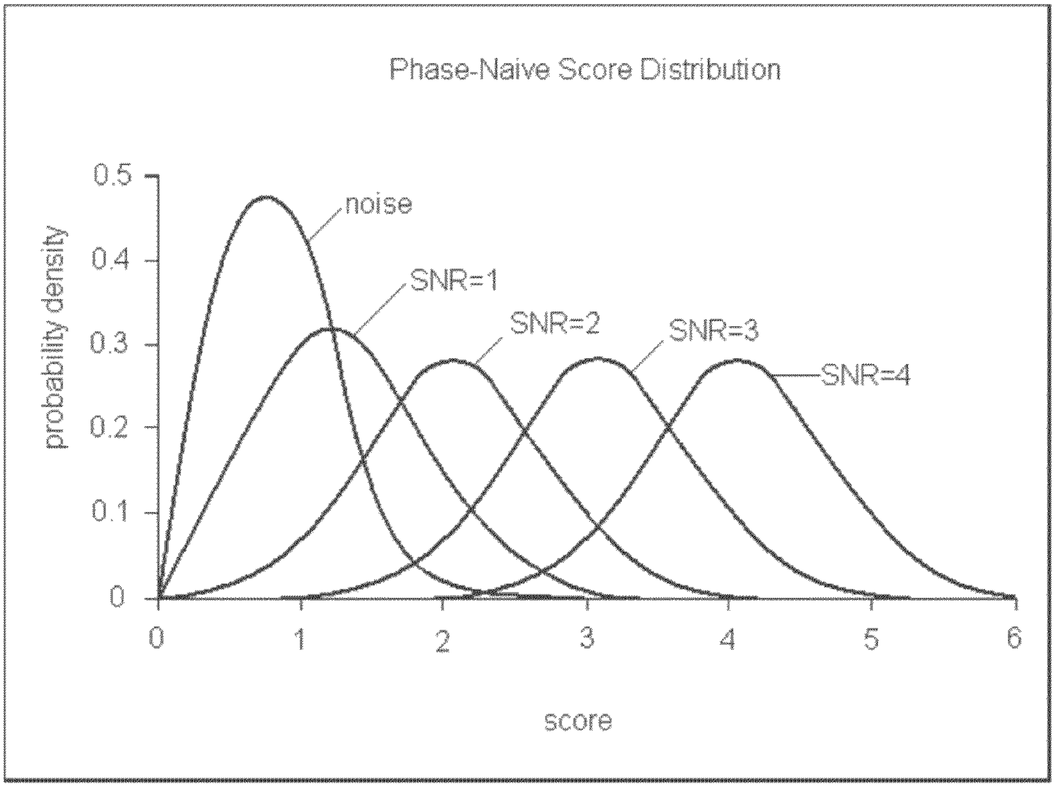
FIG. 14 depicts a graph in accordance with an embodiment of Component 3 of the present invention, in which the distribution of |S| for |A|=0, 1, 2, 3, and 4. The case of |A|=0 corresponds to noise alone. The probability of false alarm $P_{FA}$ is given by the integral under the black curve to the right of a vertical line at threshold T. The probability of detection $P_D$ for a signal of with SNR=1, 2, 3 or 4 is given by the integral under the corresponding colored curve.
Figure 15:
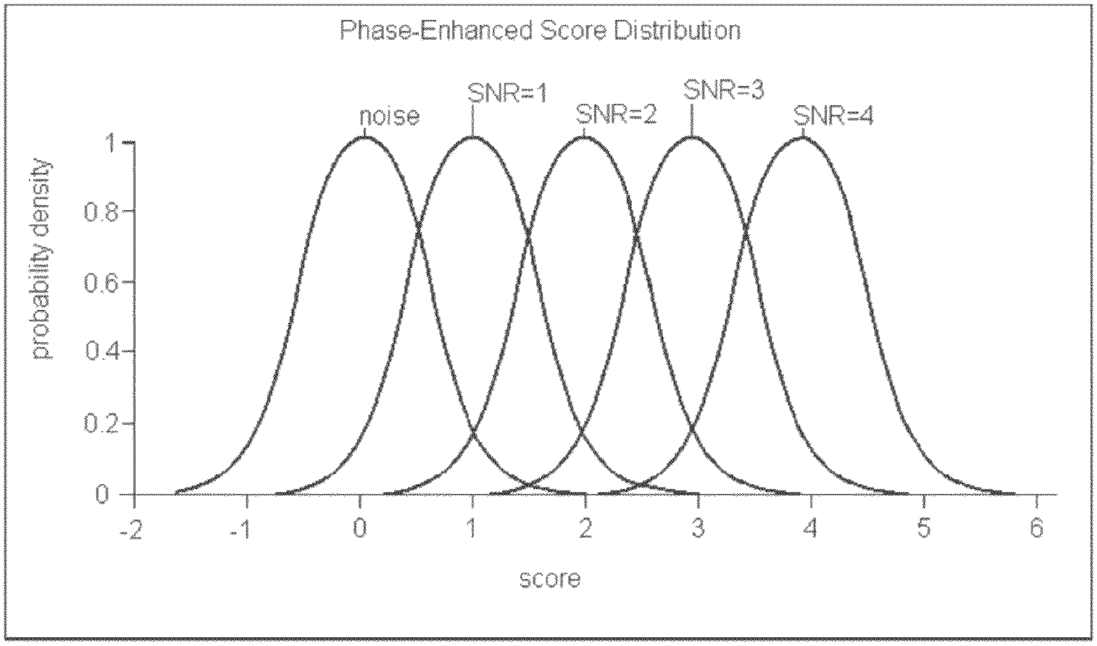
FIG. 15 depicts a graph in accordance with an embodiment of Component 3 of the present invention, in which the distribution of Re[S] for |A|=0, 1, 2, 3, and 4. The distribution of Re[S] for |A|=0 (noise alone) has mean zero. The analogous curve in panel (a) has a mean of ½. The colored curves (signal present) have means of 1, 2, 3, and 4, while the analogous curves have means slightly greater, but with shifts less than ½. The greater separation between the black curve and the colored curves rationalizes the improved performance of the phase-enhanced detector for detection of weak signals.

Plots of the detector criterion, |S| and Re[S], for the phase-naïve and phase-enhanced detector respectively are shown in FIGS. 14 and 15. Curves with the same SNR are shifted to the left in panel b relative to their panel a. The shift is largest for SNR=0 (noise only) and successively less for larger signals. As a consequence, there is greater separation between signal and noise curves for the phase-enhanced detector, which leads to improved performance.

ROC curves for the phase-naive and phase-enhanced detectors for signals with SNR values of 1, 2, and 3 demonstrate the superiority of the phase-enhanced detector. The gains appear largest for weak signals.

An ROC curve shows all possible choices for the threshold. In practice, a particular threshold is chosen to optimize a set of performance criteria. In FTMS, we may be willing to tolerate some false alarms in exchange for more sensitive detection. When FTMS is coupled to liquid chromatography, it is possible to screen out false alarms by requiring a signal to be present in spectra from multiple elutions. However, a threshold that is too low will overwhelm the system with false alarms that may require subsequent filtering that is computationally expensive.

In FTMS, the number of independent measurements (time-sampled voltages) is on the order of $10^6$. If we are willing to tolerate 100 false alarms per spectrum, the desired false alarm rate is $10^{-4}$. The threshold values that achieve this target for the phase-naïve and phase-sensitive detectors are determined by Equations 10 and 15 respectively, where the value of T is expressed in units of the noise magnitude.

The relative gain in sensitivity depends upon both the chosen threshold and the SNR of the signal. The ROC curves for false alarms rates at or below $10^{-4}$ are for signals with SNR of 2, 3, and 4.

At a false alarm rate of $10^{-4}$, the phase-enhanced detector would detect approximately 19, 70, and 98 percent of signals with SNR of 2, 3, and 4 respectively. The phase-naïve detector has detection rates of approximately 9, 50, and 92 percent. At SNR=2, the gain in detection is approximately two-fold.

Figure 16:
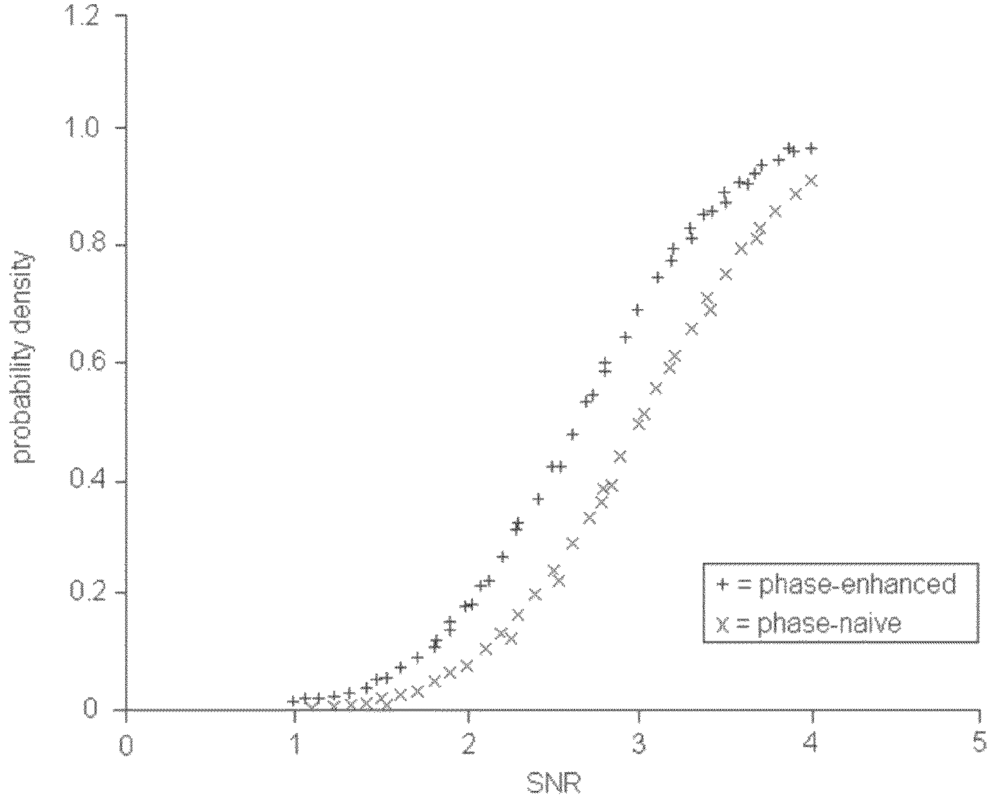
FIG. 16 depicts a graph in accordance with an embodiment of Component 3 of the present invention, in which $P_D$ vs SNR for $P_{FA}=10^{-4}$ for the phase-enhanced (depicted by "+") and phase-naïve (depicted by "x") detectors.
Figure 17:
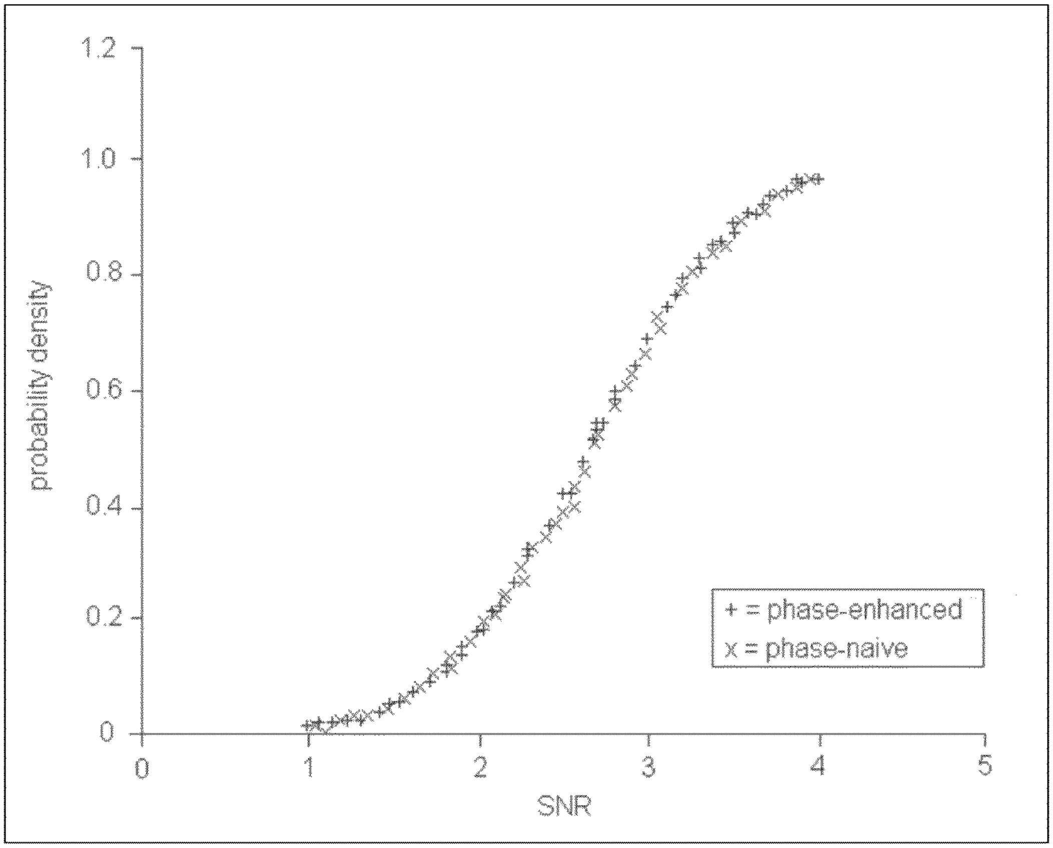
FIG. 17 depicts a graph in accordance with an embodiment of Component 3 of the present invention, in which a shift of 0.35 SNR units places the phase-enhanced curve (depicted by "+") into alignment with the phase-naïve curve (depicted by "x") (further seen in FIG. 16). This shift quantifies the improved detector performance that accompanies the use of a model predicting ion resonance phases.

FIG. 16 shows a plot of detection rate for each detector as a function of SNR for a fixed false alarm rate of $10^{-4}$. FIG. 17 shows that shifting the phase-enhanced curve to the right by 0.35 SNR units results in a good alignment of the two curves. This indicates, for example, that the phase-enhanced detector can detect signals with SNR=2 about as well as the phase-naïve detector detects signals with SNR=2.35.

The nature of the SNR shift is possibly explained by the observation that the magnitude of noise is always positive while a projection of noise assumes positive and negative values with equal likelihood. Because the phase-enhanced detector is able to look at a projection of the noise, it is better able to separate signals from noise. While it is true that noise also adds a positive bias to the observed magnitude of the signal, this effect is smaller than the magnitude bias of noise, resulting in relatively less separation between signals and noise.

It is important to note that in highly complex mixtures (e.g., blood, petroleum, etc.), abundance histograms are exponential. That is, the majority of signals have low SNR and the number of signals found at higher SNR values decreases exponentially. In spite of the relatively low rate of detection of signals at low SNR, the absolute number of detected signals may be relatively large. Consequently, small gains in sensitivity at low SNR can result in relatively large gains in the number of successfully detected signals.

In Component 3, a phase model relating ion resonance phases and frequencies described in Component 1 is used to construct a phase-enhanced detector that matches a phased signal to observed FTMS data and selects the real component of the overlap as a detection criterion. The ability to phase the signal before matching results in superior detection performance relative to an analogous matched-filter detection that did not make use of a phase model, especially in detecting signals whose magnitude is less than 3-4 times the noise level. The performance gain is roughly 0.35 SNR units. Gains in detecting weak signals could result in large gains in coverage of the low-abundance species in a sample.

Component 4: Phase-Enhanced Detection of Isotope Envelopes in FTMS Spectra

Component 4 elaborates on Component 3 on phase-enhanced detection of individual ion resonances in FTMS. Component 3 relates to the design and performance of a matched-filter detector that uses a phase model that specifies the phase of any ion resonances as a function of its frequency in detection. This detector distinguishes true ion resonances from noise using estimates of both phase and magnitude of the putative ion resonance, rather than just its magnitude.

Component 4 relates to the construction of isotope filters that can be used with the same detector as in Component 3 to detect isotope envelopes rather than individual resonances. In the isotope-envelope detector, the signal model (or matched filter) is a superposition of ion resonances from the multiple isotopic forms that have the same elemental composition, rather than a single ion resonance. The phase model is used to calculate the phase of each individual ion resonance in the isotope envelope. The relative magnitudes of the ion resonances are determined by the elemental composition of the species and the isotopic distribution of each element.

The performance gain increases with the spreading of the isotope envelope. For a molecule of a particular class (i.e., peptide), isotopic spreading increases with size. The isotope-based detector is able to capture weak signals that could be missed by detectors looking for individual resonances. For disperse envelopes, no single individual resonance may be strong enough for detection.

There are two cases to consider: detection of a known elemental composition and detection of a known class of molecules. Detection of a known elemental composition is easier and will be described first. Suppose a molecule consists of M types of elements; for instance, peptides are made of five {C,H,N,O,S}. Suppose that the elemental composition can be represented by an M-component vector of integers denote by n. Let P denote the fractional abundance of each type of isotopic species of a molecule. Equation 1 demonstrates that P for a molecule can be computed by taking the product of the fractional abundances for the pool of atoms of each elemental type.

$$P((E_1)_{n1}(E_2)_{n2} \ldots (E_M)_{nM}) = P(E_1;n_1)P(E_2;n_2) \ldots P(E_M;n_M) \quad (1)$$

This is a statement of statistical independence in the sampling of isotopes.

Suppose that a given element has q different stable isotopes with fractional abundances indicated by vector p. It is assumed that p is known to high accuracy. Then, Equation 2 shows how to compute the distribution of isotopes, denoted by vector k, observed when n atoms of the elemental type appear in a molecule. These are the factors that appear in Equation 1.

$$P(E;n) = (p_1x_1 + p_2x_2 + \ldots\ p_qx_q)^n = \sum_{(\sum ki=n)} P(k,p)x_1^{k1}x_2^{k2} \ldots x_q^{kq} \quad (2)$$

$$P(k,p) = M(n;k_1,k_2, \ldots k_q)p_1^{k1}p_2^{k2} \ldots p_q^{kq}$$

$$M(n;k_1,k_2, \ldots k_q) = \begin{pmatrix} & n & \\ k_1 & k_2 & \ldots & k_q \end{pmatrix} = \frac{n!}{k_1!k_2! \ldots k_q!}$$

The binomial distribution in Equation 2 reflects independent selection of each atom in a molecule. Fast calculation of the quantities in Equation 2 is described in Component 17.

Now suppose that the isotopic forms of an elemental composition are enumerated 1 . . . K with fractional abundances given by vector a. Because ion resonance signals (i.e., complex-valued frequency spectra) are additive, the total signal from the entire population of isotopes can be written as a weighted sum of the individual signals.

$$Y = \sum_{q=1}^{Q} c_q Y_q \tag{3}$$

The individual ion resonances Yq are characterized by four parameters in the MC model that was used in Component 3. These parameters are relative abundance (given by c), frequency, phase, and decay. It is assumed that the decay rate is the same for all isotopic forms and known. The frequency is calculated from the isotopic mass, which can be computed directly, and mass calibration parameters, which are assumed to be known. The phase of each ion can be computed from its frequency, as shown in Component 1. With these simple assumptions, one can compute the isotope envelope indicated by Equation 3.

To construct a matched filter, the signal in Equation 3 must be normalized to unit norm (Equation 4).

$$Y' = \frac{Y}{\sum_k |Y[k]|^2} \tag{4}$$

In general, it is not convenient to express the sum in the denominator of Equation 4 in terms of the individual isotope species because of peak overlaps between isotopes of the same nominal mass (e.g., C-13 and N-15).

In the case where the elemental composition is not known, one can calculate an approximate isotope envelope as a function of mass for a molecule of a given type. For peptides, a method was described by Senko ("averagine") to calculate an average residue composition from which an estimate of elemental composition for a peptide can be computed from its mass. For detection by this method, a family of matched filters is constructed to detect molecules in different mass ranges. The detection criterion should also reflect the uncertainty in the elemental composition that results from this estimator.

The performance gain that results from detection of entire isotope envelopes rather than individual resonances is simply due to increasing the overlap between the signal and the filter. In both cases, the matched filter is chosen to have unit power. Any projection of zero-mean white Gaussian noise with component variance $\sigma^2$ through a linear filter with unit power is a random variable with zero-mean and variance $\sigma^2$. Thus, the noise overlap has the same statistical distribution for any normalized matched filter.

Consider the (fictional) case where the isotope envelope of species X consists of two non-overlapping peaks of equal magnitude. Suppose that the two isotopes are present and each produces a non-overlapping ion resonance of magnitude s. The ion resonance matched filter consists of a single peak and produces a score of s at either of the two peaks. In contrast, the isotope envelope detector (that detects multiple peaks simultaneously) uses a matched filter comprised of two peaks of equal magnitude. For the matched filter to have unit magnitude, each peak must have a squared magnitude of ½; that is, each peak has a magnitude of $\sqrt{2}/2$. The isotope envelope matched filter produces a score of $\sqrt{2}$s. For the same observed spectrum, the signal-to-noise ratio is greater by a factor of $\sqrt{2}$ when the "signal" is considered to be the isotope envelope of species X rather than an individual ion resonance.

At first glance, it would appear that the isotope envelope detector would have enhanced sensitivity to weak signals, picking up peaks with SNR=x at the same detection rate that the single resonance detector would detect peaks with SNR=$\sqrt{2}$x. The actual performance of the single resonance detector is not quite so bad because the detector has two independent chances to find the signal. If the probability of detecting either signal is p, the probability of detecting at least one of the two signals is $2p-p^2$.

The derivation of the probability of detection and false alarm are given in Component 3, Equations 14 and 15. The results are repeated here.

$$P_D^{iso\_env}(|A|, T) = P(\mathrm{Re}[S] > T) = \frac{1}{\pi}\int_T^\infty e^{-[x-|A|]^2}dx = \frac{1}{\pi}\int_{T-|A|}^\infty e^{-x^2}dx = \frac{1}{2}\mathrm{erfc}(T-|A|) \tag{3.14}$$

erfc denotes the two-sided complementary error function, T denotes the detector threshold, and |A|>0 is the SNR.

The special case |A|=0 in (3.14) gives the probability of false alarm.

$$P_{FA}(T) = P_D(0, T) = \frac{1}{2}\mathrm{erfc}(T) \tag{3.15}$$

The probability of detection for the single ion resonance detector is formed by substituting $|A|/\sqrt{2}$ for |A| to generate p, the probability of detecting either of the two peaks in isolation, and then calculating $2p-p^2$, the probability of detecting at least one of the two peaks.

$$P_D^{single\_ion}(|A|, T) = 2p - p^2 \tag{7}$$
$$p = \frac{1}{2}\mathrm{erfc}\left(T - \frac{|A|}{\sqrt{2}}\right)$$

Figure 18:
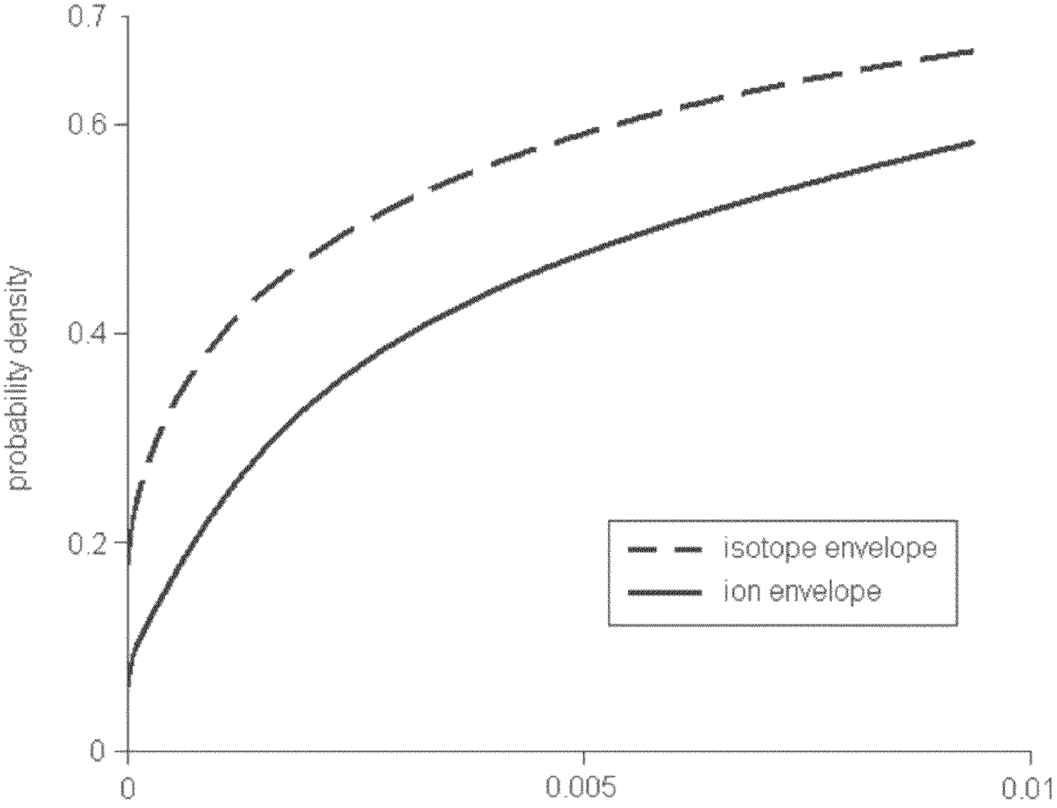
FIG. 18 depicts that the ROC curve for the isotope envelope detector (dotted line) for SNR=2 lies above the ROC curve for the single ion resonance detector (solid line) for a "toy" isotope envelope of two equal peaks, in accordance with an embodiment of Component 4 of the present invention. This demonstrates that the isotope envelope detector is superior. The "toy" isotope envelope chosen for this analysis bears some resemblance to that isotope envelope for peptides of mass 1800. Curves are calculated using Equations 3.14, 3.15, and 7 with |A|=2.
Figure 19:
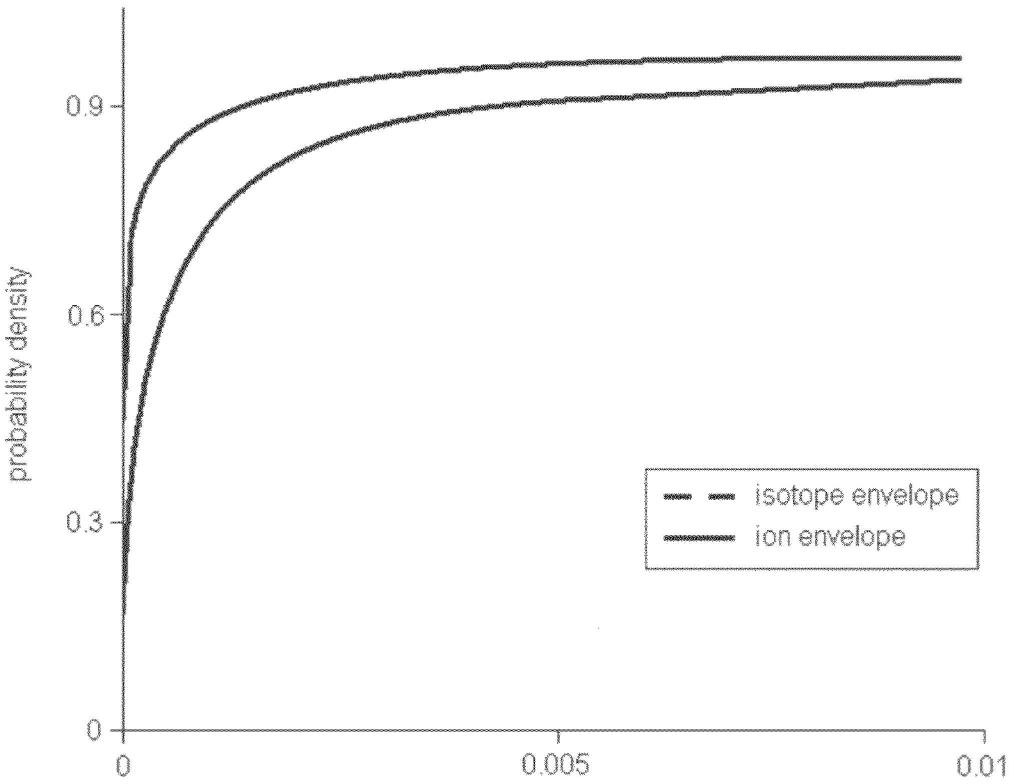
FIG. 19 depicts that the ROC curve for the isotope envelope detector (dotted line) for SNR=2 lies above the ROC curve for the single ion resonance detector (solid line) for a "toy" isotope envelope of two equal peaks, in accordance with an embodiment of Component 4 of the present invention. This demonstrates that the isotope envelope detector is superior. The "toy" isotope envelope chosen for this analysis bears some resemblance to that isotope envelope for peptides of mass 1800. Curves are calculated using Equations 3.14, 3.15, and 7 with |A|=3.

The ROC curves for the isotope envelope detector and the single ion resonance detector for the above example are shown in FIGS. 18 and 19. The probability of detection in FIG. 18 refers to an isotope envelope of two identical peaks, each with SNR=$\sqrt{2}$, so that the isotope envelope has SNR=2. FIG. 19 shows detection of isotope envelopes with SNR=3.

Figure 20:
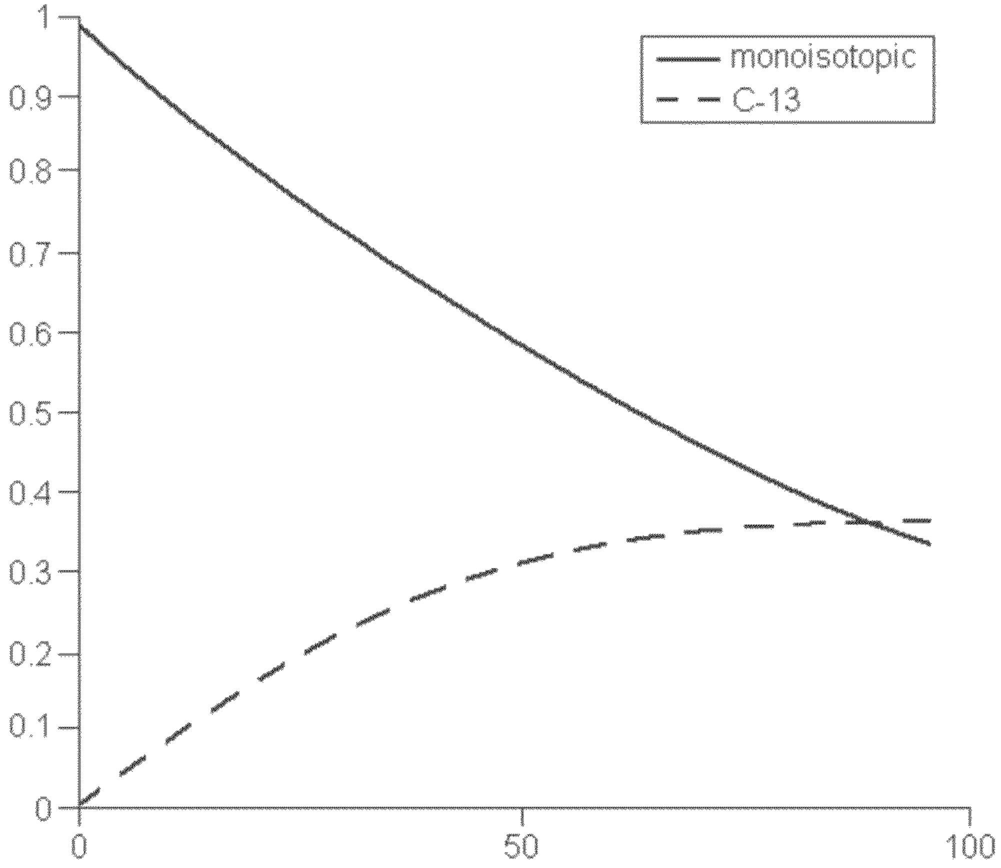
FIG. 20 depicts fractional abundances of monoisotopic and C-13 Peak versus (# of Carbons), in accordance with an embodiment of Component 4 of the present invention.

The fictional isotope envelope described above is similar to the actual isotope envelope of a peptide with 93 carbons. The peptide isotope envelope for this peptide, and for any peptide of similar size and smaller, is dominated by the monoisotopic peak and the peak corresponding to molecules with one C-13 isotope. At 93 carbons, these two peaks are roughly identical (FIG. 20).

In general, a matched filter that provides a more extensive match with the signal, matching multiple peaks rather than just one, provides better discrimination. Matched filter detector of isotope envelopes rather than single ion resonances is an example of this general property.

Component 5: Phase-Enhanced Frequency Estimation

Successful identification of the components in a mixture is the primary goal of mass spectrometry. In mass spectrometry, identifications are possible as a result of accurate determination of mass-to-charge ratio of ionized forms of the mixture components. Estimation of the frequency of an ion resonance from an observed FTMS signal is the first of two calculations required to determine the mass-to-charge ratio of an ion. An algorithm for estimating frequency, jointly with other parameters describing the resonant signal, is described in international PCT patent application No. PCT/US2007/069811. The second calculation is mass calibration, a process that is discussed in international PCT patent application No. PCT/US2006/021321, filed May 31, 2006, which is incorporated herein by reference in its entirety, and Component 9, described below.

Although the observed FTMS signal is a superposition of signals from ions of various mass-to-charge ratios (and noise), the Fourier transform separates signals on the basis of their resonant frequencies. The result is a set of peaks at various locations along the frequency axis. The precise position of the peak indicates the resonant frequency of the ion. Determining the peak position is confounded by the sampling of the signal in the frequency domain (caused by the finite observation duration) and the presence of noise in the time-domain measurements. The frequency estimation problem can be viewed in terms of recovery of a continuous signal from a finite number of noisy measurements.

One way to improve an estimator (e.g., the frequency estimator in international PCT patent application No. PCT/US2007/069811) would be to impose additional constraints upon the estimator by introducing a priori knowledge about the parameters or their interdependence. In particular, the relationship between the phase and frequency of an ion resonance can be inferred from a FTMS spectrum, as demonstrated in Component 1, which showed that the relationship between the phases and frequencies of ion resonances can be computed from an FTMS spectrum and validated by theory. The rmsd error between the phase model and observed phases was 0.079 radians in a FT-ICR spectrum and about 0.017 radians in an Orbitrap™ spectrum.

The phase of an FTMS signal changes very rapidly with frequency near the resonant frequency. It has been determined that for 1-second scans with typical signal decay rates that the phase of the FTMS signal (on either instrument) changes approximately linearly with frequency near the resonant frequency with a slope of about −2.26 rad/Hz. This suggests that even a small error in the estimate of the resonant frequency would result in significant error in the phase estimate. This suggests that a priori information about the phase of the resonance could be used to correct errors in the frequency estimate. Because of the rapid change in phase with frequency, if the a priori value for the phase were reasonably accurate, the phase-enhanced frequency estimate would have considerably higher accuracy.

The Orbitrap™ phase accuracy of 0.017 radians would translate to frequency accuracy of 0.0081 Hz. An ion with m/z of 400 resonates at about 350 kHz in the Orbitrap™ instrument, so the resulting mass accuracy (in the absence of calibration errors) would be 46 ppb. The FT-ICR instrument, phase accuracy of 0.079 radians would yield a frequency accuracy of 0.038 Hz. An ion with m/z of 400 resonates at about 250 kHz in the FT-ICR, so the resulting mass accuracy (in the absence of calibration errors) would be 150 ppb.

Calibration errors limit mass accuracy on both instruments, so it may not be possible to routinely achieve the benchmarks cited above. However, the ability to estimate frequencies with very high accuracy would make it possible to identify systematic errors in the mass calibration relation for a given instrument. Correction of these errors with improved machine-specific calibration relations could bring mass accuracy close to the theoretical limits imposed by measurement noise.

It has been shown previously, international PCT patent application No. PCT/US2007/069811, that the MC model provides a highly accurate characterization of FTMS data collected on both FT-ICR and Orbitrap™ instruments. The MC model for the time-domain signal is shown in Equation 1.

$$y(t) = \begin{cases} Ae^{-t/\tau}\cos(2\pi f_0 t - \phi) & t \in [0, T] \\ 0 & \text{else} \end{cases} \quad (1)$$

A denotes the initial amplitude of the oscillating signal, τ denotes the decay time constant for the signal amplitude, $f_0$ denotes the frequency of oscillation, and ϕ denotes the initial phase of the oscillation. The phase ϕ also refers to the position of the ion in its oscillation cycle. For example, the phase in FT-ICR is equal to the angular displacement of the ion in its orbit relative to a reference detector. T is the duration of the observation interval, which is assumed to be known. The word "initial" refers to the beginning of the detection interval.

Frequency spectrum Y is calculated from the time-dependent signal y (Equation 1) by discrete Fourier transform. The result is shown in Equation 2.

$$Y[k] = Ae^{-i\phi}\frac{1-e^{-q}}{1-e^{-q/N}} = Ae^{-i\phi}Y_0[k] \quad (2)$$

$$q = \left[\frac{1}{\tau} + i2\pi\left(\frac{k}{T} - f_0\right)\right]T$$

$Y_0$ in Equation 2 denotes the zero-phase signal. The signal can be separated into a factor that contains the amplitude and phase (a complex-valued scalar) and a factor that contains the peak shape $Y_0$, which depends upon τ, T, and $f_0$. The symbol N denotes the number of time samples in y, and for large N, linearly scales Y.

The observed spectrum can be modeled as the ideal spectrum plus white Gaussian noise.

Therefore, a maximum-likelihood estimator finds the vector of values for A, ϕ, τ, and $f_0$ that minimizes the sum of squared magnitude differences between model and observed data. The maximum-likelihood estimate vector is the value for which the derivative of the error function with respect to each of the four parameters is equal to zero. This corresponds to solving four (non-linear) equations in four unknowns. International PCT patent application No. PCT/US2007/069811 describes an iterative process to solve these equations.

In Component 5, the relationship between the phase and frequency of an ion resonance is exploited. As shown in Component 1, phase can be expressed as a function of the frequency. Therefore, there are three, rather than four, independent parameters to estimate. The complete derivation of the estimator is given in international PCT patent application No. PCT/US2007/069811. In Component 5, the new aspects are highlighted.

Let Z denote a vector containing samples of the Fourier transform of time-domain measurements. We assume that Y corresponds to a region of the spectrum containing a single ion resonance (i.e., the contributions from other resonances is effectively zero). Let e denote the squared magnitude of the difference between vectors Y and Z, model and observed data (Equation 3).

$$e(p) = \|Y(p)-Z\|^2 = (Y(p)-Z)^*(Y(p)-Z) \quad (3)$$

Let p denote the vector of unknown model parameters, e.g. $(A, \phi, f_0, \tau)$. The dependence of the model and the error upon p are explicitly noted in Equation 3. The subscript * denotes the conjugate-transpose operator; both Y and Z are complex-valued vectors.

Let $p^{ML}$ denote the maximum-likelihood estimate of p. The derivative of the error with respect to the parameters evaluated at $p^{ML}$ is equal to zero (Equation 4).

$$\left.\frac{\partial e}{\partial p}\right|_{p^{ML}} = 0 \tag{4}$$

The derivative of the error can be expressed in terms of the derivative of the model function (Equation 5).

$$\left.\frac{\partial e}{\partial p}\right|_{p^{ML}} = (Y-Z)^{*}\left.\frac{\partial Y}{\partial p}\right|_{p^{ML}} \tag{5}$$

In the derivation of the estimator described in international PCT patent application No. PCT/US2007/069811, the parameter vector p included both the frequency and the phase of the ion resonance as independent parameters. Now, the phase is assumed to be determined by the resonant frequency, as specified by the phase model function $\phi(f_0)$. The derivative of the model function with respect to frequency is given by Equation 6.

$$\left.\frac{\partial Y}{\partial f_0}\right|_{p^{ML}} = A\left[Y_0\frac{\partial}{\partial f_0}\left(e^{-i\phi(f_0)}\right) + e^{-i\phi(f_0)}\frac{\partial Y_0}{\partial f_0}\right] = Ae^{-i\phi(f_0)}\left[\frac{\partial Y_0}{\partial f_0} - iY_0\frac{\partial \phi}{\partial f_0}\right] \tag{6}$$

Equation 6 is one of the three component equations of Equation 4. The other two components, derivatives with respect to signal magnitude and decay, are the same as in the previous estimator and not repeated here. In Component 5, Equation 4 represents three non-linear equations in three unknowns, rather than four equations in four unknowns as before. These are solved numerically using Newton's method as before.

As demonstrated in Component 1, the true phase of a resonant ion varies slowly with frequency. On the Orbitrap™ instrument, there is a 20 ms delay between injection and excitation, corresponding to a complete phase cycle every 50 Hz, a rate of change of 0.12 radians/Hz. On the FT-ICR instrument at NHMFL analyzed in Component 1, the rate of change of the phase ranged from 0.013 to 0.025 radians/Hz. Therefore, the phase model is not sensitive to small errors in frequency. That is, the phase specified by the model for a particular ion resonance would not change very much in the presence of frequency errors of typical size (e.g., 0.1 Hz).

In contrast, the error in the estimate of the phase from the observed peak (in the absence of a phase model) would change dramatically in the presence of a small error in frequency. To see this, consider a sinusoid of frequency $f_0$ defined over the region [0,T] with phase zero. Now consider the problem of aligning a second sinusoid of frequency $f_0+\Delta S$ to the first. Consider the case where $\Delta f \ll 1/T$ so that the total phase swept out by the two sinusoids differs by less than 2p. The best alignment of the two waves would match the phase of the second to the first at the midpoint, resulting in a phase error of $-/+\pi T(\Delta f)$ at the beginning and end of the interval respectively. This suggests that for small Δf, that the phase error for a 1-second scan (actually 0.768 sec of observation on Thermo instruments), is 2.41 radians/Hz. This is 20-200 times greater than the rate of change of the phase model.

In general, ion resonances are decaying sinusoids, and the best alignment of two waves, as considered above, places more weight at the beginning of the observation interval. This has the effect of reducing the error in the initial phase estimate that results from an error in the frequency estimate.

An estimate of the phase error in the presence of signal decay as a result of frequency estimation error is the rate of change of $Y_0$ with respect to f evaluated at $f_0$. Equation 7 shows the first of a succession of approximations. The denominator in Equation 2 can be simplified for large N (i.e., small q/N).

$$Y_0(\Delta f) \cong \frac{1-e^{-q}}{q} \qquad q = a+bi \qquad a = \frac{T}{\tau};\ b = 2\pi\Delta f T \tag{7}$$

For small Df (i.e., small b), the exponential can be replaced with a linear approximation; the numerator and denominator are multiplied by the complex conjugate of the denominator; the result is shown in Equation 8.

$$Y_0(\Delta f) \cong \frac{1-e^{-a}e^{-bi}}{a+bi} \cong \frac{1-e^{-a}(1-bi)}{a+bi} = \frac{[(1-e^{-a})-be^{-a}i](a-bi)}{a^2+b^2} = \frac{[a(1-e^{-a})+b^2e^{-a}]+ib[ae^{-a}-(1-e^{-a})]}{a^2+b^2} \tag{8}$$

The phase of $Y_0$ at a small displacement Δf from the resonant frequency can be approximated by the ratio of the imaginary and real components, for small phase deviations. Terms depending upon $\Delta f^2$, i.e. $b^2$, can be ignored for small Δf. An approximation for the phase that is linear in Df is shown in Equation 9.

$$\begin{aligned}\arg[Y_0(\Delta f)] &= \tan^{-1}\left(\frac{\mathrm{Im}[Y_0(\Delta f)]}{\mathrm{Re}[Y_0(\Delta f)]}\right) \cong \frac{\mathrm{Im}[Y_0(\Delta f)]}{\mathrm{Re}[Y_0(\Delta f)]} = \\ &= \frac{b[ae^{-a}-(1-e^{-a})]}{a(1-e^{-a})+b^2e^{-a}} \cong \frac{b[ae^{-a}-(1-e^{-a})]}{a(1-e^{-a})} \\ &= b\left(\frac{e^{-a}}{(1-e^{-a})}-\frac{1}{a}\right) = 2\pi\Delta f T\left(\frac{e^{-T/\tau}}{(1-e^{-T/\tau})}-\frac{\tau}{T}\right) \\ &= 2\pi\left(\frac{Te^{-T/\tau}}{(1-e^{-T/\tau})}-\tau\right)\Delta f\end{aligned} \tag{9}$$

For τ=2 s and T=0,768 s, the constant in front of Δf in Equation X is −2.26 rad/Hz. In the limit as τ goes to infinity, the constant is −2.41 rad/Hz, the value determined by the analysis of the simple case above.

Figure 21:
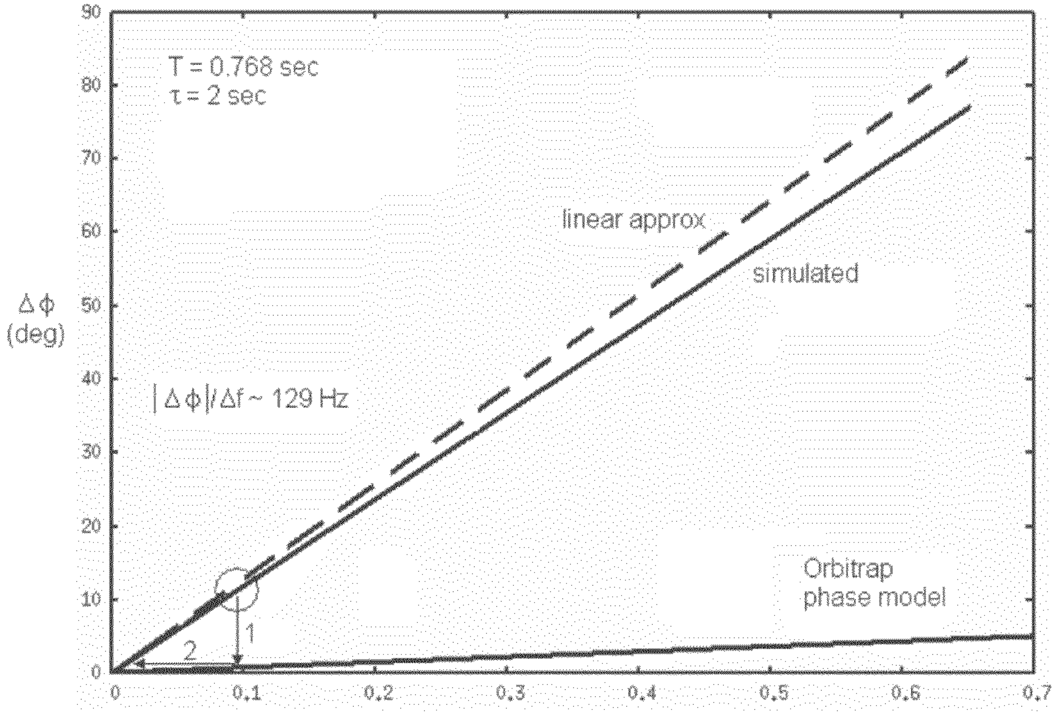
FIG. 21 depicts a plot in accordance with an embodiment of Component 5 of the present invention, in which the solid curve shows the phase shift of the sinusoid of best fit (i.e., induced phase error) as a function of frequency error. A linear approximation to this curve is shown in the dotted line. Typical errors in frequency are on the order of 0.1 Hz. The Orbitrap™ phase model can be seen below both linear and simulated lines ("Orbitrap Phase model"). The relatively small slope of this line suggests that errors in frequency estimation will not significantly change the estimate of the phase that comes from the phase model. An error in frequency of 0.1 Hz is depicted by the black circle. The error in frequency would be expected to induce a phase error of approximately 13 degrees (the y-displacement of the circle). However, the phase model provides a much better estimate of the true phase (arrow #1) because of its low sensitivity to frequency error. The apparent phase error can be used to infer the error in the frequency estimate, allowing an appropriate correction (arrow #2). Phase-enhanced frequency estimation thus results in improved accuracy. The above explanation is a rationale for the enhancement provided by a phase model. The actual mechanism for phase-enhanced frequency is that (frequency, phase) estimates are constrained to lie on the Orbitrap Phase model line). Estimates that were previously allowed by the unconstrained estimator (international PCT patent application No. PCT/US2007/069811) are no longer allowed. The constraint that the phase is accurately specified by the model prevents errors in the frequency estimation. Errors in the frequency estimation tend to follow the solid line, a direction that is not tolerated by the phase model. The process is exactly specified by Equation 6.

FIG. 21 graphically illustrates the implications of the above analysis for phase-enhanced frequency estimation. The phase that is associated with a given frequency is represented by the phase model (blue line). Errors in frequency tend to cause errors in phase so that (frequency, phase) estimation papers tend to move along the red line. However, because the slopes of these lines are substantially different (20-200×), the phase model is highly intolerant to large-scale movement along the line of estimation errors, resulting in a powerful constraint on the frequency estimate.

Errors in frequency estimates can be substantially reduced by a phase model. The phase model can be constructed from the observed resonances and validated by theory. Thus, a phase model provides an additional constraint on the phase estimate. Small errors in frequency produce substantially larger errors in phase. The phase model is intolerant to even small errors in phase. Therefore, the errors in phase-enhanced frequency estimation will be very low. Mass accuracies at or below 100 ppb may be possible; particularly if the accuracy of the frequency estimates can be used to develop better calibration functions. It may be possible to learn the reproducible systematic errors in the mass-frequency relations that result from subtle differences in the manufacture of instruments. Elimination of these effects would be an important step toward achieving mass accuracy that is limited only by the noise in the measured signal.

Component 6: Detecting and Resolving Overlapping Signals in FTMS

Signal overlap presents a challenge for characterization of samples by mass spectrometry. When two signals overlap, it becomes difficult to estimate the mass-to-charge ratio of either signal; potentially resulting in misidentification of both species. If the overlapping signals are being used for calibration, the distortion may produce errors in many additional mass estimates and cause systemic misidentification.

In many cases, the overlap of two signals is easily detected and identification confidence can be appropriately reduced. However, in some cases, the overlap may involve a relatively small signal producing a subtle distortion in a larger signal with a very similar m/z value. The overlap may render the smaller signal undetectable, yet create a distortion in the peak shape of the larger peak. This may result in a slight shift apparent position of the peak and subsequent misidentification.

In international PCT patent application No. PCT/US2006/021321 and Component 9, we have described real-time calibration methods that use identifications of all ions in the sample to self-calibrate a spectrum. Such methods can be confounded if signal overlap is not properly addressed. Component 6 provides a method for detecting overlaps and a method for decomposing the overlapped signal into individual ion resonance signals that can be successfully identified.

Figure 22:
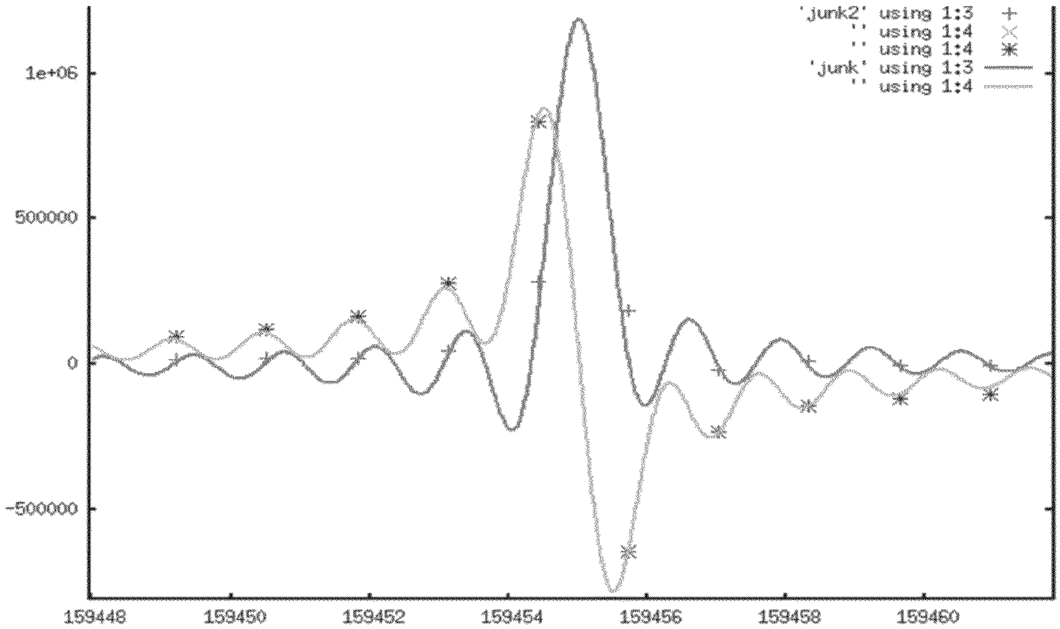
FIG. 22 depicts that a model curve for the real (dotted line) and imaginary (solid line) fits the observed samples of the Fourier transform, real (indicated by "+") and imaginary (indicated by "x") to very high accuracy, validating the MC model for spectra collected on the Thermo LTQ-FT, in accordance with an embodiment of Component 6 of the present invention.

In international PCT patent application No. PCT/US2007/069811, we described an estimator that models each detected resonance in an FTMS spectrum by four physical parameters: magnitude, phase, frequency, and decay. The patent application demonstrated the estimator was capable of modeling signals to very high accuracy (FIG. 22). Unlike other estimators that fit resonance signals only near the peak centroid, our model seemed to fit many samples away from the centroid into the tails of the peak. In most cases, the accuracy was limited only by noise in the measurement of the time-domain signal. In some isolated cases, the model did not seem to fit the peak well. Furthermore, the deviation seemed to be concentrated on a region of the peak, rather than the entire peak; suggesting the presence of a second overlapping signal.

Figure 23:
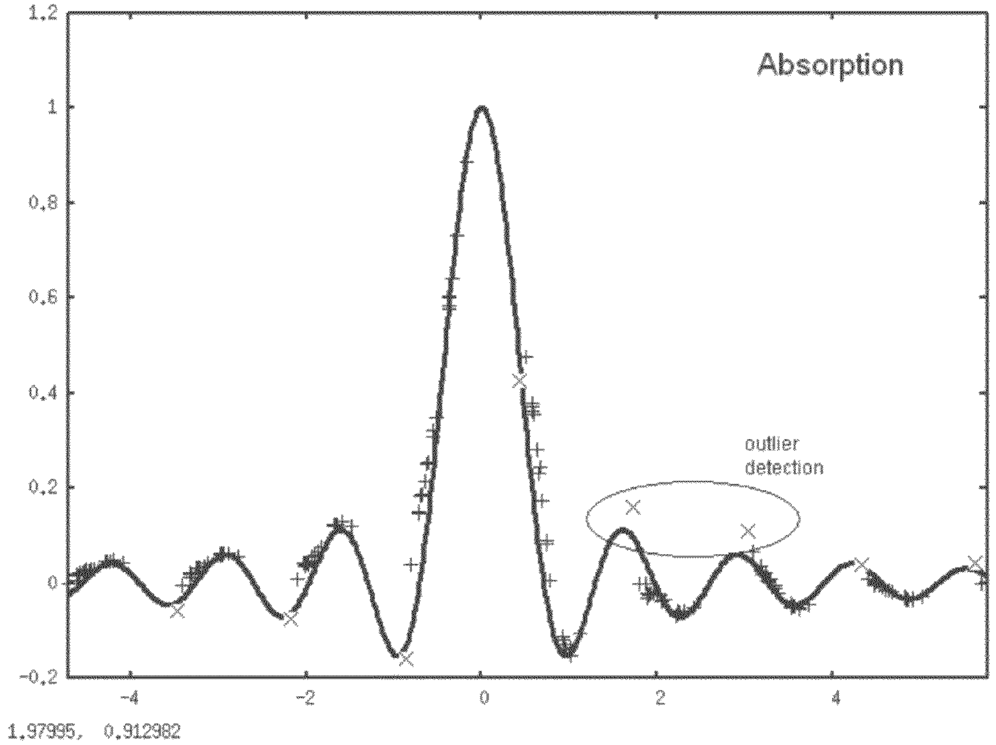
FIG. 23 depicts that 20 of 21 peaks lie on the standard curve, in accordance with an embodiment of Component 6 of the present invention (Absorption). The other peak (indicated by "x") does not. Furthermore, the difference between the data and model of best fit is concentrated on two samples, suggesting the presence of signal overlap.
Figure 24:
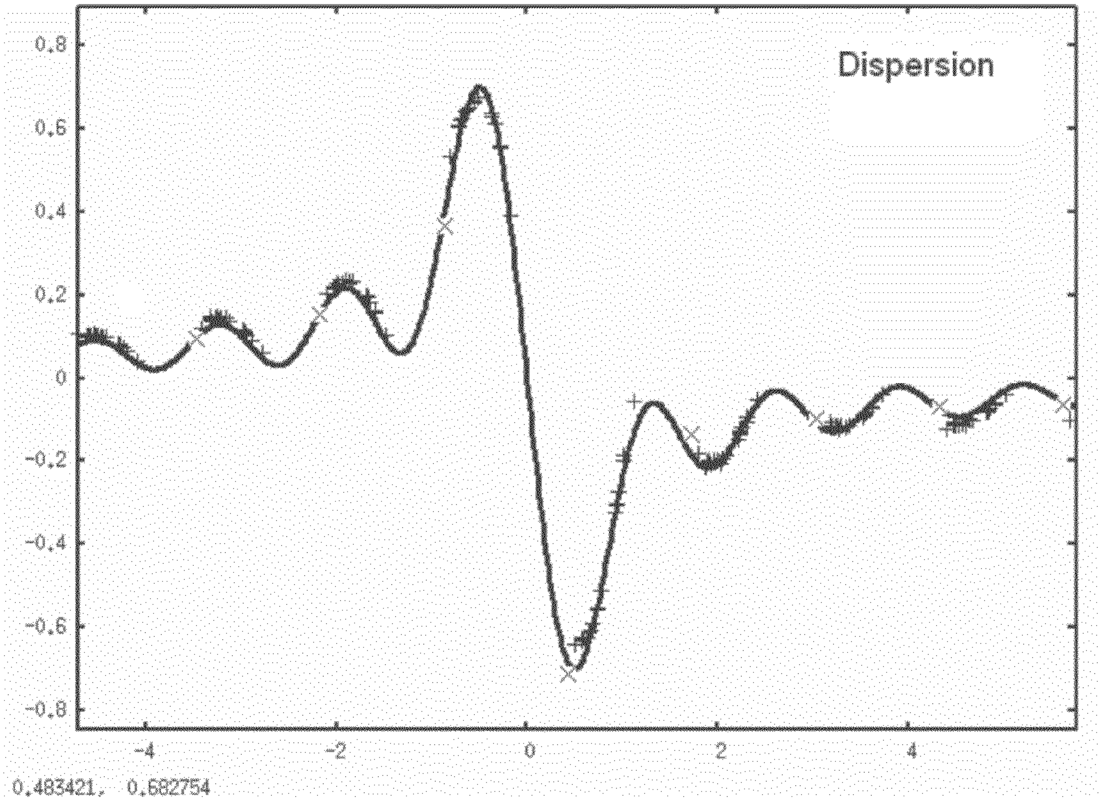
FIG. 24 depicts that 20 of 21 peaks lie on the standard curve, in accordance with an embodiment of Component 6 of the present invention (Dispersion).

FIGS. 23 and 24 shows the superposition of 21 peaks corresponding to the same ion observed in 21 successive scans. The superposition was achieved by using the estimated parameters to shift and scale each peak to maximize their alignment. One of the peaks shows a systematic deviation from the others and that the remaining 20 peaks show reasonably good correspondence with the theoretical model curve.

This analysis is based upon the assumption that there are three effects that produce differences between the observed data and the model of best fit: 1) measurement noise, 2) model error, and 3) signal overlap. In addition, the noise is assumed to be additive, white Gaussian noise. A detector for signal overlap would compute a statistic that varies monotonically with the probability that the observed difference was caused by only the first two effects, and not signal overlap. When the statistic exceeds an arbitrary threshold, then signal overlap is judged to have occurred. The probability value associated with this threshold gives the probability of false alarm.

First, consider a simpler problem: the case where there is no model error. Let y denote a vector of N samples of the frequency spectrum containing a single ion resonance. Let x denote an analogous vector of N samples and unit norm containing a signal model, which when scaled appropriately, gives rise to the maximum-likelihood, least-squares, model of the observed data.

In the absence of model error, y can be written as a scalar A times the model vector x plus a vector n that contains N samples of additive, white Gaussian noise (Equation 1). Each sample is complex-valued and the components are independent and identically distributed with zero mean and variance $\sigma^2/2$.

$$y=Ax+n \tag{1}$$

The scaled model of best fit to the data (i.e., maximum-likelihood and least-squares) is the projection of data vector y onto signal model x times vector x. Equation 2 shows the projection calculation, which also gives the maximum-likelihood estimate of A, denoted by $\hat{A}$.

$$\hat{A} = \langle y, x\rangle = \sum_{k=1}^{N} y_k x_k^* = \langle Ax+n, x\rangle = A\langle x, x\rangle + \langle n, x\rangle = A + \langle n, x\rangle = A + \Delta A \tag{2}$$

Noise causes an error in the estimate of A, denoted by ΔA. Because the error is the projection of white Gaussian noise onto a unit vector, the error is a Gaussian-distributed complex number with mean zero and component variance $\sigma^2/2$, just like each sample of the original noise vector.

Let vector Δ denote the difference between the observed data and the scaled model of best fit (Equation 3).

$$\Delta=y-\hat{A}x=(Ax+n-(A+\Delta A)x)=n-(\Delta A)x \tag{3}$$

A represents a projection of n onto the 2N−2 dimensional subspace normal to vector x. Therefore, Δ is Gaussian distributed with the same mean and component variances. The probability density of Δ is a monotonic function of the squared norm of Δ. Therefore, the squared norm of delta, denoted by S, is a sufficient statistic for detecting signal overlap (Equation 4).

$$S = \|\Delta\|^2 = \sum_{k=1}^{N} |\Delta_k|^2 = \sum_{k=1}^{N} \left|y_k - \hat{A}x_k\right|^2 \tag{4}$$

That is, when S>T, where T is an arbitrary threshold, then signal overlap is judged to be present. The probability of false alarm is the probability that S>T when S does not contain overlapping signals (i.e., S is distributed as in Equation 4). S has the same distribution as the sum of 2N−2 independent Gaussian random variables with zero mean and identical variance. This is a chi-squared distribution with 2N−2 degrees of freedom, scaled by $\sigma^2/2$. Because the chi-squared distribution is tabulated, the probability of false alarm can be computed for any given threshold T.

The detection problem becomes more complicated when model error must also be considered. To distinguish signal overlap from model error, one must assume that the model error for every signal is identical in nature. Assume that the true signal of unit amplitude is given by a vector x, and that observed data vector y is given by Equation 1, as before. In this case, the signal model is given by a vector x', which is not equal to x. The maximum-likelihood, least-squares estimate of A is given by the projection of data vector y onto signal model x', as in Equation 2, with x' in place of x (Equation 5).

$$\hat{A}=\langle y,x'\rangle=\langle Ax+n,x'\rangle=A\langle x,x'\rangle+\langle n,x'\rangle \quad (5)$$

Then the difference vector Δ reflects both noise and model error (Equation 6).

$$\Delta=y-\hat{A}x'=Ax+n-\langle y,x'\rangle x' \quad (6)$$

The detection criterion S, the squared norm of D, is calculated in Equation 7.

$$S=\|\Delta\|^2=\|y-\langle y,x'\rangle x'\|^2=\|y\|^2-\|\langle y,x'\rangle|^2 \quad (7)$$

It is necessary to introduce noise vector n into Equation 7 to calculate the distribution of S. Each of the two terms in Equation 7 can be calculated separately.

$$\|y\|^2=\langle Ax+n,Ax+n\rangle=|A|^2+2\mathrm{Re}[A\langle x,n\rangle]+\|n\|^2 \quad (8)$$

$$\begin{aligned}|\langle y,x'\rangle|^2&=|\langle Ax+n,x'\rangle|^2=|A\langle x,x'\rangle+\langle n,x'\rangle|^2 \quad (9)\\&=|A|^2|\langle x,x'\rangle|^2+2\mathrm{Re}[\langle x,x'\rangle\langle x',n\rangle]+|\langle n,x'\rangle|^2\end{aligned}$$

Using Equations 8 and 9 to rewrite Equation 7 yields Equation 10.

$$S=|A|^2(1-|\langle x,x'\rangle|^2)+Re[\langle n,(2A(x-\langle x,x'\rangle x'))\rangle]+\|n\|^2-|\langle n,x'\rangle\| \quad (10)$$

The first term in Equation 10 is deterministic; the second is a projection of noise, a Gaussian random variable; the third and fourth are each chi-squared random variables, scaled by $\sigma^2/2$ and with 2N and 2 degrees of freedom, respectively. The distribution of a sum of random variables is the convolution of their distributions. However, when all the random variables are Gaussian distributed, the result is Gaussian distributed. The chi-squared distribution is asymptotically normal for large N. The distribution of S, therefore, is approximately normal. The mean and variance are the sum of the means and variances of the individual terms respectively.

$$\mathrm{mean}[S]=|A|^2(1-|\langle x,x'\rangle|^2)+0+(2N-2)(\sigma^2/2)=|A|^2e^2+(N-1)\sigma^2 \quad (11)$$

$$\mathrm{var}[S]=0+4|A|^2e^2(\sigma^2/2)+(2N+2)(\sigma^2/2)^2=2|A|^2e^2\sigma^2+\frac{N+1}{2}\sigma^4 \quad (12)$$

e denotes the model error: the norm of the difference between x (the true signal) and the projection of x onto x' (the signal model) (Equation 13).

$$e^2=|x-\langle x,x'\rangle x'|^2=1-|\langle x,x'\rangle|^2 \quad (13)$$

Equations 11 and 12 cannot be used to calculate false positive rates because the mean and the variance depend upon the signal magnitude |A| and the model error e, which are unknown. The estimate of |A| can be used in place of |A| and the model error can be inferred from observations. A more fundamental issue is that each value of |A| demands its own detection threshold; otherwise, the detector would produce variable false positive rates for different signal magnitudes.

When signal overlap is detected, we wish to estimate parameters describing the (two) individual resonances. We begin by computing a rough initial estimate which we then refine to produce maximum-likelihood estimates. Without a sufficiently accurate initial estimate of the parameters, the refinement may converge to a local, rather than a global, maximum.

In computing the initial estimate, we assume that the two resonances have identical phases and decay, but different magnitudes and frequencies. We require four observations to determine four unknown parameters. We propose using the four moments (0, 1, 2, 3) of the observed complex-valued signal in a window containing the overlapped peaks. The zero-order moment gives an estimate of the sum of the signal magnitudes. The first-order moment and zero-order moment together give an estimate of the magnitude-weighted frequency average. The first three moments together give an estimate of the inertia, the weighted squared separation of the frequencies from the centroid. If the magnitudes were equal, these three observables would determine that magnitude and the individual frequencies. The third-order moment is needed to determine the magnitude ratio.

The initial estimate is then submitted to an iterative algorithm that finds the values of eight parameters (four for each peak) that maximize the likelihood of the observed data. This involves numerically solving eight equations in eight unknowns. Because the complex-valued signals resulting from two signals can be modeled as the sum of the individual signals, the equations are analogous to those that appear in the single-resonance estimator, described in our earlier paper. The system of non-linear equations can be solved, as before, using Newton's method, iterating from the initial estimates to a converged set of estimates, which should give the maximum-likelihood values of the parameters.

Component 7: Linear Decomposition of Very Complex FTMS Spectra into Molecular Isotope Envelopes Component 7 addresses analysis of spectra obtained by FTMS that contain a very large number of distinct ion resonances. Such spectra contain many overlapping peaks, including clusters containing many peaks that mutually overlap. In addition, it is assumed that the ion resonances represent a relatively limited set of possible m/z values.

The approach of Component 7 is top-down spectrum analysis, not to be confused with top-down proteomic analysis that refers to intact proteins. In top-down analysis, all potential elemental compositions are assumed to be present in the spectrum. The goal is to assign a set of abundances to each elemental composition. The abundance assignments—with some species assigned zero abundance—are used to construct a model spectrum that is compared to the observed spectrum.

The model spectrum, when it is expressed as a vector of complex-valued samples of the Fourier transform, is simply a weighted sum of the spectra of the individual components. It is important to emphasize that the linearity problem that makes complex-valued spectra relatively easy to analyze does not hold for magnitude-mode spectra.

Abundances are assigned to the set of elemental compositions in order to maximize the likelihood that the data would be observed if the putative mixture were analyzed by FTMS. Because variations in calibrated, complex-valued FTMS spectra can be modeled as additive white Gaussian noise, maximizing likelihood is equivalent to minimizing the squared difference between the model and observed spectra. The least-squares solution involves projecting the data onto the space of possible model spectra, parameterized by a vector of abundances, whose components represent the elemental compositions of species possibly present in the mixture. For a complex-valued spectrum, or any of its linear projections, including the absorption spectrum, the optimal abundances satisfy a linear matrix-vector equation. The equation can be solved efficiently using numerical techniques designed for sparse matrices.

The requirement for high-resolution is encoded in the matrix equation. The entries in the matrix are the overlap integrals between the model spectra for the various elemental compositions present in the mixture. The situation where there are (essentially) no overlaps, results in a diagonal matrix, resulting in a trivial solution for the abundances. Alternatively, if two species have virtually identical m/z values, they would have virtually identical model spectra. Two species with identical spectra would have identical rows in the matrix, resulting in a singularity. As the similarity between two species increases, the matrix becomes increasingly ill-conditioned, resulting in solutions that are sensitive to small noisy variations in the observed data. The mass resolving power of the instrument ultimately determines the smallest m/z differences that can be discerned by this method. Smaller differences would need to be collapsed into a single entry representing the sum of the abundances of the indistinguishable species.

Figure 25:
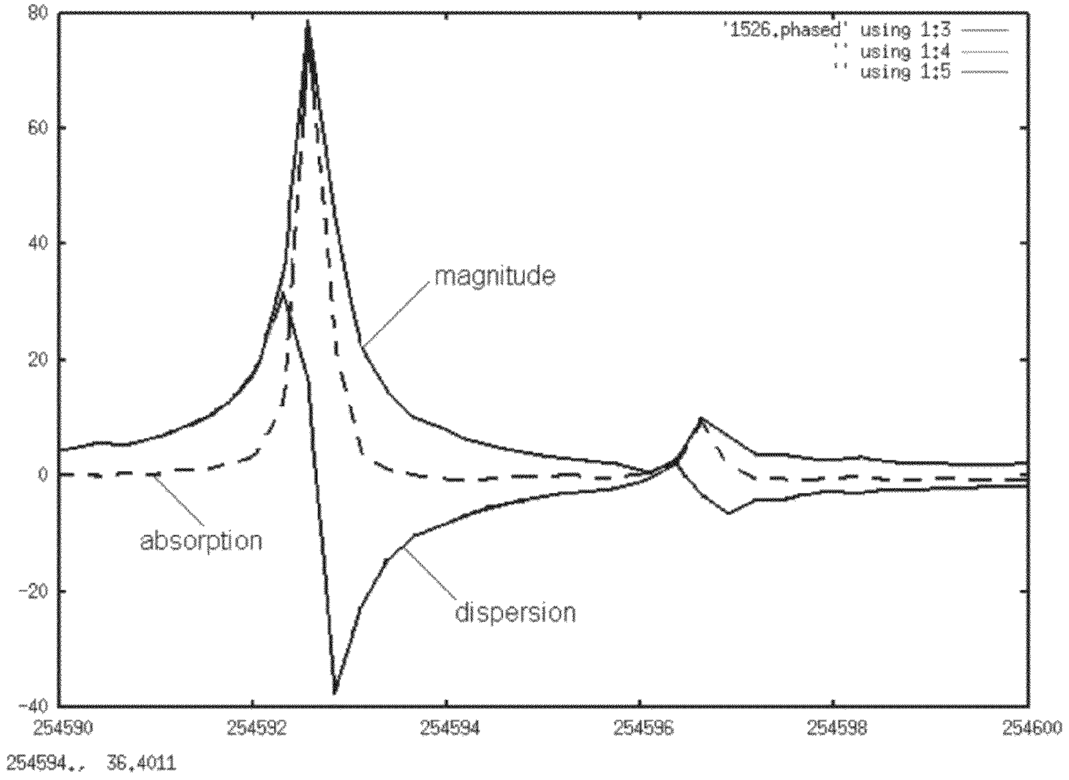
FIG. 25 depicts a chart where the magnitude, absorption, and dispersion spectra are shown for a region of a petroleum spectrum containing two ion resonances, in accordance with an embodiment of Component 7 of the present invention. The absorption peak is significantly narrower than the magnitude peak (1.6×) at FWHM. The tail of the absorption peak decays as $1/\Delta f^2$, while the magnitude tail decays as $1/\Delta f$. As a result, absorption peaks have significantly reduced overlap, resulting in improved detection and mass determination of low-intensity peaks adjacent to a high-intensity peak.
Figure 26:
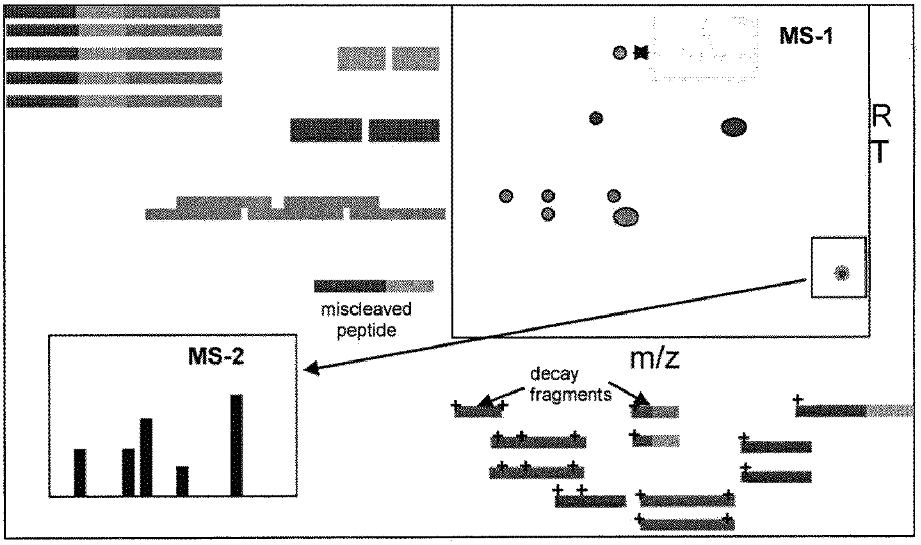
FIG. 26 depicts a schematic of a protein image in accordance with an embodiment of Component 8 of the present invention. This figure shows a hypothetical model for the contribution of a particular protein to a proteomic LC-MS run involving tryptic digestion. The sequences of tryptic peptides can be predicted and coordinates (m/z, RT) may be assigned to each—a first-order model. With experience, and with particular analysis goals in mind, reproducible deviations from the first-order model may be learned, including enzymatic miscleavages, ionization decay products, systematic errors in retention time prediction, relative charge-state abundances, MS-2 spectra, etc. The model may be continuously refined until it provides a highly accurate descriptor of the protein. The process of developing such a model would be accelerated by repeated analysis of purified protein. These models can also be inferred from protein mixtures. The ability to clearly delimit which LC-MS features belong to a certain protein makes it easier to detect other proteins. The general strategy provides a method to use experience from previous runs to improve analysis of subsequent ones.

Two important developments improve the prospects for resolving species with similar m/z values. The first is the ability to model the relationships between the phases and frequencies of ion resonances, demonstrated in Component 1, and then to use this model for broadband phase correction, shown in Component 2. The absorption spectrum that results from broadband phase correction has peaks that are only 0.4 times the width of apodized magnitude-mode spectra observed in XCalibur™ software at FWHM. Perhaps more importantly, peaks in an absorption spectrum have tails that vanish as $1/(\Delta f)^2$, where $\Delta f$ represents the distance from the peak centroid in frequency space. Magnitude peaks decrease as $1/\Delta f$. The slower decrease is most noticeable in the large shadow cast by intense magnitude-mode peaks, obscuring detection of or distorting adjacent peaks of smaller intensity. These "shadows" are greatly reduced in absorption-mode spectra. (FIG. 25).

The second development is the use of phased isotope envelopes, described in Component 3 in the context of detection. Although two isotopic species may have considerable overlap, the entire isotope envelopes may have considerably less overlap. This is most evident for species whose monoisotopic masses differ by approximately one or two Daltons. However, it is also true for species whose monoisotopic masses are nearly identical, but have distinguishable isotope envelopes (e.g., a substitution of $C_3$ for $SH_4$; Δ32 3.4 mDa). Phased isotope envelopes accurately capture the composite signals produced by overlapping resonances (e.g., C-13 vs. N-15). Overlapping resonances add like waves; magnitudes do not add. Therefore, it is necessary to consider the phase relationships between overlap signals to model observed spectra.

Let vector y denote a collection of voltage measurements at uniformly spaced time intervals over some finite duration. Suppose that the data contains M distinct signals, one signal for each group of related resonating ions. Let $\{x_1 \ldots x_M\}$ denote the individual signals. The data collected when an M-component mixture is analyzed by Fourier-transform mass spectrometry can be modeled by Equation 1.

$$y = \sum_{m=1}^{M} a_m x_m + n \tag{1}$$

It has been shown that FTMS is well approximated by a linear process. The right-hand side of Equation 1 represents a random model for generated the observed voltages. The corresponding factor $a_m$ is a scalar that corresponds to the number of ions. In fact, $a_m$ denotes relative rather than an absolute abundance because our signal model contains an unknown scale factor.

The vector n represents a particular instance of random noise in the voltage measurements. We assume that n can be modeled as white, Gaussian noise with zero mean and component variance $\sigma^2$. The observed signal is modeled as the sum of an ideal noise-free signal plus random noise.

Estimation of Abundances

Suppose we are given a set of potential mixture components, indexed 1 through M. We wish to estimate the abundance of each component given observed FTMS data. Let $a_m$ denote the true abundance of component m. (If component m is not present, then $a_m=0$.) Let $\hat{a}_m$ denote the estimated abundance of component m. The estimated value $a_m$ differs from the true abundance $a_m$ because of noise in the observations. If the same mixture is analyzed repeatedly, a collection of distinct observation vectors is produced with differences due to random noise. When the estimator is applied to the collection of observation vectors, a collection of distinct values for $a_m$ is produced. An unbiased estimator has the property that the expected value of the estimated abundance $a_m$ is equal to the true abundance $a_m$. The construction of an unbiased estimator is described below.

Because Fourier transformation is a linear operator, Equation 1 also holds when y denotes samples of the discrete Fourier transform. In this case, the vectors y, {x1 . . . xM}, and n each have N/2 complex-valued components. Therefore, either time-domain observations (transient) or frequency-domain observations (spectrum) can be expressed as linear superpositions of corresponding signal models. The estimator is virtually identical for either representation of the signal. However, for reasons that will be made clear below, the implementation of the estimator is more efficient in the frequency domain.

Let <a|b> denote the inner product of two vectors as defined by Equation 2.

$$\langle a \mid b \rangle = \sum_{k=1}^{K} a_k b_k^* \tag{2}$$

The subscript * denotes the complex-conjugate operator.

Now, suppose we take the inner product of both sides of Equation 1 with $x_k$, the spectrum model for mixture component 1, as shown in Equation 5a.

$$\langle y \mid x_k \rangle = \left\langle \left( \sum_{m=1}^{M} a_m x_m + n \right) \middle| x_k \right\rangle \tag{3}$$

Because inner product is a linear operator, we can rewrite the right-hand side of Equation 3 as shown in Equation 4.

$$\langle y \mid x_k \rangle = \sum_{m=1}^{M} a_m \langle x_m \mid x_k \rangle + \langle n \mid x_k \rangle \quad (4)$$

If we take the inner product of both sides of Equation 3 for each $x_M$, for m=1 . . . M, then we have M independent linear equations in M unknowns. The model signals must be distinct.

These M equations can be represented as a single matrix equation (Equation 5).

$$\begin{bmatrix} \langle y \mid x_1 \rangle \\ \vdots \\ \langle y \mid x_M \rangle \end{bmatrix} = \begin{bmatrix} \langle x_1 \mid x_1 \rangle & \dots & \langle x_M \mid x_1 \rangle \\ \vdots & \ddots & \vdots \\ \langle x_1 \mid x_M \rangle & \dots & \langle x_M \mid x_M \rangle \end{bmatrix} \begin{bmatrix} a_1 \\ \vdots \\ a_M \end{bmatrix} + \begin{bmatrix} \langle n \mid x_1 \rangle \\ \vdots \\ \langle n \mid x_M \rangle \end{bmatrix} \quad (5)$$

Next, take the expected value of each side of Equation 5 to produce Equation 6. Let E denote the expectation operator.

$$E \begin{bmatrix} \langle y \mid x_1 \rangle \\ \vdots \\ \langle y \mid x_M \rangle \end{bmatrix} = E \left( \begin{bmatrix} \langle x_1 \mid x_1 \rangle & \dots & \langle x_M \mid x_1 \rangle \\ \vdots & \ddots & \vdots \\ \langle x_1 \mid x_M \rangle & \dots & \langle x_M \mid x_M \rangle \end{bmatrix} \begin{bmatrix} a_1 \\ \vdots \\ a_M \end{bmatrix} + \begin{bmatrix} \langle n \mid x_1 \rangle \\ \vdots \\ \langle n \mid x_M \rangle \end{bmatrix} \right) \quad (6)$$

Expectation is also a linear operator. Because n is a zero-mean random vector and inner product is a linear operator, the expectation of the each noise component is zero. Application of these two properties to Equation 6 yields Equation 7.

$$\begin{bmatrix} \langle E[y] \mid x_1 \rangle \\ \vdots \\ \langle E[y] \mid x_M \rangle \end{bmatrix} = \begin{bmatrix} \langle x_1 \mid x_1 \rangle & \dots & \langle x_M \mid x_1 \rangle \\ \vdots & \ddots & \vdots \\ \langle x_1 \mid x_M \rangle & \dots & \langle x_M \mid x_M \rangle \end{bmatrix} \begin{bmatrix} a_1 \\ \vdots \\ a_M \end{bmatrix} \quad (7)$$

The true abundances of the mixture components could be obtained by solving Equation 7 provided that the expected value of the observed data y were known. If we replace E[y], the expectation of a random vector, with y, taken to denote the particular outcome of a given FTMS experiment, and replace each $a_m$ with $\hat{a}_m$, we have an unbiased estimator for the abundances (Equation 8).

$$\begin{bmatrix} \langle y \mid x_1 \rangle \\ \vdots \\ \langle y \mid x_M \rangle \end{bmatrix} = \begin{bmatrix} \langle x_1 \mid x_1 \rangle & \dots & \langle x_M \mid x_1 \rangle \\ \vdots & \ddots & \vdots \\ \langle x_1 \mid x_M \rangle & \dots & \langle x_M \mid x_M \rangle \end{bmatrix} \begin{bmatrix} \hat{a}_1 \\ \vdots \\ \hat{a}_M \end{bmatrix} \quad (8)$$

Maximum-Likelihood Criterion

We can also show that the estimator described by Equation 8 provides abundance estimates that maximize the likelihood of observing data vector y.

The probability density of the observation vector is given by the multivariate normal distribution. The value evaluated at y, for this case, is shown in equation 9.

$$P(y) = (\pi o^2)^{-M/2} \exp\left( -\frac{1}{o^2} \left\| y - \sum_{m=1}^{M} a_m x_m \right\|^3 \right) \quad (9)$$

The maximum-likelihood estimate is the value of the vector $a=[a_1 \dots a_M]^T$ that maximizes P(y). The maximum-likelihood estimate, denoted by $a^{ML}$ must satisfy Equation 10.

$$\left. \frac{\partial P}{\partial a} \right|_{a_{ML}} = 0 \quad (10)$$

Taking the derivative with respect to a of both sides of Equation 9 and evaluating at $a^{ML}$ yields Equation 11.

$$\left. \frac{\partial P}{\partial a} \right|_{a_{ML}} = \frac{2P}{o^2} \mathrm{Re} \begin{bmatrix} \left\langle y - \sum_{m=1}^{M} a_m^{ML} x_m \middle| x_1 \right\rangle \\ \vdots \\ \left\langle y - \sum_{m=1}^{M} a_m^{ML} x_m \middle| x_M \right\rangle \end{bmatrix} \quad (11)$$

Setting the right-hand side of Equation 11 to zero yields Equation 8, with $a^{ML}$ in place of $\hat{a}$.

To show that the extremum value of P satisfying Equation 11 is indeed a maximum (rather than a minimum), note that the second derivative of P with respect to a (Equation 12) is a negative scalar times a Hermitian matrix $\langle x_i | x_j \rangle = \langle x_j | x_i \rangle^*$, and therefore negative definite.

$$\left. \frac{\partial^2 P}{\partial a^2} \right|_{a_{ML}} = -\frac{2P}{o^2} \begin{bmatrix} \langle x_1 \mid x_1 \rangle & \dots & \langle x_M \mid x_1 \rangle \\ \vdots & \ddots & \vdots \\ \langle x_1 \mid x_M \rangle & \dots & \langle x_M \mid x_M \rangle \end{bmatrix} \quad (12)$$

Equivalence of Estimator Equation (Equation 8) in Time and Frequency

To show that Equation 8 describes an equivalent estimation process in either the time or frequency domain, it is sufficient to show that each inner product in the matrix and vector is identical. A fundamental property of inner products is that the inner product of two vectors is invariant under a unitary transformation, e.g. rotation. The Fourier transform is an example of such a transformation.

Let a and b denote N-dimensional vectors of real-valued components. Let a' and b' denote their respective Fourier transforms. For example, $$a'_k = \frac{1}{\sqrt{N}} \sum_{n=0}^{N-1} a_n e^{-i2\pi kn} \quad (13)$$

Equation 14 shows that the inner product <a|b> of the time-domain signals is equivalent to the inner product <a'|b'> of the frequency-domain signals.

$$\langle a' \mid b' \rangle = \left\langle \frac{1}{\sqrt{N}} \sum_n a_n e^{-i2\pi kn} \middle| \frac{1}{\sqrt{N}} \sum_n b_n e^{-i2\pi kn} \right\rangle = \quad (14)$$

$$\frac{1}{N} \sum_k \sum_n \sum_{n'} a_n e^{-i2\pi kn} b_{n'}^* e^{+i2\pi kn'} =$$

-continued $$\frac{1}{N}\sum_{n}\sum_{n'}a_n b_{n'}^*\sum_{k}e^{-i2\pi k(n-n')} =$$

$$\frac{1}{N}\sum_{n}\sum_{n'}a_n b_{n'}^*(N\delta_{n,n'}) = \sum_{n}a_n b_n^* = \langle a \mid b\rangle$$

It is important to note that the spectra a' and b' are complex-valued functions. In the typical practice of FTMS, spectra consist of the magnitude of the complex-valued Fourier transform samples. However, magnitude spectra are not additive. That is, the magnitude spectrum resulting from two signals with similar, but not identical frequencies (i.e., overlapping peaks) is not the sum of the individual magnitude spectra. The estimation process described above requires the use of complex-valued spectra. None of the above equations, starting with Equation 1, are valid for magnitude spectra.

Frequency-Domain Implementation of Estimator

We have demonstrated that the estimator equation (Equation 8) holds when the data and signal models are represented either by transients or (complex-valued) spectra. We will show that an accurate approximate solution of Equation 8 using spectral representations produces a computational savings of over four orders of magnitude over the direct solution in the time-domain.

The calculation of the inner product (Equation 2) in the time-domain involves the sum of T products of real numbers, while calculation of the inner product in the frequency-domain involves the sum of T/2 products of complex numbers. Each complex operation involves four real-valued products. An exact calculation of the inner product in the time-domain would yield a two-fold savings in computation time. However, as we will demonstrate below, signals in the frequency domain decrease rapidly away from the fundamental frequency, and can be approximated with reasonable accuracy by functions defined over small support regions. (i.e., less than 100 samples vs. an entire spectrum of $10^6$+ samples), producing a computational savings of 10,000 fold or greater.

Another important implementation issue also results from the narrow peak shape in the frequency domain. In theory, the spectrum of any time-limited signal has infinite extent, and therefore every pair of model signals has non-zero overlap. In practice, the overlap between most pairs of signals is so small that it can be neglected. Only signals whose fundamental frequencies are very similar have significant overlap. When we approximate model spectra by neglecting values outside a finite support region, only signals whose fundamental frequencies differ by less than twice this extent have non-zero overlaps. Therefore, the M×M matrix of inner products is quite sparse. If the peaks are sorted by either mass or frequency, non-zero terms are clustered around the diagonal. Use of absorption spectra also reduces the number of overlaps, resulting in fewer non-zero, off-diagonal terms. In any case, it is important to use an algorithm adapted for sparse matrices to efficiently calculate the solution of Equation 8.

Calculating the Matrix Entries in the Estimator Equation (Equation 8)

The MC model for FTMS signals has been described elsewhere. Here, the key results are given. The time domain signal of a single ion resonance is given by Equation 15

$$x(t) = \begin{cases} A\cos(2\pi f_0 t - \phi)e^{-t/\tau} & t \in [0, T] \\ 0 & \text{else} \end{cases} \tag{15}$$

There are five parameters in the description of the signal. T is the observation duration, assumed to be known for a given spectrum. The signal is non-zero only over the observation duration. During observation, the signal is the product of a sinusoid function and a decaying exponential. A and $\phi$ are the (initial) amplitude and phase, and $f_0$ is the frequency of the sinusoid. Initial refers to the beginning of the detection interval. $\tau$ is a time constant characterizing the signal decay.

Suppose that the continuous signal is sampled at N discrete time points $\{t_n = nT/N : n\in[0 \ldots N-1]\}$. The discrete Fourier transform of the sampled function $\{x(t_n) : n\in[0 \ldots N-1]\}$ is given by Equation 16.

$$\begin{aligned} x'(f) &= \sum_{n=0}^{N-1} x(t_n)e^{-i2\pi f t_n} \\ &= Ae^{-i\phi}\sum_{n=0}^{N-1} e^{-i/\tau}e^{i2\pi f_0 t_n}e^{-i2\pi f t_n} \\ &= Ae^{-i\phi}\frac{1-e^{-(1/\tau+i2\pi(f-f_0))T}}{1-e^{-(1/\tau+i2\pi(f-f_0))T/N}} \end{aligned} \tag{16}$$

The factor $Ae^{-i\Phi}$ is a scale factor and $f_0$ shifts the centroid of the peak. T is the same for all peaks in a spectrum. If we make the additional simplifying assumption that $\tau$ is fixed for all peaks in the spectrum, then all peaks have the same shape, differing only by scaling and shifting. Therefore, we replace set $f_0$ to zero, set $Ae^{-i\Phi}$ to one, and define a canonical signal model function $$s(f) = c\frac{1-e^{-(1/\tau+i2\pi f)T}}{1-e^{-(1/\tau+i2\pi f)T/N}} \tag{17}$$

The constant c is necessary to normalize s.

$$c = \left[\sum_{n=0}^{N-1}\left|\frac{1-e^{-(1/\tau+i2\pi f_n)T}}{1-e^{-(1/\tau+i2\pi f_n)T/N}}\right|^2\right]^{-1/2} \tag{18}$$

In practice, the sum in Equation 18 is computed over a small region near the centroid (e.g., 100 samples), rather than over the entire spectrum.

First, we will compute the overlap between individual ion resonances. Then, we will compute the overlaps between entire isotope envelopes. The latter quantities are the matrix entries of Equation 8.

The overlap between two signals, each described by Equation 17 and with $\tau$ constant, depends only the frequency shift between the signals. In Equation 19, S denotes the overlap integral between two signals shifted by $\Delta f$.

$$S(\Delta f) = |c|^2\sum_{n=0}^{N-1}\left(\frac{1-e^{-(1/\tau+i2\pi f_n)T}}{1-e^{-(1/\tau+i2\pi f_n)T/N}}\right)\left(\frac{1-e^{-(1/\tau+i2\pi f_n+\Delta f)T}}{1-e^{-(1/\tau+i2\pi f_n+\Delta f)T/N}}\right)^* \tag{19}$$

S can be precomputed and stored in a table for a predefined set of values.

To compute the overlap between two ion resonances, each with known M/z, the first step is to compute their resonant frequencies, take the difference Δf, and then look up the value of S in a table for that value of Δf.

To compute the resonant frequencies of the ions, the mass of the ion and the mass calibration relation are required. In this Component 7, it is assumed that the mass calibration relation is known.

Equation 20 is used to calculate the resonant (cyclotron) frequency of an ion with a given mass-to-charge ratio, denoted by M/z.

$$f = \frac{A}{M/z} + \frac{B}{A} \tag{20}$$

This equation comes from rearranging the more familiar calibration equation for FTMS (Equation 21): solving for f, taking the larger of two quadratic roots (the cyclotron frequency), and approximating by first-order Taylor series.

$$\frac{M}{z} = \frac{A}{f} + \frac{B}{f^2} \tag{21}$$

The monoisotopic mass of an ion of charge z is calculated from summing the masses of its atoms, indicated by its elemental composition and then adding the mass of z protons.

The second step in computing the overlap is to calculate the phase difference between the ion resonances. Ions with different resonant frequencies also have different phases, and this affects the overlap between the signals. The phase difference can be calculated when a model relating the phases and frequencies of ion resonances is available. Construction of a phase model is described in Component 1.

S in equation 17 denotes the overlap between two zero-phase signals. Let S' denote the overlap between signals with phases $\phi_1$ and $\phi_2$ respectively. Factors $e^{-i\Phi 1}$ and $e^{-i\Phi 2}$ would multiply the two factors in the sum in Equation 17. These factors can be pulled outside the sum as shown in Equation 22.

$$S'(\Delta f) = |c|^2 \sum_{n=0}^{N-1} \left( e^{-i\phi_1} \frac{1 - e^{-(1/\tau + i2\pi f_n)T}}{1 - e^{-(1/\tau + i2\pi f_n)T/N}} \right) \left( e^{-i\phi_2} \frac{1 - e^{-(1/\tau + i2\pi f_n + \Delta f)T}}{1 - e^{-(1/\tau + i2\pi f_n + \Delta f)T/N}} \right)^* = e^{-i\phi_1}(e^{-i\phi_2}) * S(\Delta f) = e^{-i(\phi_1 - \phi_2)} S(\Delta f) \tag{22}$$

The structure of Equation 22 allows the use of a single table to rapidly calculate overlaps between signals by accounting for the phase difference in a second step after table lookup.

Isotope envelopes are linear combinations of individual ion resonances, weighted by the fractional abundance of each isotopic species. The masses of the isotopic forms of a molecule are calculated as above, substituting the masses of the appropriate isotopic forms of the element as needed.

The model isotope envelope for elemental composition m and charge state z is a sum over the isotopic forms, indexed by parameter q.

$$x_{mz}(f) - c_{mz} \sum_{q=1}^{Q} \alpha_q e^{-1\phi_{mzq}} s(f - f_{mzq}) \tag{23}$$

The vector a denotes the fractional abundances of the isotopic forms of the molecule.

This calculation is described below in connection with Component 17 and is not repeated here. The frequency fmzq and phase fmzq of each isotopic form are computed as described above. The normalization constant cmz is analogous to Equation 18. After normalization, the overlap of a signal with itself is equal to one.

The overlap between two isotope envelopes can be calculated using the linearity property that was exploited in Equation 22.

$$\langle x_{mz}(f) \mid x_{m'z'}(f) \rangle = \left\langle c_{mz} \sum_{q=1}^{Q} \alpha_q e^{-i\phi_{mzq}} s(f - f_{mzq}) \,\middle|\, c_{m'z'} \sum_{q'=1}^{Q'} \alpha_{q'} e^{-i\phi_{m'z'q'}} s(f - f_{m'z'q'}) \right\rangle = c_{mz}(c_{m'z'}) * \sum_{q=1}^{Q} \sum_{q'=1}^{Q'} \alpha_q \alpha_{q'} e^{-i(\phi_{mzq} - \phi_{m'z'q'})} S(f_{mzq} - f_{m'z'q'}) \tag{24}$$

Equation 24 demonstrates that the overlap between isotope envelopes can be computed as the sum of QQ' terms—the product of the number of isotopic species represented in each envelope. It is not necessary to explicitly compute the envelope. The calculation requires the envelope normalization constants and the fractional abundances, frequencies, and phases of the isotopic species. These values are computed once and stored for each elemental composition. Note that the normalization constant cmz can be computed by using Equation 24 to compute the overlap between the unnormalized signal with itself and then taking the −½ power.

Calculating the Vector Entries in the Estimator Equation (Equation 8)

The vector entries in Equation 8 are the overlaps between the observed spectrum and the model isotope envelope spectra for the various elemental compositions thought to be present in the sample. The linearity of the inner product can be exploited to avoid explicit calculation of isotope envelopes, as in Equation 24.

$$\langle y \mid x_{mz}(f) \rangle = \left\langle y \,\middle|\, c_{mz} \sum_{q=1}^{Q} \alpha_q e^{-i\phi_{mzq}} s(f - f_{mzq}) \right\rangle = (c_{mz}) * \sum_{q=1}^{Q} \alpha_q e^{i\phi_{mzq}} \langle y \mid s(f - f_{mzq}) \rangle \tag{25}$$

The estimator was applied to a petroleum spectrum collected on a 9.4 T FT-ICR mass spectrometer. The spectrum was provided by Tanner Schaub and Alan Marshall of the National High Magnetic Field Laboratory. Analysis on this spectrum (performed at the National High Magnetic Field Laboratory) identified 2213 isotope peaks, corresponding to 1011 elemental compositions, all charge state one, ranging in mass from 300 to 750 Daltons. As a proof of concept, the abundance estimator was applied to the spectrum to decompose it into isotope envelopes corresponding to the 1011 identified elemental compositions. The estimates were computed in a few seconds, solving the 1011×1011 matrix directly, without using sparse matrix techniques. Part of the model spectrum is shown in FIGS. 29 and 30.

Figure 29:
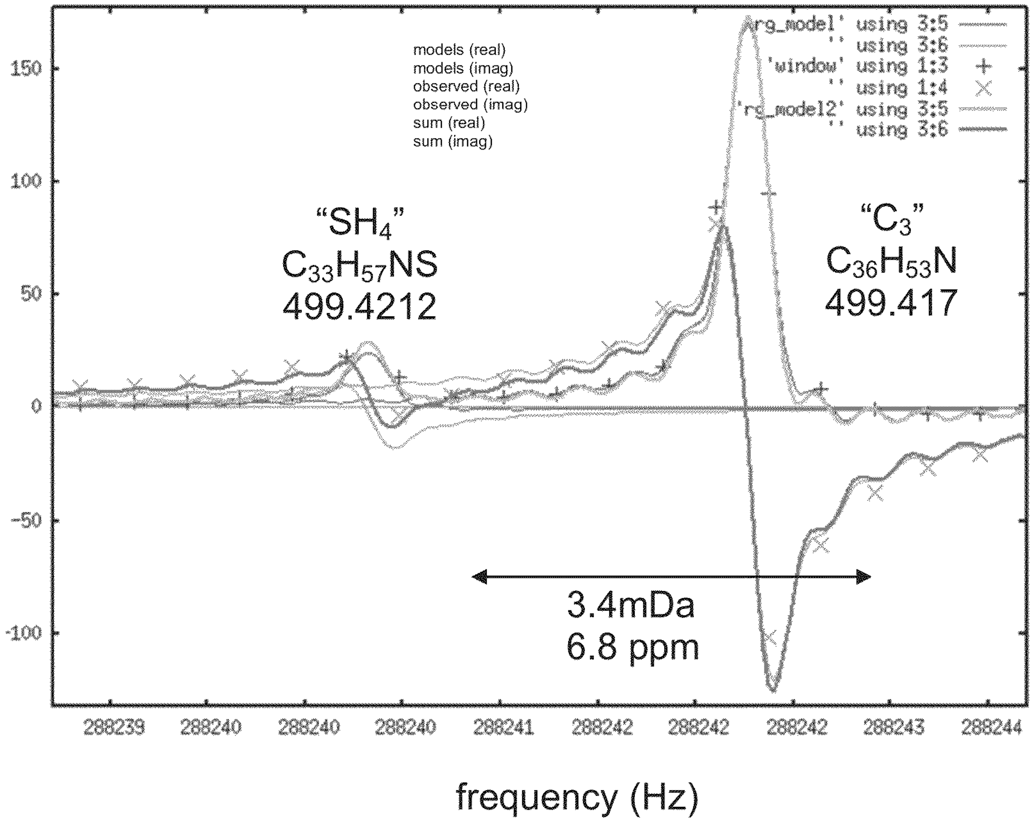
FIG. 29 depicts linear decomposition of two overlapping signals, in accordance with an embodiment of Component 7 of the present invention. The real and imaginary components of each signal (two red and two green curves) sum to give the total real and imaginary components (blue and brown curves). These curves pass through the observed real and imaginary components (blue crosses and pink x's). The real (red) and imaginary (green) components approximately resemble absorption and dispersion curves, suggesting that the resonance has approximately zero phase. Notice the significant overlap between the two green curves (approximately dispersion) from the CH3 peak and the greatly reduced overlap of the red curves (approximately absorption).

FIG. 29 demonstrates the ability to separate overlapped signals into the contributions from individual ion resonances. The two peaks shown were chosen because of their small difference in mass (3.4 mDa). This is one of the smallest mass differences routinely encountered in petroleum analysis. These two peaks were chosen also because each resonance has approximately zero phase. Thus, the real and imaginary components roughly correspond to the absorption and dispersion spectra. The overlap between the real components (absorption) is substantially less than the overlap between the imaginary components (dispersion) as expected. The performance of the algorithm is validated by finding two signal models whose sum shows good correspondence with the observed data.

Figure 30:
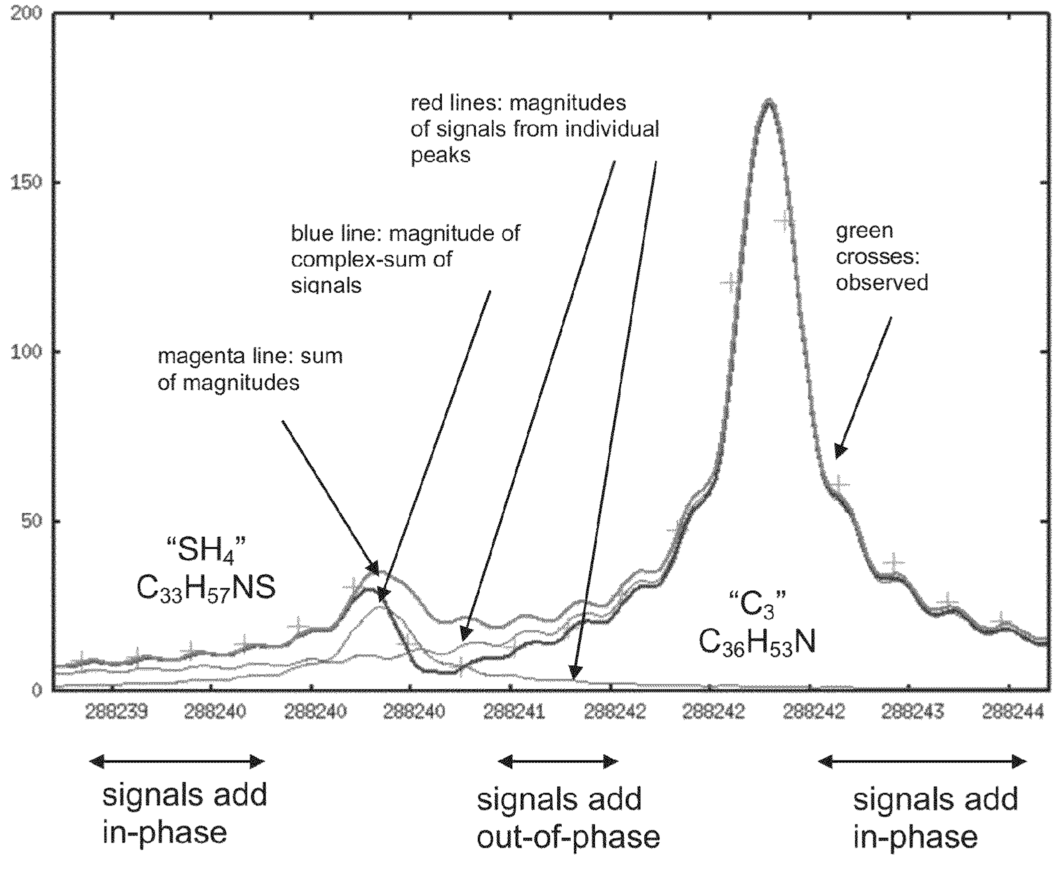
FIG. 30 depicts, in accordance with an embodiment of Component 7 of the present invention, observed magnitude spectrum (magenta), superimposed with magnitude spectra constructed from linear decomposition of real and imaginary parts—sum (blue) and individuals (two red curves). This figure reveals a general property of overlapping FTMS signals. In the region between two resonances, the signals add approximately 180 degrees out-of-phase (blue=|red1−red2|). In the region outside the two resonances, the signals add approximately in-phase (blue=red1+red2). Notice that the blue curve passes through the observed magnitudes (green crosses) for all regions. In contrast, the magenta curve passes through the observed magnitudes only outside the overlapped regions. Because the magnitude sum (magenta=red1+red2) corresponds to in-phase addition of signals, the magnitude sum overestimates the true magnitude in the overlap region. Furthermore, the red curve is the reconstructed magnitude spectrum of the $SH_4$ following linear decomposition. The blue curve shows the superposition of both signals. The phase relationships between the signals cause deconstructive interference on the side of $SH_4$ facing $C_3$ and constructive interference on the other side. This results in an apparent shift in the peak position away from $C_3$.

FIG. 30 shows the observed magnitude spectrum and four other magnitude spectra that were computed from the complex-valued decomposition. These four curves are the magnitude spectra of the individual resonances and the magnitude of the complex sum of the individual resonances and the real sum of the magnitudes of the individual resonances. The complex-sum magnitude passes through the observed magnitudes as expected. Interestingly, the real sum of the individual magnitudes matches the observed magnitudes outside the region between the resonances, but not in between. This is because of the general property that resonances add in-phase outside and out-of-phase inside. Thus, the sum of the magnitudes overestimates the observed magnitude in the region where the signals add out of phase. A consequence of this general phase relationship is the apparent outward shift in the position of both peaks; however, it is much more apparent in the smaller peak. This is due to eroding of the inside of the peak and building up of the outside of the peak due to destructive and constructive interference.

These phase relationships are explicitly accounted for in the decomposition method, and so the method is unaffected by, and in fact predicts, this phenomenon. The method should not be prone to misidentification as a result of spectral distortions induced by peak overlap.

Mass spectrometry analysis of petroleum is a suitable application for this method due to its high sample complexity and the inherent difficulty of separating the sample into fractions of lower complexity. Petroleum is not compatible with chromatographic separation. Therefore, a single spectrum reflects the entire complexity of the sample. In contrast, very complex mixtures of tryptic peptides, arising from protein digests, are easily separated by reverse-phase high-performance liquid chromatography (RP-HPLC), resulting in a large number of spectra of low to moderate complexity.

Another favorable property of petroleum samples is the large ratio of elemental compositions that have been observed versus the number that are theoretically possible. As many as 28,000 distinct elemental compositions have been identified from a signal spectrum. The number of potential elemental compositions in a petroleum sample can be estimated by allowing between 1 and 100 carbon atoms, 0 and 2 nitrogen atoms, 0 and 2 oxygen atoms, 0 and 2 sulfur atoms, and 20 different double-bond equivalents, which determines the number of hydrogen atoms after the other atoms have been specified. This gives $(100)(3^3)(20)=54,000$ elemental compositions. Whether or not these boundaries are precisely correct, the point is that a significant fraction of the elemental compositions that are possible are actually present in the sample.

Another application whose analysis can be improved by this method is the analysis of mixtures of intact proteins. Like petroleum, large proteins are not easily fractionated by chromatography. In addition, large molecules (>10 kD) present an additional challenge by having a large number of isotopic forms and producing ions with a large number of distinct charge states. Thus, each protein generates a large number of peaks. However, the family of peaks can be predicted and used to estimate the total protein abundance.

The estimation method has been described in terms of analysis of MS-1 spectra. However, the estimation equation can be used to accommodate additional sources of information. For example, chromatographic retention time or MS-2 can be used to distinguish isomers. When such data is available, Equation 8 can be used to estimate abundances, but the inner product must be redefined in terms of the additional dimensions provided by the new data. These exciting possibilities are discussed in the context of proteomic analysis in Component 8.

Component 8: Linear Decomposition of a Proteomic LC-MS Run into Protein Images

The prevailing strategy for analyzing "bottom-up" proteomics data is inherently bottom-up; that is, tryptic peptide signals are detected, m/z values are estimated, peptides are sequenced, and the peptide sequences are matched to proteins. Component 8 elaborates on a top-down approach to analysis, first described in Component 7. The general aim of the top-down approach is to assign abundances to a predetermined list of molecular components. This is achieved by finding the best explanation of the data as a superposition of component models. In Component 7, these component models were phased isotope envelopes in a single spectrum. In Component 8, the models are generally more expansive—entire LC-MS data sets that would result from analyzing individual proteins.

The top-down approach described here is not to be confused with the notion of analysis of intact proteins, commonly called "top-down proteomics." The top-down approach of Component 8 is compatible with analysis of intact proteins or tryptically digested ones. Here "top-down" means that each component thought to be in a sample is actively sought in the data, rather than detecting peaks and inferring their identities.

Linearity is a key property that enables top-down FTMS analysis. The observed data, vector y, is the superposition of component models $\{x_1 \ldots x_M\}$ scaled by their abundances $\{a_1 \ldots a_M\}$ plus noise, vector n. (Equation 1)

$$y = \sum_{m=1}^{M} a_m x_m + n \tag{1}$$

Because n is white Gaussian noise, maximum likelihood parameter estimation is equivalent to least-squares estimation. Linear least-squares estimation involves solving a linear matrix equation, and so the optimal solution is obtained relatively easily (Equation 2).

$$\begin{bmatrix} \langle y \mid x_1 \rangle \\ \vdots \\ \langle y \mid x_M \rangle \end{bmatrix} = \begin{bmatrix} \langle x_1 \mid x_1 \rangle & \dots & \langle x_M \mid x_1 \rangle \\ \vdots & \ddots & \vdots \\ \langle x_1 \mid x_M \rangle & \dots & \langle x_M \mid x_{1M} \rangle \end{bmatrix} \begin{bmatrix} \hat{a}_1 \\ \vdots \\ \hat{a}_M \end{bmatrix} \quad (2)$$

Equation 2 was derived in Component 7, and that derivation will not be repeated here. The vector on the left-hand side of the equation contains the overlap (inner product) between the observed data and the data model for each component. This formalism can accommodate many different types of data, as long as linearity (Equation 1) is satisfied. For example, y can contain one or more MS-1 spectra, MS-2 spectra of selected ions, and other types of information. The type of data contained in y dictates the form of the data models x. The data model for a given component must specify the expected outcome of any given experiment when that component is present.

The matrix in the right-hand side of Equation 2 contains the overlaps between the various components. Two components are indistinguishable if their overlaps with all components are identical. This would lead to two identical rows in the matrix, leading to a singularity, so that Equation 2 would not have a unique solution. As the similarity between two models increases, the matrix becomes increasingly ill-conditioned. The abundance estimates become increasingly sensitive to even small fluctuations in the measurements.

The concept of overlap is both simple and powerful. If two species are indistinguishable in light of the current data vector y (i.e., same overlap), an additional experiment must be performed that distinguishes them (i.e., different overlap). For example, two molecules with similar mass may result in models that have very large overlap in an instrument with low mass resolving power (e.g., ion trap), but significantly smaller overlap in an instrument with high resolving power (e.g., FTMS). The ability to make distinctions between molecules can be quantitated by the overlap between their data models.

Another example is the case of molecular isomers. Isomers have the same MS-1 data model, and thus cannot be distinguished in a single MS-1 spectrum. However, if the data also includes the chromatographic retention time or perhaps an MS-2 spectrum of the parent ion, models for the two isomers are now distinct (i.e., non-overlapping) and the two species can be distinguished.

Another illustrative example is the idea of the image of a tryptic digest of a protein in an LC-MS run. Two protein images would overlap if the proteins contained the same tryptic peptide. Similarly, overlap would occur if each protein had a tryptic peptide so that the pair had similar m/z and chromatographic retention time (RT); thus producing overlapping peaks in the 2-D m/z×RT space.

Images with high overlap (e.g., isoforms of the same protein) would have the least stable abundance estimates; that is, small amounts of noise could lead to potentially large errors. However, it is possible to reduce the extent of overlap between images of similar proteins by augmenting the LC-MS data with an experiment that would distinguish them. An example would be to identify peptides that distinguish two isoforms and collect MS-2 spectra on features that have LC-MS attributes (m/z, RT) consistent with the desired peptides. The idea of active data collection is discussed in greater depth in Component 12.

In this Component 8, the parameters to be estimated are, for instance, the abundances of proteins (denoted by vector d in Equation 2), and the data might be, for instance, a collection of FTMS spectra of eluted LC fractions of tryptically digested proteins and perhaps also collections of MS-2 spectra. Therefore, we require a model for what each protein looks like in an LC-FTMS run and MS-2 spectra. A research program for top-down proteomic data could involve purifying each protein in the human proteome, preparing a sample of each purified protein according to the standard protocol, and analyzing the sample using LC-MS. Neglecting variability between runs and variability among proteins that we identify as the same for the moment, ideal data sets generated in this way would include protein images of the human proteome.

Given these images, the entries in the matrix and vector of Equation 2 may be calculated. Matrix entries involve overlap between models; vector entries involve overlap between the observed data and the models. The abundances may be determined by solving the resulting equation directly.

When we superimpose the protein image upon the observed data, we would expect some correspondence overlap if the protein were present in the sample at detectable levels. We would also expect some spots to be slightly out of alignment due to errors in estimating m/z from the FTMS data and errors in predicting retention time. We would expect some spots to be missing perhaps due to the inability to form a stable ion of a given charge or even the absence of the peptide from the sample as a consequence of sequence variation, in vivo processing such as splicing or post-translational modification, or unpredicted trypsin cleavage patterns. We would also expect our model to be missing some of the peaks that actually arise from the protein resulting from any of the factors described above as well as decay products of predicted ions. Observations of reproducible systematic variations may be used to update the model. Characterizing the extent of random, non-systematic variations is also an important part of the modeling process.

If the image of a protein is not directly available, then a model may be constructed from observed data. The data available typically consist of complex mixtures of proteins. A de novo model may be created, enumerating predicted tryptic peptide sequences. For each sequence, the mass and m/z values for various values of z may be computed and retention time may be predicted. Each tryptic peptide ion may be assigned a coordinate (m/z, RT), and the protein image may be a collection of spots at these coordinates.

In building up protein images, goals may include finding the most likely explanation for every detected peak in an LC-MS run and/or explaining the absence of peaks in the observed data that have been included in the models. Construction of these models is very much a bottom-up process. Peaks that can be confidently assigned to a particular protein can be used to correct the de novo model. For example, the observed retention time may replace the predicted value.

The relative abundances of peaks belonging to the same protein may be included in the model. Presumably, variations in protein concentration would affect all peaks arising from the same protein in the same proportion. In addition, variations in peak abundance corresponding to the same ion observed over multiple runs may be carefully recorded and analyzed. Peaks that have correlated abundances across runs can be inferred to arise from the same protein.

As the model image of a protein becomes an increasingly rich descriptor, it can be used to extract increasingly accurate estimates of the abundance of that protein in a sample from LC-MS data. It also becomes easier to detect and accurately estimate the abundances of other proteins with overlapping images. For example, part of the intensity of a peak may be assigned to one protein using the observed abundances of other peaks from that same protein, and then assign the rest of the intensity to another protein. Abundance relationships may also be used to improve matching model and observed peaks in the data.

The ability to match features across runs of related samples (e.g., blood from two patients) is essential to biomarker discovery. Features that do not match must be categorized as either biological differences or measurement fluctuations. Determining the magnitude and nature of differences in the absolute and/or relative positions of peaks or in their relative abundances that are due to the experiment is vital to making this key distinction. Some of these differences will be systematic across the entire run. If these systematic variations can be characterized, they can be corrected by calibration. The ability to reduce independent random fluctuations makes it possible to detect (and correct) smaller systematic variations.

Top-down analysis has as its goal the systematic study of protein images under certain types of experiments. The analysis of the distinguishing features among protein images makes it possible to actively interrogate the data for evidence of the presence of each protein in a mixture and to validate its presence by finding multiple confirming features. The digestion of proteins into tryptic peptides increases the complexity of the data. However, mathematical analysis performed at the protein level, rather than individual peptides, will be much more robust to variations in the data and sensitive to low-abundance proteins. A protein image provides a mechanism for combining multiple weak signals to confidently infer the abundance (or presence) of a protein. If each of the signals is too weak to independently provide strong evidence, the presence of the protein would not be detected by the currently employed bottom-up strategy of detecting peptide peaks and matching them to proteins.

Calibration Methods

In mass spectrometry, molecules are identified indirectly by measurements of their attributes. In FTMS, the fundamental measurement is the frequency of an ion's oscillation. A calibration step is necessary to convert frequency into mass-to-charge ratio (m/z). The estimators described above are designed to achieve accurate frequency estimations. But even if the estimators were capable of inferring the precise values of ion resonant frequencies, incorrect calibration would lead to errors in the estimates of m/z, and possibly incorrect determination of the ion's elemental composition.

Work in real-time calibration was motivated by the observation that repeated scans of the same ion resulted in fluctuations in the observed frequency that averaged about 1 ppm, much larger than the errors in the frequency estimates. This suggested that the standard protocol of weekly calibration of the instrument, together with an automatic gain control mechanism designed to limit fluctuations in ion loading to maintain proper calibration were inadequate. It was clear that a mechanism for calibrating individual scans in real-time was desirable. The need is most pronounced for applications like proteomics where high mass accuracy (sub-ppm) is necessary for identification.

International PCT patent application No. PCT/US2006/021321 describes an iterative method that, using the Expectation-Maximization (EM) Algorithm, alternates between calibration and identification steps. This application demonstrated that the constraint that masses must belong to a finite set of values could be enough to calibrate spectra given only an initial estimate of the frequency-mass calibration relation and accurate, but imperfect, frequency estimates. The particular application of interest was calibrating spectra from tryptic digests of human proteins. A test case used a database of 50,000 human protein sequences and generated an (ideal) in silico tryptic digest of 2.5 million tryptic peptides—over 350,000 distinct masses. Fifty peptides were selected at random and frequency measurements were simulated using a realistic, but arbitrary relationship between m/z and frequency and additive Gaussian distributed errors about 0.5 ppm. This data represented the ion resonance frequencies that might be extracted from an FTMS spectrum. An arbitrary initial estimate of the calibration parameters was deliberately chosen to have errors of 1-2 ppm. The algorithm was able to calibrate a spectrum to an accuracy that was approximately the same as the errors in the frequency estimates. That is, systematic calibration errors were not evident, only frequency fluctuations.

In reality, the model used in international PCT patent application No. PCT/US2006/021321 may not be adequate: spectra contain resonances from ions that are not only ideally digested, intact peptides from unmodified proteins with consensus sequences. Enforcing the constraint that the masses of these ions should conform to a limited database could cause the algorithm to fail. Therefore, a second method for real-time calibration, described in Component 9, was designed to match spectra from successive elution fractions in an LC-MS experiment. The basic underlying concept was that frequency variations are caused by variations in the space-charge effect. Space-charge variations, according to the standard calibration equation, should cause all ion frequencies to shift by the same amount. The shift in m/z, on the other hand, would vary with m/z squared. The fact that all ion frequencies shift by the same amount suggests that matching spectra to correct for space-charge variations would involve finding the frequency shift that produces the best superposition of one spectrum onto another. Because the frequency shifts are much smaller than the spacing between samples, it would be necessary to compare interpolated spectra. Instead, the present invention approximates the overlap of the entire spectra by the overlap between the detected ion resonances, whose estimated frequencies reflect accurate interpolation of local regions of the spectra.

In addition to m/z determination, measurements of other attributes may be useful in identifying molecular ions. Peptide retention time is one example. Current methods for retention time prediction have limited accuracy. Variability in retention time among runs is a confounding factor due to variations in chromatographic conditions. In Component 10, a method is described for estimating the chromatographic state vector for a given LC-MS run. The state vector is the retention time for each individual amino acid residue; the predicted retention time for a peptide is the sum of the retention times of the residue it contains.

Component 11 describes a similar strategy for identifying peptides by their observed charge states. The estimator has an identical form to the one in Component 10, except that the average charge state of a peptide is used in place of retention time. The link between charge state and peptide sequence has not yet been exploited in peptide identification. The present invention describes how charge-state information may be used to identify peptides. As in Component 10, the method in Component 11 actively corrects for variations in conditions among different runs.

Component 9: Space-Charge Correction by Frequency-Domain Correlation in LC-FTMS

A key problem in FTMS is scan-to-scan variations in the frequency of a given ion. A basic goal in LC-FTMS is to match a feature in one scan to a feature in another scan; that is, to be able to confidently determine that both features are the signals produced by the same ion. The variations in frequency that confound our ability to solve this simple matching problem are caused by the so-called "space-charge effect."

The space-charge effect can be described briefly as the modulation of the oscillation frequency of an ion due to electrostatic repulsion by other ions in the analytic cell. The repulsive force among ions of the same polarity counteracts the inward force due to the magnetic field (in FT-ICR cells) or a harmonic electrical potential (in Orbitrap™ cells). In either case, the oscillation frequency is reduced. It has been shown that the frequency decrease is linear in the number of ions in the analytic cell.

Figure 27:
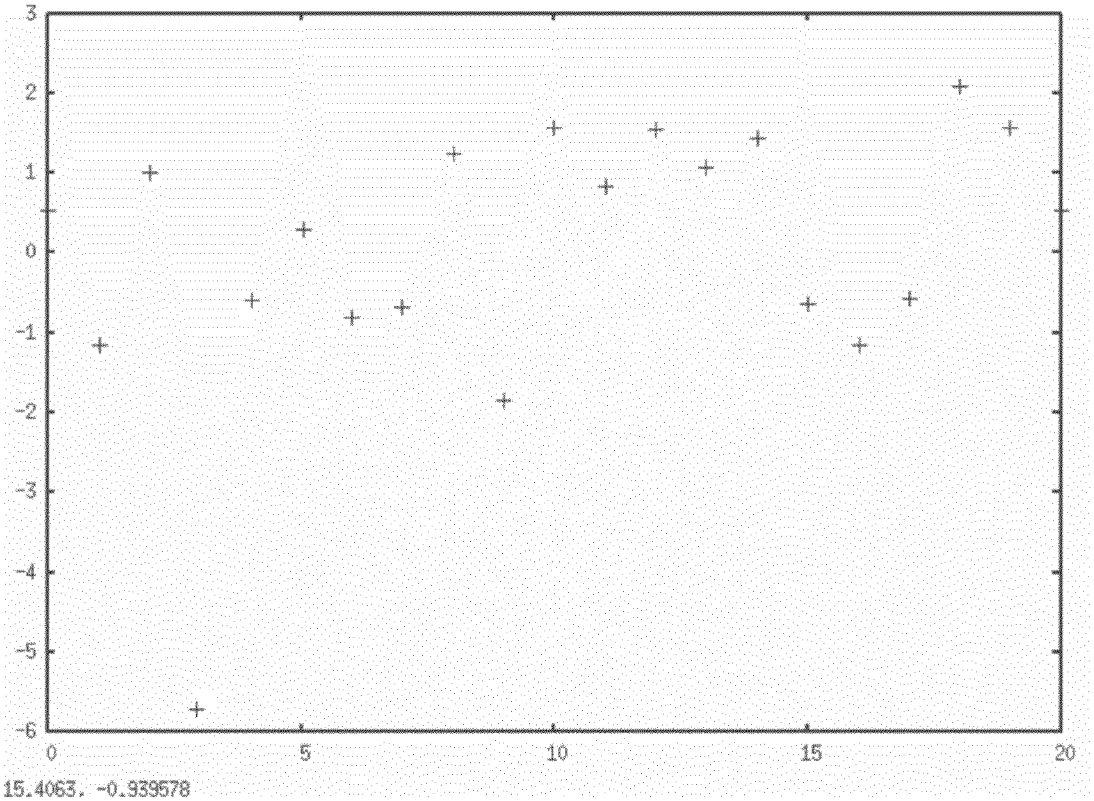
FIG. 27 depicts frequency estimates for the monoisotopic Substance P (2+) ion across 20 replicate scans, in accordance with an embodiment of Component 9 of the present invention.

In the LTQ-FT, ThermoFisher Scientific has designed an automatic gain control ("AGC") mechanism to attempt to load the cell with the same number of ions in every scan; thus eliminating variations in the space-charge effect. In spite of these efforts, variations remain unacceptably large. In FIG. 27, the observed frequency of the same ion (Substance P 2+) is shown, analyzed in a simple mixture of five peptides on the LTQ-FT. The scans represent 20 repeated, direct infusions over a period of less than one minute. The inter-scan frequency variation is about 1 part-per-million. The size of this variation is significant compared with the 1-2 ppm specification for mass accuracy on the machine. Correcting, or even eliminating, this variation would improve the mass accuracy of the instrument.

Variations in the space-charge effect can be corrected by mass calibration in real time, as described in international PCT patent application No. PCT/US2006/021321. Real-time calibration is in stark contrast to the typical protocol of performing mass calibration once a week or once a month. It is clear from FIG. 27 that it is beneficial to perform calibration on each scan (e.g., every second).

The procedure described in international PCT patent application No. PCT/US2006/021321 may be at least somewhat limited to the analysis of tryptic peptides. Component 9 describes a more fundamental approach to calibration that is applicable to any set of FTMS spectra. In LC-FTMS, a mass spectrum is generated for each elution fraction of a sample. The contents of each fraction are, in general, highly correlated because the same molecule gradually elutes off the column over many fractions (e.g., >10). Therefore, an algorithm to match mass spectra from adjacent elution fractions would be expected to correct for space-charge variations.

To "match" spectra, one needs a way to predict the coordinated shifts between multiple peaks from one scan to the next due to changes in the space-charge effect. The relationship between frequency f and mass-to-charge ratio (m/z) that is most widely-used in FT-ICR is the LRG equation shown in Equation 1.

$$\frac{m}{z} = \frac{A}{f} + \frac{B}{f^2} \tag{1}$$

The coefficient A is proportional to the magnetic field strength. The coefficient B is proportional to the space-charge effect. On the ThermoFisher LTQ-FT, which has a magnetic field strength of 7 Tesla, typical values for A and B are $1.05*10^8$ Hz-Da/chg and $-3*10^8$ $Hz^8$/Da-chg, respectively. An ion with m/z=1000 Da/chg has a frequency about $10^5$ Hz (100 kHz). The first term in Equation 1 is about 1000 Da/chg; the second term is about 30 mDa/charge. Therefore, the second term can be thought of as a correction term, which for an ion with m/z=1000 Da/chg is about 30 ppm. Therefore, for purposes of mathematical analysis (but not mass spectrometric analysis), the approximation in Equation 2 may be used, which is accurate to tens of ppm.

$$\frac{m}{z} \approx \frac{A}{f} \tag{2}$$

The magnetic field is expected to be quite stable, so A is effectively constant over long periods of time. The variations in space charge that cause scan-to-scan fluctuations in the observed frequency of an ion are due to changes in the value of B. Scan-to-scan fluctuations in the apparent m/z of an ion are due to the failure to properly adjust the value of B used to convert frequency to mass.

For example, suppose the estimated value of B differs from the true value of B by ΔB. Then, the error in mass is given by $\Delta B/f^2$. Using the approximation in Equation 2, we have the approximation shown in Equation 3.

$$\Delta\frac{m}{z} = \frac{\Delta B}{f^2} \approx \frac{\Delta B}{A^2}\left(\frac{m}{z}\right)^2 \tag{3}$$

Assuming very accurate frequency estimates and the absence of other confounding effects, a plot of D(m/z) (the difference in the apparent mass for the same ion in two different scans) versus m/z should yield a parabola. For example, the same space-charge variation would produce an error four times as large for an ion with m/z=800 as it would for an ion with m/z=400. It would be possible to correct for the space-charge variation by finding the parabola of best fit and subtracting the value of the parabolic curve at each m/z.

A simpler approach results from looking at the influence of the space-charge effect upon frequency spectra, rather than mass spectra. We rearrange Equation 1 by solving for f.

$$f = \frac{A \pm \sqrt{A^2 + 4B(m/z)}}{2(m/z)} \tag{4}$$

There are two solutions to Equation 4. The larger one is the cyclotron frequency; the one we desire. The smaller one is the magnetron frequency.

If we expand the square root in the numerator as a Taylor series, we have $$\sqrt{A^2 + 4B(m/z)} \approx A + \frac{1}{2A}\left(4B\frac{m}{z}\right) + \frac{1}{2}\frac{-1}{4A^3}\left(4B\frac{m}{z}\right)^2 + \ldots \tag{5}$$

The first term has a magnitude of about $10^8$, and for m/z~1000, the second term has a magnitude of about $10^3$, and third term about $10^{-2}$. When we insert this expansion back into Equation 4, we will divide by m/z, and so the third term will correspond to a shift of $10^{-5}$ Hz, which is 0.1 ppb. We will not be able to observe the effect of this term and higher order terms, so we neglect them, resulting in Equation 6.

$$f \approx \frac{A + A + \frac{1}{2A}\left(4B\frac{m}{z}\right)}{2(m/z)} = \frac{A}{m/z} + \frac{B}{A} \tag{6}$$

When B/A is replaced by c, this equation is known as the Francl equation. B/A is a frequency shift (about −3 Hz on the ThermoFisher LTQ-FT) due to electrostatic repulsion that does not depend upon m/z. If A is constant, one would predict from Equation 6 that space-charge variation from one scan to the next would cause every ion to shift by the same frequency, a constant offset ΔB/A. A better label for this term in the Francl equation would be Δf. The variation between two scans can be estimated by simply sliding one spectrum over the other and finding the value of Δf that produces the greatest overlap.

In practice, the frequency spectra are not continuous, but instead sampled every 1/T, where T is the duration of the observed time-domain signal. For T=1 sec, the sampling of the frequency spectrum would be 1 Hz. For m/z~1000, f~$\mathbf{10}^5$, and 1 Hz represents a spacing of 10 ppm, much larger than the deviations we want to correct. Therefore, the overlap may need to be performed on highly interpolated spectra.

Another, perhaps better approach is to estimate the overlap of two spectra by constructing continuous parametric models of the largest peaks in the spectra, as described in international PCT patent application No. PCT/US2007/069811. Assuming that the peak shape is invariant and that the peak is merely shifted and scaled, the overlap can be computed by table-lookup of the overlap between two unit-magnitude peaks as a function of their frequency difference, as described in Component 7, and multiplying by the (complex-valued) scalars.

Because the calibration equation (Equation 1) is not a perfect representation of reality, there may be additional fluctuations in the peak positions not captured by this model. It may be unwise to place too much weight on the largest peaks in the spectrum. Therefore, a more robust, and computationally simpler approach is to find the shift that minimizes the sum of the squared differences between frequency estimates of ions that can be matched across two scans. The squared differences can be weighted according to an estimate of the variance in the frequency estimate. For weak signals, the variance in the estimate is probability due to noise in the observations. For stronger signals, the variance reflects higher order effects in the frequency-m/z relationship not included in our model.

It may be possible to the Expectation-Maximization (EM) algorithm to jointly estimate the variances in the frequency estimates simultaneously with the estimated frequency shift. The variance would reflect the magnitude of the difference between the observed spectrum and the model peak shape. See Component 6.

The correlation-based algorithm (Equation 7) was tested using estimated frequencies of 13 monoisotopic ions across 21 replicate scans of a 5-peptide mix. Each line represents the frequency variations of a different monoisotopic ion across multiple scans. The frequency values observed in the first scan were used as a baseline for comparison of frequencies observed in other scans.

The approximately uniform shift of multiple ions in a given scan is reflected by the superposition of the lines. The shape of the consensus line reflects the space-charge variation across multiple scans. Presumably, scans that have points above the x-axis had a smaller number of ions, reducing the space-charge effects, and resulting in the same positive shift in the frequencies of all ions in that scan.

The systematic scan-to-scan variation in the ion frequencies is no longer apparent. The remaining variations appear to be random fluctuations, but of significantly reduced magnitude relative to the errors in the uncorrected frequencies.

Space-charge variations cause large scan-to-scan variations in ion frequencies. As predicted by theory, space-charge variation causes approximately the same frequency shift in all ions in the scan. A simple algorithm that calculates the average shift of ions in a given scan and then corrects all the frequencies by this amount eliminates the systematic variation and reduces the overall variation significantly. The ability to compensate for systematic variations in an ion's observed frequency across multiple scans makes it possible to average out noisy scan-to-scan fluctuations in the estimate. The subsequent estimate of the m/z value of the ion could be calculated from the average observed ion frequency, potentially improving mass accuracy.

Component 10: Retention Time Calibration

The retention time of a peptide in reversed-phase high-performance liquid chromatography ("RP-HPLC") can be predicted with moderate accuracy from its amino acid composition. Errors below 10% are routinely reported in the literature. Because of this relationship, it is possible to use the observed retention time to supplement a mass measurement to improve peptide identification confidence.

It has been observed that retention time is only moderately reproducible. Component 10 seeks to correct for the variability across LC-MS runs by determining a chromatographic state vector that characterizes each LC-MS run. The state vector for a run would be calculated using peptides that are confidently identified in that run.

Suppose a peptide is identified in run #1, but not in run #2. In retention time calibration, the retention time of the peptide in run #2 would not be predicted de novo. Instead, the change in the chromatographic state vector from run #1 and run #2 would be used to calculate a peptide-specific adjustment to the retention time observed in run #1.

The retention time can be modeled as a linear combination of the number of times each amino acid occurs in a peptide (i.e., the amino acid composition). Let n denote a vector representation of the amino acid composition. Then, the predicted retention time $t^{calc}$ can be expressed as a product of n and a vector of coefficients τ (Equation 1)

$$t^{calc} = n^T\tau = \sum_{a=1}^{20} n_a\tau_a \tag{1}$$

The coefficient in the linear combination $T_a$ can be interpreted as the retention time delay induced by adding that amino acid a to a peptide.

A linear model for chromatographic retention in terms of amino acid composition was first described by Pardee for paper chromatography of peptides. See Pardee, A B, "Calculations on paper chromatography of peptides," *JBC* 190:757 (1951). The basic idea is that the work required to move a peptide molecule from the stationary to the mobile phase can be written as a sum over the amino acid residues. In 1980, Meek reported retention coefficients for amino acid residues in RP-HPLC that predicted the observed retention times of 25 peptides. See Meek, J L, "Prediction of peptide retention times in high-pressure liquid chromatography on the basis of amino-acid composition," *PNAS* 77:1632 (1980). A number of recent publications describe neural-network based predictors that are similar to the linear model.

The chromatographic conditions during an LC-MS experiment can be characterized by the retention time delays of each amino acid. The vector τ in Equation 1 can be thought of as the chromatographic state vector for a given LC-MS experiment.

We can use identified peptide sequences in a run to estimate $\tau$. Let $T^{obs}$ denote a vector of M observed retention times for identified peptides. Let N denote a matrix of M columns, with each column vector containing the amino acid composition of an identified peptide. Then, for a given state vector $\tau$, Tcalc, the vector of M calculated retention times, is given by Equation 2.

$$T^{calc}=N^T\tau \quad (2)$$

Equation 2 is simply a matrix version of Equation 1.

We wish to find the value of $\tau$ that minimizes the sum of the squared differences between the M observed retention times in $T^{obs}$ and the M calculated retention times in $T^{calc}$.

Let e denote the squared error.

$$e = \sum_{m=1}^{M} [(T^{calc})_m - (T^{obs})_m]^2 = [T^{calc} - T^{obs}]^T[T^{calc} - T^{obs}] \quad (3)$$

Let $\tau^*$ denote the value of $\tau$ that minimizes e. $\tau^*$ satisfies Equation 4.

$$\frac{\partial e}{\partial \tau}\Big|_{\tau^*} = 0 \quad (4)$$

The left-hand side of Equation 4 can be calculated from Equations 2 and 3.

$$\frac{\partial e}{\partial \tau}\Big|_{\tau^*} = 2\left[\frac{\partial T^{calc}}{\partial \tau}\right]^T [T^{calc} - T^{obs}] = 2N[N^T\tau^* - T^{obs}] \quad (5)$$

By combining Equations 4 and 5, we have an equation for $\tau^*$, the least-squared estimate of the chromatographic state vector as a function of the amino acid compositions of identified peptides and their observed retention times.

$$\tau^*=(NN^T)^{-1}NT^{obs} \quad (6)$$

The predicted retention time for a peptide of amino acid composition n would be calculated by substituting $\tau^*$ for $\tau$ in Equation 1. If a mass measurement cannot distinguish between peptide a and peptide b, then the observed retention time would be compared to $n_a^T\tau$ and $n_b^T\tau$.

However, suppose that peptide a and peptide b were both observed in run 1 and a feature in run 2 with retention time $t_2$ could not be unambiguously assigned to one of these peptides. If the observed retention times of peptide a and b in run 1 are denoted by $t_{a1}$ and $t_{b1}$, and the chromatographic state vector in runs 1 and 2 are denoted by $\tau^*_1$ and $\tau^*_2$, then $t_2$ would be compared to $t_{a1}+n_a^T(\tau^*_2-\tau^*_1)$ and $t_{b1}+n_b^T(\tau^*_2-\tau^*_1)$.

Component 11: Identification of Peptides by Charge-State Prediction and Calibration A typical bottom-up proteomic LC-MS experiment provides a variety of different types of information about peptides in a sample. Most notably, MS measures the mass-to-charge ratio of intact peptide ions and their various isotopic forms. Sometimes, these measurements are sufficient to determine the mass of the monoisotopic species to sufficient accuracy that the peptide's elemental composition can be determined with high confidence. Sometimes, the elemental composition is sufficient to determine the sequence of the peptide and the protein from which it was cleaved by trypsin digestion. In other cases, additional information is necessary. In such cases, analysis of fragmentation spectra (MS-2) or retention time can be used to rule out some of the candidate identifications.

In Component 11, the peptide's observed average charge state is used as an identifier. Like retention time, the average charge state of a peptide depends upon its amino acid composition. For example, a peptide with basic residues (e.g., histidine) would tend to have a higher average charge state than a peptide with acidic residues (e.g., glutamate and aspartate). Therefore, observation of the charge state of an unknown peptide provides information about its identity.

Suppose a peptide is observed in a spectrum and multiple charge states 1 . . . M with relative abundances $A_1 \ldots A_M$. The average charge state, denoted by $\bar{z}^{obs}$ is given by Equation 1.

$$\bar{z}^{obs} = \sum_{z=1}^{M} zA_z \quad (1)$$

The basic assumption is that each amino acid type has an intrinsic ability to pick up a proton during electrospray ionization and to hold on to that charge in a stable peptide ion. We assume that this propensity to harbor a proton is constant for an amino acid, regardless of the other amino acids in the peptide. This assumption is not strictly true, but allows us to construct a model that balances accuracy and computational convenience.

We are interested in how this propensity changes when the experimental conditions are varied across runs. Let $\zeta_i$ denote the average charge state of an amino acid residue of type i under a particular set of conditions. The vector $\zeta$ has 20 components—one for each amino acid—and characterizes the dependence of charge state on experimental conditions. The value of $\zeta$ must be estimated from identified peptides in a given run.

The second assumption is that the average charge state of a peptide ion can be modeled as the sum of average charge state of its residues. Equation 2 gives the average charge of peptide P as a weighed sum of the average amino acid charge states $z_i$. Each weight $n_i$ is the number of amino acids of type i in peptide P.

$$\bar{z}^{calc}(P) = \sum_{i=1}^{20} n_i z_i \quad (2)$$

We can represent the amino acid composition of P by the 20-component vector v. In fact, in this model, we do not distinguish between sequence permutations, so we can identify the peptide P by its amino acid composition, represented by vector v. Then, we can rewrite Equation 2 as the inner product between vectors $\zeta$ and v.

$$\bar{z}^{calc}(v)=v^T\zeta \quad (3)$$

Suppose that we have identified M peptides and their observed average charge states are contained in an M-component vector $Z^{obs}$. Suppose that the amino acid compositions are stored in the columns of a matrix N, where N has M columns and 20 rows. If we knew the value of the charge state vector $\zeta$, then we could compute a vector $Z^{calc}$ whose M components are the estimates of the average charge states of the peptides.

$$Z^{calc}=N^T\zeta \quad (4)$$

To estimate ζ, for a given run, we wish to obtain the value of ζ that minimizes the sum of the squared differences between the observed and calculated values for the M identified peptides. We denote the sum of squared differences by e in equation 5.

$$e(\zeta)=(Z^{calc}(\zeta)-Z^{obs})^T(Z^{calc}(\zeta)-Z^{obs}) \quad (5)$$

We calculate the derivative of e with respect to ζ.

$$\frac{\partial e}{\partial \zeta} = 2N(Z^{calc}(\zeta) - Z^{obs}) \quad (6)$$

Then, we set the derivative equal to zero, and solve for ζ. We denote the least-squares estimate of ζ by $\hat{\zeta}$.

$$\hat{\zeta}=(NN^T)^{-1}NZ^{obs} \quad (7)$$

This same equation appears in Component 10 on retention-time calibration because both predictors use the same linear model.

The unweighted least-squares estimate corresponds to the maximum-likelihood estimate when the errors in the observation are Gaussian distributed with zero mean and equal variances.

We can use an estimate of ζ to distinguish between multiple candidate identifications of a peptide by comparing $z^{calc}$, computed via Equation 3, for each candidate to $z^{obs}$. This situation corresponds to identification by charge-state prediction.

An alternative way to identify peptides in comparing multiple samples (e.g., in biomarker discovery) is to match a peptide in one run to a peptide that was identified in a previous run. Suppose we have identified a peptide in one run and wish to find the same peptide in a second run. Suppose we have detected a peptide in the second run that we cannot confidently identify, but feel that it might be the same peptide by virtue of its similar apparent m/z, retention time, and isotope distributions. We could increase the confidence of our match by verifying that each observed peptide has a similar average charge state in each run.

The average charge state, like retention time, is reasonably reproducible across replicate experiments, assuming that the experimental conditions were designed to be the same. Reproducibility can be improved by charge-state calibration that uses the observed charge state of the peptide in one run $(Z^{obs})_1$, and predictions of the charge state in both runs $Z^{calc}(\zeta_1)$ and $Z_{calc}(\zeta_2)$ to predict the charge state of the peptide in the second run, denoted by $(Z^{calc})_2'$ (Equation 8).

$$(Z^{calc})_2'=(Z^{obs})_1+(Z^{calc}(\zeta_2)-Z^{calc}(\zeta_1))=Z^{calc}(\zeta_2)+((Z^{obs})_1-Z^{calc}(\zeta_1)) \quad (8)$$

Equation 8 illustrates two equivalent ways to interpret charge-state calibration. The first is that the observation in one run is shifted by a term that reflects the change in the charge state due to the different conditions between runs. The second is that the calculated charge state in the second run is corrected by the prediction error that was observed in the first run—with the expectation that the systematic error in the prediction will be similar in all runs.

In addition to correcting for variations in data that has already been corrected, analysis of estimates of ζ across multiple runs may lead to data collection protocols that improve data quality. For example, one goal may be to reduce charge-state variations. Variations in ζ can be correlated with observations in the experimental parameters (e.g., temperature, humidity, counter-current gas flow). Then, the tolerances on each experimental parameter that are required to achieve a desired maximum level of charge-state variation may be determined. Another application is to control the experimental parameters to achieve a targeted average charge state for some subset of peptides or proteins. The predicted average charge for a particular peptide or protein could be predicted from ζ, which may, in turn, be predicted for a set of experimental conditions.

Yet another application is to intentionally modify the charges on peptides across two runs. Running the same sample under two different experimental conditions designed to produce a large change in ζ (i.e., from ζ to ζ') would provide an additional observation that could be used to identify the peptide. The information provided increases as the angle between ζ and ζ' approaches 90 degrees. One way to do this is by changing experimental conditions surrounding the ionization process. Another way is to chemically modify the peptides with a residue-specific agent to introduce a charged group at selected types of residues.

Charge state prediction and calibration is currently an untapped source of information for identifying peptides. Component 11 provides an approach to exploit the dependence of a peptide's average charge state and its amino acid composition to improve identification. A method for estimating this dependence for an individual run is provided, to provide robust predictions in spite of experimental variability. When multiple runs of similar samples are available (e.g., clinical trials), charge state calibration can be applied to improve matches between peptides across multiple runs. Charge state calibration provide a better estimate of the charge state of a peptide in a current run than either the observation of its charge state identified in a previous run or prediction using only information from the current run.

Adaptive Data-Collection Strategies

The next set of Components (12-14) explores the possibilities that follow from the ability to assign candidate identities to tryptic peptides from MS-1 spectra in real-time. "Real time" refers to completing analysis in less than one second; the same time-scale as successive fractions are eluted in LC-MS. Candidate assignments, together with probability estimates, indicate where supplemental data collection would provide useful information about the sample.

Component 12 suggests a strategy for optimal use of MS-2 on a hybrid instrument among ion resonances detected in an MS-1 scan. The optimality criterion is information—the reduction of uncertainty about the protein composition of the sample. This method prescribes not only the list of ions to be sequenced by MS-2, but also the duration of the analysis of the fragment ions. MS-2 scan time is viewed as a finite resource to be allocated among competing candidate experiments that provide differing amounts of information. That is, there is roughly one second to analyze ions in a particular LC elution. Roughly speaking, the resource allocation (e.g., MS-2 scan time) would be favored for an ion for which knowledge of the sequence is needed to, and would be expected to, identify a protein in the mixture. The inherent difficulty in identifying a protein from an MS-2 experiment given a pool of candidates can be estimated in advance and used to determine the optimal scan duration. For example, distinguishing between two candidate sequences that map to different proteins could require identification of a single fragment. In this case, a scan of very short duration may suffice.

An alternative type of information would be address identifying differences in a sample relative to a population. In this case, resources would be allocated preferentially to ions that have unusual abundances or that possibly represent species that are not usually present. This intelligent, adaptive approach is in stark contrast to current methods for MS-2 selection, which focus resources on the most abundant species. This prior art approach has not provided the depth of coverage of low abundance species that is necessary for biomarker discovery from proteomic samples.

Component 13 explores new applications for a chemical ionization source currently used for electron transfer dissociation (ETD) and proton transfer dissociation (PTR) (available from ThermoFisher Scientific, Inc.), and involves adaptively introducing one or more of a stable of anion reagents designed to perform sequence-specific gas-phase chemistry upon ions. The basic concept, as in Component 12, would be to analyze one elution fraction from an LC-MS run in real-time, identifying peptides and also identifying ions with ambiguous identity.

When a short list of candidate sequences can be enumerated for certain ions, one or more gas-phase reagents may be identified whose reaction (or lack of reaction) with the ion of interest could rule out one or more of these candidates; thereby potentially identifying the ion. Given highly selective reagents, multiple peptide ions may be identified from a single spectrum of gas-phase products. The products may include either dissociation fragments or altered charge states. In connection with this embodiment of the invention, the chemical ionization source currently in use for ETD/PTR might be partitioned into multiple components; each with its own valve that would be controlled by instrument control software. Real-time analysis may trigger one or more of these valves in such a way to maximize the amount of information that can be inferred from various gas-phase reactions.

Component 14 is another method for adaptively improving the information content of FTMS spectra. A small number of highly abundant ion species obscure detection of a relatively large number of species present at low abundances. Characterization of highly abundant species is relatively simple because their high SNR makes them easier to identify and they have likely been characterized in runs of related samples. In connection with this embodiment of the invention, these ions may be eliminated in successive scans after they have been characterized. Elimination would be performed by ejecting them from the ion trap using the quadrupole before injecting the remaining set of ions into the analytic cell.

Component 14 also includes a strategy for "overfilling" the ion trap by an amount that exceeds the loading target for the FTMS cell by the predicted abundance of ejected ions. The resulting enrichment of low abundance ions can be used effectively in conjunction with depletion/enrichment sample-preparation strategies to discover many additional species that could not be characterized using previous methods.

Component 12: Maximally Informative MS-2 Selection in Proteomic Analysis by Hybrid FTMS Instruments MS-2, the analysis of the masses of fragment ions of a larger molecular ion, is a powerful method for identification by mass spectrometry. The richness of information, measurements of a large number of predictably formed fragments, in a high-quality MS-2 spectrum, makes false positive identification unlikely. However, the information comes at the cost of analytic throughput. While an MS-1 spectrum provides information about every molecule in the sample in parallel, an MS-2 spectrum, as it is most commonly implemented, provides information about only one molecule in the sample.

The most widely used protocols for proteomic analysis on hybrid FTMS machines involve a cycle time in which an accurate mass scan is performed in the FT (or Orbitrap™) cell (e.g., for 1 second) while, at the same time, multiple short MS-2 scans (e.g., 3×200 ms) are performed in the ion trap. The relatively low mass accuracy of the ion trap is still sufficient to identify molecules when enough predicted fragments are present. Therefore, MS-2 is a valuable resource in identification.

A problem in the application of MS-2 to proteomic analysis is one of resource allocation. Current strategies involve selecting the most intense signals in an MS-1 spectrum for MS-2 analysis, with the sole caveat that the same signal should not be fragmented again for some specified time duration (e.g., 30 seconds). This strategy has the advantage that strong signals are more likely to yield interpretable MS-2 spectra, as the intensity of the fragments are only a fraction of the intensity of the parent ion, given the multiplicity of possible fragmentation patterns. However, the disadvantages of selecting the most abundant signals for MS-2 are severe. One is a bias towards identifying the most abundant species in the sample. The most abundant species tend to be very well-characterized across a population of samples. In clinical trials, these species have not led to useful biomarkers; suggesting that better coverage of low-abundance species is needed. From an information standpoint, it seems that repeated MS-2 of these same species would not be necessary for identification and represent a poor allocation of a valuable, limited resource.

An alternative strategy is to view the time available for MS-2 scans over one cycle (e.g., 1 sec) as a channel transmitting information about the peptide identities in the fraction. Alternatively, the channel could be thought of at a higher level about transmitting information about which proteins are in a sample or even how the given sample differs from the members of a larger population of similar samples. Then, the goal is to partition the time available for MS-2 scans among the peptides detected in the MS-1 scan to maximize information.

In spite of the rather vague way that information is described in common usage, information has a precise mathematical description—it is the reduction of uncertainty (i.e., entropy) in the value of one variable that results from knowledge of the value a second (related) variable. The entropy of a discrete random variable is the expected value of the logarithm of probability mass function.

For example, suppose two coins are flipped. Let X denote the outcome of the first coin flip. If the coin is fair, the entropy of X is $\frac{1}{2}\log\frac{1}{2}+\frac{1}{2}\log\frac{1}{2}=1$. Let S denote the total number of heads. If S=0 or S=2, the value of X can be inferred: tails in the first case, heads in the second. In either of these cases, the entropy of X is zero. If S=1, the value of X remains completely undetermined; the entropy of X remains 1. The entropy of X given S is the entropy resulting from each outcome weighted by the probability of each outcome: $\frac{1}{4}(0)+\frac{1}{4}(0)+\frac{1}{2}(1)=\frac{1}{2}$. Therefore, the information between X and S is $1-\frac{1}{2}=\frac{1}{2}$. We say that knowing the value of S reduces the expected entropy of X by ½.

Similarly, an MS-2 spectrum may give partial information about the identity of a peptide. To develop a scheduling protocol for MS-2, we need to model the information provided by an MS-2 spectrum as a function of what is known, a priori, about the peptide and the duration of MS-2 acquisition. Interestingly, the mass accuracy of an MS-2 scan (whether collected on an ion trap or FT cell) improves with duration in a similar way: the mass error is inversely proportional to the duration (for short durations, e.g., <1 second). Each two-fold reduction in the mass error corresponds to an additional bit in the representation of the m/z ratio. Therefore, the number of bits per peak grows like log 2(T). There is a diminishing return which suggests that most of the information is acquired at the beginning of a scan.

In fact, the ability to confirm the identity of a species from an MS-2 scan is less dependent upon the mass accuracy of the peaks than the number of predicted peaks (a, b, c, x, y, z ions) and the number of unpredicted peaks (everything else). A very short MS-2 scan may be sufficient either to identify a peptide or to determine how much information a longer scan would provide.

Finally, LC-MS data (i.e., MS-1) collected by FTMS provides considerable information about peptide identities. To assess the role of mass accuracy in identification of human tryptic peptides, we modeled identification success on a sequence database as a function of rmsd mass error.

The sequence database was constructed by in silico digestion of the International Protein Index human protein sequence database. 50,071 sequences were digested to form 2.5 M peptide sequences, 808,000 distinct sequences, and 356,000 distinct masses. We found that if one of the 808,000 distinct sequences is selected uniformly at random (i.e., a detected peak in an LC-MS run) that 21% of the time knowing the exact mass of the peptide (i.e., its elemental composition) would identify the protein it came from. An additional 37% of the time, the sequence would identify the protein to which the peptide belongs. The remaining 42% of the time, the peptide sequence occurs in multiple proteins; in this case, successful MS-2 identification of the peptide sequence would not lead (directly) to protein identification.

The next question is how much mass accuracy is required to determine exact mass. To address this question, we calculated the result of the following experiment (i.e., without actually performing the experiment). We simulated mass measurements of the 356,000 distinct exact masses generated above by adding a Gaussian random variable to each. Then, we determined the maximum-likelihood value of the exact mass from the measurement, by computing the probability that each exact mass in our database would have produced the "measured" value. Separate trials were performed at different levels of mass accuracy.

We conclude from the above results that mass accuracy of 1 part per million identifies about half the tryptic peptide elemental composition successfully on average. Even when identification fails, the remaining number of candidates—the entropy in the elemental composition—is quite low. In many cases, this is sufficient to identify a protein. In a slightly larger number of cases, MS-2 is required to resolve distinguish isomeric sequences or to clarify ambiguity in the elemental composition. In some cases, MS-2 provides no further information. This technique has particular import for MS-2 scheduling because these scenarios can be evaluated in real-time for individual measurements.

Component 13: Adaptive Strategies for Real-Time Identification Using Selective Gas-Phase Reagents Reagents designed to predictably modify peptides have been demonstrated to improve peptide identification. The rationale is to target a particular functional group on the peptide (e.g., the N-terminal amine or the cysteine sulfhydryl group) and to introduce a chemical group that can be selected either by affinity or by software that detects an effect is easily identifiable in a spectrum.

One example of an effect that is easily identifiable is a spectrum is the isotope envelope of bromine. The nearly equal natural abundances of Br-79 and Br-81 gives brominated peptides an isotope envelope that has the appearance of two non-brominated peptide isotope envelopes duplicated with a spacing of roughly two Daltons. Brominated peptides can be easily filtered from the spectrum by software that recognizes this pattern. If the brominating reagent is designed to react specifically with N-terminal peptides, then N-terminal peptides can be identified from analysis of the spectrum after the sample has been incubated with the reagent.

Another type of easily identifiable effect follows from "mass-defect" labeling. The regular chemical composition of peptides results in a regular pattern of masses. The mass defect of a peptide—the fractional part of the mass—falls into a rather narrow band whose limits can be computed as a function of the nominal mass. Addition of a chemical group with an unusually positive or (more likely) negative mass defect would cause modified peptides to fall outside the band of typical mass defect values for unmodified peptides. Thus, modified peptides would be identifiable directly by analysis.

Yet another type of labeling is based upon the concept of "diagonal chromatography," an idea so old that it was initially implemented using paper for chromatographic separation. In the original implementation, components in a sample would be separated along one axis, exposed to a special reagent, and then separate along the perpendicular direction. The reagent is designed to react specifically with selected groups and to introduce a moiety that significantly alters the mobility of the molecule. Unmodified molecules will have identical mobilities in both axes and thus lie along a diagonal line. Modified molecules will lie off the diagonal, thus identifying molecules that originally contained the reactive group.

Component 13 involves a novel strategy for adaptive labeling using selective gas-phase chemistry. Selective chemistry, targeted to any group for which a selective reagent can be found, can be used to introduce a group that causes an observable, reproducible, and predictable change in a subset of ions, including dissociation, mass shift, isotope envelope variation, or charge state increase or decrease. As in the other examples cited above, the presence or absence of the reactive group in the original molecule can be used to select or rule out candidate identifications.

The mechanism for introducing reagents to modify ion charge states has already been demonstrated by ThermoFisher Scientific in its chemical ionization sources used to implement electron transfer dissociation ("ETD") and proton-transfer reactions ("PTR"). In ETD or PTR, anions are combined with the ions in the ion trap where gas-phase reactions occur before analysis. The same mechanism might be used with reagents that show specific or even partial preferences for particular functional groups. Such reagents could be introduced in solution prior to ionization. However, introducing reagents through the chemical ionization source creates interesting possibilities.

A stable of anion reagents with different selectivities may be housed in parallel compartments with openings controlled by independently operable valves. Real-time analysis may be used to assign candidate identifications to detected peaks in a spectrum as soon as a fraction elutes from a column in an LC-MS run. That is, peptide identifications can be made from the MS-1 spectrum from one fraction before the next fraction is analyzed. This real-time analysis will identify some ions with confidence, but may find other ions to have ambiguous identities. Instrument control software can trigger the release of one or more suitable reagents that will rule out or select candidate identifications for one or more of the peptide ions. Reagents could be chosen adaptively according to a criterion for maximizing information. Unlike ETD, the entire population of ions, rather than one selected ion, would be exposed to the reagent, allowing multiple identifications to proceed in parallel.

For example, suppose that one peptide ion has two potential candidate identifications, exactly one of which contains a cysteine. When such a situation is encountered, instrument control software may trigger release of a reagent with specificity for cysteine to react with ions produced by the next elution fraction. Assuming that the same ion is present in the following fraction, the two candidate identifications may be disambiguated by the appearance of the ion or a modified form of the ion in the subsequent spectrum.

We have demonstrated methods for assigning candidate identities to peptides in real time from FTMS spectra. ThermoFisher Scientific has proven the utility of a chemical ion source capable of performing gas phase reactions for ETD and PTR. The application of a gas-phase labeling method would be limited only by the availability (and discovery) of anions with gas-phase reactivity that is selective for particular functional groups. It is possible that currently used gas-phase ions exhibit some selectivity that has not been well characterized, but could be discovered and exploited for identification.

Component 14: Adaptive Dynamic Range Enhancement in a Hybrid FTMS Instrument by Notch-Filtering in a Quadrupole Ion Trap A fundamental limitation of mass spectrometry is the dynamic range of the instrument. Mass spectrometers can analyze on the order of $10^6$ ions, suggesting that it could be possible to detect species in the same spectrum that differ by six orders of magnitude. In fact, Makarov et al. demonstrated mass accuracy better than five parts per million for ions in the same spectrum varying in abundance over four to five orders of magnitude. Even so, proteins in human plasma are known to vary over ten to twelve orders of magnitude. Fractionation and depletion techniques have been used to enrich species of relatively low abundance. Further improvements would increase coverage of the plasma proteome and possibly lead to the first clinically important biomarker discovered by mass spectrometry.

Component 14 provides an adaptive strategy to use instrument control software to eliminate high-abundance species as soon as they are identified. The ability to deplete species adaptively may allow the instrument to use its limited dynamic range optimally to find species of relatively low abundance.

In this embodiment of the invention, the high capacity of the quadrupole ion trap to store ions and its selectivity to eliminate ions before injecting them into an FTMS cell that has much lower capacity are exploited. Typically, the quadrupole ion trap on a hybrid instrument is used in a wide band-pass mode (e.g., allowing ions of m/z between 200 and 2000 to enter the FTMS cell). In this embodiment of the invention, the quadrupole ion trap is operated as a notched-filter, eliminating one or more narrow bands of the spectrum. The quadrupole is thus used to destabilize trajectories of ions in selected ranges to cause their ejection from the ion trap before injecting the remaining ions into the FTMS cell for analysis.

In connection with earlier-described Components, the ability to perform analysis of MS-1 spectra in real-time has been demonstrated. The identification of high abundance species is relatively simple because the high SNR of the resonance signal results in highly accurate mass estimates. Furthermore, the peak can be confidently matched to runs of similar samples in which the same peak has already been identified. In this embodiment of the invention, such species are eliminated (and the narrow band of m/z values that surrounds them) as soon as they are identified.

In a typical LC-MS run, the same species elutes over several fractions. If a high abundance species (e.g., with mass to charge ratio M) has been identified in fraction n, it can be eliminated from analysis in the fractions n+1 through n+k by destabilizing the trajectories of ions with m/z values near M. The goal is to load the same number of ions into the analytic cell, enriching the concentration of the less abundant ions by ejecting the highly abundant ions. The ion trap may be loaded with a number of ions that exceeds the analytic target by the number of ejected ions. To achieve this goal, the number of ions that are to be ejected by the quadrupole may be estimated. The estimate can be made either by a short survey scan and/or extrapolation of the elution profile of each ejected species.

The ion loading procedure employed in this method would be have some similar features to the AGC mechanism currently used for ion loading in hybrid instruments. However, the relatively larger uncertainty in estimating the number of ejected ions would be expected to introduce larger fluctuations in the ion loading and thus in the space-charge effect. However, earlier-described Components have demonstrated how to correct for these fluctuations by real-time calibration of individual scans. Given these calibration corrections, minimizing space-charge variations among scans is not believed to be a crucial issue. Even so, precise ion loading would still be desirable so that the analytic cell operates close to the number of ions that achieves the optimal balance of sensitivity and mass accuracy.

For example, suppose that the target number of ions is $1e^6$, and a survey scan indicates that 20% of the ions come from the most abundant species. In this case, the ion trap would be loaded with $1e^6/(1-0.2)=1.25e^6$ ions. The most abundant species would be eliminated, accounting for $1.25e^6*0.2=2.5e^5$ ions, leaving $1e^6$ ions. A low abundance species that previously accounted for 1% of the ions would now account for $1\%/(1-0.2)=1.25\%$, a 25% gain in the SNR for that peak.

In a case where 90% of the ions are contributed by a few species of high abundance that can be identified with high confidence, the ion trap would be loaded with ten times the target number of ions for the analytic cell. After ejection of the high-abundance species, analysis of the remaining ions may benefit from a full order of magnitude gain in the effective dynamic range.

The instrument-based method for dynamic range enhancement is completely independent of, and therefore compatible with, sample-preparation techniques of depletion and fractionation that also attempt to improve identification of low-abundance species. Ejection of significant numbers of high-abundance ions before analysis would shift the capacity bottleneck from the analytic cell to the ion trap. Depletion of the dominant species in sample preparation may ease the capacity requirements placed upon the ion trap. Furthermore, the ion trap would eliminate "leakage" that is a common problem with depletion-based strategies.

Instrument-based elimination of high abundance ions has the flaw of eliminating bystander ions with m/z values that are similar to the targeted ions. However, the potential to boost the signals of ions across the entire spectrum would appear to outweigh obscuration of small regions of the spectrum. There is a design tradeoff in the filtering time and the precision with which m/z values may be targeted; the width of the notch filter depends inversely upon the filtering time.

Methods for Peptide Identification and Analysis

The last four Components (15-18) describe various auxiliary tools useful for MS-1 analysis of proteomic samples.

Component 15 describes construction of a database of tryptic peptide elemental compositions that makes it possible both to identify new peptide isoforms that have yet to be reported while still making use of the wealth of available prior information about the human proteome. De novo identification approaches represent an overreaction to the limitation imposed by finite databases. Biomarker discovery, in particular, demands the ability to identify species that have not been seen before. However, to assign equal a priori probability to all possible interpretations of data introduces an unacceptably large number of misidentifications. Instead, it is important to devise a scheme that assigns non-zero a priori probability to things that are possible, even if they have never been observed. At the same time, one must acknowledge that, without compelling evidence to the contrary, one should favor more commonly observed outcomes.

Component 15 demonstrates the calculation of the tryptic peptide elemental compositions ("TPEC") distribution that would result from randomly shuffling the sequences in the human proteome and digesting (ideally) with trypsin. The distribution relies upon the use of the Central Limit Theorem to approximate the EC distribution of long tryptic peptides. Because peptides are made of five elements, the total number of possible TPECs less than mass M is proportional to $M^5$. Component 15 produced a promising result for proteomic analysis: the number of typical TPECs (e.g., those that would include all but 1 in 1000 or 1 in 10000 of randomly selected outcomes) grows only as $M^3$. The success rate of TPEC identification would not be limited by excluding atypical outcomes.

A database designed to capture 99.9% of possible outcomes for peptides up to length 30 has been tabulated and contains only 7.5 million entries. The entries in the database are not assigned equal weight, but have a probability estimate associated with them. Two entries in the database with nearly indistinguishable masses may have probabilities that differ by as much as five orders of magnitude. Even if the inventive mass measurement alone is unable to distinguish between the two ions, common sense dictates that the ion's identity is almost certainly the more likely of these two possibilities. Component 16 formalizes the notion of "common sense" with a Bayesian estimation strategy. An important feature of Component 15 was that the observed distribution of human TPECs was in close correspondence with values predicted by the inventive model. This result suggests that the model provides a powerful method for extending the information in the human proteome for biomarker discovery.

Component 16 describes how to use the database in Component 15 along with other databases and other sources of information to identify peptides using Bayesian estimation.

Component 17 describes an algorithm for fast computation of the distribution of molecular isotope abundances for a molecule of a given elemental composition. The ability to perform large numbers of these calculations rapidly is important in Component 7, where the spectrum is written as the sum of isotope envelopes of known species. A key insight is that the problem can be partitioned into the distribution of isotopic species for a given number of atoms for each individual element. These distributions can be computed rapidly using recursion and stored in tables of reasonable size (e.g., 1 MB) even when very large molecules are considered and very high accuracy (0.01%) is required.

Component 18 describes Isomerizer—an algorithm for generating all possible amino acid compositions that have a given elemental composition. This particular program may be useful in, for instance, hypothesis testing. For example, one might be interested in studying the distribution of retention times or charge states for a peptide with a given elemental composition. Such a distribution would be useful in determining the confidence for assigning a particular sequence to a peptide of known elemental composition given measurements of retention time and charge state. The program may also have applications is computing distributions of MS-2 fragments when the elemental composition of the parent ion is known.

Component 15: A Database of Typical Elemental Compositions for Random Tryptic Peptides and their Probabilities of Occurrence The most likely elemental compositions of tryptic peptides can be mapped to the region of the 5-D lattice (C,H,N,O,S) enclosed by a series of overlapping ellipsoids, one for each peptide length. This simple geometric treatment allows us to correct an important misconception in proteomic mass spectrometry: peptide identification from accurate mass measurements can be extended to larger peptides without exponential gains in mass accuracy.

In connection with Component 15, it is demonstrated analytically that the number of quantized mass values, or equivalently elemental compositions, of tryptic peptides less than mass M increases only as $M^3$, not as $e^{kM}$, as previously reported. As a proof of concept, a database of 99.9% of tryptic peptides of 30 residues or less was constructed, quantized to 10 ppb (QMass). The database matched an accurately measured mass to a short list of entries with similar masses; each entry contained a quantized mass value, an elemental composition, and an estimate of its a priori frequency of occurrence.

Because the peak density of mass values at nominal mass M increases only as $M^{3/2}$, peptide identification may benefit substantially from anticipated improvements in mass accuracy. Improved performance may extend to protein identification by mass fingerprinting or tandem mass spectrometry and proteomic spectrum calibration.

FT-ICR mass spectrometers can measure masses with 1 ppm accuracy. The mass of a peptide can be computed to better than 10 ppb accuracy from its elemental composition. Roughly speaking, it is possible to distinguish between two peptides whose masses differ by greater than 1 ppm. It has been demonstrated that all peptides less than 700 Daltons can be identified with certainty by a mass measurement with 1 ppm accuracy. However, the number of distinct peptide mass values (i.e., elemental compositions) increases with mass. As a result, one can make only probabilistic statements about the elemental compositions of larger peptides. Because the average mass of a tryptic peptide is about 1000 Daltons, absolute identification requires improvement in mass accuracy.

It is of important theoretical and practical interest to know how the number of elemental compositions increases as a function of mass. Roughly speaking, when the density of mass values increases to the point that the mean spacing between values is less than the measurement accuracy, it becomes difficult to identify distinct values with certainty.

Mann recognized that peptide mass values are distributed in clusters; one cluster per each nominal mass value. He noted that each cluster is approximately Gaussian and provided two linear equations for estimating the centroid and the width of each cluster as a function of nominal mass value M. Zubarev built on this work by examining how many elemental compositions there are at each nominal mass. He determined the number of elemental compositions for nominal mass values between 600 and 1200 Daltons and fit an exponential curve to the data. Spengler addressed the same issue; namely, what mass accuracy is necessary to resolve peptide elemental compositions. He enumerated peptide mass values for nominal mass values between 200 and 1500 D in increments of 100 D. Three or four values were chosen from near the center of each cluster. The separations between adjacent mass values were plotted. An exponential relationship was shown between the required accuracy (separation between adjacent values) and the nominal mass value.

Previous methods for estimating the number of elemental compositions for medium to large peptides relied upon sampling and extrapolation because direct enumeration of peptide elemental compositions is difficult. One approach is to enumerate all residue compositions up to a certain peptide length and group these into residue compositions. The number of residue compositions of peptides no longer than length L is N1=(L+20)!/(L!20!). For small L, N1 grows almost exponentially, and for large L, grows asymptotically as $L^{20}$. For L=20, N=1.4*1011. Since the smallest 20-residue peptide has a mass of 1158 Daltons, it is clear that this approach is not practical for enumerating all peptide elemental compositions. The situation improves only slightly if we restrict our attention to tryptic peptides. The number of tryptic peptides up to length L is N2=2(L+17)!/(L−1)!18!. The number of elemental compositions is considerably smaller because many of these residue compositions have the same elemental composition, but the number of calculations is proportional to the much larger number of residue compositions.

It is clear, without detailed analysis that the number of elemental compositions cannot increase exponentially with mass M. First, the number of peptide residue compositions grow only as M20 and the number of tryptic peptides grows as M18, since mass and length are linearly related. The number of elemental compositions of the five elements C, H, N, O, and S (of which peptides are a small subset) of less than mass M can be approximated by (M+5)!/(M!*5!*12*1*14*16*32), which for large M is approximately 10-7 M5.

A summary of the key experimental results for Component 15 is given below.

| | | |
|---|---|---|
| number of "typical" tryptic peptides of | length = N | $k_1N^{5/2}$ |
| | length < N | $k_2N^3$ |
| | nominal mass = M | $k_3M^2$ |
| | nominal mass < M | $k_4M^3$ |
| peak density of "typical" mass values for nominal mass = M | | $k_5M^{3/2}$ |

The results refer, not to every peptide, but instead to typical tryptic peptides. Typical peptides are the set of the most frequently occurring peptides. The typical set is chosen so that the probability of occurrence of a peptide outside the typical set is arbitrarily small (e.g., 0.1%). It is believed that exclusion of these peptides does not significantly affect the results of most analyses for which peptide masses are employed. Furthermore, these results are asymptotic upper bounds on the actual values. The accuracy of these bounds increases for larger peptides.

The implications of the above mathematical results on proteomic mass spectrometry are significant. For example, the density of mass values indicates how many candidate elemental compositions remain indistinguishable following a measurement with a given uncertainty. It has been stated previously that this quantity depends exponentially upon M. As a consequence, it was stated that while 1 ppm accuracy would be sufficient to identify most elemental compositions of 1000 Dalton peptides, similar success in determining the elemental compositions of 2600 Dalton peptides would require 1.6 part per billion accuracy—a factor of 600 improvement. In fact, the required gain in accuracy is only $2.6^{3/2}$, about 4.2.

The number of mass values whose nominal mass is less than some upper limit M indicates the number of entries in the database needed to identify the elemental composition from any measured mass less than M. If the table size is X for M=1000 Daltons, a table of size $2.6^3$×, about 18× would be needed to analyze peptides up to 2600 Daltons.

The time required to construct the database of mass values is proportional to the sum over residue lengths N of the number of elemental compositions for an N-residue peptide. If the database covering peptides up to length 10 can be constructed in time t, it would take time $2^{7/2}$t, about 28t, to cover length 26. If the average time to search the 10-residue database is T, the time to search the 26-residue database is log $2(2.6^3)$+T, about three additional steps.

The above analysis demonstrates the scalability of an approach to enumerate all possible elemental compositions (and mass values) for tryptic peptides in a table, and to determine elemental composition(s) from an observed mass value by table look-up. Below, the calculations are demonstrated showing that the constants of proportionality in these relationships are small enough that it is feasible to apply this approach to proteomic mass spectrometry on a modern workstation.

For example, there are 382 tryptic peptides with an atomic mass number of 500. These peptides can be grouped into 34 distinct residue compositions. These 34 groups can be further subdivided into 10 distinct elemental compositions (groups of isomers).

| | | | |
|---|---|---|---|
| CGGKN | 12 | $C_{19}H_{32}N_8O_6S$ | 500.21655 |
| CHKN | 6 | | |
| DGGPR | 12 | $C_{19}H_{32}N_8O_8$ | 500.23431 |
| DNPR | 6 | | |
| YYR | 1 | $C_{24}H_{32}N_6O_6$ | 500.23833 |
| CGKPP | 12 | $C_{21}H_{36}N_6O_6S$ | 500.24170 |
| AEGKP | 24 | $C_{21}H_{36}N_6O_8$ | 500.25946 |
| AADKP | 12 | | |
| EKPQ | 6 | | |
| AGPRT | 24 | $C_{20}H_{36}N_8O_7$ | 500.27070 |
| AAPRS | 12 | | |
| PQRT | 6 | | |
| AKPW | 6 | $C_{25}H_{36}N_6O_5$ | 500.27472 |
| GKPTV | 24 | $C_{22}H_{40}N_6O_7$ | 500.29585 |
| GKLPS | 24 | | |
| AKPSV | 24 | | |
| GIKPS | 24 | | |
| GGLRV | 12 | $C_{21}H_{40}N_8O_6$ | 500.30708 |
| AGRVV | 12 | | |
| GGIRV | 12 | | |
| LNRV | 6 | | |
| INRV | 6 | | |
| AAALR | 4 | | |
| AAAIR | 4 | | |
| QRVV | 3 | | |
| AGIKL | 24 | $C_{23}H_{44}N_6O_6$ | 500.33223 |
| AGKLL | 12 | | |
| AAIKV | 12 | | |
| AAKLV | 12 | | |
| AGIIK | 12 | | |
| IKLQ | 6 | | |
| GKVVV | 4 | | |
| KLLQ | 3 | | |
| IIKQ | 3 | | |

Therefore, there are 10 exact mass values for tryptic peptides with a nominal mass of 500. These can be easily distinguished by a measurement with 1 ppm accuracy: the closest pair of values involves exchanging $SH_4$ for C, a mass difference of 0.00337 D, or 6.74 ppm. Therefore, a measurement with 1 ppm accuracy of a tryptic peptide with nominal mass 500 is equivalent to a quantum or exact mass measurement, because the elemental composition can be determined with virtual certainty.

For larger values of nominal mass, multiple exact mass values may inhabit the same 1 ppm window. In this case, the precise value of the mass measurement and additional information may be used to assign probabilities to a finite number of exact mass values. Consider the case of a measurement of a tryptic peptide ion with +1 charge state of 1000.3977. There are three exact mass values within 1 ppm of the measured value.

| | | | | | |
|---|---|---|---|---|---|
| 1000.39558 | 2.12 | 0.4 | C43H62N13O9S3 | 1260 | $2.0e^{-9}$ |
| 1000.39719* | 0.51 | 29.1 | C38H58N13O19 | 48279 | $1.5e^{-7}$ |
| 1000.39759* | 0.11 | 37.3 | C39H70N9O13S4 | 2310 | $7.2e^{-9}$ |
| 1000.39806* | 0.36 | 33.2 | C39H62N13O14S2 | 1410732 | $6.0e^{-7}$ |
| 1000.40056 | 2.86 | 0.01 | C35H62N13O19S1 | 19698 | $1.3e^{-8}$ |

Without additional information about the exact mass values, one would assume that the most likely elemental composition would be $C_{39}H_{70}N_9O_{13}S_4$ because it is closest to the measured value. But given the uncertainty in the measurement, all three values are reasonably likely. However, there are over one million tryptic peptides with chemical formula $C_{39}H_{62}N_{13}O_{14}S_2$ and merely a few thousand with the formula $C_{39}H_{70}N_9O_{13}S_4$.

Even when an accurate mass measurement does not identify a single elemental composition, the remaining uncertainty has been transformed from continuous to discrete in nature.

By restricting attention to the exact mass values (or elemental compositions) of peptides, rather than all possible combinations of members of the Periodic Table, the number of unique masses is reduced considerably. Peptides, however, have very limited elemental compositions. Zubarev reported that elemental compositions could be uniquely determined for peptides up to 700-800 Dalton from measurements with 1 ppm accuracy.

Peptide identification in bottom-up proteomic mass spectrometry requires a list of possible peptide candidates. The number of peptide sequences of length N grows exponentially with N, and even the number of amino acid residue compositions (collapsing the permutational degeneracy) grows as $N^{19}$, making enumeration possible for only short peptides. However, the chemical formulas of peptides can be partitioned into groups of isomers, with each group identified by a unique chemical formula and exact mass value. The average number of isomers in a group grows exponentially with N, but the number of groups grows much more slowly: the set of "typical" chemical formulas (all but a set whose total probability can be made arbitrarily small) grows as $N^{5/2}$. This makes it possible to enumerate the entire set of typical chemical formulas for even the longest peptides ones would expect to encounter in a tryptic digest.

The list of typical peptide masses makes it possible to translate an accurate mass measurement of a monoisotopic peptide into a small number of possible exact mass values, or equivalently, chemical formulae. Furthermore, these values can be weighted by probability estimates, which can be routinely estimated from the chemical formula. This list of masses, chemical formulae, and probabilities can be applied to several fundamental problems in proteomic mass spectrometry: identifying peptides from accurate mass measurements, identifying the parent proteins that contain the peptide fragments, and in the fine calibration of mass spectra. Furthermore, it is relatively straightforward to use this table to detect and identify post-translationally modified peptides.

Moreover, a fundamental limitation of mass spectrometry is the inability to distinguish isomeric species directly. The structural formula of a molecule can be inferred only by weighing the masses of its fragments, a process that must be performed one molecule at a time. This is the major bottleneck in high-throughput proteomics.

From another perspective, this limitation can be viewed as a blessing in disguise. Peptides can be grouped into isomeric species of equivalent mass. The groups are large: the average number of isomers for an N-residue peptide grows exponentially with N. However, the number of distinct groups, or chemical formulae, or exact mass values, grows only as $N^{5/2}$, as shown below. As a result, the continuous nature of a mass measurement is effectively reduced to a quantum measurement.

Stated in another way, given a mass measurement alone, the distribution of possible values for the true mass is continuous, centered on the measured value and whose width characterizes the measurement accuracy. When the constraint that the measured molecule is a peptide is enforced, the distribution of possible values for the true mass is discrete; if the measurement is accurate, a small number of candidate values have non-negligible probabilities.

Furthermore, the number of candidate values that must be considered in inferring the exact mass of a peptide from an accurate mass measurement grows in a very manageable way. For example, let M denote the average number of candidate exact mass values for an N-residue peptide whose mass is measured with some given accuracy. Then the average number of candidate values for peptides of length 2N is only $2^{5/2}M\sim5.6M$. It has been recognized previously that for peptides of length six or seven, a mass measurement of 1 ppm accuracy on average identifies a single exact mass value. Then, for peptides of length 13, about six candidates would need to be considered. For peptides of length 26, a 1 ppm measurement would rule out all but about 30 candidate chemical formulae.

In fact, the value of such a measurement is even greater than suggested by the number of candidate solutions. In the worst case, a guess among M candidates with equal a priori probability that are not distinguishable by a measurement would produce the right answer on average with probability 1/M. However, the a priori distribution of peptide mass values is far from uniform, as shown below. It is typical to observe differences greater than 10-fold in a priori probabilities among adjacent chemical formulae. Remarkably, in many cases, it is possible to infer the exact mass with high probability for even the largest tryptic peptides.

In any case, given a list of peptide masses and probabilities, subsequent interpretation of an accurate mass measurement involves considering a finite and enumerable number of candidate solutions. Subsequent interpretation might involve tandem mass-spectrometry, additional biophysical measurements (e.g., isoelectric point), or search against a genomic sequence. All of these problems are simplified by having a list of peptide masses and probabilities.

For very small peptides, it is possible to enumerate all peptide sequences. There are 20 sequences of length 1: A, C, D . . . There are 400 of length 2: AA, AC, AD . . . There are 20N of length N. It is impossible to enumerate all peptide sequences for lengths typical of tryptic peptides, since 5% are longer than 20 residues.

For a larger set of peptides, it is possible to enumerate all amino acid residue compositions. This can be represented by vectors with 20 non-negative components. For example, a peptide with 2 Ala residues and 1 Cys residue could be represented by the vector (2, 1, 0, 0 . . . ). There are 20 compositions of length 1: (1, 0, 0 . . . ), (0, 1, 0, . . . ), . . . There are 210 compositions of length 2. There are (N+19)!/(N!19!) compositions of length N. This is a reduction from exponential to polynomial, since the number of residue compositions grows as N19 for large N. Still, it is impossible to enumerate all peptide sequences for peptides with lengths typical of proteomic experiments.

The number of peptide elemental compositions, however, is considerably smaller. Because peptides are made from five elements (C, H, N, O, S), chemical formulae can be represented as five-dimensional vectors with non-negative integer components. Because the maximum possible value of each component for an N-residue peptide is linear in N, the number of possible chemical formulae grows no faster than $N^5$. This is a significant reduction over the number of residue combinations, but we still need to do better in order to make it practical to generate a list of peptide chemical formulas.

The key insight comes from information theory and also from statistical mechanics. The concept is that the properties of a random variable or the behavior of a physical system can be well approximated by considering only its "typical" values or physical states. Atypical values or states—those defined by occurrence probabilities less than some threshold—can be thrown away without changing overall macroscopic properties. This property makes possible accurate, yet simple mathematical modeling of many physical systems.

To identify typical chemical formulae, it is necessary to assign probabilities to them. It turns out that these probability values will be very useful later, too.

Probabilistic Model for Tryptic Peptides

The construction of a peptide sequence is modeled by independent, identical trials of drawing at random an amino acid residue from an arbitrary distribution. Let A denote the set containing the 20 naturally occurring amino acids: A={Ala,Cys,Asp, . . . }. Let $p_a$ denote the probability of an amino acid residue a in A. These probabilities are equated with the frequencies of occurrences of amino acids in the human proteome. These values are taken from the Integr8 database, produced by EBI/EMBL.

| | |
|---|---|
| Ala | 7.03 |
| Phe | 3.64 |
| Lys | 5.61 |
| Pro | 6.44 |
| Thr | 5.39 |
| Cys | 2.32 |
| Gly | 6.66 |
| Leu | 9.99 |
| Gln | 4.75 |
| Val | 5.96 |
| Asp | 4.64 |
| His | 2.64 |
| Met | 2.15 |
| Arg | 5.72 |
| Trp | 1.28 |
| Glu | 6.94 |
| Ile | 4.30 |
| Asn | 3.52 |
| Ser | 8.39 |
| Tyr | 2.61 |

To model tryptic peptides, rather than infinite sequences of residues, the rule is added that a tryptic sequence terminates after an Arg or Lys residue is drawn. Let T denote the set of terminal residues: T={Arg, Lys}, and let N denote the set of non-terminal residues: N=A−T. Let $p_t$ denote the probability of drawing a terminal residue at random, and let $p_n$ denote the probability of drawing a non-terminal residue.

$$p_T = p_{Arg} + p_{Lys}$$

$$p_N = 1 - p_T$$

The probability of generating a sequence of tryptic peptide of length N using this model is the probability of drawing N−1 consecutive "non-terminal" residues followed by a terminal residue.

$$p(N)=p_N^{N-1}p_T$$

The distribution of tryptic peptide lengths is exponential. It is straightforward to compute the expected length of ideal trypic peptides.

$$<N>=\sum_n \mathrm{Np}(N) = p_T\sum_n \mathrm{Np}_N^{N-1} = \frac{p_T}{(1-p_N)^2} = \frac{1}{p_T}$$

Because $p_T$ is about 0.11, the average length of a tryptic peptide is about 9 residues.

We can also compute the probability that the length is greater than some positive integer M.

$$p(N \geq M) = \sum_{n>M} p(N) = p_T\sum_n \mathrm{Np}_N^{N-1} = p_T p_N^M \sum_{k\geq 0} p_N^k = \frac{p_T}{(1-p_N)} p_N^M = p_N^M$$

For example, about 9% of tryptic peptides are longer than 20 residues and about 3% are longer than 30 residues.

Let S denote a sequence generated by our random model. Let N denote the length of S. The probability of generating S is the product the probability of drawing each of its residues in sequence.

$$p(S) = \prod_{n=1}^{N} p_{S_n}$$

Notice that the same probability would be assigned to any permutation of sequence S.

Let R denote a 20-component vector of non-negative integers, representing the residue composition of a tryptic peptide; let $R_a$ denotes the number of occurrences of the amino acid a in R. For tryptic peptides, $R_{Arg}+R_{Lys}=1$. Let R(S) denote the residue composition of sequence S above.

$$R_a = \sum_{n=1}^{N} \delta_{S_n,a}$$

Let L(R) denote the number of residues in R.

$$L(R) = \sum_{a\in A} R_a$$

For example, L(R(S))=N.

The probability of generating a sequence S can be expressed in terms of its residue composition R(S).

$$P(S) = \prod_{a \in A} p_a^{[R(S)]_a}$$

Let D(R) denote the degeneracy of residue composition R (i.e., the number of sequences with residue composition R).

$$D(R) = \frac{L(R)!}{\prod_{a \in A} R_a!}$$

Then, the probability of generating a sequence with residue composition R is the probability of any individual sequence that has residue composition R times the number of such sequences D(R). For example, $$P(R(S))=D[R(S)]P(S)$$

Note that the probability of residue composition R can be expressed directly by combining the three equations immediately above.

$$P(R) = \frac{L(R)!}{\prod_{a \in A} R_a!} \prod_{a \in A} p_a^{R_a}$$

Let $E=(E_1, E_2 \ldots E_5)$ denote an elemental composition of a peptide. E is a five-component vector of non-negative integers that denote the number of carbon, hydrogen, nitrogen, oxygen, and sulfur atoms, respectively. Let E(S) denote the elemental composition of sequence S. Let $E^{(i)}$ denote the elemental composition of the $i^{th}$ residue in the sequence. Let $e_a$ denote the elemental composition of the (neutral) amino acid residue a.

| | |
|---|---|
| Ala | (3,5,1,1,0) |
| Phe | (9,9,1,1,0) |
| Lys | (6,12,2,1,0) |
| Pro | (5,7,1,1,0) |
| Thr | (4,7,1,2,0) |
| Cys | (3,5,1,1,1) |
| Gly | (2,3,1,1,0) |
| Leu | (6,11,1,1,0) |
| Gln | (5,8,2,2,0) |
| Val | (5,9,1,1,0) |
| Asp | (4,5,1,3,0) |
| His | (6,7,3,1,0) |
| Met | (5,9,1,1,1) |
| Arg | (6,12,4,1,0) |
| Trp | (11,10,2,1,0) |
| Glu | (5,7,1,3,0) |
| Ile | (6,11,1,1,0) |
| Asn | (4,6,2,2,0) |
| Ser | (3,5,1,2,0) |
| Tyr | (9,9,1,2,0) |

E(S) is the sum of the elemental compositions of the residues plus two hydrogen atoms on the N-terminus and an oxygen atom on the C-terminus Let $e_{H2O}$=(0, 2, 0, 1, 0).

$$E(S) = \sum_{i=1}^{N} E^{(i)} + e_{H_2O}$$

Let S(E) denote the set of sequences with elemental composition E (i.e., tryptic peptide isomers). The probability of generating a sequence with elemental composition E is the sum of probabilities of all sequences in S(E).

$$p(E) = \sum_{S \in S(E)} p(S)$$

We can also express the probability of an elemental composition in terms of the sum of the probabilities of residue compositions. Let R (E) denote all residue compositions with elemental composition E.

$$p(E) = \sum_{R \in R(E)} p(R)$$

Let M(E) denote the (monoisotopic) mass of a molecule of elemental composition E. Define μ as the 5-component vector whose components are the masses of $^{12}C$, $^{1}H$, $^{14}N$, $^{16}O$, and $^{32}S$ respectively.

$$M(E) = \sum_{i=1}^{5} \mu_i E_i$$

There is a one-to-one correspondence between exact mass values and elemental compositions. Therefore, the probability of generating a peptide of mass M' is the same as the probability of generating an elemental composition E if M(E)=M'.

Analysis of Elemental Composition Probabilities

Let S denote a random tryptic peptide sequence generated by the process described above. Then, E(S) is also a random variable, defined by the same equation where the right-hand side is now randomly determined. The values of the elemental compositions of the individual residues $\{E^{(i)}, i=1 \ldots N\}$ are mutually independent. The values of $E^{(1)} \ldots . E^{(N-1)}$ are drawn from the non-terminal residues. The value of $E^{(N)}$ is drawn from the terminal residues.

$$p(E^{(k)} = e_a) = \begin{cases} p_i / p_{non} & k \in [1 \ldots N-1], a \in N \\ 0 & k \in [1 \ldots N-1], a \in T \\ p_i / p_{term} & k = N, a \in T \\ 0 & k = N, a \in N \end{cases}$$

It is useful to decompose the elemental composition of an N-residue tryptic peptide in terms of the sum of N'1 non-terminal residues and a terminal residue. Let E denote an elemental composition of an N-residue tryptic peptide, and let E' denote the elemental composition of its first N'1 residues. Then, we can express the probability that random elemental composition E is equal to a fixed elemental composition x in terms of E'.

$$p(E=x)=p\lfloor E'=x-(e_{Lys}+e_{H_2O})\rfloor p_{Lys}+p\lfloor E'=x-(e_{Arg}+e_{H_2O})\rfloor p_{Arg}$$

The Central Limit Theorem may be used to model the distribution of random variable E'; the sum of N−1 independent, identically distributed random variables. The Central Limit Theorem states that for large N, the distribution of the sum of N independent, identically distributed random variables tends to a normal distribution.

The probability density for an d-dimensional continuous random variable, calculated at an arbitrary point x, can be expressed in terms of an d-dimensional vector m and an d×d matrix K, which denote the mean and covariance of the random variable.

$$p(x) = (2\pi)^{-N/2}|K|^{-1/2}e^{-\frac{1}{2}(x-m)^T K^{-1}(x-m)}$$

Elemental compositions are 5-dimensional. Although the components are non-negative integers rather than continuous, real values, we can use the continuous model to assign probabilities. Each elemental composition sits on a lattice point in the continuous space. Each lattice point can be centered within a (hyper)cubic volume of one unit per edge (i.e., volume=1 unit$^5$). When the probability function is roughly constant over these volume elements, assigning the values of the continuous probability densities calculated on the lattice points to probabilities of discrete elemental compositions is acceptable.

Let $E_N$ denote a random variable, resulting from selecting a non-terminal residue at random.

$$p(e_a) = \begin{cases} p_i / p_N & a \in N \\ 0 & a \in T \end{cases}$$

The mean $m_N$ and covariance $K_N$ of random variable $E_N$ can be computed in terms of weighed sums over the 18 non-terminal residues.

$$m_N = \frac{1}{p_N}\sum_{a \in N} p_a E_a$$

$$K_N = \left(\frac{1}{p_N}\sum_{a \in N} p_a E_a E_a^T\right) - m_N m_N^T$$

The result of this calculation, using the tables of amino acid probabilities and elemental combinations provided above, is shown below.

$$m_N = \begin{bmatrix} 4.78 \\ 7.22 \\ 1.17 \\ 1.54 \\ 0.05 \end{bmatrix} \quad K_N = \begin{bmatrix} 3.42 & 3.36 & 0.14 & -0.16 & -0.04 \\ 3.36 & 5.61 & 0.02 & -0.44 & -0.01 \\ 0.14 & 0.02 & 0.20 & 0.03 & -0.01 \\ -0.16 & -0.45 & 0.00 & 0.51 & -0.03 \\ -0.04 & -0.01 & -0.01 & -0.03 & 0.05 \end{bmatrix}$$

The first component of m, for example, indicates the probability-weighted average number of carbon atoms among the non-terminal amino acid residues (4.78). The most abundant atom is hydrogen (7.22), and the least abundant is sulfur (0.05), which occurs once for each Cys and Met (about 5% of residues). K is a symmetric 5×5 matrix. The diagonal entries indicate variances, the weighted squared deviation from the mean. For example, the upper-left entry is the variance in the number of carbon atoms among the non-terminal residues (3.42). Hydrogen has the most variance (5.61), followed by carbon, oxygen (0.51), nitrogen (0.20), and sulfur (0.05). The off-diagonal entries indicate covariances between elements. For example, the strongest covariance is between carbon and hydrogen (column one, row two=3.36). This relatively large positive value reflects the trend that hydrogen atoms usually accompany carbon atoms in residue side-chains. While numbers of carbon and hydrogen atoms are strongly coupled, the other atoms are relatively uncorrelated.

The mean and covariance of E' are equal to N−1 times the mean and covariance of $E_N$.

$$m = (N-1)m_{E_{non}}$$

$$K = (N-1)K_{E_{non}}$$

For example, a sequence of 10 non-terminal residues would have an average of 48 carbon atoms with a variance of 34 (i.e., a standard deviation about 6). Therefore, a tryptic peptide of length 11 would have an average of 54 carbon atoms with the same variance, because a tryptic peptide sequence would be formed by adding either Lys or Arg and $H_2O$, and Lys and Arg each have 6 carbon atoms. It would also have 86+/−7 hydrogen atoms, 15+/−2 nitrogen atoms, 16+/−2 oxygen atoms, and 0.5+/−0.5 sulfur atoms.

The probability density for a continuous random variable evaluated at x can also be expressed in terms of the chi-squared function.

$$p(x) = (2\pi)^{-N/2}|K|^{-1/2}e^{-\frac{1}{2}\chi^2(x;m,K)}$$

The function $\chi^2(x;m,K)$ has the interpretation of normalized squared distance between a vector x and the mean vector m;

$$\chi^2(x;m,K)=(x-m)^T K^{-1}(x-m)$$

The normalization is with respect to the variances along the principal components of the distribution—the eigenvectors of the covariance matrix K. Let unit vectors $v_1 \ldots v_5$ denote the eigenvectors of K. The eigenvectors form a complete orthonormal basis for the continuous space of 5-dimensional real-valued vectors. Because $v_1 \ldots v_5$ form a complete basis, we can write any elemental composition as a linear combination of these basis vectors.

$$x=a_1v_1+a_2v_2+a_3v_3+a_4v_4+a_5v_5$$

The scalar values $a_1 \ldots a_5$ are the projections of x onto the respective component axes. For example, $$v_1^Tx=v_1^T(a_1v_1+a_2v_2+a_3v_3+a_4v_4+a_5v_5)=a_1v_1^Tv_1+a_2v_1^Tv_2+a_3v_1^Tv_3+a_4v_1^Tv_4+a_5v_1^Tv_5=a_1$$

Similarly, we can express m and x−m in terms of these basis vectors.

$$m = b_1v_1 + b_2v_2 + b_3v_3 + b_4v_4 + b_5v_5$$

$$x - m = d_1v_1 + d_2v_2 + d_3v_3 + d_4v_4 + d_5v_5$$

The values $d_1 \ldots d_5$ represent (unnormalized) distances between x and m along the principal component axes.

Let $\lambda_1 \ldots \lambda_5$ denote the eigenvalues of K. By definition, for i=1 . . . 5, $$Kv_i\lambda_iv_i$$

We can show that these eigenvalues are the variances of the projections along the component axes. For example, $$\sigma_{d_1}^2 = \langle d_1^2\rangle - \langle d_1\rangle^2 = \langle[v_1^T(x-m)]^2\rangle - \langle v_1^T(x-m)\rangle^2 = \langle[v_1^T(x-m)][(x-m)^T v_1]\rangle - \langle[v_1^T(x-m)]\rangle\langle[(x-m)^T v_1]\rangle = v_1^T[\langle(x-m)(x-m)^T\rangle - \langle(x-m)\rangle\langle(x-m)\rangle^T]v_1 = v_1^T K v_1 = v_1^T\lambda_1 v_1 = \lambda_1(v_1^T v_1) = \lambda_1$$

Also, note that the eigenvectors of K are also eigenvectors of $K^{-1}$, and the eigenvalues are $1/\lambda_i$.

$$K^{-1}v_i = K^{-1}\left(\frac{1}{\lambda_i}\lambda_i v_i\right) = \frac{1}{\lambda_i}K^{-1}(\lambda_i v_i) = \frac{1}{\lambda_i}K^{-1}(Kv_i) = \frac{1}{\lambda_i}(K^{-1}K)v_i = \frac{1}{\lambda_i}v_i$$

The eigenvalues are the normalization factors in the calculation of $\chi^2$. Now we can express $\chi^2$(x;m,K) as the sum of the squared normalized distances.

$$\chi^2(x;m,K) = (x-m)^T K^{-1}(x-m) = (d_1v_1 + d_2v_2 + d_3v_3 + d_4v_4 + d_5v_5) TK^{-1}(d_1v_1 + d_2v_2 + d_3v_3 + d_4v_4 + d_5v_5) = (d_1v_1 + d_2v_2 + d_3v_3 + d_4v_4 + d_5v_5) T(d_1K^{-1}v_1 + d_2K^{-1}v_2 + d_3K^{-1}v_3 + d_4K^{-1}v_4 + d_5K^{-1}v_5) = (d_1v_1 + d_2v_2 + d_3v_3 + d_4v_4 + d_5v_5)T\left(d_1\frac{1}{\lambda_1}v_1 + d_2\frac{1}{\lambda_2}v_2 + d_3\frac{1}{\lambda_3}v_3 + d_4\frac{1}{\lambda_4}v_4 + d_5\frac{1}{\lambda_5}v_5\right) = \frac{d_1^2}{\lambda_1} + \frac{d_2^2}{\lambda_2} + \frac{d_3^2}{\lambda_3} + \frac{d_4^2}{\lambda_4} + \frac{d_5^2}{\lambda_5}$$

The above result has both theoretical and practical value in our development.

In many problems, algorithms can achieve tremendous savings in time and memory usage without sacrificing much accuracy by considering only the most probable states of a system. In this problem, the above analysis suggests how to generate a list of the most probable elemental compositions of N-residue tryptic peptides.

We say that x is a typical elemental composition for an N-residue tryptic peptides is the probability of x exceeds some arbitrary threshold value T.

$$p(x) > T$$

This is equivalent to saying that the $\chi^2$-value of x, with respect to m,K for N-residue tryptic peptides is less than a related threshold t.

$$\chi^2(x;m,K) < 2\log(T/k) = t$$

Using the result above, we can show that the typical elemental compositions lie in the interior of a 5-dimensional ellipsoid.

$$\frac{d_1^2}{\lambda_1} + \frac{d_2^2}{\lambda_2} + \frac{d_3^2}{\lambda_3} + \frac{d_4^2}{\lambda_4} + \frac{d_5^2}{\lambda_5} < t$$

Usually, we choose T (or t) so that the total probability mass of non-typical elemental compositions is less than some arbitrarily small value e. The values of t necessary to achieve various values of e for N degrees of freedom (e.g., 5) are tabulated. The $\chi^2$-value is frequently used to compute the probability that an observation was either drawn or not drawn from a normal distribution with known mean and covariance. For example, if we choose t=20.5150, then the resulting ellipsoid will encapsulate 99.9% of the elemental compositions, weighted by probability.

Next, we would like to know how many typical elemental compositions there are for N-residue tryptic peptides (e.g., needed to comprise 99.9% of the distribution). This is closely related to the volume of the ellipsoid for arbitrary t.

$$V = V_s t^{5/2}(\lambda_1\lambda_2\lambda_3\lambda_4\lambda_5)^{1/2}$$

$$V_s = 8\pi 2/15$$

$V_s$ is the volume of the 5-dimensional unit sphere.

The product of the eigenvalues is also equal to the determinant of the covariance matrix K. Let U denote the matrix formed by stacking the eigenvectors as column vectors.

$$U = [v_1\ v_2\ v_3\ v_4\ v_5]$$

Recall that eigenvectors form an orthonormal basis.

$$U^TU = \begin{bmatrix} v_1^T \\ v_2^T \\ v_3^T \\ v_4^T \\ v_5^T \end{bmatrix}[v_1\ \ v_2\ \ v_3\ \ v_4\ \ v_5] = \begin{bmatrix} 1 & 0 & 0 & 0 & 0 \\ 0 & 1 & 0 & 0 & 0 \\ 0 & 0 & 1 & 0 & 0 \\ 0 & 0 & 0 & 1 & 0 \\ 0 & 0 & 0 & 0 & 1 \end{bmatrix} = I$$

From this, we conclude $$U^T = U^{-1}$$

The eigenvector equation can be written in matrix form in terms of $\Lambda$, the diagonal matrix of eigenvalues.

$$KU = K[v_1\ \ v_2\ \ v_3\ \ v_4\ \ v_5] = [Kv_1\ \ Kv_2\ \ Kv_3\ \ Kv_4\ \ Kv_5] = [\lambda_1v_1\ \ \lambda_2v_2\ \ \lambda_3v_3\ \ \lambda_4v_4\ \ \lambda_5v_5] = [v_1\ \ v_2\ \ v_3\ \ v_4\ \ v_5]\begin{bmatrix} \lambda_1 & 0 & 0 & 0 & 0 \\ 0 & \lambda_2 & 0 & 0 & 0 \\ 0 & 0 & \lambda_3 & 0 & 0 \\ 0 & 0 & 0 & \lambda_4 & 0 \\ 0 & 0 & 0 & 0 & \lambda_5 \end{bmatrix} = U\Lambda$$

We solve for L by multiplying both sides by U-1.

$$\Lambda = U^{-1}KU.$$

By taking the determinant of both sides of the above equation, we obtain the desired result, that the determinant of a matrix is the product of its eigenvalues.

$$|\Lambda| = |U^{-1}KU| = |U^{-1}||K||U| = |U^{-1}||U||K| = |U^{-1}U||K| = |K|$$

Thus, the volume of the ellipsoid can be expressed in terms of the determinant of the covariance matrix.

$$V = V_s t^{5/2}|K|^{1/2}$$

Now, recall that the covariance matrix for E' is (N−1) times the covariance matrix for Enon. Note that multiplying a 5-D matrix by a scalar multiplies its determinant by the scalar raised to the $5^{th}$ power.

$$V = V_s t^{5/2}|(N-1)K_{E_{non}}|^{1/2} V_s t^5 |K_{E_{non}}|^{1/2}(N-1)^{5/2}$$

Let E'(N−1) denote the set of elemental compositions for sequences constructed from (N−1) non-terminal residues, and let Z' denote the size of set E'.

$$Z' \approx \frac{1}{2}V$$

The approximation improves as N increases. The correspondence between the volume and the number of elemental compositions arises because elemental compositions live on an integer lattice, with one lattice point per unit volume. The factor of ½ arises from the fact that the elemental compositions of neutral molecules have a parity constraint, so that half the compositions on the integer lattice are not allowed. For atoms made from C, H, N, O, S, the number of hydrogen atoms must have the same parity as the number of nitrogen atoms.

Let E (N) denote the set of elemental compositions of N-residue tryptic peptides, and let Z denote the size of set E. There are at most two N-residue tryptic peptide elemental compositions for each elemental composition of N−1 non-terminal residues—formed by adding either Lys or Arg. Many of these elemental compositions are duplicates. Elemental composition E is a duplicate if both E−(eArg+eH2O) and E−(eLys+eH2O) are in E'(N−1).

Let r denote the ratio of the number of (unique) elements in E(N) to the number of elements in E'(N−1).

$$Z = rZ' \approx \frac{1}{2}V$$

It is expected that r will be no greater than 2 and to decrease towards 1 with large N. Its value is estimated presently. Duplicate elemental compositions formed by adding Lys and Arg are contained within two ellipsoids, one centered at m+eArg+eH2O and the other centered at $m+e_{Lys}+e_{H2O}$. Arg and Lys have very similar elemental compositions: Arg=(6, 12, 4, 1, 0), Lys=(6, 12, 2, 1, 0)—the displacement between the centroids is two nitrogens. The overlapping volume between two ellipsoids can be computed rather easily if the displacement is along one of the axes. Because eigenvector $v_4$ is very nearly parallel to the nitrogen axis (8° deviation), we will simplify our calculation by assuming the displacement is along $v_4$.

Let $y=x-e_{Lys}+e_{H2O}$. Let d denote the separation (along the $v_4$ axis). In this case, d=2. We will plug in this value for d at the end of the calculation. The intersection of the ellipsoid volumes satisfies the two inequalities below.

$$\frac{y_1^2}{\lambda_1}+\frac{y_2^2}{\lambda_2}+\frac{y_3^2}{\lambda_3}+\frac{y_4^2}{\lambda_4}+\frac{y_5^2}{\lambda_5}<t$$

$$\frac{y_1^2}{\lambda_1}+\frac{y_2^2}{\lambda_2}+\frac{y_3^2}{\lambda_3}+\frac{(y_4-d)^2}{\lambda_4}+\frac{y_5^2}{\lambda_5}<t$$

Equivalently, $$\frac{y_1^2}{\lambda_1}+\frac{y_2^2}{\lambda_2}+\frac{y_3^2}{\lambda_3}+\frac{y_5^2}{\lambda_5}<\left(t-\frac{y_4^2}{\lambda_4},\ t\frac{(y_4-d)^2}{\lambda_4}\right)$$

Let z denote the normalized separation between the ellipsoids (i.e., d in units of the ellipsoid axis in the direction of the separation).

$$z=\frac{d}{\sqrt{t\lambda_4}}$$

If z is greater than 2, the ellipsoids do not intersect. Even though the variance of nitrogen atoms among non-terminal residues is relatively small, there is considerable intersection between the ellipsoids, even for small values of N.

$$z \cong \frac{2}{\sqrt{0.18t}}(N-1)^{-1/2} \cong \frac{4.7}{\sqrt{t(N-1)}}$$

For example, for t=20.515 (99.9% coverage) and N=10, z~0.35.

Let $q(y_4)$ denote the function on the right-hand side. $q(y_4)$ is symmetric about $y_4=d/2$. When $y_4>d/2$, $q(y_4)$ is positive when $y_4<(t\lambda_4)^{1/2}$. For each value of $y_4$ in this range, the solution to the above inequality is the interior of a 4-dimensional ellipsoid with axes $(q(z_4)\lambda_1)^{1/2}$, $(q(z_4)\lambda_2)^{1/2}$, $(q(z_4)\lambda_3)^{1/2}$ and $(q(z_4)\lambda_5)^{1/2}$. Let $V_4(y_4)$ denote the volume of this ellipsoid. Let $V_I$ denote the volume inside the intersection of the ellipsoids.

$$V_I = 2\int_{d/2}^{\sqrt{t\lambda_4}} V(y_4)\,dz_4 = 2\frac{\pi^2}{2}\sqrt{\lambda_1\lambda_2\lambda_3\lambda_5}\int_{d/2}^{\sqrt{t\lambda_4}} q(y_4)\,dz_4 =$$

$$\pi^2\sqrt{\lambda_1\lambda_2\lambda_3\lambda_5}\int_{d/2}^{\sqrt{t\lambda_4}}\left(t-\frac{y_4^2}{\lambda_4}\right)^2 dy_4 =$$

$$\pi^2\sqrt{\lambda_1\lambda_2\lambda_3\lambda_4\lambda_5}\,t^{5/2}\left[\frac{8}{15}-\frac{z}{2}+\frac{z^3}{12}-\frac{z^5}{160}\right]$$

Now, we have the ratio of the union of the ellipsoid interiors to the volume of an ellipsoid.

$$r=\frac{2V-V_I}{V}=\frac{\frac{8}{15}+\frac{z}{2}-\frac{z^3}{12}+\frac{z^5}{160}}{8/15}=1+\frac{15z}{16}-\frac{5z^3}{64}+\frac{3z^5}{256}$$

For small z, we can approximate r by the first two terms of the right-hand side. For the example above, when z~0.35, r~1.32.

The determinant of KN is 0.0312. For t=20.5150 (99.9% coverage), the product of the constant terms (with c=1) is roughly 1800. We can increase our coverage to 99.99% by choosing t=25.7448. In this case, the constant term increases to 3100. In other words, by doubling the number of elemental compositions in our list, we can reduce the rate of missing compositions by more than 10-fold.

For N=10, N5/2~316. Less than million elemental compositions of 11 N-residue tryptic peptides would cover greater than 99.99% of the probability mass. For each doubling of N,N5/2 increases by about 5.7.

Turning now to the eigenvectors and eigenvalues of KN.

$$\begin{bmatrix}\lambda_1\\ \lambda_2\\ \lambda_3\\ \lambda_4\\ \lambda_5\end{bmatrix}=\begin{bmatrix}8.08\\ 1.03\\ 0.45\\ 0.18\\ 0.05\end{bmatrix}$$

$$\begin{bmatrix}v_1^T\\ v_2^T\\ v_3^T\\ v_4^T\\ v_5^T\end{bmatrix}=\begin{bmatrix}0.59 & 0.81 & 0.01 & -0.06 & -0.00\\ 0.79 & -0.55 & 0.12 & 0.24 & -0.03\\ 0.16 & -0.18 & 0.06 & -0.97 & 0.05\\ 0.12 & -0.07 & -0.99 & -0.03 & 0.04\\ 0.02 & 0.00 & 0.04 & 0.06 & 1.00\end{bmatrix}$$

Sampling

The elemental compositions of N−1 non-terminal residues are enumerated by traversing the region of the 5-D lattice that is bounded by the ellipsoid described above. These are transformed into the elemental compositions of N-residue tryptic peptides by adding either eLys+eH2O or eArg+eH2O and then removing duplicates from the list.

Note that sampling a multi-dimensional lattice delimited by boundary conditions is non-trivial in many cases. The simplest case is rectangular boundary conditions, when the edges are parallel to the lattice axes. The reason for its simplicity is that sampling a rectangular volume of an N-dimensional lattice can be conveniently reduced to sampling rectangular volume set of a set (N−1)-dimensional lattices. Fortunately, ellipsoids have the same property: that cross sections of ellipsoids are ellipsoids.

Sampling the region of a lattice enclosed by an ellipsoid in five dimensions is accomplished by successively sampling a set of lattices enclosed by four-dimensional ellipsoids. Dimensionality is reduced is subsequent steps until only the trivial problem of sampling a 1-D lattice remains.

The mechanism for sampling the lattice is demonstrated by rewriting the equation for $\chi^2$ in terms of two terms, one that involves only one of the five elements and another that involves only the other four.

First, we define vectors 4-dimensional vectors x', and m', and 4×4 matrix K' to contain only entries from x, m, and $K^{-1}$ involving the first four components.

$$x'=\begin{bmatrix}x_1\\ x_2\\ x_3\\ x_4\end{bmatrix}\quad m'=\begin{bmatrix}m_1\\ m_2\\ m_3\\ m_4\end{bmatrix}\quad K'=\begin{bmatrix}(K^{-1})_{11} & (K^{-1})_{12} & (K^{-1})_{13} & (K^{-1})_{14}\\ (K^{-1})_{21} & (K^{-1})_{22} & (K^{-1})_{23} & (K^{-1})_{24}\\ (K^{-1})_{31} & (K^{-1})_{32} & (K^{-1})_{33} & (K^{-1})_{34}\\ (K^{-1})_{41} & (K^{-1})_{42} & (K^{-1})_{43} & (K^{-1})_{44}\end{bmatrix}$$

We also define a 4-dimensional vector v which contains the cross terms of $K^{-1}$ between the first four components and the last one.

$$v^T=\lfloor (K^{-1})_{51}(K^{-1})_{52}(K^{-1})_{53}(K^{-1})_{54}\rfloor$$

Then, we rewrite x, m, and K in terms of these newly defined quantities.

$$x=\begin{bmatrix}x'\\ x_5\end{bmatrix}\quad m=\begin{bmatrix}m'\\ m_5\end{bmatrix}\quad K^{-1}=\begin{bmatrix}K' & v^T\\ v & (K^{-1})_{55}\end{bmatrix}$$

Now we rewrite $\chi^2$ (x,m,K) in terms of these quantities.

$$\chi^2(x;m,K)=$$

$$(x-m)^TK^{-1}(x-m)=\begin{bmatrix}x'-m'\\ x_5-m_5\end{bmatrix}^T\begin{bmatrix}K' & v^T\\ v & (K^{-1})_{55}\end{bmatrix}\begin{bmatrix}x'-m'\\ x_5-m_5\end{bmatrix}=$$

$$(x'-m')^TK'(x'-m')+2(x_5-m_5)v^T(x'-m')+(K^{-1})_{55}(x_5-m_5)^2$$

Finally, we want to complete the square to express $\chi^2$ (x;m,K) as a symmetric quadratic form in the first four components plus a scalar term that depends only on the last component. To do so, we identify the symmetric quadratic form that has the same first two terms as in the above equation $$[(x'-m')+(x_5-m_5)(K')^{-1}v]^TK'[(x'-m')+(x_5-m_5)(K')^{-1}v]=$$

$$(x'-m')^TK'(x'-m')+2(x_5-m_5)v^T[(K')^{-1}K'](x'-m')+$$

$$(x_5-m_5)^2v^T[(K')^{-1}K'(K')^{-1}]v=$$

$$(x'-m')^TK'(x'-m')+2(x_5-m_5)v^T(x'-m')+(x_5-m_5)^2v^T(K')^{-1}v$$

Combining the two equations above, we have the desired result.

$$\chi^2(x;m,K)=(x'-m')^TK'(x'-m')+2(x_5-m_5)v^T(x'-m')+\big[$$

$$(x_5-m_5)^2v^T(K')^{-1}v-(x_5-m_5)^2v^T(K')^{-1}v\big]+(K^{-1})_{55}(x_5-m_5)^2=$$

$$[(x'-m')+(x_5-m_5)(K')^{-1}v]^TK'[(x'-m')+(x_5-m_5)(K')^{-1}v]+\big[$$

$$(K^{-1})_{55}-v^T(K')^{-1}v\big](x_5-m_5)^2$$

We introduce a new quantity m" to simplify the above equation.

$$m'=m'-(x_5-m_5)(K')^{-1}v$$

Now, we apply our new result to the inequality that defines the interior of the ellipsoid.

$$\chi^2(x;m,K)=(x'-m'')^TK(x'-m'')+\lfloor (K^{-1})_{55}-v^T(K')^{-11}v\rfloor (x_5-m_5)^2<t$$

The above equation suggests how to reduce the sampling of a 5-D lattice to sampling a set of 4-D lattices. First, we note that K' is non-negative definite since (K')−1 is non-negative definite and is therefore the covariance matrix of some 5-dimensional random variable. K' would be the covariance matrix of a 4-dimensional random variable that is generated by throwing out the last component.

Since K' is non-negative definite, the quadratic form involving K' is non-negative definite. Therefore, we have a constraint on possible values of $x_5$.

$$\big[(K^{-1})_{55}-v^T(K')^{-1}v\big](x_5-m_5)^2<t$$

$$(x_5-m_5)^2<\frac{t}{(K^{-1})_{55}-v^T(K')^{-1}v}$$

$$x_5\in\left(m_5-\sqrt{\frac{t}{(K^{-1})_{55}-v^T(K')^{-1}v}},\ m_5+\sqrt{\frac{t}{(K^{-1})_{55}-v^T(K')^{-1}v}}\right)\cap Z$$

So, in sequence, we set $x_5$ to each non-negative integer in the interval above. For a particular value of $x_5$, we have a resulting constraint on x' (i.e. the values of the other four components of x).

$$(x'-m'')^TK'(x'-m'')<t-\lfloor (K^{-1})_{55}-v^T(K')^{-1}v\rfloor (x_5-m_5)^2=t'$$

The above equation defines the interior of a 4-dimensional ellipsoid. In general, the axes of this ellipsoid will not correspond to the axes of the parent ellipsoid unless the coordinate axis happens to be an eigenvector. The volume of the ellipsoid is maximal when $x_5$ is equal to its mean, $m_5$.

We sample the lattice contained in this ellipsoid using the same technique, sampling a set of 3-D lattices. We continue to reduce the dimensionality at each step until we have a 1-D lattice; this can be sampled trivially.

To make this process as efficient as possible, the components may be ordered so that the component with the least variance is sampled first and the component with the most variance is sampled last (i.e., first sulfur, then nitrogen, oxygen, carbon, and hydrogen).

Elemental Compositions with a Given Mass

Let μ denote the 5-component vector of monoisotopic masses of carbon, hydrogen, nitrogen, oxygen, and sulfur respectively. Let x denote an arbitrary elemental composition of an N-residue peptide. Let M denote the mass of this peptide. As noted before, mass M can be expressed in terms of x and μ.

$$M = \sum_{i=1}^{5} \mu_i x_i$$

Let $u_M$ denote the unit vector parallel to μ.

$$u_M = \frac{\mu}{|\mu|}$$

Then, we can interpret the above equation for M in terms of the length of the projection of vector x onto $u_M$.

$$M = \sum_{i=1}^{5} \mu_i x_i = \mu \cdot x = |\mu|(u_M \cdot x)$$

Choose unit vectors $u_1 \ldots u_4$ so that together with $u_M$, these five vectors form a complete orthonormal basis for the five-dimensional vector space. Then, we can write x in terms of these basis vectors.

$$x = c_M u_M + \sum_{i=1}^{4} c_i u_i$$

Let U denote the matrix formed by stacking uM in the first column and u1 . . . u4 in the remaining four columns.

$$U=[u_M u_1 u_2 u_3 u_4]$$

We can write the above equation for x in matrix form.

$$x = Uc$$

$$c = U^T x$$

Now, substituting this representation for x into the mass equation, we see that mass M is independent of coefficients $c_1 \ldots c_4$.

$$M=|\mu|(u_M \cdot x)=|\mu|u_M{}^T Uc=|\mu|[1\ 0\ 0\ 0]c=|\mu|c_M$$

In other words, we can generate new vectors with the same mass by replacing $c_1 \ldots c_4$ in the above equation. The linear combinations of $c_1 \ldots c_4$ represent a 4-D plane; each arbitrary value of M describes a different parallel 4-D plane. However, most of these planes will not intersect the 5-D lattice (i.e., most planes will contain no points whose five components (in terms of the original C,H,N,O,S coordinate system) are all non-negative integers).

Now consider elemental compositions that are typical of N-residue peptides and also have masses in [M,M+D]. The region of space for which these constraints are satisfied approximately describes a (hyper)cylinder with special axis $Du_M$. The "base" of the cylinder is a 4-D ellipsoid. This ellipsoid is characterized immediately below.

Let b denote the vector of coefficients of m, the mean elemental composition of N-residue tryptic peptides, in terms of the coordinate system described by basis vectors U. Then, we write the inequality for typical elemental compositions in terms of U.

$$(x'-m'')^T K'(x'-m'')=(Uc-Ub)^T K^{-1}(Uc-Ub)=(c-b)^T (U^T KU)^{-1}(c-b)<t$$

If the mass of x equals M, then $c_M=|\mu|M$. Let U' denote the vector formed by stacking column vectors $u_1 \ldots u_4$ and c' and b' denote the components of $u_1 \ldots u_4$ in x and m respectively. Fixing one component reduces a 5-D ellipsoid to a 4-D ellipsoid.

$$(c-b)^T(U^T KU)^{-1}(c-b) = (c_M - b_M)^2(u_M^T K^{-1} u_M) + (c'-b')^T(U'^T KU')^{-1}(c'-b') < t$$

$$(c'-b')^T(U'^T KU')^{-1}(c'-b') < t - (c_M - b_M)^2(u_M^T K^{-1} u_M)$$

For adjacent values of M, the resulting ellipsoid will have slightly shorter or longer axes, but for small D, this effect can be ignored, resulting in a region of cylindrical geometry. We will describe how to identify elemental compositions in this region later, but for now, let's explore the density of elemental compositions per unit mass.

It is not straightforward to sample the lattice of elemental compositions enclosed by this cylinder. However, we can construct a lattice from $u_1 \ldots u_4$ as shown below. Let $n_i \ldots n_4$ denote arbitrary integer values. s denotes a scaling factor on the lattice basis vectors whose necessity will be explained shortly.

$$L = \left\{ \sum_{i=1}^{4} n_i(su_i) \,\middle|\, n_i \in Z \right\}$$

This lattice is relatively easy to sample. In general, none of the values on this lattice represent elemental compositions, but it is easy to find the nearest elemental composition by rounding each component to the nearest integer. To find an arbitrary elemental composition x whose mass is within ε (ε<½ Dalton) of M by this procedure, it is necessary that all components (in the original 5-D atom number coordinate system) differ by less than ½. We can guarantee this if the spacing between points on the sampling lattice is small enough so that there must be a lattice point within ½ unit of x.

Given lattice spacing s, we use the Pythagorean Theorem first to bound $d_{\|}$, the distance between x and the plane and then d, the distance between x and the closest lattice point on the plane.

$$d_{\parallel}^2 < 4\left(\frac{s}{2}\right)^2$$

$$d^2 = d_{\parallel}^2 + d_{\perp}^2 < 4\left(\frac{s}{2}\right)^2 + \varepsilon^2 = s^2 + \varepsilon^2$$

We require that d<1/2. Given ε, we set the right-hand side of the above equation to ¼ and solve for s to determine the lattice spacing necessary that guarantees finding all typical N-residue tryptic peptide elemental compositions whose mass is within ε Daltons of M.

$$s = \frac{\sqrt{1 - 4\varepsilon^2}}{2}$$

The above equation indicates that e<½ and s<½.

This exercise above motivates the construction of a table of typical elemental compositions. The above procedure involves sampling multiple 4-D lattices (for different peptide lengths) to find elemental compositions satisfying a single mass value. Alternatively, a database of all typical peptide masses can be constructed by sampling a set of 5-D lattices one time. Each elemental composition entry includes its mass and probability. The entries are sorted by mass.

To find the elemental composition closest to a given value of mass requires a binary search of the sorted entries. The number of iterations required to find an element is the logarithm base-two of the number of entries. Twenty iterations are sufficient to search a database of one million entries, thirty iterations for one billion.

A mass accuracy of roughly one part per thousand allows us to see that the mass of an atom is not the sum of the masses of the protons, neutrons, and electrons, from which it is composed. For example, a 12C atom contains six protons, six neutrons, and six electrons. The total mass of these eighteen particles is 12.099 atomic mass units (amu), while the mass of 12C is exactly (by definition) 12 amu. The deviation (824 ppm) is a consequence of mass-energy conversion, described by Einstein's celebrated equation $E=mc^2$. This effect is shown below for several isotopes below.

| | | | | |
|---|---|---|---|---|
| 1H | 1p1e | 1.007825 | 1.007825 | 0 |
| 12C | 6p6n6e | 12.098938 | 12 | 824 |
| 14N | 7p7n7e | 14.115428 | 14.003074 | 802 |
| 16O | 8p8n8e | 16.131918 | 15.994915 | 856 |
| 32S | 16p16n16e | 32.263836 | 31.972071 | 913 |

A mass accuracy of roughly one part per billion would be required to detect conversion of mass to energy in the formation of a covalent bond. The mass equivalent of a covalent bond (about 100 kcal/mol) is on the order of $10^{-8}$ atomic mass units. Therefore, we will not consider the effects of covalent bonding in calculation of molecular masses.

We will represent the exact mass of a molecule by the sum of the masses of the atoms from which the molecule is composed. Numerical representations of the exact mass will be considered to be accurate to at least 10 parts per billion. The masses of 1H, 12C, 14N, and 16O are known to better than one part per billion and the mass of 32S is known to about four parts per billion. Even if the atomic masses were known to greater accuracy, mass conversion associated with covalent bond formation would limit the accuracy of our simple model to about one part per billion. In this model, the exact masses of different isomers are represented by the same value. Therefore, there is a one-to-one correspondence between exact mass values and elemental compositions. This allows us the convenience of identifying exact masses by elemental compositions.

Consider the use of exact mass values in protein identification by peptide mass fingerprinting. This conventional application of this technique can be enhanced by the use of exact masses rather than measured masses. Suppose we have a list of nucleotide sequences of all human genes. From this, we construct a list of amino acid sequences resulting from translation of each codon in each gene. Then we construct a list of (ideal) tryptic fragments by breaking each amino acid sequence following each instance of Lys or Arg. Next to each entry we add the exact mass (i.e., accurate to 10 ppb) of each tryptic peptide. An observed exact mass value would be compared to each entry in the genomic-derived database by subtraction of masses. A difference of zero would receive a high score, indicating a perfect match of the elemental composition of the observed molecule and the in silico tryptic fragment derived from the canonical sequence of the gene. Differences equal to certain discrete values would suggest particular modifications of the canonical fragment (e.g., sequence polymorphism or post-translational modification). The score associated to such outcomes would indicate the relative probability of that type of variation. The statistical significance of a particular interpretation of the exact mass would be determined in the context of the relative probabilities of assigned to alternative interpretations.

Another application for exact mass values is spectrum calibration. In this case, suppose that some measurements of limited accuracy could be converted into exact mass values by some method. Calibration parameters would be adjusted to minimize the sum of squared differences between measured and exact mass values. Presumably, improved calibration would result in the ability to identify additional exact mass values. These additional values could be used to further improve the calibration in an iterative process. This method would allow calibration of each spectrum online, use all the information in each spectrum, and avoid the many drawbacks associated with adding calibrant molecules to the sample.

An exact mass value identifies the elemental composition. It is possible to produce a set of residue compositions for any given elemental composition. These compositions can include various combinations of post-translational modifications (that is, modifications involving C, H, N, O, and S). A list of residue compositions alone is no more informative about protein identity than an exact mass value, but does provide information when combined with fragmentation data. Information about the residue composition of a peptide improves confidence in identifying fragments measured with limited accuracy. When the fragmentation spectrum is incomplete, definite identification of even a few residues (perhaps aided by a list of candidate residue compositions) may be sufficient to identify the correct residue composition from the list. Given the residue composition, it may be possible to extract enough additional information from the spectrum to identify a protein.

Additional information can be found in the genome sequence, restricting the set of peptides one would expect to see in a proteomic sample. Canonical tryptic peptides, resulting from translation of the nucleotide sequence into an amino acid sequence and cleaving after lysine and arginine residues, are the most likely components of such a sample, but many variations are possible. Failure to consider sequence polymorphisms, point mutations, and post-translational modifications results in the inability to assign any identity to some peptides and misplaced confidence in those that are assigned. Construction of a database by directly enumerating possible variants would be prohibitively computationally expensive.

An alternative approach is to enumerate peptide elemental compositions. The set of elemental compositions contains all possible sequence variations and post-translational modifications involving the elements C, H, N, O, and S. With additional processing, the database can be used to consider modifications involving other elements also. The additional coverage provided by enumerating all elemental compositions comes at some cost in computation and memory. However, this cost is not as great as directly applying numerous modifications to each canonical peptide, since this method would count the same elemental composition each time it is generated by variation of a peptide.

Suppose we have a database for identifying the elemental compositions of peptides. If the mean spacing between mass values in the database is small compared with typical errors in measuring mass, it will be hard to identify peptides. Roughly speaking, two elemental compositions can be distinguished only if their mass separation exceeds the nominal mass accuracy of the measurement. The key question is how the density of elemental compositions varies with mass.

Identifiability is not an all-or-one phenomenon as suggested by this criterion. For example, suppose a mass value x were bracketed by values x−d and x+d. Measurement and subsequent identification of x would require a measurement error of less than d/2. A measurement accuracy of 1 ppm suggests that the measurement error is normally distributed with a standard deviation of 1 ppm. If d corresponds to 1 ppm of x, x would be identified measurement with 1 ppm accuracy less than 31% of the time. Now consider a set of values placed at random along a line with uniform density. The resulting distribution of spacings between adjacent points is exponential. As a result, if the mean spacing between points is 1 ppm, more than 13% of the spacings will be 2 ppm or greater. However, about 10% of the spacings will be 0.1 ppm or less. Finally, suppose that object A occurs with frequency 0.9 and ten other objects each occur with frequency 0.1. When an object is drawn, a guess that object A was drawn will be correct 90% of the time, even in the absence of a measurement that distinguishes the object.

Variations in the spacing between element compositions and in their frequencies produce variations in identifiability among them. A peptide with relatively low frequency must have significant spacing from its neighbors relative to the measurement error in order to be identifiable. A peptide occurring at relatively high frequency may be identifiable from a measurement with low accuracy. Furthermore, identifiability is not a binary property. Posterior probabilities that take into account both the evidence from the measurement and a priori knowledge are computed for all candidates. Identifiability depends upon the resulting discrete probability distribution.

Component 16: Bayesian Identifier for Tryptic Peptide Elemental Compositions Using Accurate Mass Measurements and Estimates of a priori Peptide Probabilities In bottom-up mass spectrometry, the proteomic composition of an organism is determined by identifying peptide fragments generated by tryptic digestion. Typically, peptide identification by mass spectrometry involves mass measurements of many "parent" ions in parallel (MS-1) followed by measurements of fragments of selected peptides one-at-at-time (MS-2). When the organism's genome sequence is known, peptides are identified from MS data by database search and subsequently matched to one or more proteins.

Because FTMS is capable very high mass accuracy (e.g., 1 ppm), a single (parent) mass measurement (MS-1) is often sufficient to determine a tryptic peptide elemental composition ("TPEC"). A TPEC often uniquely identifies a protein. Component 16 relates to the ability of accurate mass measurements to identify proteins in terms of a hypothetical benchmark experiment. Suppose we make mass measurements of 356,933 human tryptic peptides—one for each of the distinct TPECs derived from the IPI database of 50,071 human protein sequences. How many TPECs can be correctly determined given 1 ppm mass accuracy? How many proteins? How do the success rates vary with mass accuracy?

Describe herein is a Bayesian identifier for TPEC determination from a mass measurement. The performance of the identifier can be calculated directly as a function of mass accuracy. The success rate for identifying TPECs is 53% given 1 ppm rms error, 74% for 0.42 ppm, and 100% for perfect measurements. This corresponds to 28%, 43%, and 64% success rates for protein identification. The ability to identify a significant fraction of proteins in real-time by accurate mass measurements (e.g., by FTMS) enables new approaches for improving the throughput and coverage of proteomic analysis.

Cancer and other diseases are associated with abnormal concentrations of particular proteins or their isoforms. Therapeutic responses are also correlated to these protein concentrations. The ability to identify the protein composition of a complex proteomic mixture (e.g., serum or plasma collected from a patient) is the key technological challenge for developing protein-based assays for disease status and personalized medicine.

In parallel with proteomic methods, genome-wide assays have also been developed and demonstrated some success for probing disease. In some cases, the measurement of a gene transcript level is a good surrogate for the concentration of the corresponding protein. In other cases, however, variations in protein modification, degradation, transport, sequestration, etc., can cause large differences between relative transcript level and relative protein abundance. Furthermore, these variations themselves are often indicative of disease and would be missed in genomic assays.

Proteomic analysis in personalized medicine faces two related challenges: throughput and coverage. The ability to analyze proteomic samples rapidly is critical to using proteomic assays in clinical trials with a sufficiently large number of patients to discover factors present at low prevalence. In direct tension with the goal of high throughput is the need for a comprehensive view of the proteome that analyzes as many proteins as possible. The mismatch between the dynamic range of protein concentrations (10-12 orders of magnitude) and the dynamic range of a mass spectrometer (3-4 orders of magnitude) makes it impossible to analyze all proteins simultaneously. Separation of the sample into a large number of fractions is necessary to isolate and detect low abundance species.

"Bottom-up" proteomic mass spectrometry is a widely used method for identifying the proteins contained in a complex mixture. The proteolytic enzyme trypsin is added to a mixture of proteins to cleave each protein into peptide fragments. Trypsin cuts with high specificity and sensitivity following each arginine and lysine residue in the protein sequences, resulting in a set of peptides with exponentially distributed lengths and with an average length of about nine residues. Longer peptides are increasingly likely to appear in only one protein from a given proteome. Thus, identification of the peptide is equivalent to identifying the protein.

The typical method for identifying peptides by mass spectrometry is to separate a mixture of ionized peptides on the basis of mass-to-charge ratio (m/z) and then to capture a select ion, break it into fragments by one of a variety of techniques, and use measurements of the fragment masses to infer the peptide sequence. The two steps in this process are referred to as MS-1 and MS-2 respectively.

The most common method for sequencing peptides is tandem mass spectrometry (MS2). An MS2 experiment follows a typical MS1 experiment, in which all components in a fraction are analyzed (i.e., separated on the basis of mass-to-charge (m/z) ratio). Ions with a narrow window of m/z values are can be selected by the instrument with the goal selecting a single peptide of interest for further analysis by MS2. In the MS2 experiment, the peptide is broken into fragments, and the fragment masses are analyzed. In some cases, the peptide sequence can be correctly reconstructed de novo from the collection of fragment masses. Sometimes, it is possible to identify post-translationally modified peptides. In many cases, de novo sequencing does not succeed, but the most likely sequence can be inferred in the context of the putative protein sequences of an organism Peptide sequences provide considerable information about protein identity, but the information is gained at a considerable cost. A MS2 experiment dedicates an analyzer to determination of a single peptide. In contrast, the MS1 experiment is obtaining information about dozens, perhaps hundreds, of peptides in parallel. The mass accuracy of measurements performed by FTMS is on the order of 1 ppm. Mass accuracy of 1 ppm is sufficient in many cases to single out one peptide from an in silico digest of the human proteome.

An alternative to peptide sequencing is determining the elemental composition of the peptide by an accurate mass measurement. Peptide sequencing by tandem mass spectrometry has the drawback that collection of a spectrum is dedicated to the identification of a single peptide. In contrast, accurate mass measurements can be used to identify many peptides from one spectrum, resulting in higher throughput. It may seem that a peptide's sequence would provide substantially more information than an accurate mass measurement, because, at best, an accurate mass measurement can provide only the elemental composition of a molecule. In general, a very large number of sequences would have the same elemental composition. However, when there are a relatively small number of candidate sequences (e.g., human tryptic peptides), the elemental composition provides nearly as much information as the sequence, as demonstrated below.

Smith and coworkers defined the concept of an accurate mass tag ("AMT")—a mass value that occurs uniquely in an ideal tryptic digest of an entire proteome. Because an AMT could be mapped unambiguously to a single protein, detection of the AMT by an accurate mass measurement is essentially equivalent to detection of the protein that contained the fragment. The utility of the AMT approach has been demonstrated in small proteomes. Furthermore, the detection of AMTs has been used to estimate the mass accuracy requirements for analyzing various proteomes.

In larger proteomes, there are more tryptic peptides, leading to a larger number of distinct elemental compositions and also more occurrences of isomerism. The increased number of distinct elemental compositions increases the need for mass accuracy; the increased number of isomers does not. Isomers cannot be distinguished by mass, regardless of the mass accuracy. However, a fragmentation experiment that can distinguish isomers does not require high mass accuracy. Therefore, the requirement for mass accuracy depends only upon the number of distinct tryptic peptide masses (or elemental compositions).

Described below is a probabilistic version of an accurate mass tag approach and a demonstration of its utility in human proteome analysis. A good metric for assessing the performance of a proteomic experiment is the fraction of correct protein identifications. It is fundamentally problematic to perform this assessment in a real proteomic experiment because correct protein identities cannot be known with certainty (i.e., by another approach). Instead, it is useful to create a realistic simulation in which the correct answer is known but concealed from the algorithm, and data is simulated from the known state according to some model. An even better approach is to construct such a simulation as a thought experiment and to directly calculate the distribution of outcomes of the simulation (without actually performing the simulation repeatedly).

Suppose that a mixture consists of every human protein represented by a database of consensus human protein sequences. Suppose these proteins are digested ideally by trypsin; that is, each protein is cut into peptides by cleaving the sequence at each peptide bond following either an arginine or lysine residue, except when followed by proline. Then, suppose that the resulting mixture of peptides is sufficiently well fractionated so that the density of peaks is low and that the mass spectrometer has sufficiently high mass resolving power that peak overlap is rare. Although it may be possible to separate isomers by chromatography, we assume that peptides with the same elemental composition are not resolvable. Therefore, analysis of the tryptic peptide mixture results in one accurate mass measurement for each distinct elemental composition or mass value.

Measured masses reflect the true mass value and may lead to identification of a peptide. However, each mass measurement has an error, and the errors may be large enough to confound peptide identification. We assume that the errors in the mass measurements are statistically independent. We also assume that each measurement error is normally distributed, has zero mean (e.g., following proper calibration), and root-mean-squared deviation (rmsd) is proportional to the mass. The typical specification of an instrument's measurement accuracy is the constant of proportionality between the error and the actual mass. In FTMS, the mass accuracy is commonly expressed in ppm.

The aim is to identify the protein from which any given peptide was liberated by trypsin cleavage. First, we use a mass measurement derived from a spectrum to predict the elemental composition. We assume that the molecule giving rise to the observed peak resulted from ideal tryptic cleavage of a protein whose sequence appears in the database of human protein sequences. This assumption constrains the prediction, which would otherwise require significantly higher mass accuracy to discriminate the much larger set of possible elemental compositions. We construct a maximum-likelihood estimator to choose the most probable elemental composition of the peptide giving rise to each measured mass as described below.

Assume that the calculated tryptic peptide elemental compositions have been sorted by mass from smallest to largest, and have been enumerated (e.g., from 1 to N). Suppose that the mass of a peptide is measured with elemental composition of index i (in the sorted database) and mass $m_i$. Suppose that mass accuracy is x ppm. Let M denote the outcome of this measurement. Given the assumption that the error is normally distributed with zero mean and standard deviation $\sigma_x$ determined by the peptide mass and the mass accuracy (Equation 1b), the values of M are characterized by the probability density given by Equation 1a.

$$p(M \mid i; x) = \frac{1}{\sigma_i \sqrt{2\pi}} e^{-(M-m_i)/2\sigma_x^2} \tag{1a}$$

$$\sigma_i = \frac{x}{10^6} m_i \tag{1b}$$

Now, suppose that a value M represents the measurement of an unknown elemental composition, and a probability is to be assigned to each entry in the database (i.e., that the measured peptide has a given elemental composition). If all elemental compositions were equally likely before the measurement, the probability of any given peptide would be proportional to Equation 1a, where the index i takes on all values from 1 to N. In fact, peptides are not equally likely a priori: some peptides belong to proteins whose abundance is known to be relatively high; other peptides might be predicted to elute at a certain retention time; other peptides might be predicted not to elute at all or to ionize well. Even randomly generated peptides have a highly non-uniform distribution of elemental compositions.

None of the above information is assumed, but instead it is assumed that the probability that a given elemental composition is observable is proportional to the number of times it occurs in the proteome. This model describes a situation where the probability of observing any particular peptide is low. For example, most proteins may have abundances that are below the instrument's limit of detection. It has been suggested there is a relatively small fraction of proteotypic peptides (i.e., peptides observable by a typical mass spectrometry experiment). Therefore, the probability that a mass value M corresponds to a peptide with elemental composition i given is given by Equation 2.

$$p(i \mid M; x) = \frac{n_i p(M \mid i; x)}{\sum_{j=1}^{N} n_j p(M \mid j; x)} \tag{2}$$

The sum in the denominator is taken over all elemental compositions in the proteome so that when the expression is summed over all values of i from 1 to N, the result is one.

Now, a maximum-likelihood estimator is defined (Equation 3). Given measurement M and mass accuracy x, the prediction for the elemental composition, denoted by I(M;x), an index in the range from 1 to N, is the elemental composition with the highest probability, as computed in Equation 2.

$$I(M; x) = \underset{i \in [1 \ldots N]}{\operatorname{argmax}} [p(i \mid M; x)] \tag{3}$$

Equation 3 can be rewritten in terms of the masses and number of occurrences of the tryptic peptide elemental compositions. The denominators in the right-hand sides of Equations 1 and 2 are constant over various candidates and can be removed when evaluating the maximum.

$$I(M) = \underset{i \in [1 \ldots N]}{\operatorname{argmax}} [n_i p(M \mid i)] = \underset{i \in [1 \ldots N]}{\operatorname{argmax}} \left\lfloor n_i e^{-(M-m_i)/2\sigma_x^2} \right\rfloor \tag{4}$$

Each possible value for a mass measurement (i.e., the real line) can be mapped to an elemental composition that is most probable for that measurement. Let $R_i$ denote the set of values for which the maximum-likelihood estimator returns elemental composition i.

$$R_i = \{M : I(M) = i\} \tag{5}$$

The boundaries between regions for adjacent elemental compositions i and k with masses $m_i$ and $m_k$ respectively are determined by solving Equation 6.

$$p(i|M) = p(k|M) \Longleftrightarrow n_i e^{-(M-m_i)/2\sigma_x^2} = n_k e^{-(M-m_k)/2\sigma_k^2} \tag{6}$$

Because $m_i$ and $m_j$ differ by parts-per-million, it is a very good approximation to set $\sigma_k = \sigma_i$. Let M(i,k) denote the value of M that solves Equation 6.

$$M(i, k) = \frac{m_i + m_k}{2} + \sigma_i^2 \frac{\log(n_k / n_i)}{m_i - m_k} \tag{7}$$

Because Equation 6 has exactly one solution, each region $R_i$ is an open interval of the form $(M_i^{lo}, M_i^{hi})$ where $M_i^{lo}$ and $M_i^{hi}$ are given by Equations 8ab.

$$M_i^{lo} = \max_{k<i} [M(i, k)] \qquad M_i^{hi} = \min_{k>i} [M(i, k)] \tag{8ab}$$

The $M_i^{hi} < M_i^{lo}$ is interpreted to mean that $R_i$ is an empty interval.

A special case of Equation 7 is equal abundances (i.e., $n_i = n_k$). In this case, M(i,k) is the midpoint between $m_i$ and $m_k$. When all abundances are equal, the maximum-likelihood estimator can be specified simply and intuitively: "Choose the peptide mass closest to the measured value."

When the abundances of two peptides differ, the decision rule is less obvious. The value of M(i,k)—the boundary for the decision rule—moves closer to the less abundant mass value. The size of the shift away from the midpoint is linear in the log-ratio of the abundance ratio and the error variance. A peptide mass of low abundance may be overshadowed by neighbors of high abundance, so that, at a given mass accuracy, there are no measurement values for which that peptide is the maximum likelihood estimate. It would be said that this elemental composition is unobservable at this mass accuracy; improved mass accuracy would be necessary to identify such a peptide.

For each observable elemental composition, it is desirable to know how often a measurement of that elemental composition results in a correct identification by the estimator described above. Consider elemental composition k with mass $m_k$. Let M denote the (random) outcome of a measurement of the peptide. Let P(k;x) denote the probability that the elemental composition k is correctly estimated from random measurement M (i.e., that I(M)=k). This is also the probability that M, drawn randomly from p(M|k;x), is in $R_k$.

$$p(k;x)=\int_{R_k}p(M\mid k;x)\,dM=\int_{M_k^{lo}}^{M_k^{hi}}p(M\mid k;x)\,dM \tag{9}$$

For unobservable peptides, p(k;x)=0.

Because p(M|k;x) is Gaussian (Equation 2), Equation 9 is written in terms of the error function.

$$p(k;x)=\frac{1}{2}\left[erf\left(\frac{M_k^{hi}}{\sqrt{2}\,\sigma_k}\right)-erf\left(\frac{M_k^{lo}}{\sqrt{2}\,\sigma_k}\right)\right] \tag{10a}$$

$$erf(z)=\frac{2}{\sqrt{\pi}}\int_{-\infty}^{z}e^{-t^2}\,dt \tag{10b}$$

If there is one mass measurement for each human tryptic peptide elemental composition, the expected fraction of correct identifications at mass accuracy x is the average of p(k;x) over k.

$$\langle f_{correct}^{EC}(x)\rangle=\frac{1}{N}\sum_{k=1}^{N}p(k;x) \tag{11a}$$

The standard deviation in the fraction of correct identifications can be computed.

$$\sigma_{f_{correct}^{EC}}=\frac{1}{N}\left[\sum_{k=1}^{N}p(k;x)-\sum_{k=1}^{N}p(k;x)^2\right]^{1/2}<\frac{1}{\sqrt{N}} \tag{11b}$$

The maximum-likelihood prediction of the elemental composition is used to predict the protein that contained the peptide. If the elemental composition occurs once in the proteome, the protein identity is unambiguous. In general, suppose that $N_k$ denotes the number of proteins that contain a tryptic peptide with elemental composition k. If it is assumed that all proteins containing that peptide are equally likely to be present, a random guess among $N_k$ proteins would be correct with probability $1/N_k$. In an alternate embodiment of the invention, the odds can be improved by taking into account other identified peptide masses from the candidate proteins.

To calculate the expected fraction of correct protein identifications from measurements of the entire complement of human tryptic peptides, Equation 11a is used, replacing p(k; x) with p(k;x)/$N_k$.

$$\langle f_{correct}^{P}(x)\rangle=\frac{1}{N}\sum_{k=1}^{N}\frac{p(k;x)}{N_k} \tag{12}$$

In the case of unlimited mass accuracy, x=0 and p(k;x)=1 for all k. That is, all elemental compositions are determined with certainty. Because some proteins contain tryptic peptides with the same elemental composition, proteins are not determined with certainty even for perfect mass measurements. Replacing the numerator of the summand in Equation 12 with 1 defines a limit on protein identification from a single accurate mass measurement.

Finally, suppose that the sequence (rather than an accurate mass measurement) is available. If $N'_s$ denotes the number of proteins containing a tryptic peptide with sequence s, and S denotes the number of distinct tryptic peptide sequences, the expected fraction of correct protein identifications can be computed, given sequence information.

$$\langle f_{correct}^{S}(x)\rangle=\frac{1}{S}\sum_{s=1}^{N}\frac{1}{N'_s} \tag{13}$$

In Silico Tryptic Digest of Human Protein Sequences

A list of human protein sequences was downloaded from the International Protein Index. All subsequent operations on this data were performed by in-house programs written in C++, unless otherwise indicated. First, an in silico protein digest was performed on the "mixture" of proteins in the database. Each protein sequence (represented by a text string of one-letter amino acid codes) was partitioned into a set of substrings (each representing an ideal tryptic peptide sequence) by breaking the string following each K or R except when either was followed by P; representing the idealized selectivity of trypsin cleavage.

The sequence of each tryptic peptide was converted into an elemental composition by summing the elemental compositions of each residue in the peptide. The elemental composition was used to calculate the "exact mass" of the monoisotopic form of the peptide by summing the appropriate number of monoisotopic atomic masses. The UNIX commands sort and uniq were used, respectively, to sort the peptides by mass and to count the number of peptides of each distinct mass value. A list of distinct peptide sequences using the uniq command was also generated.

Exact Mass Determination by Maximum Likelihood

The list of distinct tryptic peptide mass values was used to calculate the expected fraction of correct elemental composition identifications from mass measurements as a function of mass accuracy. The first step was to calculate the boundaries of the regions that map measurements into maximum-likelihood elemental composition predictions (Equation 8).

This calculation was performed by first initializing $M_1^{lo}$ to zero and calculating the boundary M(1,2) between peptide mass $m_1$ and its neighbor above $m_2$ (Equation 7). It is not necessary to compute the boundary M(i,k) for every pair i and k. Instead, we loop through the values of k from 2 to N. For each value of k, we loop through values of i starting with k−1 and decrementing i as necessary until finding a value for which $M(i,k)>M_i^{lo}$. When $M(i,k)<M_i^{lo}$, then peptide mass i is unobservable, and $M_i^{hi}$ is set to $M_i^{lo}$ (i.e., to specify an empty interval). When $M_i^{lo}>M(i,k)$, then $M_k^{lo}$ and $M_i^{hi}$ are both set to M(i,k), completing the inner loop on index i.

After completing the outer loop (on index k), the boundaries of all maximum-likelihood regions $R_k$ are defined. Next, for each elemental composition k, p(k;x) was calculated (Equations 9 and 10)—the probability that a measurement of a peptide of elemental composition k would result in a correct identification. The probability is the integral of the probability density function p(M|k,x) (Equation 2) inside the boundary region $R_k$ (Equation 5).

Performance Metrics

For various mass accuracies, denoted by x ppm rmsd, the expected fraction of correct identifications of the peptide elemental composition was computed (Equation 11). The proteome average for correct identifications of the protein from which the peptide originated was also computed (Equation 12) as a function of mass accuracy x. Finally, the fraction of correct protein identifications that would result from the known sequence of the peptide was computed (Equation 13).

In Silico Digest of the Human Proteome

Summary statistics of the tryptic peptides resulting from an in silico digest of the human protein sequences listed in the International Protein Index are given in table below. The database contains 50,071 human protein sequences. Ideal tryptic digest generated 2,516,969 peptides. Of these, 1181 peptides contain uncertainties in amino acid residues denoted by codes X, B, or Z in the database; these peptides are eliminated. The remaining 2,515,788 peptides range in mass from 238 (C-terminal) occurrences of G (75.03202841 Da) to a 237 kD peptide of 2375 residues, containing 100 23-residue repeats.

TABLE

| Ideal Human Tryptic Peptides | | |
|---|---|---|
| Protein sequences | 50,071 | |
| Tryptic peptides | 2,516,969 | |
| Tryptic peptides of unambiguous sequence | 2,515,788 | |
| Distinct sequences | 808,076 | |
| Uniquely occurring sequences | 471,572 | (58.4%) |
| Distinct elemental compositions | 356,933 | |
| Uniquely occurring elemental compositions | 166,813 | (46.7%) |

Among the tryptic peptides, there are 808,076 distinct sequences. Short sequences occur many times in the proteome. The most extreme examples are K and R, which occur 135,611 and 131,338 times, respectively. Highly degenerate sequences like these provide essentially no information about protein identity. However, 471,572 of these sequences (58.4%) occur once in the proteome, indicating that the peptide arose from a particular protein.

There are 356,933 distinct mass values or elemental compositions. 166,813 of these distinct mass values (46.7%) occur once in the proteome. The remaining 53.3% of elemental compositions represent groups of two or more isomers. Some isomers are related by sequence permutation; many of these are short sequences. For example, the sequence DECK and the five other tryptic peptides that result from shuffling DECK (DCEK, EDCK, ECDK, CEDK, and CDEK) all occur in the database. Other isomers have distinct combinations of amino acid residues, but the same elemental composition. For example, six other peptides (DTQM, DVCAS, EGSVC, ENMT, GSEVC, TEAAC) also occur in the database. Like DECK, these six also have the chemical formula $C_{18}H_{31}N_5O_9S$ and mass 493.1842483 Da. These isomers can be thought of as shuffling DECK at the atomic level, rather than the amino acid residue level.

Expected Number of Correct Identifications

Correct identification of an elemental composition, roughly speaking, requires that the measured mass lie closer to the true mass value than to the mass values of the elemental compositions of other tryptic peptides in the proteome. The rate of correct identifications depends critically upon the distribution of tryptic peptide masses.

A distribution of ideal human tryptic peptide masses from the IPI database, first with all peptides represented equally and then with groups of multiple isomeric peptides each collapsed to a single count (i.e., the distribution of distinct peptide masses) was created (not shown). The distribution of tryptic peptide masses is approximately exponential when all peptides are represented equally, as would be expected for any homogeneous fragmentation process. The parameter of the exponential distribution λ (the mean and variance of peptide mass) agrees with the theoretical value calculated in Equation 14.

$$\lambda = \frac{\langle \text{residue mass} \rangle}{(f_R + f_K)(1 - f_P)} \tag{14}$$

The corresponding distribution of distinct peptide masses is suppressed in the low mass region by collapsing very large groups of isomers into single counts. The density of distinct peptide masses can be thought of as the ratio of the number of tryptic peptides per unit mass divided by the average isomeric degeneracy of each elemental composition. At the peak density (about 1500 Da), the exponential drop in the number of large peptides overtakes the polynomial decrease in elemental composition degeneracy.

In a zoomed-in view (not shown) of the mass distribution in the region around 1000 Da, at each (integer-valued) nominal mass, there is a bell-shaped distribution of mass values, first noted by Mann. This is a consequence of the nearly integer values of the atomic masses and the regularity of peptide elemental compositions. The clustering of peptide masses reduces the average spacing between adjacent masses; higher mass accuracy is required to identify human tryptic peptides than would be needed to identify the same number of uniformly spaced masses.

In a view (not shown) of the same mass distribution at the highest level of magnification, five discrete peptide masses are present in the range 1000.44-1000.45 Da, labeled A-E. Peptide mass B is separated from its nearest neighbors by several parts per million and thus easily identified by a measurement with 1 ppm accuracy. In contrast, peptide D is so close to its nearest neighbors that it would require much higher mass accuracy to identify.

In the unnormalized identification probabilities (the numerator of Equation 2) for each of the five elemental compositions A-E as a function of measurement value, each curve is a Gaussian, centered at the peptide mass, having a width proportional to the measurement error (10ˆ6 xm), and scaled by the number of occurrences of the elemental composition in the proteome. Curves for 0.42 ppm mass accuracy and 1 ppm mass accuracy were created (not shown). These two values represent respectively the mass accuracy achieved on a ThermoFisher LTQ-FT under typical proteomic data-collection conditions.

Based on maximum-likelihood decision regions for peptide masses A-E (not shown), it was determined that peptide D is completely overshadowed by adjacent peptides. An empty decision region indicated that there was no measurement for which D was the most likely elemental composition; it was unobservable at 1 ppm mass accuracy. However, at 0.42 ppm mass accuracy, 46% of the random measurements of peptide D would result in correct identification.

The probability of a correct identification (not shown), given that the actual peptide elemental composition is i, is the probability that the measurement of peptide i lies inside the region ($M_i^{lo}$, $M_i^{hi}$).

To provide a model simple enough to allow the calculations performed above, the result of tryptic digest of a human proteomic sample (e.g., serum or plasma) was modeled by an in silico digest of a human protein sequence database. The differences between an in silico digest and an actual digest of a proteomic sample were addressed to assess the validity of these calculations. An important difference was that for each protein sequence in the database, there is a very large number of variant protein isoforms within a population and perhaps coexisting within the same sample. Biological factors causing these differences include somatic mutations, alternative splicing, sequence polymorphisms, and post-translational modification. In addition, experimental factors including incomplete or non-specific trypsin cleavage, ion fragmentation, chemical modifications, and adduct formation can cause further confounding differences in elemental composition. The very large number of potential peptides would seem to dramatically reduce identifiability. To achieve better coverage of the proteome, one would need to account for variant peptides.

Ironically, the enormous number of potential variant peptides makes the vast majority of them unobservable. There are two factors reducing observability: the very low a priori probability that any given variant peptide will be present in a sample and the relatively low abundance of most variant peptides that are present. Most peaks that are large enough to be observed are likely to be unmodified peptides. To address variant peptides, one would assign an intensity distribution to each modified peptide—perhaps using semi-empirical rules—to allow a probabilistic interpretation of any given peptide based upon identity.

It was recognized that the error rate in peptide identification from real tryptic digests is reduced by a multiplicative factor from the error rate computed from an ideal digest of consensus protein sequences. Every variant protein would be misidentified in the current scheme, if not in the elemental composition, then certainly in the protein identity. Therefore, if the fraction of observed peaks arising from variant peptides is p, then the actual success rate in identifying proteins is reduced by a multiplicative factor of (1-p). The value of the crucial parameter p depends not only upon the sample and the data collection protocol, but also upon the sensitivity and resolving power of the instrument; the ability to detect low abundance species will discover an increasing proportion of modified peptides. Estimates of p can be obtained by careful analysis of de novo identification trials by tandem mass spectrometry.

Even when dealing with ideal tryptic peptides, there are two factors that lead to incorrect protein identifications from accurate mass measurements: limited mass accuracy and degeneracy in the mapping from peptide masses to proteins. Given limited mass accuracy, measurement error can shift the measured value of the peptide mass closer to the mass of another peptide elemental composition in the database, resulting in error in identifying the elemental composition. Even when the elemental composition has been correctly determined, protein identification is confounded when multiple proteins contain tryptic peptides with the same elemental composition, and even the same sequence.

The probabilistic approach described in Component 16 recognizes the uncertain nature of protein identification. For example, mass accuracy of 1 ppm does not mean that two peptides with spacing greater than 1 ppm can be discriminated with 100% accuracy or conversely that two peptides with spacing less than 1 ppm cannot be discriminated at all.

It was also recognized that peptide masses that occur multiple times in the proteome are informative when they can be identified. Even though mass values shared by two peptide isomers do not satisfy the stringent criterion to be an AMT, one bit of information is all that is needed to distinguish them. Such properties include the chromatographic retention time, properties of the isotope envelope, or a single sequence tag obtained by multiplexed tandem mass spectrometry.

The amount of additional information needed to identify a protein following an accurate mass measurement can be determined in real-time and used to guide subsequent data collection and analysis to optimize throughput. For example, some measurements will identify a protein directly; others will not provide much information; but still others belong to an intermediate class of measurements that rule out all but a small number of possible proteins whose identity can be resolved by an additional high-throughput measurement. The method for discrimination is indicated by the number and particular proteins involved. In this way, the present analysis demonstrates the capacity not only to identify proteins directly, but also to guide a strategy for optimizing the success rate of protein identifications at a given throughput rate by making selected supplemental observations.

Another important consideration, not directly addressed in this analysis, is that a protein of typical length will be cleaved by trypsin into about 50 peptides. Some of these peptides are not observable for a variety of reasons, including extreme hydrophobicity or hydrophilicity that prevents chromatographic separation, extremely low or high mass, or inability to form a stable ion. Suppose that a protein yields N tryptic peptides that are abundant enough to be detectable as a peak in a mass spectrum. Suppose that the success rate for identifying peptides is (uniformly) p. Then, the probability that at least one of these peptides leads to a correct identification is $1-(1-p)N$. For example, for $N=5$ and $p=0.2$, the probability of a correct protein identification is 67%. For $N=5$ and $p=0.5$, it increases to 97%.

Proteins in a biological sample will be represented by widely varying numbers of observable peptides. For example, one would expect many, perhaps most, proteins to have abundances below the limit of detection. In general, the distribution of abundances would be expected to be exponential. The fact that the distribution of observable peptides per protein is non-uniform also provides information that can be used to link peptides to proteins: it is more likely that a peptide whose origin is uncertain came from a protein for which there is evidence of other peptides than from a protein not linked to any observed peptides. Probabilistic analysis allows information from the entire ensemble of peptides to be integrated in identifying proteins. It is believed that the presence of multiple peptide observations for many proteins will considerably boost protein identifications above the values computed for single peptide observations.

Mass accuracy requirements for peptide identification have been examined independently of proteomes. Zubarev et al. observed that mass accuracy of 1 ppm is sufficient for determination of peptide elemental composition up to a mass limit of 700-800 Da and determination of residue composition up to 500-600 Da. However, the vast majority of the peptides considered in the present analysis are unlikely to be observed in a given proteome, or perhaps in any proteome. Furthermore, the criterion of absolute identifiability is unnecessarily stringent.

In Component 16, it is possible to identify elemental compositions in the limited context of ideal human tryptic peptides; that is, only ideal tryptic cleavages of the consensus human sequences listed in a database are considered. As a result, there is a rather small pool of candidate elemental compositions. Many of these elemental compositions have masses separated from their nearest neighbors by several ppm, allowing confident identification by a measurement with 1 ppm mass accuracy. For a given mass accuracy, the ability to discriminate among elemental compositions depends crucially upon the distribution of masses.

Genomic analysis, while less informative, avoids many of the technical difficulties of proteomics. The ability to amplify transcripts present at low-copy number by PCR does not have a protein analog. As a result, the detection of low-abundance proteins, especially in the presence of other proteins at very high abundance, is a severe limitation of proteomic analysis.

Component 17: A Fast Algorithm for Computing Distributions of Isotopomers

A fundamental step in the analysis of mass spectrometry data is calculating the distribution of isotopomers of a molecule of known stoichiometry. A population of molecules will contain forms which have the same chemical properties, but varying isotopic composition. These forms (isotopomers), by virtue of their slightly varying masses, are resolved as distinct peaks in a mass spectrum. The positions and amplitudes of this set of peaks provide a signature, from which a signal arising from a molecular species can be distinguished from noise and from which, in principle, the stoichiometry of an unknown molecule can be inferred.

Component 17 describes an efficient algorithm for computing isotopomer distributions, designed to compute the exact abundance of each species whose abundance exceeds a user-defined threshold. Various aspects of this algorithm include representing the calculation of isotopomers by polynomial expansion, extensive use of a recursion relation for computing multinomial expressions, and a method for efficiently traversing the abundant isotopic species.

Polynomial Representation of Isotopomer Distributions

In the development of this algorithm, it is assumed that each atom appearing in a molecule is selected uniformly from a naturally occurring pool of isotopic forms of that element and that the abundance of each isotopic species is known for each element. The table below provides a partial list of isotopes, their masses, and relative abundances given as percentages.

| | | | | |
|---|---|---|---|---|
| C | 12.000000 | 98.93 | 13.003355 | 1.07 |
| H | 1.007825 | 99.985 | 2.014102 | 0.015 |
| N | 14.003074 | 99.632 | 15.000109 | 0.368 |
| O | 15.994915 | 99.757 | 16.999131 | 0.038 |
| | 17.999159 | 0.205 | | |
| S | 31.972072 | 94.93 | 32.971459 | 0.76 |
| | 33.967868 | 4.29 | 35.96676 | 0.02 |
| P | 30.973763 | 100.00 | | |

The distribution of isotopomers can be represented elegantly using a polynomial expansion. This is most easily demonstrated by example. The distribution of the 10 isotopomers of methane ($CH_4$) can be computed as shown in Equation 1.

$$\begin{aligned} P(CH_4) = P(C)*[P(H)]^4 &= [0.9893(^{12}C) + 0.0107(^{13}C)]* \quad \text{Equation 1}\\ &[0.99985(^1H) + 0.00015(^2H)]^4 = \\ &(0.9893(^{12}C) + 0.0107(^{13}C))*((0.99985)^4(^1H)_4 + \\ &4(0.99985)^3(0.00015)(^1H)_3(^2H) + \\ &6(0.99985)^2(0.00015)^2(^1H)_2(^2H)_2 + 4(0.99985) \\ &(0.00015)^3(^1H)(^2H)_3 + (0.00015)^4(^2H)_4) = \\ &(0.9893)(0.99985)^4((^{12}C)(^1H)_4 +) + \\ &(0.0107)(0.99985)^4((^{13}C)(^1H)_4) + \\ &4(0.9893)(0.99985)^3(0.00015)((^{12}C)(^1H)_3(^2H)) + \\ &4(0.0107)(0.99985)^3(0.00015)((^{13}C)(^1H)_3(^2H)) ++ \\ &(0.9893)(0.99985)^2(0.00015)^2((^{12}C)(^1H)_2(^2H)_2) + \end{aligned}$$

-continued $$\begin{aligned} &6(0.0107)(0.99985)^2(0.00015)^2((^{13}C)(^1H)_2(^2H)_2) + \\ &4(0.9893)(0.99985)(0.00015)^3 \\ &((^{12}C)(^1H)(^2H)_3 + 4(0.0107)(0.99985) \\ &(0.00015)^3((^{13}C)(^1H)(^2H)_3) + \\ &(0.9893)(0.00015)^4((^{12}C)(^2H)_4) + \\ &(0.0107)(0.00015)^4((^{13}C)(^2H)_4) \\ &0.988707((^{12}C)(^1H)_4) + 0.0106936((^{13}C)(^1H)_4) + \\ &0.000593313((^{12}C)(^1H)_3(^2H)) + \\ &6.41711\cdot 10^{-6}((^{13}C)(^1H)_3(^2H)) + \\ &1.33515\cdot 10^{-7}((^{12}C)(^1H)_2(^2H)_2) + \\ &1.44407\cdot 10^{-9}((^{13}C)(^1H)_2(^2H)_2) \\ &1.33535\cdot 10^{-11}((^{12}C)(^1H)(^2H)_3) + \\ &1.44428\cdot 10^{-13}((^{13}C)(^1H)(^2H)_3) + \\ &5.00833\cdot 10^{-16} + 5.41687\cdot 10^{-18}((^{13}C)(^2H)_4) \end{aligned}$$

The abundance of each isotopic species appears as the coefficient of the corresponding term in the polynomial.

In general, the isotopomer distribution for a molecule with arbitrary chemical formula ($E_1n_1\ E_2n_2 \ldots E_Mn_M$) can be calculated by expanding the polynomial in Equation 2.

$$P((E_1)_{n1}(E_2)_{n2} \ldots (E_M)_{nM}) = (P(E_1))^{n1}(P(E_2))^{n2} \ldots (P(E_M))^{nM} \quad (2)$$

If element E has q naturally occurring isotopes with mass numbers $m_1, m_2, \ldots m_q$ and abundances $p_1, p_2, \ldots p_q$ respectively, the expression P(E) has the form $p_1\ (^{m1}E)+p_2\ (^{m2}E)+ \ldots p_q\ (^{mq}E)$ Multinomial Expansion The calculation of factors of the form $P(E)^n$, which appear on the right-hand side of Equation 2, is a key step in the isotopomer distribution calculation. The interpretation of $P(E)^n$ is as follows: sample n atoms of the same element type uniformly from the naturally occurring isotopic variants of this element and group the atoms by isotopic species. For example, a possible result is $n_i$ atoms of species 1, $n_2$ atoms of species 2, etc. The terms in the expansion of the polynomial $P(E)^n$ represent all possible outcomes of this experiment and the coefficient associated with each term gives the probability of that outcome. For even picomolar quantities of a substance, the numbers of molecules are so large that observed abundances and calculated probabilities are essentially equivalent.

The representation of isotopomers by polynomials is compact, but for operational purposes, cannot be taken too literally. For large molecules, the values of $n_1 \ldots n_M$ may be so large that direct expansion of the polynomial would be computationally intractable. For example, direct expansion of the polynomial representing the partitioning of 100 carbon atoms into isotopic species would require $2^{100}$ ($\sim 10^{30}$) multiplications.

Rather than brute-force calculation of the polynomial by n-fold multiplication, the multinomial expansion formula is used to evaluate these coefficients. The multinomial expansion formula is given by the Equation 3a-c, $$(p_1x_1 + p_2x_2 + \ldots p_qx_q)^n = \sum_{(\sum ki=n} P(k,\ p)x_1^{k1}x_2^{k2} \ldots x_q^{kq} \quad (3abc)$$

-continued $$P(k,\ p) = \ < (m; k_1, k_2, \ldots\ k_q) p_1^{k1} p_2^{k2}\ \ldots\ p_q^{kq}$$

$$M(n; k_1, k_2, \ldots\ k_q) = \begin{pmatrix} n \\ k_1\ k_2\ \ldots\ k_q \end{pmatrix} = \frac{n!}{k_1!k_2!\ \ldots\ k_q!}$$

where k denotes the vector of exponents ($k_1$, $k_2$, . . . $k_q$) and p denotes the vector of probabilities ($p_1$, $p_2$, . . . $p_q$). The multinomial expression M(n;$k_1$, $k_2$, . . . $k_q$) in equation 3c gives the number of ways that n distinguishable objects can be partitioned into q classes with $k_1$, $k_2$, . . . $k_q$ elements in the respective classes.

Avoiding Overflow and Underflow in Calculating Multinomials

In general, the right-hand side of Equation 3c can not be calculated directly. For large values of n, calculation of n! would produce overflow errors. In fact, the value of the right-hand side of Equation 4 often would produce an overflow for most states associated with large n.

However because the values of P(k,p) (Equation 3b) represent probabilities, these terms must be less than one so these can be computed without overflow if the various multiplicative factors are introduced judiciously. To compute P(k,p), first three lists of factors are made:

$$v_1 = [\,n \quad n-1 \quad \ldots \quad n-k_1+1\,],$$

$$v_2 = [\,k_2 \quad k_2-1 \quad \ldots \quad 2 \quad k_3 \quad k_3-1 \quad \ldots \quad 2 \quad \ldots \quad k_q \quad k_q-1 \quad \ldots \quad 2\,]$$

$$v_3 = [\,p_1 \quad p_1 \quad \ldots \quad p_1 \quad p_2 \quad p_2 \quad \ldots \quad p_2 \quad \ldots \quad p_q \quad p_q \quad \ldots \quad p_q\,]$$

In $v_3$, $p_1$ appears $n_1$ times, $p_2$ appears $n_2$ times, etc. Without loss of generality, $k_1$ is chosen to be the largest component of k (i.e., sort of the isotopes by abundance). Then, $v_1$ has n-$k_1$ elements, $v_2$ has (n−$k_1$)−(q−1) elements, and $k_3$ has n elements.

To avoid overflow errors, P(k,p) is computed as an accumulated product, introducing factors from each list in sequence as follows: multiply by a factor from $v_1$ if the accumulated product is less than or equal to one and divide by a factor from $v_2$ or multiply by a factor from $v_3$ whenever the list is greater than one or after all the terms from $v_1$ have been used.

Calculation of P(k,p) involves at most 3n multiplies and divides. However, only P(k,p) need be computed in this way for one value of k and successive applications of the recursion relation, given in equation 4, can be used to compute all other values of k.

$$p(k_1, \ldots (k_i+1), \ldots (k_j-1), \ldots k_q, p_1, p_2, \ldots p_q) = \left(\frac{k_j}{k_i+1}\right)\left(\frac{p_i}{p_j}\right) P(k_1, \ldots k_i, \ldots k_j, \ldots k_q, p_1, p_2, \ldots p_q) \tag{4}$$

The recursion relation allows the computation of a state probability from the probability of a "neighboring" state using a total of four multiplies and divides.

Efficient Sampling of Abundant Isotopomers

In realistic situations, most of the probability mass in an isotopomer distribution resides in a relatively very small fraction of the terms. While arbitrary precision is desirable, it may be undesirable to spend most of the time computing terms with vanishingly small probabilities.

A reasonable solution is to allow the user to specify a threshold probability t so that no terms with probability below the threshold are to be returned by the algorithm. In fact, it may be desirable for the algorithm to avoid computing such terms as much as possible. This requires a traversal of the state vectors k=($k_1$, $k_2$, . . . $k_q$) that satisfy the constraint that $k_1$+$k_2$+ . . . $k_q$=n and with P(k,p)>t. Each time a new state is encountered, its probability is calculated and the process terminated when all states with P(k,p)>t have been visited.

A key property of an efficient method for traversing the states is maximizing the number of moves between connected states to allow use of the recursion relation to compute state probabilities P(k,p). Moves between states that are not connected require storing previously computed values of the probabilities. Another important property is to minimize collisions (i.e., moving to the same state multiple times during the traversal). Another important property is to minimize the number of moves to states with P(k,p)<t. This requires a way of "knowing" when all states with P(k,p)>t have been visited.

A sketch of the traversal algorithm is given below:

```
0) Let Poly = "a null polynomial"
1) Sort the components of p in decreasing order , i.e. p[1] >=
p[2] >=. . .p[q]
2) For r = 1 to q, { let c[r] = int(np[r] + 0.5) }
3) Let pc = prob(c,p) (See note 1.)
4) For i = 1 to 2^(q-1) {
   a) Let b denote the binary representation of i-1
   b) For r = 1 to q-1 {
      i) Let v[r] = [+1,0,0, . . . -1 (at position r), 0, . . .0]
      ii) If b[r]=0, s=1, else s=-1
      iv) Let w[r]=s*v[r]
      }
   c) Let x = c; let px = pc.
   d) For r = 1 . . q-1 {
      i) If (b[r]==1), let x = x+w[r]
      ii) Let px = prob_recursive(x+w[r],x;p,px) (See note 3)
      }
   e) Let state = x; let pstate = px; let r = q.
   f) While (pstate<t) {
      i) Append (pstate,state) to P
      ii) For m = 1 to r-1 {
         1) Let stored_state[m] = state.
         2) Let stored_prob[m] = pstate.
         }
      iii) Let r = 1
      iv) Do {
         1) Let prev_state = stored_state[r]
         2) Let prev_p = stored_p[r]
         3) Let state = stored_state[r] + dir[r]
         4) If (state "is connected to" prev_state) (See note 2)
            let pstate = prob_recursive(state,prev_state;p,prev_p)
               else pstate = 0
         5) Let r = r+1
         }While (pstate<t and r<q-1)
      }
   }
5) Return P
```

Notes:

1) The probability at the centroid is computed without the benefit of the recursion relation, avoiding overflow errors as described above.

2) b "is connected to" a if for some i, j in 1. .q−1, 1) b[i] = a[i]+1, 2) b[j] = a[j]−1, and 3)a[r]=b[r] for r!=i or j and r in 1. .q−1

3) Let pa = P(a,p) as defined in Equation 3.

For i, j as defined above, p_recursive(a,b;p,pb) computes P(b,p) via Equation 4:

$$P(b,p) = pa*(p[i]/p[j])*(a[j]/b[i])$$

Analysis of the Traversal Algorithm

The possible outcomes of drawing n objects (atoms) of q types (isotopic species) lie on a (q−1)-dimensional plane embedded in q-dimensional Cartesian space. The maximum probability is roughly at the centroid of the distribution and falls monotonically every direction moving away from the maximum. The probability decreases with distance from the centroid most rapidly for the least abundant species.

A suitable basis for the plane on which the possible outcomes lie is given by the set of q−1 q-dimensional vectors {(1, −1, 0, 0, . . . 0), (1, 0, −1, 0, 0, . . . 0), (1, 0, 0, −1, 0, 0, . . . 0), . . . (1, 0, 0, . . . 0, −1)}. Taking the centroid as the origin, the q−1 dimensional plane contains $2^{q-1}$ "quadrants" which can be defined by the $2^{q-1}$ combinations formed by assigning a + or − to each basis vector. We define the quadrants formally below.

For r in {1 . . . q−1}, let $v_r$ denote the (q−1)-component vector with $v_{r1}$=1, $v_{rr}$=−1, and $v_{rm}$=0 for m in {2 . . . r−1, r+1, . . . q}. These are the set of basis vectors of the plane described above.

For i in {1 . . . $2^{q-1}$}, let $b_i$ denote the (q−1) component vector with $b_{im}$=((i−1)/2m−1%2), for m in {1 . . . q−1} where "/" denotes integer divide and "%" denotes modulus. That is, the $m^{th}$ component of $b_i$ is equal to the $m^{th}$ bit of the binary representation of i−1.

For i in {1 . . . $2^{q-1}$}, let $s_i$ denote the (q−1) vector generated from $b_i$ by the formula $s_{im}$=1−2*$b_{im}$, i.e. a component of $s_i$ is assigned to 1 or −1 when the corresponding component of $b_i$ is 0 or 1, respectively.

For i in {1 . . . $2^{q-1}$}, let $w_{ir}$ denote the $r^{th}$ basis vector for quadrant i. $w_{ir}$=$s_{ir}$*$v_r$. It corresponds to the $r^{th}$ basis vector of the plane multiplied by +1 or −1 as specified by the value of $Si_r$.

Then, the $i^{th}$ quadrant is defined as the set of points $$Q_i = \left\{ x_i + \sum_{r=1}^{q-1} u_r \cdot w_{ir} : u \in \{0, 1, \ldots\}^{q-1} \right\},\ i \in \{1 \ldots 2^{q-1}\}$$

So that the quadrants are disjoint, $x_i$ is defined, the origin of Qi as $$x_i = \sum_{r=1}^{q-1} b_{ir} \cdot w_{ir}$$

The traversal specified in the above algorithm search involves $2^{q-1}$ trajectories that start at or near the centroid, each covering all the states in a quadrant whose probability exceeds the threshold one of these quadrants.

The trajectory in a quadrant i starts at $x_i$ and moves between states in one unit steps along $w_{i1}$ (the direction for which the probability associated with each state decreases the most slowly). At each step away from the centroid, the probability decreases and can be computed using the recursive formula given in Equation 3. When the probability drops below the user-specified threshold, the sequence of steps in this direction is halted, since it is guaranteed that any states further along this line will have even lower probabilities.

The next state in the trajectory is $x_i$+$w_{i2}$, one step from the start state in the direction of the second basis vector—the second most slowly varying direction. Then the trajectory continues by making steps along the fastest varying direction (i.e., $x_i$+$w_{i2}$+$w_{i1}$, $x_i$+$w_{i2}$+2$w_{i1}$, etc.). In order to use the recursive formula to calculate the probability at $x_i$+$w_{i2}$, the value of the probability at $x_i$ was previously stored. In fact, the last state encountered along each of the q−1 search directions was kept track of. That is, q−1 values were stored during each scan so that all successive states can be computed using the recursion relation. When a subthreshold probability is encountered, the algorithm tries to make a step along the next component direction, backtracking to the last step taken in that direction, until it finds a new state with probability above the threshold, or terminates when all directions are exhausted.

The recursion relation is also used to compute the probability at each $x_i$, the start of the $i^{th}$ scan, from the stored value of the probability at c, the centroid. Because $x_i$ is not connected to c, in general, this calculation is iterative, but takes at most q−1 iterations.

Combining Multinomials to Generate Isotopomer Distributions

Finally, after the multinomial distribution has been calculated for each element, these are multiplied together (as in Equation 2) to generate the isotopomer distribution. For efficiency, each term in the multinomial may be sorted from high to low abundance. At each multiplication step, terms below the threshold can be eliminated without introducing errors. Truncation is allowed because successive multiplications (involving different elements) will not involve any of these terms.

The algorithm in Component 17 finds all isotopic species with abundance above a user-defined threshold in an efficient manner, visiting each desired state only once, visiting a minimum of states with sub-threshold probability, using a insignificant amount of memory overhead above what is required to store the desired states, and using a recursion relation to calculate all but the first state probability Component 18: Peptide Isomerizer: an Algorithm for Generating all Peptides with a Given Elemental Composition Peptide Isomerizer generates an exhaustive list of amino acid residue compositions for any given elemental composition. The algorithm exploits the natural grouping of amino acids into eight distinct groups, each identified by a unique triplet of values for sulfur atoms, nitrogen atoms, and the sum of rings and double bonds. A canonical residue-like constructor element is chosen to represent each group. In a preliminary step, combinations of these eight constructors are generated that, together, have the required numbers of sulfur atoms, nitrogen atoms, and rings plus double bonds. Because of the way these constructors were chosen, the elemental composition of these constructor combinations differs from the target elemental composition only by integer numbers of methylene groups ($CH_2$) and oxygen atoms. Remaining $CH_2$ groups and oxygen atoms are partitioned among the constructors to produce combinations of 16 residues (plus the pseudo-residue Leu/Ile) that have the desired elemental composition. Four residues (Leu, Ile, Gln, and Asn) each have an isomerically degenerate elemental composition and are treated separately. The final step steps of the algorithm yield residue combinations including all 20 residues.

Peptide Isomerizer can also be used to enumerate all isomeric peptides that contain arbitrary combinations of post-translational modifications. The program was used to correctly predict the frequencies with which various elemental compositions occur in an in silico digest of the human proteome. Applications for this program in proteomic mass spectrometry include Bayesian exact-mass determination from accurate mass measurements and tandem-MS analysis.

Motivation for Peptide Isomerizer

Proteins in a complex mixture can be identified by identifying one or more peptides that result from a tryptic digest of the proteins in the mixture. Peptides can be identified with reasonably high confidence by accurate mass measurements, given sufficient additional information. The uncertainty in the peptide's identity is due both to the uncertainty about its elemental composition that results from measurement uncertainty and the existence of multiple peptide isomers for virtually every elemental composition.

The accuracy required to identify the elemental composition of a peptide by measuring its mass increases sharply with the mass of the peptide. Roughly speaking, an elemental composition can be identified if its mass differs from all other distinct peptide mass values by more than the measurement error. The density of distinct peptide mass values increases roughly as the mass squared, so that peptides with larger mass tend to have closer neighbors. FTMS machines measure mass with an accuracy of 1 ppm. It has been shown that this mass accuracy is sufficient for absolute determination of peptide elemental compositions below 700 Da. Additional information is required to determine elemental compositions for larger peptides.

The elemental composition of a peptide does not, in general, specify its sequence. For nearly every elemental composition, there are multiple peptide isomers with the same elemental composition. Permutation of the order of the amino acids produces isomeric peptides. Exchanging atoms between residue side chains can produce peptide isomers with new residue compositions, including residues altered by post-translational modifications.

Given so many possibilities, identification of a peptide is not absolute, but rather addressed in terms of statements of probability. For example, given a peptide mass measurement M, peptides with masses near M (e.g., within 1 ppm) would be expected to have relatively high probability. In some cases, there may be a very large number of peptides with masses near M, but a much smaller number of distinct elemental compositions. In some cases, the peptide's elemental composition can be determined with high probability because one elemental composition is the closest to the measured value. In other cases, when several candidate elemental compositions are roughly the same distance from the measured value, one is distinguished by association with a relatively very large number of isomers, and thus is most likely to be the correct elemental composition.

Peptide Isomerizer provides a way to assign a priori probabilities to each elemental composition. The program enumerates all peptide isomers associated with any given elemental composition, even including post-translational modifications. The probability of an elemental composition is the sum of residue composition probabilities, summed over the isomeric combinations identified by Peptide Isomerizer.

Considering the a priori probabilities of elemental compositions improves both the determination of a peptide's elemental composition and interpreting the observed peptide as a member of the dynamic proteome (all proteins plus all possible modifications). A peptide's elemental composition provides a convenient way of matching the peptide to the proteome. A difference between an observed elemental composition and one representing a protein in its canonical form suggests a possible modification.

The ultimate goal in protein identification is an accurate estimate of the probability that an observed peptide is derived from a particular protein given a measurement of the peptide's mass. Such probabilities allow objective assessment of alternative interpretations of an observed peptide mass and provide a confidence metric for a chosen interpretation. Peptide Isomerizer is a useful tool in the calculation of these probabilities.

Problem Statement

Let F denote the elemental composition of a peptide made up of M elements: $n_1$ atoms of element $E_1$, $n_2$ atoms of $E_2$, . . . $n_M$ atoms of $E_M$. Then, F is represented by the N-component vector of non-negative integers.

$$F=(n_{E_1}, n_{E_2}, \ldots n_{E_M}) \quad (1)$$

Peptide isomers with elemental composition F are solutions to Equation 2 of the form ($a_1$, $a_2$, . . . $a_L$; $M_1$, $M_2$, . . . $M_L$).

$$F = \left( \sum_{i=1}^{L} f_{a_i} + M_i \right) + f_{H_2O} \quad (2)$$

L is a positive integer that denotes the length of the peptide. $a_i$ denotes the amino acid residue in position i of the sequence, and $f_{ai}$ denotes the elemental composition of this amino acid residue in its neutral, unmodified form. The elemental compositions of the twenty standard amino acids, represented by three-letter and one-letter codes, are shown below in the table below.

TABLE

Elemental Compositions of the Neutral Amino Acid Residues

| | | | |
|---|---|---|---|
| Ala(A) $C_3H_5NO$ | Gly(G) $C_5H_7NO_3$ | Met(M) $C_5H_9NOS$ | Ser(S) $C_3H_5NO_2$ |
| Cys(C) $C_3H_5NOS$ | His(H) $C_6H_7N_3O$ | Asn(N) $C_4H_6N_2O_2$ | Thr(T) $C_4H_7NO_3$ |
| Asp(D) $C_4H_5NO_3$ | Ile(I) $C_6H_{11}NO$ | Pro(P) $C_5H_7NO$ | Val(V) $C_5H_9NO$ |
| Glu(E) $C_5H_7NO_3$ | Lys(K) $C_6H_{12}N_2O$ | Gln(Q) $C_5H_7N_2O_2$ | Trp(W) $C_{11}H_{10}N_2O$ |
| Phe(F) $C_9H_9NO$ | Leu(L) $C_6H_{11}NO$ | Arg(R) $C_6H_{12}NO$ | Tyr(Y) $C_9H_9NO_2$ |

In Equation 2, $M_i$ denotes the elemental composition of the modification (if any) of residue i (i.e., the difference between the modified and unmodified residue). The values of Mi are also restricted to a set of allowed modifications not specified here. $f_{H2O}$ is the elemental composition of water: two hydrogen atoms are added to the N-terminal residue; one hydrogen and one oxygen atom are added to the C-terminal residue to make a string of residues into a peptide.

Attention is restricted to the special case M=5, and $E_1$=C, $E_2$=H, $E_3$=N, $E_4$=O, $E_5$=S. In this case, F=($n_C$,$n_H$,$n_N$,$n_O$,$n_S$). For example, $f_{H2O}$=(0, 2, 0, 1, 0), and $f_{Ala}$=(3, 5, 1, 1, 0). Even so, post-translational modifications involving atoms other than these five can be addressed.

Algorithm Design

Sequence Permutations

Peptide isomers can be related by three types of transformation: sequence permutation, exchange of atoms between unmodified residues, and introduction of post-translational modifications to unmodified peptides. It is trivial to enumerate sequence permutations, and so Peptide Isomerizer lists only one representative sequence among all possible permutation. One choice for such a representative sequence is the one with residues listed in non-ascending order by one-letter amino acid codes. For example, the set of 720 permutations of the sequence CEDARS would be represented by ACDERS.

Post-translational Modifications

The Peptide Isomerizer algorithm was guided by the insight that the generation of isomeric peptides could be divided into sequential steps. Treatment of post-translational modifications is the first such step. Any combination of post-translational modifications can be handled by simply subtracting out the necessary atoms from a given elemental composition and generating combinations of unmodified residues from the remaining atoms. For example, to generate singly-acetylated ($C_2H_2O$ added) peptide isomers with elemental composition $F=(n_C,n_H,n_N,n_O,n_S)$, unmodified peptide isomers are generated with elemental composition $F'=(n_C-2, n_H-2, n_N, n_O-1, n_S)$.

An Alternative Representation of Elemental Compositions

Not all combinations of five non-negative integers specify a peptide elemental composition. One constraint dictated by chemistry is that neutral species must satisfy Equation 3 for some non-negative integer k.

$$n_H=2n_C+n_N-2k \quad (3)$$

The number of hydrogen atoms must have the same parity as the number of nitrogen atoms (i.e., both are even or both are odd). For saturated molecules (i.e., no rings or double-bonds), k=0. Each ring or double-bond introduced into a molecule must be accompanied by the removal of two hydrogens, incrementing k by one. Therefore, k is the sum of the number of rings and double bonds.

$$k = \frac{2n_C + n_N - n_H}{2} \quad (4)$$

It is demonstrated below that the five component vector $(n_C, k, n_N, n_O, n_S)$ is a more useful representation of peptide elemental compositions. k is a non-negative integer, related to the original representation as defined by Equation 4.

Isomerically Degenerate Amino Acid Residues: Asn, Gln, Leu and Ile

The elemental composition of the amino acid residue Asn is the same as that of two Gly residues. Similarly, the elemental composition of the Gln is the same as the sum of the elemental compositions of the residues Gly and Ala. This property is exploited in the inventive algorithm as follows: first, all peptide isomers are generated from residues excluding the residues Gln and Asn; then, for each of these residue combinations of 18 residues, Asn and Gln residues are substituted for Gly and Ala to generate all possible combinations that include all 20 residues.

Let G and A denote the number of occurrences of Gly and Ala respectively in a residue combination. Let I denote the number of isomeric combinations that result from zero or more substitutions of Gln and Asn. The value of I is given by Equation 5.

$$I = \sum_{N=0}^{\lfloor G/2 \rfloor} 1 + \min(A, G-2N) = \begin{cases} \left\lfloor \frac{G}{2} \right\rfloor \left\lceil \frac{G}{2} \right\rceil + A + 1 - \left\lfloor \frac{G-A}{2} \right\rfloor \left( \left\lceil \frac{G-A}{2} \right\rceil - 1 \right) & G > A \\ \left( \left\lfloor \frac{G}{2} \right\rfloor + 1 \right) \left( \left\lceil \frac{G}{2} \right\rceil + 1 \right) & G \le A \end{cases} \quad (5)$$

The elemental compositions of Leu and Ile are identical, as suggested by their names. This property is exploited in the algorithm as well. A pseudo-residue "Leu/Ile" is created with elemental composition identical to Leu and Ile and undetermined covalent structure. The algorithm generates peptide isomers using Leu/Ile, but excludes the residues Leu and Ile. Then, for each of these residue combinations, Leu and Ile are substituted to generate all possible residue combinations that include these residues.

Let N denote the number of occurrences of Leu/Ile. Then, it is possible to generate N+1 distinct residue combinations by substituting as many as N and as few as zero occurrences of Leu and substituting Ile for the rest.

Classification of Residue Elemental Compositions to Define Constructor Elements

Figure 28:
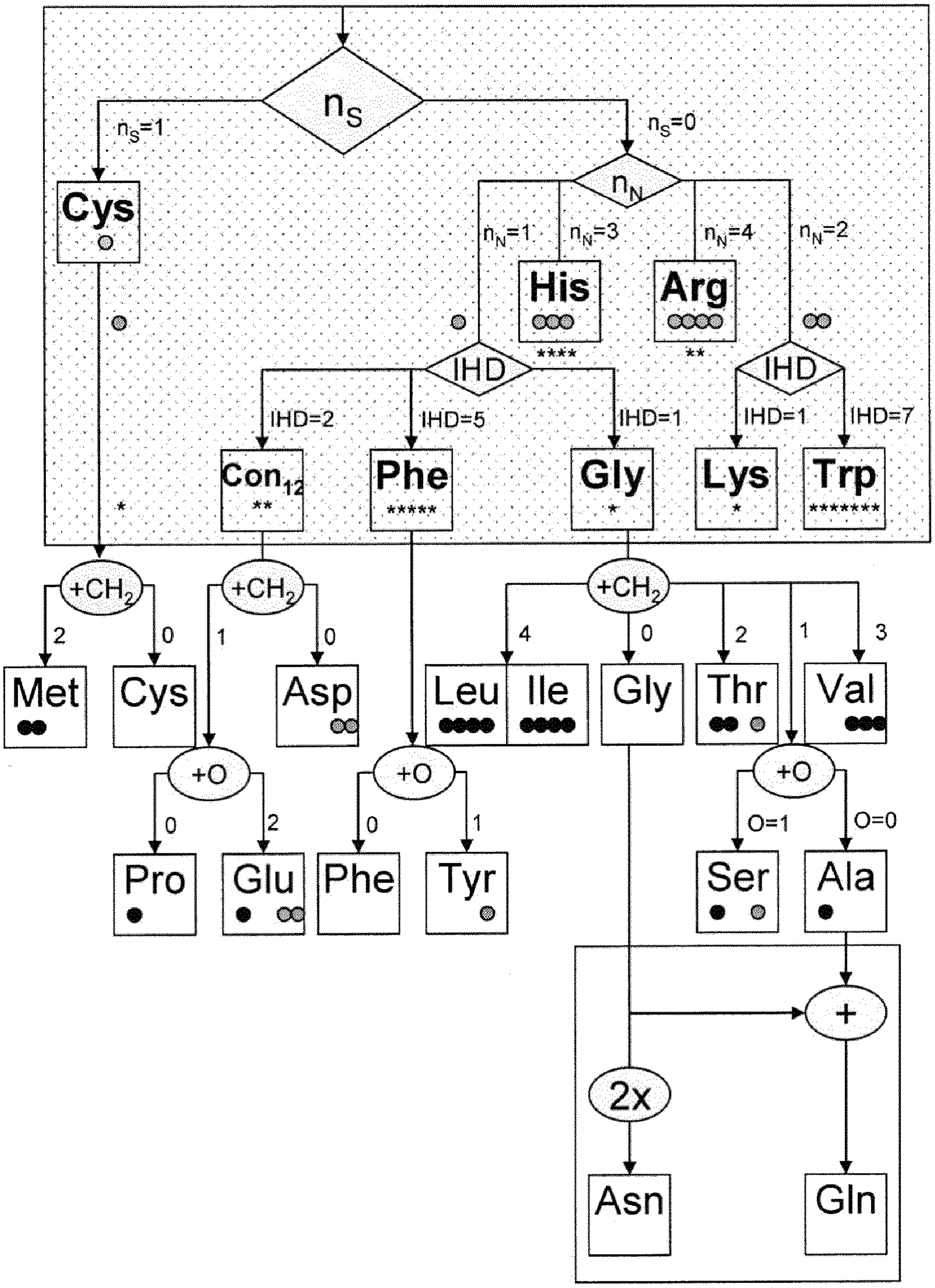
FIG. 28 depicts a classification of amino acid residues, in accordance with an embodiment of Component 18 of the present invention. A decision tree can be used to classify the chemical formulae of the amino acids residues into one of eight constructor groups (first boxed region). Constructor groups are identified by number of sulfur atoms (nS), number of nitrogen atoms (nN), and index of hydrogen deficiency (IHD, stars). Constructor groups H is, Arg, Lys, and Trp are singleton sets of their respective residues. Residues belonging to a given constructor group are built by adding the specifying number of methylene groups ($CH_2$) and oxygen atoms (O) to the canonical constructor element. Asn and Gln can be built from two copies of the constructor element Gly (lower right box): Asn=2*Gly, Gln=2*Gly+CH2=Gly+Ala.
Figure 31:
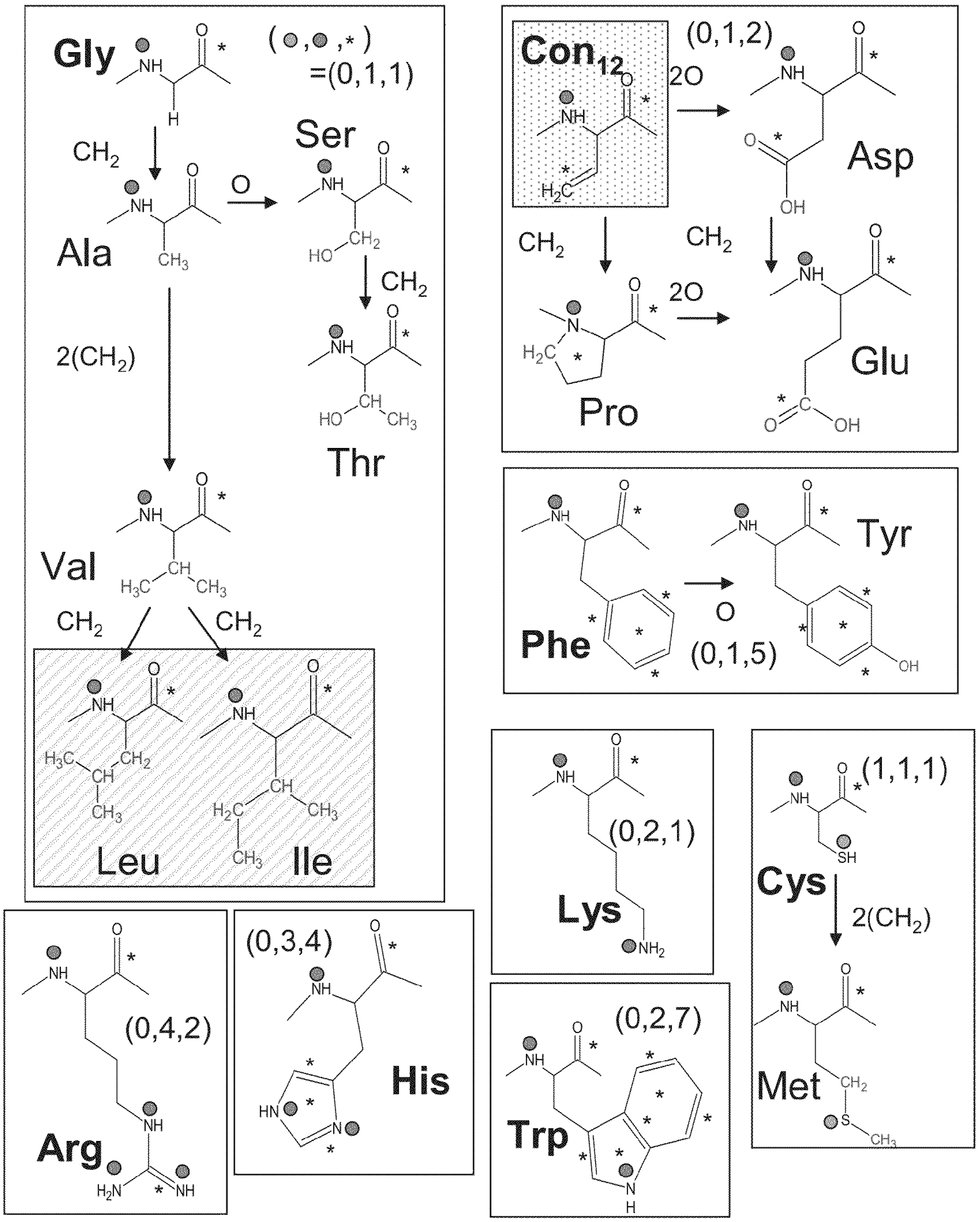
FIG. 31 illustrates that 18 amino acid residues can be divided in 8 groups, in accordance with an embodiment of Component 18 of the present invention. Each group is identified by a unique triplet (nS,nN,IHD), where nS=# of sulfur atoms (yellow balls), nN=# of nitrogen atoms (blue balls), and IHD=index of hydrogen deficiency (rings and double bonds, stars). Each group contains a constructor element (denoted in bold). Other members of the group can be "built" from the constructor by adding $CH_2$ and O (and rearrangement). Seven of the eight constructors are amino acid residues. The other (Con12, shaded) is the "lowest common denominator" of Glu and Pro. Leu and Ile (striped) are isomeric. Asn and Gln are excluded: they can be generated from combinations of Gly and Ala, i.e. Asn=Gly+Gly and Gln=Gly+Ala.

The amino acid residues (excluding Asn and Gln) can be divided into eight classes based upon the number of sulfur atoms ($n_s$), the number of nitrogen atoms ($n_N$), and the sum of the number of rings and double bonds (k) (FIGS. 28 and 31). A constructor element is chosen to represent each group. The constructor element is a "lowest common denominator" elemental composition that has the correct number of sulfur atoms, nitrogen atoms, and rings plus double bonds. The constructor element is chosen so that the elemental composition of each member of the group it represents can be constructed by adding a non-negative number of methylene ($CH_2$) groups and oxygen atoms to it. The defining properties of each group ($n_S$, $n_N$, and k) are invariant upon addition of $CH_2$ or O.

Seven of the eight constructor elements are identical to the elemental compositions of amino acid residues. Constructors are identified by the use of boldface font to distinguish them from residues. Four constructor elements Arg, His, Trp, and Lys represent groups with only one element, the corresponding residue. Three other constructors Cys, Gly, and Phe represent groups that contain not only these residues, but other residues whose elemental compositions that can be constructed from them. For example, the residue Ala is constructed from the constructor element Gly by adding $CH_2$.

The last constructor element has the elemental composition $C_4H_5NO$, and is labeled $Con_{12}$, denoting that it has one nitrogen atom and a sum of rings and double bonds of two. $Con_{12}$ represents the lowest-common denominator structure between Glu and Pro. Adding two oxygen atoms to $Con_{12}$ produces Asp, adding $CH_2$ produces Pro, and adding both $CH_2$ and two oxygen atoms produces Glu.

The residues Gln and Asn can be thought to belong to the Gly group. The elemental composition of Gln can be constructed from two copies of the constructor Gly. The elemental composition of Asn can be written as the sum of Gly and Ala, or equivalently twice Gly plus $CH_2$.

The relationships among constructor groups and residues are shown schematically in FIG. 28.

Solving Three Components of Equation 2 to Generate Constructor Combinations

The overall design of Peptide Isomerizer is to find solutions of Equation 2 (with no modifications; i.e., $M_i=0$) one component at a time, using the representation where $n_H$ is replaced by k, the sum of the number of rings and double bonds. The solutions for a given component are constrained by the distribution of that component among the amino acid residues, and by the solutions determined for the previous components. For example, amino acid residues may have one, two, three, or four nitrogen atoms, but if an amino acid residue is known to have a sulfur atom (from a previous step), then it must have one nitrogen atom.

The order in which the component equations are solved has a large impact upon the performance of the algorithm. Each component equation, in general, has multiple solutions. Each of these solutions is applied as a constraint in solving the next component equation. These constrained equations may also have multiple solutions, leading to a tree of candidate solutions. Many of these candidate solutions will lead to discovery of peptide isomers. An efficient algorithm minimizes the production of candidate solutions which do not lead to peptide isomers.

Using this rationale, it may be logical to solve the component equation involving the sulfur atoms first because this indicates with certainty the sum of Cys and Met residues;

these residues have one sulfur atom and the other residues have none. Thus, every subsequent solution must have $n_s$ copies of the Cys constructor.

The choice of the next constraint is less clear, but $n_N$ was chosen. Amino acid residues may have one, two, three, or four nitrogen atoms. After assigning one nitrogen atom for each Cys constructor, the algorithm generates all possible partitions of the remaining nitrogen atoms into "residues" so that each has no less than one and no more than four (i.e., $n_{min}$=0, $n_{max}$=4). Each partition of nitrogen atoms specifies a peptide of a particular length and a variety of lengths are possible.

The resulting distribution of nitrogen atoms among residues is approximately exponential, so that most residues have one nitrogen atom, fewer have two, still fewer have three, and the fewest have four. This distribution roughly reflects the actual distribution of amino acids since most have one nitrogen atom, a few have two, only His has three, and only Arg has four. The partitions of nitrogen atoms (without considering hydrogen, carbon, and oxygen) are fairly representative of the actual distributions of isomers that will be discovered, and thus does not lead to a lot of wasted calculations. In each partition of nitrogen atoms, every residue that has three or four nitrogen atoms is replaced by the Arg or His constructor, respectively.

Next, the component equation involving rings and double bonds was solved. In the first step, the number of Cys constructors in each isomer was identified. In the second step, combinations of various, but defined lengths, containing some unresolved constructors, but with defined numbers of Arg and His constructors were created. The identification of these constructors specifies the assignment of some of the rings and double bonds. The remaining rings and double bonds, or generically, unsaturation units, must be assigned to undetermined residues that have each one or two nitrogen atoms. These assignments determine the identity of these constructors. Two-nitrogen residues become Trp constructors when assigned seven unsaturation units and Lys when assigned one. One-nitrogen residues become Gly, $Con_n$, and Phe when assigned one, two, and five unsaturation units, respectively.

Adding $CH_2$ and O to Constructors to Form Residues

The solutions of three components of Equation 2—$n_S$, $n_N$, and k—represent a set of constructor combinations. The elemental composition of each of constructor combination can be calculated and compared to the desired value, the input elemental composition. By construction, the numbers of sulfur and nitrogen atoms are identical. Also, the difference in the number of hydrogen atoms is twice the difference in the number of carbon atoms, because k is also identical. Thus, the difference in the elemental combination can be written as the sum of an integer number of $CH_2$ groups and an integer number of O atoms. If the constructor combination contains too many carbon or oxygen atoms, it must be removed from consideration as a source of potential peptide isomers. Otherwise, any $CH_2$ groups and O atoms that remain must be added to the various constructor elements to form residues.

The eight constructors have varying capacities for $CH_2$ groups and oxygen atoms. Four constructors—Arg, His, Trp, and Lys—cannot take any additional atoms. Cys can take two $CH_2$ groups or none, becoming residues Met or Cys, respectively. Phe can accept one oxygen atom or none, becoming residues Tyr or Phe, respectively. A number of possible assignments of $CH_2$ and oxygen are possible with Gly and $Con_{12}$. Gly can take between zero and four $CH_2$ groups and one oxygen atom or none. $Con_{12}$ can take one $CH_2$ group or none and one oxygen atom or none. The minimum and maximum number of $CH_2$ groups and oxygen atoms that each constructor combination can accept is calculated. If the number of remaining $CH_2$ groups or oxygen atoms is outside this range, the constructor combination is discarded.

For each remaining constructor combination, $CH_2$ groups are partitioned among the Cys, $Con_{12}$, and Gly constructors. After this step, one or more candidate solutions (constructors plus varying arrangements of $CH_2$ groups) have been constructed. For each of these candidates, the minimum and maximum number of oxygen atoms that the constructors can accept is recalculated. If the number of remaining oxygen atoms is outside this range, that candidate is discarded.

Partitions of the remaining O atoms among the constructors in the remaining candidates produces all possible isomers constructed from 16 residues, excluding Asn, Gln, Leu, and Ile, but including the pseudo-residue Leu/Ile (Gly+4 CH2 groups). Isomers including all 20 residues are constructed by incorporating the four previously excluded residues as described above.

Probability Model

Applications of Peptide Isomerizer involve assigning probabilities to elemental compositions. The estimated frequency of occurrence of a residue composition is the sum of the frequencies of occurrence of all peptide sequences with that residue composition. The estimated frequency of occurrence of a peptide sequence is the product of the frequency of occurrences of the amino acid residues. Let S=($a_1$, $a_2$, . . . $a_n$) denote an n-residue peptide sequence. Let $p_k$ denote the probability of each amino acid residue, where k is the index denoting the amino acid type.

$$P(S) = \prod_{i=1}^{n} p_{a_i} \tag{6}$$

The values of $p_k$ are taken from the frequencies of the amino acid residues observed in the human proteome (Integr8 database, EBI/EMBL), shown in the table below.

TABLE

| Observed Amino Acid Frequencies in the Human Proteome | |
|---|---|
| Ala | 7.03 |
| Cys | 2.32 |
| Asp | 4.64 |
| Glu | 6.94 |
| Phe | 3.64 |
| Gly | 6.66 |
| His | 2.64 |
| Ile | 4.30 |
| Lys | 5.61 |
| Leu | 9.99 |
| Met | 2.15 |
| Asn | 3.52 |
| Pro | 6.44 |
| Glu | 4.75 |
| Arg | 5.72 |
| Ser | 8.39 |
| Thr | 5.39 |
| Val | 5.96 |
| Trp | 1.28 |
| Tyr | 2.61 |

The probabilities assigned to peptide sequences (and thus residue compositions) are equivalent to the frequencies that would be observed when sequences are generated by drawing residues at random from the above distribution.

Any model for generating peptides of finite length also requires a termination condition. One example is the rule that a peptide terminates following an Arg or Lys residue (i.e., idealized trypsin cleavage). In this model, any peptide that has does not end in an Arg or Lys residue or has an internal Arg or Lys residue would be assigned zero probability. But all peptides obeying these constraints would have properly normalized probabilities that are given by the equation above. Other rules for terminating sequences could also be implemented.

In this model, the probability assigned to a peptide sequence is invariant under permutation of the sequence. Let R denote a twenty-component vector that represents the residue composition of sequence S. The value of $R_k$, the kth component of R, represents the number of occurrences in S of amino acid type k. Note that n, the length of sequence S, is the sum of the components of R.

$$n = \sum_{k=1}^{20} R_k \tag{7}$$

Let N denote the number of distinct sequences with residue composition R. These are the district permutations of S.

$$N = \frac{n!}{\prod_{k=1}^{20} R_k!} \tag{8}$$

Then, the probability assigned to residue composition R is the probability of S times the number of permutations of S. This probability can be expressed entirely in terms of R without reference to sequence S or its length n.

$$p(R) = Np(S) = \frac{n!}{\prod_{k=1}^{20} R_k!} \prod_{i=1}^{n} P(S_i) = \frac{\prod_{k=1}^{20} R_k}{\prod_{k=1}^{20} R_k!} \prod_{k=1}^{20} p_k^{R_k} \tag{9}$$

Implementation Details

The inventive algorithm was implemented in C++. A few implementation details are provided below.

Partition Subroutine

The workhorse of the Peptide Isomerizer program is a subroutine for determining solutions to the general problem: "Find all partitions of N balls into M urns, with the constraint that each urn has at least $n_{min}$ balls and no more than $n_{max}$ balls." Solutions to the problem can be represented by vectors of $n_{max}$+1 non-negative integers, where the first component represents the number of urns with $n_{min}$ balls and the last component the number of urns with $n_{max}$ balls. The algorithm is the implementation of a recursive equation.

$$P(N, M, n_{min}, n_{max}) = \begin{cases} \bigcup_{n=\max(n_{min}, N-(M-1)n_{max})}^{\min(n_{max}, \lfloor \frac{N}{M} \rfloor)} e_n + P(N-n, M-1, n, n_{max}) & M > 0 \\ \emptyset & M = 0, N \neq 0 \\ \{0\} & M = 0, N = 0 \end{cases} \tag{10}$$

where $e_n$ is a unit vector of dimension $n_{max}$+1 with component n+1 equal to 1, and the operation "+" takes a vector v and a set S of vectors of the same dimension as v and adds the v to each element in S.

$$v+S=\{v+x:x\in S\}$$

There are a large number of partitions that are related by permuting the order of the urns. Unique partitions can be represented by ordering the urns in monotonically non-decreasing order, with urns containing the smallest number of balls first and largest last. By replacing the argument $n_{min}$ with n, the number of balls in the previous urn, in subsequent calls, it is ensured that all partitions are permutationally non-degenerate.

The partition subroutine is called at two places in the algorithm: partitioning of nitrogen atoms and $CH_2$ groups among Gly residues Partitioning Nitrogen Atoms Suppose there are N nitrogen atoms to be partitioned among residues. After Cys constructors are considered, allocating one nitrogen atom for each Cys residue, N=nN−nS. The subroutine is called with the arguments N balls, N urns, min=0, max=4. Each "urn" (residue) must, in fact, contain at least one "ball" (nitrogen atom), but specifying a minimum of zero, rather than one, permits the possibility of peptides of various lengths. Suppose the subroutine returns a partition has M residues with zero nitrogen atoms; we simply ignore these, leaving a partition of N-M residues each with at least one nitrogen atom.

Partitioning Rings and Double Bonds

Suppose, after assigning rings and double bonds to the Cys, Arg, and His constructors identified in previous steps, there are N additional unsaturation units to assign. If $N_{cys}$, $N_{Arg}$, and $N_{His}$ denote the numbers of Cys, Arg, and His constructors, respectively, then $N=k-N_{Cys}-2N_{Arg}-4N_{His}$. Suppose there are $N_2$ residues with two nitrogen atoms and $N_1$ residues with one nitrogen atom. The partition subroutine is not called to distribute unsaturation units. Instead, an assignment of units to constructors is represented as a five-component vector ($N_{Trp}$, $N_{Lys}$, $N_{Phe}$, $N_{Con12}$, $N_{Gly}$). $N_{Trp}$ and $N_{Lys}$ denote the number of two-nitrogen residues that receive seven units and one unit, respectively. $N_{Phe}$, $N_{Con12}$, and $N_{Gly}$ denote the number of one-nitrogen residues that receive five units, two units and one unit respectively. Since there are three constraints, represented by sums with values N, $N_1$, and $N_2$ respectively, the values of two components of the partition determine the other three. For example, if values of $N_{Trp}$ and $N_{Phe}$ are chosen, then the values of $N_{Lys}$, $N_{Con12}$, and $N_{Gly}$ are determined $$\begin{aligned} N_{Lys} &= N_2 - N_{Trp} \\ N_{Con_{12}} &= N - (N_1 + N_2 + 6N_{Trp} + 4N_{Phe}) \\ N_{Gly} &= N_1 - (N_{Phe} + N_{Con_{12}}) \end{aligned} \tag{11}$$

The set of all solutions is determined by looping over the possible values of ($N_{Trp}$, $N_{Phe}$).

$$\begin{aligned} N_{Trp} &\in \left[\max\left(0, \left\lceil \frac{N-(5N_1+N_2)}{6} \right\rceil\right), \min\left(\left\lfloor \frac{N-(N_1+N_2)}{6} \right\rfloor, N_2\right)\right] \\ N_{Phe} &\in \left[\max\left(0, \left\lceil \frac{N-(2N_1+N_2+6N_{Trp})}{3} \right\rceil\right), \right. \end{aligned} \tag{12}$$

-continued $$\min\left(\left\lfloor \frac{N-(N_1+N_2+6N_{Trp})}{4} \right\rfloor, N_1\right)\Bigg]$$

Partitioning $CH_2$ Groups

After the constructor combinations have been established in the previous steps, $CH_2$ groups are distributed among the constructors as the first of two steps towards generating residue combinations. Let N, $N_{Cys}$, $N_{Con12}$, and $N_{Gly}$ denote the total number of $CH_2$ groups to be partitioned and the number of Cys, $Con_{12}$, and Gly constructors, respectively. Let $N_{met}$ denote the number of Met residues formed and $N_{Pro/Glu}$ denote the number of $N_{Con12}$ residues that receive one $CH_2$ group. We loop over the possible values for ($N_{Met}$, $N_{Pro/Glu}$).

$$N_{Met} \in \left[\max\left(0, \left\lceil \frac{N-(4N_{Gly}+N_{Con12})}{2} \right\rceil\right), \min\left(\left\lfloor \frac{N}{2} \right\rfloor, N_{Cys}\right)\right] \tag{13}$$

$$N_{Pro/Glu} \in [\max(0, N-(2N_{Met}+4N_{Gly}), \min(N-2N_{Met}, N_{Con12})]$$

Then, for each pair of values the remaining ($N-2\,N_{Met}-N_{Pro/Glu}$) $CH_2$ groups are partitioned among the $N_{Gly}$ Gly constructors using the partition subroutine with $n_{min}=0$, $n_{max}=4$.

Partitioning Oxygen Atoms

Adding oxygen atoms to constructors, some with added $CH_2$ groups, is the final step in generating residue combinations. A Gly constructor with one $CH_2$ group requires an oxygen atom to become a Thr residue; similarly, a $Con_{12}$ constructor with no $CH_2$ groups requires two to become Asp. Let N, $N_{Thr}$, and $N_{Asp}$ denote the total number of free oxygen atoms and the number of Thr and Asp residues formed respectively. Then, there are $N-N_{Thr}-2{*}N_{Asp}$ oxygen atoms to partition among the remaining constructors that can accept oxygen atoms.

Let $N_{Pro/Glu}$, $N_{Ala/Ser}$, and $N_{Phe/Tyr}$ denote the numbers of $Con_{12}$ constructors with one $CH_2$ group, Gly constructors with one $CH_2$ group, and Phe constructors respectively. Let $N_{Glu}$, $N_{Ser}$, and $N_{Tyr}$ denote the number of Glu, Ser, and Tyr residues formed by adding oxygen atoms to the corresponding constructors. The numbers of Pro, Ala, and Phe residues ($N_{Pro}$, $N_{Ala}$, $N_{Phe}$) are determined by these values.

$$N_{Phe} = N_{Phy/Tyr} - N_{Tyr} \tag{14}$$

$$N_{Pro} = N_{Pro/Glu} - N_{Glu}$$

$$N_{Ala} = N_{Ala/Ser} - N_{Ser}$$

We loop over possible values for ($N_{Glu}$, $N_{Ser}$).

$$N_{Glu} \in \left[\max\left(0, \left\lceil \frac{N-(2N_{Asp}+N_{Thr}+N_{Ala/Ser}+N_{Phe/Tyr})}{2} \right\rceil\right), \min\left(\left\lfloor \frac{N-(2N_{Asp}+N_{Thr})}{2} \right\rfloor, N_{Pro/Glu}\right)\right] \tag{15}$$

$$N_{Ser} \in [\max(0, N-(2N_{Glu}+N_{Thr}+2N_{Asp}+N_{Phe/Tyr})), \min(N-(2N_{Glu}+N_{Thr}+2N_{Asp}), N_{Ala/Ser})]$$

The value of $N_{Tyr}$ is the number of remaining oxygen atoms.

$$N_{Tyr}=N-(2N_{Asp}+N_{Thr}+2N_{Glu}+N_{Ser}) \tag{16}$$

Experiments

To test the correctness of the algorithm and implementation, all (unmodified) residue compositions of eight residues or less were generated and grouped by elemental composition, recording the number of isomers for each elemental composition. Then, each elemental composition was submitted to Peptide Isomerizer to calculate the number of isomers and the results were compared.

To examine the rate of growth of the number of residue combinations with mass, a list of human proteins (International Protein Index) was taken, an in silico tryptic digest was performed, the resulting peptides were grouped by elemental composition, and the number of isomers and probability for each elemental composition were calculated.

Isomerization of all Peptides Up to Length Eight

There are 26,947,368,420 ($20^8$) peptides of length eight or less. These peptides can be grouped into 3,108,104 (28!/(20!8!)−1) distinct residue combinations. These distinct residue combinations can be further grouped into 188,498 distinct elemental compositions. Thus, each elemental combination represents, on average, about 16 different isomeric residue combinations and about 140,000 different isomeric peptides, length eight or less.

The Peptide Isomerizer program was validated as follows. The distinct residue combinations of peptides of length eight or less were enumerated. For each residue combination, the elemental composition and exact mass were computed. These residue combinations were then sorted by exact mass value and residue combinations that had the same elemental composition were grouped together. A table of these elemental compositions was created, and for each entry, the number of residue compositions was recorded.

Then, each elemental composition was fed to the Peptide Isomerizer program. The program counted the number of isomers for 188,498 elemental compositions in under one hour on an Ultrasparc III (800 MHz, 12 Gb RAM) machine. The results were compared to the tabulated values generated by direct enumeration.

The Peptide Isomerizer program and direct enumeration of isomeric residue compositions gave identical results for the first (lightest) 3,906 elemental compositions (masses up to 531.2 D). The first discrepancy was for the elemental composition $C_{18}H_{29}N_9O_{10}$. For this elemental composition, four isomers were found by direct enumeration Gly$(Asn)_4$, $(Gly)_3(Asn)_3$, $(Gly)_5(Asn)_2$, and $(Gly)_7$Asn. The Peptide Isomerizer found these four, plus an additional isomer $(Gly)_9$. Peptide Isomerizer found $(Gly)_9$ because it considers peptides of arbitrary length; the direct enumeration had a length cutoff of eight residues.

Peptide Isomerizer produced correct results, and direct enumeration of peptides up to length N is sufficient for identifying isomers only up to mass $(N+1)m_{Gly}$—for n=8, 531.2 D. To identify all isomers up to mass 1000D, one would need to enumerate all residue combinations up to length 16. This requires consideration of 7,307,872,109 residue combinations. This fact emphasizes the utility of the Peptide Isomerizer program.

Isomerization of Tryptic Peptides from the Human Proteome

Peptide Isomerizer was run on an ideal tryptic digest (cutting on the C-terminal side of each Arg and Lys residue) of human protein sequences. 50,071 human protein sequences were downloaded from the ENSEMBL International Protein Index (8/2005), and 2,673,065 tryptic peptides were constructed. 1194 peptides with amino acid codes X, Y, and Z were eliminated. After eliminating multiple occurrences of the same peptide, there were 831,139 distinct peptides. These peptides were sorted and peptides with identical elemental composition were eliminated. The Peptide Isomerizer was run on the resulting 342,623 elemental compositions. The first 100,000 elemental compositions (masses <1507 Da) were processed in about two hours. The next 100,000 elemental compositions (masses <2243 Da) required roughly two days.

Figure 32:
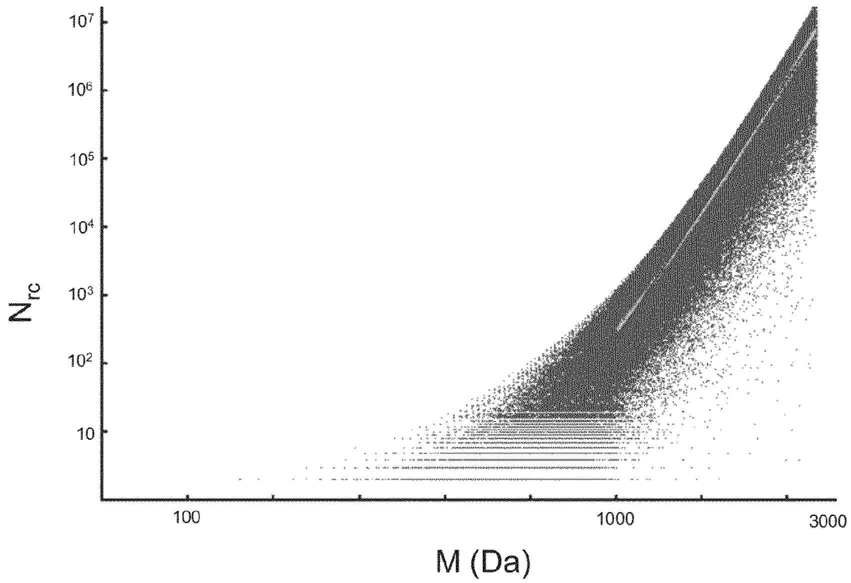
FIG. 32 depicts a log-log plot of number of residue compositions (Nrc) vs. peptide mass (M), in accordance with an embodiment of Component 18 of the present invention. Red: in silico tryptic digest of human proteome (ENSEMBL IPI), masses <3000D (N=261540). Green: average Nrc for each nominal mass. Blue: line of best fit through green dots: y=(5.31*10-27)*M9.55.
Figure 32:
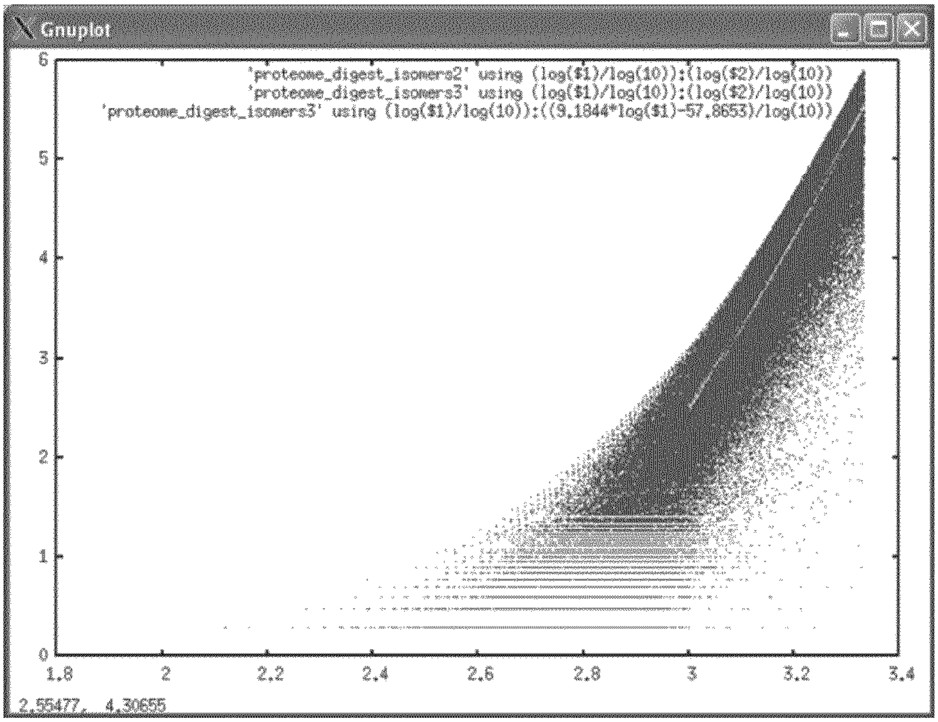

The number of isomeric residue combinations ($N_{rc}$) is plotted against the peptide mass (M) on a log-log scale (FIG. 32). There is a good linear fit of the log of the number of peptide isomers versus the log of the mass, in the mass range of 1000 to 2500 Da. The slope of the line (10×) indicates the exponent q in the relation.

$$N_{rc}=kM^{q} \quad (17)$$

Peptide Isomerizer is a multi-purpose tool with a number of possible applications. It was noted above that the initial motivation for developing this tool was to improve peptide and protein identification from an accurate mass measurement. However, at least two other applications—tandem mass spectrometry and on-line mass spectrum calibration—are contemplated.

As emphasized above, an accurate mass measurement is, in general, insufficient for peptide identification without additional information. One important source of additional information is the measurement of the masses of peptide fragment ions. A recent paper has discussed how enumeration of residue combinations can improve the interpretation of tandem mass spectra (Spengler, *JASMS* 15: 704, 2004).

The use of Peptide Isomerizer is valuable in this approach. Interpretation of fragment masses may be guided both by the fragment mass and the parent mass. Peptide Isomerizer could generate peptide isomers of various ion types (i.e., a, b, c, x, y, z), treating the effects of different types of cleavage as generic modifications. Because fragment masses are measured with low accuracy, alternative elemental compositions may need to be considered in parallel. Statistical analysis of the residue combinations of the parent peptide can be used to weigh competing interpretations of the fragment masses.

This approach is amenable to analysis of incomplete fragmentation spectra, which often cause failure of conventional methods. When fragments are identified, the Peptide Isomerizer can calculate residue combinations consistent with the remaining atoms in the unidentified regions of the peptide, bringing tighter constraints on the identification of the rest of the peptide. For example, it would be relatively easy to determine the last five or six residues after the other residues were identified by tandem MS and the parent mass were known to 1-ppm accuracy.

The ability to generate a list of isomers for any arbitrary chemical formula makes it possible to consider arbitrary combinations of arbitrary post-translational modifications. If additional information allows us to assign a priori probability to arbitrary post-translational modifications and/or sequence variations, we could formally compute probabilities for all alternative interpretations of the given chemical formula. This would form the basis of a maximum-likelihood estimate of the PMT-state of the peptide, an estimate of the probability that the estimate is correct, as well as a list of the most likely alternative interpretations.

Exact mass determination, even without identifying the sequence or much less the residue composition, can be used to calibrate the mass spectrometer (i.e., to convert observed frequencies into mass-to-charge ratios). Calibration accuracy can be improved by having a large number of correctly determined mass values. In turn, improved calibration accuracy permits the correct identification of additional mass values. Iterations between calibration and exact mass determination steps can be repeated to improve both processes. In many cases, an accurate mass measurement of a peptide does not identify the exact mass with certainty. However, consideration of the relative frequencies of occurrence of different exact mass values makes it possible to assign probabilities to them. Thus, the probabilities that come from Peptide Isomerizer can be used in calibration to enforce high-confidence assignments rigidly while other observed values would have less influence on the calibration parameters.

An issue that affects the utility of Peptide Isomerizer is the growth in the number of residue compositions with mass. It was found that the number of residue compositions grows roughly as the $10^{th}$ power of the mass over masses from 1000 to 3000 Da. For example, doubling the mass increases the number of residue compositions one thousand fold. A statistical method is needed for rapid computation of elemental composition probabilities for larger masses. Such a method can be validated using the Peptide Isomerizer as a gold standard.

One way to speed up Peptide Isomerizer is to generate only tryptic peptides. The program can be modified to do this as follows. The elemental composition of Lys and Arg residues are each subtracted from the target elemental composition. For each difference, peptide isomers are generated from the 18 amino acid residues excluding Lys and Arg. Then, for each of these two sets, either Lys or Arg are appended to the residue compositions in the corresponding set, and the two sets are combined.

Peptide Isomerizer provides an efficient enumeration of peptide isomers of a given elemental composition, with the ability to consider post-translational modifications. The program has been used to estimate the a priori probabilities with which elemental compositions are expected to occur in a tryptic digest of the human proteome. Applications for Peptide Isomerizer include probability-based approaches to peptide/protein identification, tandem mass spectrometry, and on-line mass spectrum calibration.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as “a” or “an” (e.g., “a” and/or “an” should typically be interpreted to mean “at least one” or “one or more”); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of “two recitations,” without other modifiers, typically means at least two recitations, or two or more recitations).

Accordingly, the invention is not limited except as by the appended claims

What is claimed is:

1. A method for calibrating two or more mass spectra comprising:

recording the mass spectra of at least two sample ions;

estimating the frequencies of the ion species from the mass spectra to form two frequency lists;

matching the frequencies of the ions between the two lists, wherein a frequency shift is modeled by the equation, $$f \approx \frac{A + A + \frac{1}{2A}\left(4B\frac{m}{z}\right)}{2(m/z)} = \frac{A}{m/z} + \frac{B}{A},$$

wherein m represents mass, z represents charge, f represents frequency, A is proportional to the magnetic field strength, and B is proportional to the space-charge effect, and determining the optimal frequency that best superimposes one list of frequencies on to the other.

2. The method of claim 1, wherein the mass spectra are generated by an LC-FTMS, an FT-ICR, an LTQ-FT or an Orbitrap system.

3. The method of claim 1, wherein the space-charge frequency shift is determined based on an overlap of any two frequency spectra corresponding to two of said at least two different scans, wherein the overlap is estimated by constructing continuous parametric models of the largest peaks in the spectra.

4. The method of claim 1, wherein the space-charge frequency shift is determined as the shift that minimizes the sum of the squared differences between frequency estimates of ions that can be matched across any two frequency spectra corresponding to two of said at least two different scans.

5. The method of claim 1, wherein the algorithm calculates the average space-charge frequency shift of all scans of said sample ion when there are more than two scans.

* * * * *